(12) United States Patent
Ruben et al.

(10) Patent No.: US 6,410,709 B1
(45) Date of Patent: Jun. 25, 2002

(54) CORNICHON-LIKE PROTEIN

(75) Inventors: Steven M. Ruben, Olney; Craig A. Rosen, Laytonsville; Ping Fan, Gaithersburg; Hla Kyaw, Frederick, all of MD (US); Ying-Fei Wei, Berkeley, CA (US)

(73) Assignee: Human Genome Sciences, Inc., Rockville, MD (US)

( * ) Notice: Subject to any disclaimer, the term of this patent is extended or adjusted under 35 U.S.C. 154(b) by 0 days.

(21) Appl. No.: 09/257,179

(22) Filed: Feb. 25, 1999

Related U.S. Application Data

(63) Continuation-in-part of application No. PCT/US98/17709, filed on Aug. 27, 1998.
(60) Provisional application No. 60/056,270, filed on Aug. 29, 1997, provisional application No. 60/056,271, filed on Aug. 29, 1997, provisional application No. 60/056,247, filed on Aug. 29, 1997, and provisional application No. 60/056,073, filed on Aug. 29, 1997.

(51) Int. Cl.$^7$ .............................................. C07H 21/04
(52) U.S. Cl. ....................... 536/23.5; 536/24.31; 435/6; 435/69.1; 435/70.1; 435/71.1; 435/91.2; 435/252.3; 435/320.1; 530/350
(58) Field of Search ............................. 536/23.5, 24.31; 435/6, 69.1, 70.1, 71.1, 91.2, 252.3, 320.1; 530/350

(56) References Cited

U.S. PATENT DOCUMENTS 5,968,744 A    10/1999   Hillman et al.

FOREIGN PATENT DOCUMENTS

WO    WO 00/09709    2/2000
WO    WO 00/53751    9/2000

OTHER PUBLICATIONS

Pasqualone et al., "STU1, a Suppressor of a β-Tubullin Mutation, . . .", J. of Cell Biol., 127(6):1973–1984 (Dec. 1994).
Evers et al., "Molecular coevolution of mammalian ribosomal . . .", Proc. Natl. Acad. Sci. USA, 92:5827–5831 (Jun. 1995).
Tanaka et al., "Molecular Cloning of cDNA for Vacuolar Membrane . . .", Biochem. And Biophys. Res. Comm., 190(3):1110–1114 (Feb. 15, 1993).
Lin et al., "Isolation and Characterization of C–reative Protein (CRP) . . .", J. of Biol. Chem, 268(9):6809–6815 (Mar. 25, 1993).
Colas et al., "Drosophila 5–HT$_2$ serotonin receptor: . . .", Proc. Natl. Acad. Sci. USA, 92:5441–5445 (Jun. 1995).
Zock et al., "The *Bacillus subtilis pnbA* gene encoding . . .", Gene, 151:37–43 (1994).

Lauder et al., "Dual Requirement for the Yeast MMS19 Gene in . . .", Mol. And Cell. Biol., 16(12):6783–6793 (Dec. 1996).
Dwyer et al., "Structure and expression of AtS1, an . . .", Mol. Gen. Genet., 231:442–448 (1992).
Genbank Accession No. R05785 (Apr. 3, 1995).
Genbank Accession No. AA459132 (Aug. 13, 1997).
Genbank Accession No. AA312632 (Apr. 19, 1997).
Genbank Accession No. AA530982 (Aug. 20, 1997).
Genbank Accession No. R77507 (Jun. 7, 1995).
Genbank Accession No. H97682 (Dec. 12, 1995).
Genbank Accession No. AA184809 (Jan. 7, 1997).
Genbank Accession No. AA253014 (Aug. 6, 1997).
Genbank Accession No. H04658 (Jun. 20, 1995).
Genbank Accession No. B01406 (Jun. 26, 1996).
Genbank Accession No. O95406 (May 30, 2000).
Genbank Accession No. O35372 (May 30, 2000).
Genbank Accession No. AF070654 (Mar. 21, 1999).
Genbank Accession No. AF104398 (Dec. 28, 1998).
Genbank Accession No. AF031379 (May 27, 1999).
Genbank Accession No. AF022811 (May 5, 1998).
Genbank Accession No. AF104398 (Dec. 28, 1998).
Genbank Accession No. AF031379 (May 27, 1999).
Genbank Accession No. AF022811 (May 5, 1998).
Genbank Accession No. W02973 (Apr. 18, 1996).
Genbank Accession No. AA545158 (Aug. 4, 1997).
Genbank Accession No. AA424788 (Oct. 16, 1997).
Genbank Accession No. AA309041 (Apr. 18, 1997).
Genbank Accession No. N36077 (Jan. 16, 1996).
Genbank Accession No. AA488913 (Aug. 15, 1997).
Genbank Accession No. AA488843 (Aug. 15, 1997).
Genbank Accession No. AA259744 (Mar. 18, 1997).
Genbank Accession No. N72259 (Mar. 18, 1996).
Genbank Accession No. N31510 (Jan. 10, 1996).
Genbank Accession No. AA258723 (Mar. 17, 1997).
Genbank Accession No. AA521110 (Aug. 20, 1997).
Genbank Accession No. AA139230 (Feb. 18, 1997).
Genbank Accession No. AA316187 (Apr. 19, 1997).
Genbank Accession No. W03628 (Apr. 19, 1996).
Genbank Accession No. AA305145 (Apr. 18, 1997).
Genbank Accession No. H11860 (Jun. 26, 1995).
Genbank Accession No. N35514 (Jan. 16, 1996).
Genbank Accession No. H98531 (Dec. 15, 1995).
Genbank Accession No. F02558 (Feb. 2, 1995).
Genbank Accession No. AA218033 (Feb. 6, 1997).

(List continued on next page.)

*Primary Examiner*—W. Gary Jones
*Assistant Examiner*—Janell E. Taylor
(74) *Attorney, Agent, or Firm*—Human Genome Sciences, Inc.

(57) ABSTRACT

The present invention relates to novel human secreted proteins and isolated nucleic acids containing the coding regions of the genes encoding such proteins. Also provided are vectors, host cells, antibodies, and recombinant methods for producing human secreted proteins. The invention further relates to diagnostic and therapeutic methods useful for diagnosing and treating disorders related to these novel human secreted proteins.

46 Claims, No Drawings

OTHER PUBLICATIONS

Genbank Accession No. N22845 (Dec. 28, 1995).
Genbank Accession No. AA286780 (Aug. 14, 1997).
Genbank Accession No. H39954 (Aug. 16, 1995).
Genbank Accession No. D61770 (Aug. 29, 1995).
Genbank Accession No. H18748 (Jun 29, 1995).
Genbank Accession No. AA297880 (Apr. 18, 1997).
Genbank Accession No. H85727 (Nov. 21, 1995).
Genbank Accession No. AA049525 (Sep. 9, 1996).
Genbank Accession No. N35920 (Jan. 16, 1996).
Genbank Accession No. N44081 (Feb. 7, 1996).
Genbank Accession No. AA038981 (Aug. 29, 1996).
Genbank Accession No. N28653 (Jan. 4, 1996).
Genbank Accession No. AA414260 (Aug. 4, 1997).
Genbank Accession No. AA414077 (Aug. 4, 1997).
Genbank Accession No. H58327 (Oct. 5, 1995).
Genbank Accession No. W70849 (Jun. 17, 1996).
Genbank Accession No. Z43636 (Nov. 11, 1994).
Genbank Accession No. N70237 (Mar. 14, 1996).
Genbank Accession No. F06684 (Feb. 20, 1995).
Genbank Accession No. AA415304 (Oct. 16, 1997).
Genbank Accession No. AA511617 (Jul. 8, 1997).
Genbank Accession No. F11535 (Mar. 12, 1995).
Genbank Accession No. AA405519 (May 17, 1997).
Genbank Accession No. AA258561 (Mar. 17, 1997).
Genbank Accession No. AA235046 (Aug. 7, 1997).
Genbank Accession No. F06275 (Feb. 19, 1995).
Genbank Accession No. AA652056 (Nov. 13, 1997).
Genbank Accession No. Z39700 (Nov. 7, 1994).
Genbank Accession No. H94365 (Nov. 25, 1996).
Genbank Accession No. T35223 (Sep. 6, 1995).
Genbank Accession No. N67794 (Mar. 8, 1996).
Genbank Accession No. AA510294 (Jul. 8, 1997).
Genbank Accession No. D61806 (Aug. 29, 1995).
Genbank Accession No. R01406 (Mar. 31, 1995).
Genbank Accession No. N31657 (Jan. 10, 1996).
Genbank Accession No. T97629 (Mar. 29, 1995).
Genbank Accession No. AA651834 (Nov. 13, 1997).
Genbank Accession No. D62499 (Aug. 29, 1995).
Genbank Accession No. AA297892 (Apr. 18, 1997).
Genbank Accession No. AA414376 (Aug. 4, 1997).
Genbank Accession No. AA297245 (Apr. 18, 1997).
Genbank Accession No. AA544466 (Aug. 4, 1997).
Genbank Accession No. H58716 (Oct. 5, 1995).
Genbank Accession No. N33050 (Jan. 10, 1996).
Genbank Accession No. F02949 (Feb. 2, 1995).
Genbank Accession No. AA547568 (Aug. 5, 1997).
Genbank Accession No. N39925 (Jan. 22, 1996).
Genbank Accession No. AA298181 (Apr. 18, 1997).
Genbank Accession No. H18661 (Jun. 29, 1995).
Genbank Accession No. F09197 (Feb. 23, 1995).
Genbank Accession No. T97581 (Mar. 29, 1995).
Genbank Accession No. AA681715 (Dec. 5, 1997).
Genbank Accession No. T30535 (Sep. 6, 1995).
Genbank Accession No. H11499 (Jun. 26, 1995).
Genbank Accession No. AA620005 (Oct. 9, 1997).
Genbank Accession No. R01405 (Mar. 31, 1995).
Genbank Accession No. AA237834 (Mar. 3, 1997).
Genbank Accession No. AA297587 (Apr. 18, 1997).
Genbank Accession No. D79647 (Feb. 9, 1996).
Genbank Accession No. W91723 (Jul. 9, 1996).
Genbank Accession No. AA297457 (Apr. 18, 1997).
Genbank Accession No. AA495847 (Aug. 11, 1997).
Genbank Accession No. AA287884 (Aug. 14, 1997).
Genbank Accession No. AA049433 (Sep. 9, 1996).
Genbank Accession No. T30559 (Sep. 6, 1995).
Genbank Accession No. F04288 (Feb. 19, 1995).
Genbank Accession No. D61004 (Aug. 28, 1995).
Genbank Accession No. H28462 (Aug. 16, 1995).
Genbank Accession No. AA296790 (Apr. 18, 1997).
Genbank Accession No. W18659 (Sep. 10, 1996).
Genbank Accession No. F08052 (Feb. 21, 1995).
Geneseq Accession No. Y28813 (Oct. 7, 1999).
Geneseq Accession No. Y41306 (Oct. 19, 1999).
Geneseq Accession No. Y41732 (Sep. 16, 1999).
Geneseq Accession No. Y32925 (Sep. 2, 1999).
Geneseq Accession No. Y53622 (Jul. 8, 1999).
Geneseq Accession No. Y11505 (Feb. 11, 1999).
Geneseq Accession No. X90853 (Oct. 7, 1999).
Geneseq Accession No. Z30544 (Oct. 19, 1999).
Geneseq Accession No. Z34164 (Sep. 16, 1999).
Geneseq Accession No. Z36228 (Jul. 8, 1999).
Geneseq Accession No. Z11186 (Sep. 2, 1999).
Geneseq Accession No. Z34165 (Sep. 16, 1999).
Geneseq Accession No. Z11179 (Sep. 2, 1999).

SEQUENCE LISTING

<160> NUMBER OF SEQ ID NOS: 128

<210> SEQ ID NO 1
<211> LENGTH: 733
<212> TYPE: DNA
<213> ORGANISM: Homo sapiens

<400> SEQUENCE: 1
gggatccgga gcccaaatct tctgacaaaa ctcacacatg cccaccgtgc ccagcacctg      60
aattcgaggg tgcaccgtca gtcttcctct tccccccaaa acccaaggac accctcatga     120
tctcccggac tcctgaggtc acatgcgtgg tggtggacgt aagccacgaa gaccctgagg     180
tcaagttcaa ctggtacgtg gacggcgtgg aggtgcataa tgccaagaca aagccgcggg     240
aggagcagta caacagcacg taccgtgtgg tcagcgtcct caccgtcctg caccaggact     300

-continued

```
ggctgaatgg caaggagtac aagtgcaagg tctccaacaa agcccctccca acccccatcg    360 agaaaaccat ctccaaagcc aaagggcagc ccgagaacc acaggtgtac accctgcccc     420
catcccggga tgagctgacc aagaaccagg tcagcctgac ctgcctggtc aaaggcttct    480
atccaagcga catcgccgtg gagtgggaga gcaatgggca gccggagaac aactacaaga    540
ccacgcctcc cgtgctggac tccgacggct ccttcttcct ctacagcaag ctcaccgtgg    600
acaagagcag gtggcagcag gggaacgtct tctcatgctc cgtgatgcat gaggctctgc    660
acaaccacta cacgcagaag agcctctccc tgtctccggg taaatgagtg cgacggccgc    720
gactctagag gat                                                      733
```

<210> SEQ ID NO 2
<211> LENGTH: 5
<212> TYPE: PRT
<213> ORGANISM: Homo sapiens
<220> FEATURE:
<221> NAME/KEY: Site
<222> LOCATION: (3)
<223> OTHER INFORMATION: Xaa equals any of the twenty naturally
      ocurring L-amino acids

<400> SEQUENCE: 2

Trp Ser Xaa Trp Ser
 1               5

<210> SEQ ID NO 3
<211> LENGTH: 86
<212> TYPE: DNA
<213> ORGANISM: Homo sapiens

<400> SEQUENCE: 3

```
gcgcctcgag atttccccga aatctagatt tccccgaaat gatttccccg aaatgatttc    60
cccgaaatat ctgccatctc aattag                                        86
```

<210> SEQ ID NO 4
<211> LENGTH: 27
<212> TYPE: DNA
<213> ORGANISM: Homo sapiens

<400> SEQUENCE: 4

```
gcggcaagct ttttgcaaag cctaggc                                       27
```

<210> SEQ ID NO 5
<211> LENGTH: 271
<212> TYPE: DNA
<213> ORGANISM: Homo sapiens

<400> SEQUENCE: 5

```
ctcgagattt ccccgaaatc tagatttccc cgaaatgatt tccccgaaat gatttccccg    60
aaatatctgc catctcaatt agtcagcaac catagtcccg cccctaactc cgcccatccc   120
gcccctaact ccgcccagtt ccgcccattc tccgccccat ggctgactaa ttttttttat   180
ttatgcagag gccgaggccg cctcggcctc tgagctattc cagaagtagt gaggaggctt   240
ttttggaggc ctaggctttt gcaaaaagct t                                  271
```

<210> SEQ ID NO 6
<211> LENGTH: 32
<212> TYPE: DNA
<213> ORGANISM: Homo sapiens

<400> SEQUENCE: 6

```
gcgctcgagg gatgacagcg atagaaccccc gg                              32
```

<210> SEQ ID NO 7
<211> LENGTH: 31
<212> TYPE: DNA
<213> ORGANISM: Homo sapiens

<400> SEQUENCE: 7

```
gcgaagcttc gcgactcccc ggatccgcct c                               31
```

<210> SEQ ID NO 8
<211> LENGTH: 12
<212> TYPE: DNA
<213> ORGANISM: Homo sapiens

<400> SEQUENCE: 8

```
ggggactttc cc                                                    12
```

<210> SEQ ID NO 9
<211> LENGTH: 73
<212> TYPE: DNA
<213> ORGANISM: Homo sapiens

<400> SEQUENCE: 9

```
gcggcctcga ggggactttc cggggacttt ccggggactt tccatcctg            60 ccatctcaat tag                                                   73
```

<210> SEQ ID NO 10
<211> LENGTH: 256
<212> TYPE: DNA
<213> ORGANISM: Homo sapiens

<400> SEQUENCE: 10

```
ctcgagggga ctttcccggg gactttccgg ggactttccg ggactttcca tctgccatct   60
caattagtca gcaaccatag tcccgcccct aactccgccc atcccgcccc taactccgcc  120
cagttccgcc cattctccgc cccatggctg actaatttttt tttatttatg cagaggccga  180
ggccgcctcg gcctctgagc tattccagaa gtagtgagga ggcttttttg gaggcctagg  240
cttttgcaaa aagctt                                                 256
```

<210> SEQ ID NO 11
<211> LENGTH: 866
<212> TYPE: DNA
<213> ORGANISM: Homo sapiens
<220> FEATURE:
<221> NAME/KEY: SITE
<222> LOCATION: (22)
<223> OTHER INFORMATION: n equals a,t,g, or c
<220> FEATURE:
<221> NAME/KEY: SITE
<222> LOCATION: (37)
<223> OTHER INFORMATION: n equals a,t,g, or c

<400> SEQUENCE: 11

```
tccacgtaaa tgggaacaaa ancatggacc accaccngca agtggcggcc gctctagaac   60
tagtggatcc cccgggctgc aggaattcgg cacgaggtaa tatgagtctt ccagcttcat  120 tcttttttcaa aattgctttg gtttttctac acgttttttc tgtgaacttt agaatcagct  180
tgtcagtgtc tacaagccct ctgggatttt gactggaatt gcattgaatg tatgaaacaa  240
tctggaggac agctgacatt ttaacaatac tgagtcttct gattcacaca cccataggtc  300
```

| | |
|---|---:|
| agtgatggga gcaaggctca ggctaaagca gattcagggt gtctttctgt gtggaacgtt | 360 |
| taggaaaagt atgtttgcat gccactgtct cctgaccaaa cccttcgctt ttttgtcttc | 420 |
| tagtatcttt atgtatcctt atagattatt ataggcagta atgattaatg atgagatatt | 480 |
| aaaacgcctt tgttcttttg atttaaggag agggcaagta ttgaggattt ccctcttgc | 540 |
| ttttgtattc agggccgggc gctggtkgct cacgcctgta atcccagcac tttgagaagc | 600 |
| cgaggcgggc atatcacgag gtcaagagat cgagaccatc ctggccaaca ttgtgaaacc | 660 |
| tcatctctac taaaaataca aaaattaact ggccctggtg gtgtgcgcct gtgatcccag | 720 |
| ctactcagga ggctgaggca ggagaatcgc ttgaacccgg gaggcagagg ttgcagtgag | 780 |
| ccgagatcgt gccactgcac tccagcytgg gccacagaaa gagactccgt ctcaaaaaaa | 840 |
| aaaaaaaaaa aaaaaaaaaa actcga | 866 |

<210> SEQ ID NO 12
<211> LENGTH: 651
<212> TYPE: DNA
<213> ORGANISM: Homo sapiens

<400> SEQUENCE: 12

| | |
|---|---:|
| gaattcggca cgagctatag tctcctcgta ttttcatatt ttcatagcta aattgttaaa | 60 |
| gaggcgatgg cagtgtactc atcaggagac ttgttcttgc ctcgaacatt aaaagcccaa | 120 |
| tttaagactg gagaatttct tctttgaggg ttttgtccac ccatcataag agatttcaaa | 180 |
| ctatgtaatg agtcatttta cttttcccct tttcttatgg ggacagcttc tctttaatac | 240 |
| accgtgtggt ctgccctctt ggaggttgtg tcaccattat cagtagacaa atgctgccat | 300 |
| gtgtaaaagg ctatgccagt ttctgcagtc ctgtagtttt gcccctcact agaacttcaa | 360 |
| gttgcttaac ctaatcagga atacgggcat ctttacatag gaagtgcact tcttcatcat | 420 |
| atagacatag aggtcaggta ttattatctt tggcttcctt tctcagaaat tcttaaacat | 480 |
| gaatgtctga ataaacatac agagaagagg ttgggcgctg tggctcatgc ctgtaatccc | 540 |
| agcactttgt gaggccaagg taggtggatc acctgaggtc aagagttcaa gaccagcctg | 600 |
| accaacatgg tgaaacccta tctctactaa aaaaaaaaaa aaaaaactcg a | 651 |

<210> SEQ ID NO 13
<211> LENGTH: 1336
<212> TYPE: DNA
<213> ORGANISM: Homo sapiens
<220> FEATURE:
<221> NAME/KEY: SITE
<222> LOCATION: (766)
<223> OTHER INFORMATION: n equals a,t,g, or c

<400> SEQUENCE: 13

| | |
|---|---:|
| gaattcggca cgagagtaag agtatgtttg tttacagccc caacctcagc aatgccaaag | 60 |
| gctggcatcg ggggcagtgc caagctgtcc ctggatacta tttacctttg aggaagaaca | 120 |
| gcatgggttt gccaagctca attcccaggc tggtgctcct tgaattaatc atggcacagt | 180 |
| gttcatctct ctggaaatgc ccacgccagc ccagacacag cctcararatc ctttccaaca | 240 |
| cgaccctcca ggcagcagtt accaaccatc agtcttcagc tgaagcttca agtctttgcc | 300 |
| atccttgtaa tgacagcctt aggccttgcc ccaagcattc tggactctct aacactcaga | 360 |
| attgtaatgt aatattctgc tctaatttaa attttttaaaa atatagtctc ctaattcagg | 420 |
| ataaggagta agcaaacttt ctgaaagggg ctagataata agtattttag gctttgccag | 480 |
| tcatatggtc tcttgcagct actcaactct gccactgtag tatgaaagca gccatgagta | 540 |

```
atatgttaat gaatgggaat ggctgagttc caataaagct ttatttttt ttttatttga    600 gacgggtct tgctctgttg cccaggctgg agtgcaatgg cgcaatctca gctcactgca    660
agctctgcct cctgggttca agccattctc ctgcctcagc ctcccaagta gctgcgacta    720
caggtgcgca ccacaatgcc tggctaattt tttgtatttt tagtanagac agagtttcac    780
catgttggcc aggttggtct caaactcctg attcgtgatc cacccacctt ggsctcccaa    840
agcactggga ttacaggcat gagccaccat tcccagccaa taaaacttta tttacaagaa    900
cagctggtgg gccagatttg cmaagggtca tagtttatta tcccttgagc taggctgctg    960
ctgaggttga ttcaacatcc cagctccagt caacaacaaa aattctaagt ctcccgccta   1020
atgctgctgt ggtgtgtcat gccaaaaaag tgggctactc aggttagacc aatgacttca   1080
gaaccacagg gctcagaaca ggaaggagct tctttctgca gagctgattc ctggaaagcc   1140
accagcactc caccttctgc ccagaaatgt gattcagtca atagctgatg aggaaaagca   1200
acctgcaaac attaggaaga aggagaaaaa taattcagag gtgatgatac cacctccaat   1260
gaacagggaa gcaagttcat cagtaacaaa gtcagtgagg caaaaaaaaa aaaaaaaaa   1320 aaaaaaaaaa actcga                                                  1336
```

<210> SEQ ID NO 14
<211> LENGTH: 585
<212> TYPE: DNA
<213> ORGANISM: Homo sapiens

<400> SEQUENCE: 14

```
ggcacgaggt gaggaccctg gctggactgt tacagtgaca cacagtggca tggggtgtgc     60
aggaaggaca ctacaccaca aacatttaa ggacagaatc tgaagtattt gtcaactgag    120
tgatggtgca gggctctggt ggtacctgtt taatgatgac agatttactg tttgcagtga    180
tgctagctgt catgattgag tcctgtaaaa gattatatta agctaaaact aactgtaaaa    240
atcagtatat ctgtttcttt cccttccttt ctctcacttc tttcccttct tcttccctc    300 cttccctcct tccctctctc ctatctacca ggtgctttgt gctaactttt cattcagagt    360
gttttctgtc ccttacaaag ctgacagagt tgtcaagagg tttcacccac tcaacccaca    420
ttacttgaca cacagttact tgcattacaa agcactgcat gaggagctct tggtaataaa    480
ggggtgactc aaacacagat cctcccctcc agggtcacgt ctgtgctgtt gaatgttgaa    540
ccaaatgact acattactaa ataaaaaaaa aaaaaaaaaa aaaaa                    585
```

<210> SEQ ID NO 15
<211> LENGTH: 1144
<212> TYPE: DNA
<213> ORGANISM: Homo sapiens
<220> FEATURE:
<221> NAME/KEY: SITE
<222> LOCATION: (605)
<223> OTHER INFORMATION: n equals a,t,g, or c
<220> FEATURE:
<221> NAME/KEY: SITE
<222> LOCATION: (1144)
<223> OTHER INFORMATION: n equals a,t,g, or c

<400> SEQUENCE: 15

```
gcagaatgag gaggccccg agctggctgt tctaacttag aaggaagaga agactggatg     60
ggcctgcttg ggatctaggc ctcttctaaa ccctatccta agctccagtt ccatggcaag    120
gctcagactt ttaatgccat cttaatctga tggttgagcg cttcactcta ttttctggtg    180
```

-continued

```
ctgcccagcc agtgccttct gccatggatg ttactggcta cttgagaaaa aggagagggg    240
agaacccctt ctttcattcc aactgcctcc gacccccaaag ggattcttgg ctctctggta    300
accatggata ccaccatgaa ttttatttgg atcctcagca ggttgattct ggaggcctca    360
tgctatgact ttttatttct cttcctggga tccaccaccc tctactctca gctgactgct    420
gcatttaggc caggtctcca attgctttcc tccagaaagt gtgttcccgt ctagtgaggt    480
agtattgaag cctcggcttt ccctctggag cctgggaccc tgtttacagt tgcacatctg    540 ggscccctcac tgtggggatt gatcattctc atgaaggaat cacagttata tggcaactgc    600
agaangctga gctcctcatg gtgctataac cccttgggac actcatccag acttctctga    660
agcagaaaac ctgagctccc cactcactgc cctagaattt atggcaagga gcaaatctac    720
agcattctct cccacctacg tcctgcttct tggttgagac tactgggatc cttcagaaaa    780
gaaacactgg gtcccatagc taaattctca accgccaggc accttcagaa gaatccagcc    840
taatactgga atttgtgcta ttatcttcct ctccagcccc ccaactccat ccctcaccac    900
agttgtctag gaaatgacat gaattcaata tctaatgtca accatgggg agagccacaa    960 ctccaggaga ggttcctgag ctgagtccct taatttctgg atgaagaaga ccaacaagtt   1020
ttgtccaatg tatttgtttc tcagaccttg cctaggcact aaaataaaa tactaggtca   1080 ttggaggmwa aaaaaaaaaa aaaaaaaaaa aaaaaaactc agggggagc ccgcgctaca   1140 tcan                                                                1144
```

<210> SEQ ID NO 16
<211> LENGTH: 1037
<212> TYPE: DNA
<213> ORGANISM: Homo sapiens

<400> SEQUENCE: 16

```
aattcggcag agcggctgtg ggcactggac ctagctgcta gcttgctaca tctaaggtcg     60
accagacggt tctcaccacc ggcagtactg ctcaggaat aaggtgaagg tggactcttc    120
ttgttcagtg gagcacatgt ggtcctgagc aaagctgtca cacagtggac tcagagatgt    180
ggtctacggg cactaatttc ctctcagtcc ctgcctaagc aagattcatc ttcctctgcc    240
tgctgtttca ttttttttctt ctattgtctg gtatatctta agataaaaac ttgtttccaa    300
agggaaagtt tcagaaatgt ttctaagaat aataattcaa gttggatttc caagtagtat    360
tcctgggcaa ctgattaaat tcttttgtca ataatcaaaa tctggaatgt cctggattag    420
ttccaccatt tcatcatgat aactccctct tctataatcc ctaccagaaa tgattgcttt    480
gcttaaaagc ttttccctga aagacactg gtgtgttatt tctttatcag cttatgaaaa    540
ttaattctgg ttgggtacag tggctcatgc ctgtaatccc agcactttgg gaggctgagg    600
tgggcggatc atgaggtcaa aattgagacc ttcctarcca acatggtgaa accctgtctc    660
tactaaaaat acaaaattag ctgggtgtgg tggcatgcgc ctgtagtccc agctacttgg    720
gaggctgagg caggagaatc acttgatcct gggaggcaga gggtgcagtg agccgagaga    780
gcgccactgc attgcagcct ggcgacagag cgagactcca tctaaaaata tatgtatatt    840
aattctacat atctaggatt tttactgtgc cttttgtgttt ttttaagcta ctggttttct    900
caagttaaac attaaaagta ttatggaagt actgatgatg tactcagagg aaaacaatag    960
agcatataat ttatttgtta taaaatgtaa aagttcaaaa aaaaaaaaa aaaaaaaaaa   1020 aaaaaaaaaa aactcga                                                  1037
```

<210> SEQ ID NO 17
<211> LENGTH: 925
<212> TYPE: DNA
<213> ORGANISM: Homo sapiens

<400> SEQUENCE: 17

| cggcagtggt | ggcggcggcg | gcggcggccc | gcgccgcaga | gaataactca | agtcacctgt | 60 |
| actggaaatc | agtttgctga | aattaatcaa | cgattcttga | agttgaagaa | aaggaggttc | 120 |
| cagccttggc | aagaggagtg | tggcccttcc | tggaatccct | ctggacacac | cctcctagca | 180 |
| tcctctagga | aagatgcggc | agctcaaagg | gaagcccaag | aaggagacct | ccaaggacaa | 240 |
| gaaggagcgg | aagcaagcca | tgcaggaggc | ccggcagcag | atcactacag | tggtactgcc | 300 |
| cacgctggcc | gtggtcgtgc | tcttgatcgt | ggtgtttgtg | tacgtggcca | cgcgccccac | 360 |
| catcaccgag | tgagccccgc | agccggccgc | ggaccccatc | ggcagggaga | ggaggcgcgg | 420 |
| gaggggacg | caaacaaaaa | atggctttca | tattcagaga | tgttcatgtt | gctgagctgt | 480 |
| aagcaggagc | accctgtctt | ctctggtctt | tgacttgatt | aaagtatctc | cgctttcttg | 540 |
| ggagggaata | ggggatgttt | tatcagtgaa | tgtgccatac | accttatggt | ccacttcatg | 600 |
| tgcctttcag | acttcaaarc | gcgcgcgcat | gtgtgtgtgt | gtgtgtgtgt | gtgtgtgtgt | 660 |
| gtgcttcttt | ttctctccta | aaaatcgata | agtagctcca | cctgaagagg | gatggaacct | 720 |
| ctgggtcagg | aaacagctgg | aatccacact | cacctcattc | ccattgtttg | gatcatgcct | 780 |
| ctttccaaca | cgtgttcaca | atctccaaag | ggactgtatt | tcttctctgt | gcttaatgtg | 840 |
| atttgaaata | tgttgaatca | aagtgaaata | tttatttttt | gaataaagga | gataatagcc | 900 |
| ttaaaaaaaa | aaaaaaaaaa | ctcga | | | | 925 |

<210> SEQ ID NO 18
<211> LENGTH: 1197
<212> TYPE: DNA
<213> ORGANISM: Homo sapiens
<220> FEATURE:
<221> NAME/KEY: SITE
<222> LOCATION: (25)
<223> OTHER INFORMATION: n equals a,t,g, or c
<220> FEATURE:
<221> NAME/KEY: SITE
<222> LOCATION: (36)
<223> OTHER INFORMATION: n equals a,t,g, or c
<220> FEATURE:
<221> NAME/KEY: SITE
<222> LOCATION: (92)
<223> OTHER INFORMATION: n equals a,t,g, or c
<220> FEATURE:
<221> NAME/KEY: SITE
<222> LOCATION: (1192)
<223> OTHER INFORMATION: n equals a,t,g, or c

<400> SEQUENCE: 18

| ttaatccccg | tggccctgaa | attcnacgca | taatgntgca | agaacagttg | tcgaaacttg | 60 |
| gctgggaag | aaaatgggca | gatttcctgc | ancctgaaag | aagctgagct | gtctctcttg | 120 |
| ctgcacaacg | tggtcctgct | ctccaccaac | taccttggga | caaggcgctg | aatgaaccat | 180 |
| ggagcggatg | gcattgtcct | gcagtcgtat | agtatagcag | tgcaggaaca | aacagcactt | 240 |
| gccagcaaag | tctgtgtgta | ctgttaagtg | tgtgggaggc | agagagagga | gcaggggcca | 300 |
| tgggcttcac | agcatggcac | acmtgtggga | actgcagaca | ttcctctcac | agctagaact | 360 |
| gaaacaaacc | ctcttgctag | gggtggtccg | tgtgaggtgt | catcctgtcc | ccctcataat | 420 |
| tactaatagc | tggaactggc | agcagcctct | actgggcttt | tactgtgatg | tgttcagttc | 480 |

-continued

| | |
|---|---|
| atgtcctagg aagtcagctt ttgccccagg tgggaatcct tatttggctt aggactgatc | 540 |
| cacttccatg ttacttacat ctgtgggttt ttgttgttgc tgttagaaaa tttgtggctg | 600 |
| gtgaaaacag cactcctttg gctggagcac ttgtgtccrt gcatgtactt gggtgtttcc | 660 |
| ctccatcctt tctgatatga ccaaaaatca agttgttttg ttttttgtca ccttcactgg | 720 |
| catgggctaa ccacttcttt ttcaaaccct ctgaacacct ttttctgatg ggtaacttgc | 780 |
| aggaatattc tattggaaaa gataacagga agtacaagtg cttcttgacc ccttcctcaa | 840 |
| tgtttctagc cttcactctc cattgtcttt tcctggctgt attacagccc tctgtggatc | 900 |
| ttcaactctg ctgcctccac tgtgatgcag cagtccaact gtaactgaca gtggctgcct | 960 |
| tctctgggcc atgatcaca cctgtaaggt actaattact gcccagcctg gggagatcag | 1020 |
| gagaggtctg catagttagt aagttgggtt tagcttttgt gtgtgcatca gtgacttaga | 1080 |
| gttctgtaat aacttattgt aaatgcatga agcactgttt ttaaacccaa gtaaagactg | 1140 |
| cttgaaacct gttgatggaa atgaaaaaaa aaaaaaaaaa cccgagggg gncccgg | 1197 |

<210> SEQ ID NO 19
<211> LENGTH: 1106
<212> TYPE: DNA
<213> ORGANISM: Homo sapiens
<220> FEATURE:
<221> NAME/KEY: SITE
<222> LOCATION: (318)
<223> OTHER INFORMATION: n equals a,t,g, or c
<220> FEATURE:
<221> NAME/KEY: SITE
<222> LOCATION: (509)
<223> OTHER INFORMATION: n equals a,t,g, or c
<220> FEATURE:
<221> NAME/KEY: SITE
<222> LOCATION: (523)
<223> OTHER INFORMATION: n equals a,t,g, or c

<400> SEQUENCE: 19

| | |
|---|---|
| gaattcggca cgagatgctc tcctgagtcc tctgctagtt aagctctctg aaaagaaggt | 60 |
| ggcagacccg gtttgctgat cgccccaggg atcaggaggt aagcaccata gaggagctgg | 120 |
| gttagagacg agagacttaa ccgtttctct gctgaaaaag caactgagg aaaggccagc | 180 |
| catgctgtgc acacctctga gaacctgaac ctgcaaacat ggacatcagc tctgaaagga | 240 |
| tgggttcatt tctcttttat tcactttagc catgtcctct ggtgtctctg agctggtgtt | 300 |
| ccttaaagct tcggcttncc tttgggggttt gtctatcagc ctatttgtaa ggctgacttt | 360 |
| tatgccaatm gcaaatacaa gcattttta agttaacaga tattatgaag taaaatgcaa | 420 |
| gttttttcatt tataaggcaa cataacttca gagaaaaaac tgagtcaatc atataaaatg | 480 |
| tgattaaaat gtgattgtta ttatataana gggttatagg aanattagct tcttatggac | 540 |
| aagtagaaaa gtaggaatca tccaagctga ttgtcacagt aaatattcaa caaaggtagt | 600 |
| gtccttcctt gctttcatca gtaggatggg ggcatttgga tggctttatc attgcaaata | 660 |
| tttttaatgt attccttatt ttgaaaatgg tcctgataat agttttaatt ttcactcatg | 720 |
| aactctacat gtataagtag agtttctcca gcgcttacca acatataggaa aaaacatta | 780 |
| taaggccatt aacagtgata gtttagaatt tattaacatt gactctactg atgggggtat | 840 |
| tcaagcttcc ctaaaattca caatcagtta ttttcagctc ataaacatct tttcctgttc | 900 |
| tttggcttat ttcttccact ttatatgttg ctgctctgga agtcattaat tgctaataat | 960 |
| gtcaaacatc ttttttatgt ttattggata tttgagcaaa ttgctcattc acatcttttg | 1020 |
| cacacttttc aaatagactg ttgttttctt attgatacat ggttctccat gtattccaaa | 1080 | agcaaaaaaa aaaaaaaaaa actcga                                           1106

<210> SEQ ID NO 20
<211> LENGTH: 932
<212> TYPE: DNA
<213> ORGANISM: Homo sapiens
<220> FEATURE:
<221> NAME/KEY: SITE
<222> LOCATION: (43)
<223> OTHER INFORMATION: n equals a,t,g, or c
<220> FEATURE:
<221> NAME/KEY: SITE
<222> LOCATION: (458)
<223> OTHER INFORMATION: n equals a,t,g, or c
<220> FEATURE:
<221> NAME/KEY: SITE
<222> LOCATION: (465)
<223> OTHER INFORMATION: n equals a,t,g, or c
<220> FEATURE:
<221> NAME/KEY: SITE
<222> LOCATION: (494)
<223> OTHER INFORMATION: n equals a,t,g, or c
<220> FEATURE:
<221> NAME/KEY: SITE
<222> LOCATION: (501)
<223> OTHER INFORMATION: n equals a,t,g, or c
<220> FEATURE:
<221> NAME/KEY: SITE
<222> LOCATION: (515)
<223> OTHER INFORMATION: n equals a,t,g, or c
<220> FEATURE:
<221> NAME/KEY: SITE
<222> LOCATION: (582)
<223> OTHER INFORMATION: n equals a,t,g, or c

<400> SEQUENCE: 20
attccaatca ggtaataggc agggtatagg gaaagcgggt acncctgcag gtaccggtcc        60
ggaattcccg ggtcgaccca cgcgtccggg tatgggtgt tgtcttgaat gtgtgtggtc        120
ctggggcatg gggtttggca gaacattctg tgaaaatgga atacatatat gttttttttc      180
gtgacacttt tttttttttg cttttggaga ttttcaatt tggctccagg acctgtatga        240
tgttttcaag ctttgcagag atgctcaaga tatgactgga cattttttgaa agttcctgtg     300 tcctcttcaa cacatcttct caccaaacat taattgtagt gtcttttctt ccagaaaact       360
tgcataaaat gacttcctct cctgtgaaaa cagtgtcctg ctctgaatgg gagctttaaa      420
ggagtaggca caaattgtaa gatgatgtat cttgaggnct ggggncttag agatattctg       480
ctgcctccca gagnctttgt ngcagacggg tctgnccagg gtggggaaag ggaagcctcc      540
gttctttttg gtaagctagc cataaagaca ggtaagggag tnctatttc aagaaagctg        600 gatctgtttc gtactctttc tgcccctaat cgctgtggac agctcccagc agcacaaaga       660
gatgaagggc aaaggcagga tgcagcaggc aaagttaaca ttgtatttgt gagtacagtt      720
gaggataaaa aagggatgaa atccacggtg aggaccatca tggtggggga atagtttatt      780
ctaatggatt caagagcttt ggagaccaaa ctaacacatt tatttttatg tgcagttaaa     840
gtcatagaaa cctgttttgt gaaacctcag atttctaaag aaaaccagaa gcaagacctt      900
ccttggttta aaaaaaaaaa aaagggcgg cc                                      932

<210> SEQ ID NO 21
<211> LENGTH: 1032
<212> TYPE: DNA
<213> ORGANISM: Homo sapiens

<400> SEQUENCE: 21

-continued

```
ggtcgaccca cgcgtccgaa aacgccttat gatgaatcta agttctatat tggctgtgat        60
ctttgtacta actggtatca tggagaatgt gttggcatca cagaaaagga ggctaagaaa       120
atggatgtgt acatctgtaa tgattgtaaa cgggcacaag agggcagcag tgaggaattg       180
tactgtatct gcagaacacc ttatgatgag tcacaatttt atattggctg tgatcggtgt       240
cagaattggt accatgggcg ctgcgttggc atcttgcaaa gtgaggcaga gctcattgat       300
gagtatgtct gtccacagtg ccagtcaaca gaggatgcca tgacagtgct cacgccacta       360
acagagaagg attatgaggg gttgaagagg tgctccgtt ccttacaggc cataagatg        420 gcctggcctt tccttgaacc agtagaccct aatgatgcac cagattatta tggtgttatt       480
aaggaaccta tggaccttgc caccatggaa gaaagagtac aaagacgata ttatgaaaag       540
ctgacggaat tgtgtggcaga tgaccaaaa attttgata actgtcgtta ctacaatcca       600
agtgactccc cattttacca gtgtgcagaa gttctcgaat cattctttgt acagaaattg       660
aaaggcttca agctagcag gtctcataac aacaaactgc agtctacagc ttcttaaagt       720
tcagcgtgtt aacctaacat aaaacacagc aagaatctgg ttgtctgaac tattttaaat       780
taaggagcca gatgttttta gtcaggctat cctgacaaga cttgacctaa acttcgtttt       840
tattggtcat aacagtccaa ttatattctt ggccaatttt gtccaacgga caagaaaaaa       900
gcaaagtcaa cgacaccatt atcttgtcaa gatcagatgt ttttactatt gtggcagaag       960
cgagaaaact ttgtttattg aaaaaaaaaa aaaaaaaaaa aaaaaaaaaa aaaaaaaaaa      1020
aaaagggcgg cc                                                        1032
```

<210> SEQ ID NO 22
<211> LENGTH: 487
<212> TYPE: DNA
<213> ORGANISM: Homo sapiens

<400> SEQUENCE: 22

```
acgtagtagg gaaacgtggt acgccgtgca ggtaccggtc cggaattccc gggtcgaccc        60
acgcgtccgt gtaaactgga atttgcaagg ggatgctgtg atgataaccc ctttctattg       120
ctgtaatgtt catataacct gggaaactga gagaagggga tgtgtaaata aaagcttaaa       180
cattttagta atgtgttaaa atgtcactct ctcttaccct gtttcccttt ttttgccaga       240
tgatgatttt tttatttta ttttgtactt tactggatga ctgtgaagcg atgagtattg       300
ggttggggta ggtgtgttga ttttgagagt gcatgttaag aactgaaggg gaactacttg       360
agatgactta agaagcatcc catgcaaata tcttgttttg ccctaataaa atattcagaa       420
agataaaaaa aaaaaaaaaa aaaaaaaaaa aaaaaaaaaa aaaaaaaaaa aaaaaaaag       480 ggcggcc                                                               487
```

<210> SEQ ID NO 23
<211> LENGTH: 1460
<212> TYPE: DNA
<213> ORGANISM: Homo sapiens

<400> SEQUENCE: 23

```
gaattcggca cgaggcggga aggttgtagt gccgcgagtt gagctcctct tgcctaagtg        60
gtcgcgcccc ctttaagagc agcgattgta aggagaggcg gtcccggtgt cctcgggtcc       120
caggttttca aaacaaaaat agagttgcaa tcttggcaga actggacaaa gagaaaagaa       180
aactacttat gcagaaccag tcttcaacaa atcatcctgg agctagcatt gcactctcga       240
gaccctctct taataaggac ttccgggatc acgctgagca gcagcatatt gcagcccaac       300
```

-continued

| | |
|---|---|
| agaaggcagc tttgcagcat gctcatgcac attcatctgg atacttcatc actcaagact | 360 |
| ctgcatttgg gaacttattc ttcctgtttt acctcgcctt gacccagaat gaagaaaaca | 420 |
| tttgcgatgg aaaagtgact ttgtaatatc aaatgccaaa gctactatca ttcagtgcta | 480 |
| catgaactgt gactttaaga attttggtga actttgatat ttttttgtttg tctgaaagaa | 540 |
| aggaatgtgt aagtgaaagc tgaaagaaga ataaccagga tgatgagagc tgtggaagct | 600 |
| gtatcgtcca aggaattgat tatgtaccgt gactgtaact tttttgtaat gctgtttaac | 660 |
| tctcaatcag actgtgaact ggatggtcac gaagtcattc cccaactcct agcaagtttg | 720 |
| actgaatata tcatgtccac agtagatttt caagaatcat ttatagtact taactttaaa | 780 |
| gaaacaaggc tgcttttaaa aaatgaacta ataggcttaa atcaattgca tccatatttg | 840 |
| ctgtttatag gattgctatc agtataccttt ttgcgtttat agtcaacatg tatcatcctg | 900 |
| aaatattctt tctggactta taactacttc cccctttttc actttaaaac aaacctcaag | 960 |
| aataaattac taaccagtct taaccatctt ttataaacat atgctcttat aaatgttgtg | 1020 |
| actagatgca attaaaaata atagggaatg tggtaggttt ttaatttgta catcctctta | 1080 |
| tttagtgtta ccacataaat gatgagtttg tgtggttctg ttttccattt ttgttctaac | 1140 |
| tgaaaacttt ttggctgggc acggtgcctc atgcctgtaa tcccagcact ttgggaggcc | 1200 |
| aaggcgggca gatcacttga gatcaggagt ttgagaccag cctggccaac atggtgaaac | 1260 |
| cctgtctcta ctaaaagtat aaaaaattag ccatgtgtgg tggcacacgc ctgtaatccc | 1320 |
| agctactcag gaggctgagg caggagaatc gcttgaacct gggaggcagg ggttgcagtg | 1380 |
| agctgagacg tgtcactgc actccagcct gggtgacagt gagtctttgt ctcaaagaaa | 1440 |
| aaaaaaaaaa aaaaactcga | 1460 |

<210> SEQ ID NO 24
<211> LENGTH: 1098
<212> TYPE: DNA
<213> ORGANISM: Homo sapiens

<400> SEQUENCE: 24

| | |
|---|---|
| gaattcggca cgagctgaaa tcttggaggg aagaaaacac atcccaccct gcctccggga | 60 |
| agggcctct cctggacatg tctcctgcag ctgctgctga gccagatggg gaccagcagg | 120 |
| acagacacgt cagcaaactc atcttctgct tctttgtctt cggcgccgtc ttgttgtgtg | 180 |
| tgggagtcct gctctccatc tttgggttcc aggcatgcca atataagccc ctcccagact | 240 |
| gccccatggt gctcaagtgg cggggctgca tgtgccgtgg ttgggcttgg gggctgtgat | 300 |
| cctggcccgc tcccgggcgc aacttcagct ccgtgcaagc tgcagagag gtcagcagat | 360 |
| ggaccccgac cgagccttca tctgtggaga gagccgccag tttgcccagt gccttatctt | 420 |
| tgggtttctg ttcttgacaa gcggcatgct catcagcgtc ctgggcattt gggtccctgg | 480 |
| atgtggctcc aactgggcgc aggaaccgct aaacgagaca gacactggcg actcagagcc | 540 |
| ccggatgtgt gggttccttt ctctgcagat catgggccc ttgattgtgc ttgtgggatt | 600 |
| gtgtttcttc gtggttgccc atgttaagaa gagaaacacg ctgaatgctg gccaggatgc | 660 |
| ctctgagaga gaagarggac agatccagat tatgagcct gtccaggtca ctgtagcttc | 720 |
| tgcggtcgct gagagtcctg gaactaacag tctgcttccg aatgaaaacc cccttcata | 780 |
| ttacagtatt tcaactatg ggaccccaac ttcagagggt gcagcctctg aaagagactg | 840 |
| tgaatctata tataccatttt ctgggacgaa ttcatcttct gaggcctcac acactccaca | 900 |

| | |
|---|---|
| tcttccatct gaattgcctc ctagatatga agaaaaagaa aatgctgcag ctacattctt | 960 |
| gcctctatct tctgagcctt ccccaccgta aactatggac tctagttcag ttttatatgc | 1020 |
| aatggatcac tattttattt aatttttttt aaataaaaaa tacaatagca aaaaaaaaa | 1080 |
| aaaaaaatga ccctcgaa | 1098 |

<210> SEQ ID NO 25
<211> LENGTH: 1015
<212> TYPE: DNA
<213> ORGANISM: Homo sapiens

<400> SEQUENCE: 25

| | |
|---|---|
| ggcacgagca gtattttcac tcttggaggg gcctaacact atcatgttgc cctgatttgt | 60 |
| gcctaacgct cattcataaa atgatcctga cttaaagtgg tatgtttggt gctttctttt | 120 |
| tctgtttgct ttttaaatcc tttctaaatg gcggcccatt tcatttacat ctctcatttc | 180 |
| ccctgaagtc tttgaagcct tttttgtaat gtgccttaaa caaataagtc tctctttttt | 240 |
| ctccagcagt gtgaggcttc tcaaatattt gtgttatgag ttacggacaa ggcatttcct | 300 |
| gacctgtttc cttaaaaaat ccattttag acaacctata gcattaagat tgaaatccaa | 360 |
| actatgggag tttacctgaa gctgcaagct ttcaaactgt aattttgtgg tattggtaga | 420 |
| gccatgaaag tggaagtgaa acctttttaa ttaattttct ttggcagttg aaaatggccc | 480 |
| atgttttagc tggtagcaat gtaagtttac atatgagccc aactaagctg gttcattatt | 540 |
| ctcttcagtt gtttgaaagt tggcagccat catcacaaca gcagctggat acaagataac | 600 |
| ctagccagtg ttggcacatg ttgaggcata tgggaattta ttaaatcatg caacctttgc | 660 |
| aaagaagagc gtctaaatga cttaatatac taatttaaaa cagctggcca tgagcaatca | 720 |
| tatgacttaa attattctat tcagatttat taatccaatt gaacattaac tgagtaattt | 780 |
| gatgttttta tctaaatgga taagatgatt ttttgaagta taaaatggga tttgtaggga | 840 |
| taggggaaga aactatatag aacaaagcaa gcggtgcaat tctggtttta gaaataatct | 900 |
| gtgtttggct gggtgcagtg gctgacacct gtaatcccaa cactttggga ggctgaggta | 960 |
| ggaggatcac ttgagcccag gagttccaga ccagcctgtg agaccgtatc tctac | 1015 |

<210> SEQ ID NO 26
<211> LENGTH: 1197
<212> TYPE: DNA
<213> ORGANISM: Homo sapiens

<400> SEQUENCE: 26

| | |
|---|---|
| gggttctcgc agccgtacct ttctgtcgtc ttctcgccca cgcgtccgcc cacgcgtcgc | 60 |
| gagaagacga cagaagggta cggctgcgag aagacgacag aagggtacgg ctgcgagaag | 120 |
| acgacagaag ggtacggctg cgagaagacg acagaagggt acggctgcga agaagacgaca | 180 |
| gaagggtacg gctctttctc cgctccgccc ctcctcctcg tccctccctc aaggcmcgga | 240 |
| rgcgaaacct ctccacctct tccgagcggg gtmacggccc ggcygcggta acctggtttc | 300 |
| cgagagtgcc gggcggtcgg cgggtcaggg cagcccgggg cctgacgcca tgtcccggaa | 360 |
| cctgcgcacc gcgctcattt tcggcggctt catctccctg atcggcgccg ccttctatcc | 420 |
| catctacttc cggcccctaa tgagattgga ggagtacaag aaggaacaag ctataaatcg | 480 |
| ggctggaatt gttcaagagg atgtgcagcc accagggtta aaagtgtggt ctgatccatt | 540 |
| tggcaggaaa tgagagggct gtcatcagct ctgattaaga aaggagattt cttcatgctt | 600 |
| tcgattctgc atggggtaca gccagtcacc tcaccagaga atgacggctg gagaagaaaa | 660 |

```
ctctgtaata ccataaataa gagtgcttgt aataaaagac tgtgcacaag gattaatatt      720
tcccttctta agtatcaaaa gaactctgga acaaattata ccattaggaa ggttttcatg      780
attcagttga tttccaaaa atgaagctat ctcacccagc tgggtttgga ggagcaatct      840
gcttattatt ctgtcgttac cacttactca agcgagctgt gatatgaata caagcaacca      900
gtgggctcgg gaaggtccgg gtctcttctg ccatcttcca gataagagat ttcagtaaaa      960
aactgccatg ctgagctgcc ttatagagct cttcgaaaat gttcgagttg ataaagctct     1020
ttgaggacaa ggtacttcgt gcacctcatg ctgaagattg caccatgttg gaaataaat     1080 atgaagcaag tcaaactaga tgcatacact tgtgtagaaa tcaataatca attaatagaa     1140
gtgaaaaaat agacattaaa atgatttatt tctaaaaaaa aaaaaaaaaa aactcga       1197
```

<210> SEQ ID NO 27
<211> LENGTH: 1002
<212> TYPE: DNA
<213> ORGANISM: Homo sapiens
<220> FEATURE:
<221> NAME/KEY: SITE
<222> LOCATION: (19)
<223> OTHER INFORMATION: n equals a,t,g, or c
<220> FEATURE:
<221> NAME/KEY: SITE
<222> LOCATION: (29)
<223> OTHER INFORMATION: n equals a,t,g, or c
<220> FEATURE:
<221> NAME/KEY: SITE
<222> LOCATION: (948)
<223> OTHER INFORMATION: n equals a,t,g, or c
<220> FEATURE:
<221> NAME/KEY: SITE
<222> LOCATION: (955)
<223> OTHER INFORMATION: n equals a,t,g, or c
<220> FEATURE:
<221> NAME/KEY: SITE
<222> LOCATION: (969)
<223> OTHER INFORMATION: n equals a,t,g, or c
<220> FEATURE:
<221> NAME/KEY: SITE
<222> LOCATION: (973)
<223> OTHER INFORMATION: n equals a,t,g, or c
<220> FEATURE:
<221> NAME/KEY: SITE
<222> LOCATION: (990)
<223> OTHER INFORMATION: n equals a,t,g, or c

<400> SEQUENCE: 27

```
tgcccttccc tgccctgtnt ccgccgttnt tcccccaccc ccgccccata gaccaagttc       60
gtgcagtgcc cagatgggga gctccagaaa cgcaaggagg tggtgcacac cgtgtccctg      120
cacgagatcg acgtcatcaa ctctcgcacc cagggcttcc tggcgctctt ctcaggtgac      180
acagggagga tcaagtcaga agtccgtgag cagatcaatg ccaaggtggc tgagtggcgc      240
gaggagggca aggcggagat catccctgga gtgctgttca tcgacgaggt ccacatgctg      300
gacatcgaga gcttctcctt cctcaaccgg gccctggaga gtgacatggc gcctgtcctg      360
atcatggcca ccaaccgtgg catcacgcga atccggggca ccagctacca gagccctcac      420
ggcatcccca tagacctgct ggaccggctg cttatcgtct ccaccacccc ctacagcgag      480
aaagacacga agcagatcct ccgcatccgg tgcgaggaag aagatgtgga gatgagtgag      540
gacgcctaca cggtgctgac ccgcatcggg ctggagacgt cactgcgcta cgccatccag      600
ctcatcacag ctgccagctt ggtgtgccgg aaacgcaagg gtacagaagt gcaggtggat      660
gacatcaagc gggtctactc actcttcctg gacgagtccc gctccacgca gtacatgaag      720
```

```
gagtaccagg acgccttcct cttcaacgaa ctcaaaggcg agaccatgga cacctcctga    780
gttggatgtc atccccgac cccaccctgt tttccaccag agttctgaca ctgtgactct    840
gtataaaatg gttgggaagc tgcaaaaaaa aaaaaaaaa aaactcgagg ggggccggt     900 acccaattcg ccctatagtg agtcgtatta caattcatgg ccgtcgtntt acaangtcgt   960
gactggggna aancctggcg ttacccaatn aatcgcttgc ag                     1002
```

<210> SEQ ID NO 28
<211> LENGTH: 1327
<212> TYPE: DNA
<213> ORGANISM: Homo sapiens

<400> SEQUENCE: 28

```
ggcacgagga aagtccttgc tctggtgacc tgtaagttgc agaggagggt ggagtgagag    60
tgtcatgtat tgggatagtc agggatccct gcctttggcc tttcttcttc ttcttcttcc   120
tcttccatag ttggatcatg tatatttwac ttctaaagga gagaatgtca aaaagttctg   180
tattttttta tattctatat attaggtagg tcaatcttaa ttggtctcaa gaggaagaac   240
tgtctgtcat ttcggtaagt aggatactgt gaggaagacc aaaagagat atggatgctt    300 cctcgctcag gaggcctgag cttggtcctt ttcctctctg cttggattct ggaccaccac   360
ctgggaccaa ccttcagctc tggaaccttc ataaagcagg tcagcgtggc ctgattgtcc   420
caggacctga aggagcaag gatggcctca gggcctggtg aagtctgcta ctctgtcctt    480
actgctgaac atcctgcttg tatcaggaaa ctcagaagca gtttgccttg tcaaatcaat   540
ctcaatgggc catgtccaca taactgatca cccatggctg cctctcctat tatctattat   600
cactgaaact tagtagcctg ctcttttttt ttttttttt agagctattg cgtatcttcc    660
ctgtttggga tccttgtacc tggtttgggt tttcccttcc ttgtgacaat tataatccag   720
atgcctcttc tttctgtttg aattacggta gtgcattgcc ttagtggctt gcctgtgcct   780
ctgggtggat tacatatgat agtaaagccc acctgtttgg atgggagtag aggaagttgg   840
tgtagaccag ctgtggagct gaaggcacag tctgccccac ccccacctcc ccactgtggt   900
tagtcagagg catcctgctc caagctctgc ttttccttcc tctgaaacaa tgccattctt   960
gcttctattg ctacacatct ccttctggct caggtgaaat ccatgccctt ctgcttatag  1020
acctaaagtt caggtactta ttattggcca ttgatcttga atttgccctc tcctagtgct  1080
gcagtcccac ttcaaagcca ttttctgagg aggatggttt aggtctggca attgtccttg  1140
aaaaatccca cccatgttgt accaccttgg tgagtcatat gccactcatc agcttgggaa  1200
tgatggctgc caactcccaa tctcccagga aggcaggggg cagaatcttt ttttcacttg  1260
gcctgctacc tccattaaaa aaccattctc ttacagttta aaaaaaaaa aaaaaaaa     1320 ggcggcc                                                           1327
```

<210> SEQ ID NO 29
<211> LENGTH: 668
<212> TYPE: DNA
<213> ORGANISM: Homo sapiens

<400> SEQUENCE: 29

```
tattgtcctg ctctttttt tttggatgaa aactccagcc tttcctgact cacctccatc     60
ttcggttctt cagttttctg agaagagttg ggatatgtgg gaaggggcat gggagctcgg   120
cagcctccgc ctgccaggaa ggcagtttcg cctctgcagg aaagagcaga gcccgtggga   180
agccctgggt gagggtggcg cagcggccca gcacgcatgg tattgccagc cacgggggc    240
```

-continued

```
ctgcgtgtag tctctgctcc ctgcatttca ccttctttgt tgactttcct tctctgtttt    300
cccccatctg tttgccagag gggtgggact ggcaacagaa cagccgtggc tgctttatct    360
ctcctctcca cggtgtactc aggcctgagt ggtgactcac gggagcctgg ccacctcgca    420
gctgttcgcc ccctcaacct ttgaactgga actgctggct cacacagggt tttcgacaac    480
tgcagctgaa tctcatggaa aagctggatt cctctgcctt acgcagaaac acccgggctc    540
catctgccag gtgcttgcca ctggtcctgg cagaaatggc ggctgctgaa agtgaccttc    600
caaatccttg gtggcacttc agcgccacag gctctccaat aaaaacccctt tacacacaaa   660 aaaaaaaa                                                              668
```

<210> SEQ ID NO 30
<211> LENGTH: 1243
<212> TYPE: DNA
<213> ORGANISM: Homo sapiens
<220> FEATURE:
<221> NAME/KEY: SITE
<222> LOCATION: (327)
<223> OTHER INFORMATION: n equals a,t,g, or c
<220> FEATURE:
<221> NAME/KEY: SITE
<222> LOCATION: (335)
<223> OTHER INFORMATION: n equals a,t,g, or c
<400> SEQUENCE: 30

```
ggtcgaccca cgcgtccgat tttataaaaa gtacagttta acattccatt taccttgtta     60 cttttttgact acaagtcttt gcttcccttg ccagtccctc ttcccagttc ttgaccaaat   120
acacctaaaa aaggaatgtc acatttatgg aactgtgtga tctttctttg aatctggttt    180
aacattaaac tatgggtttt ttgttgttgt tctttgtgat aagttccacc tgctatacac    240
tgttagcgca aagtattttt ttggaacact tttgtattag ttatggaaat aaattttaca    300
cattggatta aaatgtagag aaacatncat tgagnatact cagcaagtcc tgctggacta    360
gaagctgtta ctttctgtaa aatgactcta matmtctttg ctwyaaacca ctatctactg    420
tytcatagtt taactccaag agcagttttt gtttgttttc cctaagctct tagataaatc    480
ctcagggata tctcagtgct tgacatattg tattataatt gcttgtttgt ctatttctcc    540
cactagaaac tatgggatga tggtgagaat ttcacagcag gaaagattgg gaagtttaag    600
gatctgaaca ggagttaggt aggaaagtat tacatgctat gatgtagctg tatataccac    660
caaaaattct accttagaat ggtttaggtc actgaatttc ataattttac aattatttca    720 tattcctttta cataagaatt tgtatgttgc aaggcttaag aagctttaat ttatcagttc    780
ctattagcgt atcgtcctct ttttgtgtca agaaaagaaa ctcggctggg tgcggtggct    840
cacgcttgta atcccagcac tttgtgtggg aggccgaggc agcgaatgga ttgcctgagg    900
tcaggagttt gagaccagcc tggctgacat ggtgggaccc tgtctctgct aaaaataaaa    960
aagttaggtg ggtgtggtgg tgtgtgcctg tggtcccagc tactggggag gctgaggcag   1020
gagactctct tgggcctggg aggcagaggt tgcagtgggc cgaggtcatg cccgctgcac   1080
tccagcctgg gcaacagagc gagactccgt ctcaaaaaaa atataataaa cctcattctt   1140
ttatttaaaa ggtaatattt tttactggta aaaattgata aaaataagcc aaagacaacg   1200
attcaatctt aatctcatag aaaaaaaaaa aaaagggcg gcc                      1243
```

<210> SEQ ID NO 31
<211> LENGTH: 1053
<212> TYPE: DNA

<213> ORGANISM: Homo sapiens

<400> SEQUENCE: 31

| | | | | | |
|---|---|---|---|---|---|
| attacggaat | acagtagaca | ccatgtaacc | ccagtcttaa | tatttaaaga | atgttaatgt | 60 |
| tgtcacattt | ctatcttttg | tttttacatg | agaagtcaaa | cattacatta | taagtagagc | 120 |
| taaaatccaa | cctctccatc | ccctttccag | agctaatgag | gagcttgatt | gtaaatttgt | 180 |
| tgtatatcag | ctctgtgcat | ttwaaaatat | attcatccct | tatctgtatt | ggtaacaatg | 240 |
| cttattaatg | tttatctgtt | tattattttt | gttttcattc | agcttttgca | ttcctcattt | 300 |
| ctgagattag | gtcatgttga | tacatacagt | aattaaattg | ctagatagta | tttcgtcaaa | 360 |
| ttcctttact | acttgtgtgt | acttaatctt | gtttagtatt | tttttattgt | ttcattcaac | 420 |
| aatatgttct | gagattgagt | catgttgata | catatagaca | atttttatttt | tattactata | 480 |
| gaaagatctg | ttaaatgaat | atagtctatt | taccaacttc | aacagaatta | taatataatt | 540 |
| agtttttagc | tgttagagac | tctactccag | tgaacctgtt | tcctcattca | gargaatgta | 600 |
| tagtttatgt | tctcagaaac | agaatttcat | ggctgggcat | aatggctcat | gtctttggga | 660 |
| rgccaaaggt | caggartttg | agggcaacct | ggacaccaca | gcaagamccc | atctctacaa | 720 |
| aatttttttat | taaaaattaa | ccagggccgg | gtgcagtggc | tcatgcctgc | actttgggag | 780 |
| gctgaggtgg | gcggatcacc | tgaggtcagg | agtttgagac | cagcctgacc | aacatggaga | 840 |
| gaccccgtct | ctactaaaaa | tacaaaatta | gccgcgtgtg | gtggtgcatg | cctgtaatcc | 900 |
| cagctgctca | ggaggctgag | gcaggagaat | tgcttgaacc | caggagacgg | aggttgcaaa | 960 |
| gagccgagat | tgtgccattg | cactccagcc | tgggcaagaa | gagcgaaact | cggtctcaaa | 1020 |
| aaaaaaaaaa | aaaaaaaaaa | aaaaagggcg | gcc | | | 1053 |

<210> SEQ ID NO 32
<211> LENGTH: 1014
<212> TYPE: DNA
<213> ORGANISM: Homo sapiens

<400> SEQUENCE: 32

| | | | | | |
|---|---|---|---|---|---|
| ggtcgaccca | cgcgtccgaa | acttaaaaaa | atgtggccag | gcatagtagc | tcatgcctgt | 60 |
| aatcctagca | atttgggagg | ccgaggccgg | aggatccctt | gaatccagga | gttcgagacc | 120 |
| agcctgggca | acaaactgag | accctcatct | ccatatatta | aaaaaataaa | aataaataa | 180 |
| ttgtttttttt | aaaccacaca | aaaaatgtat | aaacatgtat | ccctgtact | gcaaaatctt | 240 |
| gctctcattc | ctattccttc | tgctctcttc | caaccatacc | tatgtagcta | accacattta | 300 |
| ttcattctgg | ctcattcttt | atatgtttct | tcttgcaaat | ataagcaaac | tgtatatatt | 360 |
| taatattctt | acttacagaa | aatgtagtat | atatactcct | ttgcaccttg | tattttttgtt | 420 |
| tgtttactta | agaatatatt | ccagaaatca | ttctacatta | gttcataggc | atcttttttga | 480 |
| ctattattat | ggccagtttc | ttaaatggct | gcatagtact | ctgttgtatg | gttggatctt | 540 |
| gctttagtcg | accttctgta | aatgggaatt | attatgagaga | tgtagcttta | gagtaaattc | 600 |
| ctagaagaat | gattgctggt | caaagagtaa | atgcatatgt | agttttatta | gatgttgtca | 660 |
| aatttccttc | catatgagca | gcacacaatc | acttttaaaa | ggcacttttt | tggccgggcg | 720 |
| tggtgctcac | gcctgtaatc | ccagcacttt | gggaggccag | gcaggagga | tcatgaggtc | 780 |
| aggagatgga | gactattctg | gctaacaggg | tgaaaccctg | tctctactaa | aaaatacaaa | 840 |
| aaattagccg | ggcgtgttgg | cgcatgcctg | tagtcccagc | tactcaggag | gctgaggcag | 900 |
| gagaattgct | tgaacctggg | aggcagaggt | tgcagtgagc | tgagatcgca | ccactacgcg | 960 |

```
ccagcctggg caatagagcg agattcgtct caaaaaaaaa aaaaagggc ggcc        1014
```

<210> SEQ ID NO 33
<211> LENGTH: 1373
<212> TYPE: DNA
<213> ORGANISM: Homo sapiens
<220> FEATURE:
<221> NAME/KEY: SITE
<222> LOCATION: (1373)
<223> OTHER INFORMATION: n equals a,t,g, or c

<400> SEQUENCE: 33

```
gaattcggca cgaggacgct tcggccgtaa cgatgatcgg agacatcctg ctgttcggga      60
cgttgctgat gaatgccggg gcggtgctga actttaagct gaaaaagaag gacacgcagg     120
gctttgggga ggagtccagg gagcccagca caggtgacaa catccgggaa ttcttgctga     180
gcctcagata ctttcgaatc ttcatcgccc tgtggaacat cttcatgatg ttctgcatga     240
ttgtgctgtt cggctcttga atcccagcga tgaaaccagg aactcacttt cccgggatgc     300
cgagtctcca ttcctccatt cctgatgact tcaagaatgt ttttgaccag aaaaccgaca     360
accttcccag aaagtccaag ctcgtggtgg gtggaaaagt gttcgccgag gtgtgcatgg     420
tttcccagcc acgtccctgt tttcaaagat agtttcactt tggtctctga attgaaatgc     480
tgtctactga aagggtttca ggagcgttta tgtaaggggc tgtgatgaaa ttgcattccc     540
catagataaa agaaaaatca tttctatcca gagatctgag cagaaggatt ggcttgttag     600
tttaacacag ccgtattttt ggacattcag tgttacttgc tgagtctgac agcctctggg     660
cccggccagg ggccctgtta acaaactgct ttcacatccc aacagggtct gcttggccac     720
tcagtgcagc tgcgattaac cctaaaggct ttaaggaacg ggccacctgt aacagagaca     780
ccagccttcc tgtatagaca ctaaattgtt agcaagagtg ttgagctagt tcctggtgaa     840
gtgtttccac agaagacatg tggagcagtt gtggggatat taagggaaac tttcctctgc     900
cttgaccct tgttaaata aaatgacttt gggagccatt cattgtacag ttgcaggaat       960
gagagtgatt ttatgatgtg gtacattggg accatgttct aaaaccttgg gtttctgagt    1020
ctgctttttg agtaggtgat tttgaggttg aaaaaccagg ggccttcatc taggaaatac    1080
agcatttcc agaagcttct ttgaaaggga atcctggttt tgttgccaaa atgaaacgcc     1140
cggggttggc gctgaatccc acaactgtgt gatttgcttg ttgagttttt tgttgtctgg    1200
ttttttgtt tgtttgttta taccaataag aatgagcctg aatgttggtg gtttttgaaa     1260
tcctgacttg gaggtaaacc tggaggaagg aaaaaaagta aatatgcagg ctttaggac    1320
tgagtagcct tgaaaataaa cctcatttct aaaaaggaaa aaaaaaaaa aan           1373
```

<210> SEQ ID NO 34
<211> LENGTH: 1404
<212> TYPE: DNA
<213> ORGANISM: Homo sapiens
<220> FEATURE:
<221> NAME/KEY: SITE
<222> LOCATION: (36)
<223> OTHER INFORMATION: n equals a,t,g, or c

<400> SEQUENCE: 34

```
gtggatcccc gggctgcagg aattcggcaa cggcgnccgc tccccgctcc tcctccccag      60
ccatggcgtt cacgttcgcg gccttctgct acatgctggc gctgctgctc actgccgcgc     120
tcatcttctt cgccatttgg cacattatag catttgatga gctgaagact gattacaaga     180
```

-continued

| | |
|---|---|
| atcctataga ccagtgtaat accctgaatc cccttgtact cccagagtac ctcatccacg | 240 |
| ctttcttctg tgtcatgttt ctttgtgcag cagagtggct tacactgggt ctcaatatgc | 300 |
| ccctcttggc atatcatatt tggaggtata tgagtagacc agtgatgagt ggcccaggac | 360 |
| tctatgaccc tacaaccatc atgaatgcag atattctagc atattgtcag aaggaaggat | 420 |
| ggtgcaaatt agcttttat cttctagcat tttttacta cctatatggc atgatctatg | 480 |
| ttttggtgag ctcttagaac aacacacaga agaattggtc cagttaagtg catgcaaaaa | 540 |
| gccaccaaat gaagggattc tatccagcaa gatcctgtcc aagagtagcc tgtggaatct | 600 |
| gatcagttac tttaaaaaat gactccttat tttttaaatg tttccacatt tttgcttgtg | 660 |
| gaaagactgt tttcatatgt tatactcaga taaagatttt aaatggtatt acgtataaat | 720 |
| taatataaaa tgattacctc tggtgttgac aggtttgaac ttgcacttct taaggaacag | 780 |
| ccataatcct ctgaatgatg cattaattac tgactgtcct agtacattgg aagcttttgt | 840 |
| ttataggaac ttgtagggct catttggtt tcattgaaac agtatctaat tataaattag | 900 |
| ctgtagatat caggtgcttc tgatgaagtg aaaatgtata tctgactagt gggaaacttc | 960 |
| atgggttcc tcatctgtca tgtcgatgat tatatatgga tacatttaca aaataaaaa | 1020 |
| gcgggaattt tcccttcgct tgaatattat ccctgtatat tgcatgaatg agagatttcc | 1080 |
| catatttcca tcagagtaat aaatatactt gctttaattc ttaagcataa gtaaacatga | 1140 |
| tataaaaata tatgctgaat tacttgtgaa gaatgcattt aaagctattt taaatgtgtt | 1200 |
| tttatttgta agacattact tattaagaaa ttggttatta tgcttactgt tctaatctgg | 1260 |
| tggtaaaggt attcttaaga atttgcaggt actacagatt ttcaaaactg aatgagagaa | 1320 |
| aattgtataa ccatcctgct gttcctttag tgcaatacaa taaaactctg aaattaactc | 1380 |
| aaaaaaaaaa aaaaaaact cgta | 1404 |

<210> SEQ ID NO 35
<211> LENGTH: 1093
<212> TYPE: DNA
<213> ORGANISM: Homo sapiens
<220> FEATURE:
<221> NAME/KEY: SITE
<222> LOCATION: (2)
<223> OTHER INFORMATION: n equals a,t,g, or c

<400> SEQUENCE: 35

| | |
|---|---|
| gnaattcggc acgagtgggg gtggctgccc tggcccagtg gaaggagctt ggccaagaca | 60 |
| cagcatcctg tctagcttcc taccagtaga caaagctgtc agattactta catggccacc | 120 |
| tctctgccgc agttgcttgg aagttctaaa ctaagtttca tgtttaattg ctttagcatg | 180 |
| cttcaaccag gaacatttaa tagcattttt tctctcttct ttttgtttgt aactttagtc | 240 |
| tttcatcttt atcagttgtt tttatactta ttatacctgc aatttttataa gttgcctcaa | 300 |
| attcttttt aaagcccttg agtccaaaat aaaatataat ataaaccaaa agccatttt | 360 |
| ataattaaag tagtaccaga gtcatcctcc ttaaaaatca ggtaaaatac gtgttgaata | 420 |
| gagataagag tatttgctat tacaatttta attcagtact aggcatgctt ccataaactg | 480 |
| ctcaagaata aatggtaagt attctaaatc caaggaggga aaaacaaaa ttgcattttt | 540 |
| gcagacagta ctttatgta tgtataaaat gcaatgaaat taatacaaaa gtaactggag | 600 |
| ataatgataa taatgtgata gtgttctgca gaattatagg ctaggctaaa aatctcaaaa | 660 |
| gtcaagtaag ttagtatttg ctaaagtcat gtagctgaca atatagtgat gaaagacata | 720 |
| tgagaaaaca ttgtccacat ccaaaactga acttctgtct aactacccta gtgggcctgc | 780 |

```
cctccctgca cctcttattc actatgctga ctaatggcat catccaccca ggtcatccaa      840
gcctaaacct tggaggtcat cttaagcacc acctccccag acctttacaa ctgctgaccc      900
tcagaactag tcagtcgtta accagcttct gacattacct aaatttctcc caaacccatc      960
ccaattttgt acccaattct tctgacttaa tttaagtcta tcattttgt cagaattact      1020 agatgaattc ttcagtcata tgtatagata tacacgtgct ccacaggtta aaaaaaaaa      1080 aaaaaaactc gta                                                        1093

<210> SEQ ID NO 36
<211> LENGTH: 418
<212> TYPE: DNA
<213> ORGANISM: Homo sapiens
<220> FEATURE:
<221> NAME/KEY: SITE
<222> LOCATION: (72)
<223> OTHER INFORMATION: n equals a,t,g, or c
<220> FEATURE:
<221> NAME/KEY: SITE
<222> LOCATION: (417)
<223> OTHER INFORMATION: n equals a,t,g, or c

<400> SEQUENCE: 36
aaaatgttca atcatctatg tcatttaaaa atgtttaaaa cacttttatg ctttctaaca       60
tattccccat gnaaataaaa aatgtacatg tcttatctgt ttttactctt tggatgtcac      120 gttttttaaac ttaattttttc ttttccttta aactactgtg tggactttta tcaactactg    180
ttttatattc acctaattgt gtagtaaata ttttaagata ataacctgga gaatttgagg      240
aaagtcaaat atgtgtgaaa ctcttttttc ttcccctgtt gctttaggta caaattattt      300
ggctcgactt ctagtttttg tcttatttca ggcagctctg tccagtggag tgacccgktg      360
ccagagtgca gaggtaagag ttaaaaaaac ctaagcacct ccaggatggt gaaggcng       418

<210> SEQ ID NO 37
<211> LENGTH: 1042
<212> TYPE: DNA
<213> ORGANISM: Homo sapiens
<220> FEATURE:
<221> NAME/KEY: SITE
<222> LOCATION: (222)
<223> OTHER INFORMATION: n equals a,t,g, or c

<400> SEQUENCE: 37
gaatcggcac gaggaaatat tactgaattt tcttttatta tcaaatacaa atttagcata       60
tcctatgtaa aatgctgatt gcccttttct gcatattatt tcagtcttg ttttctatac      120 ccacaaggat tttctatata ttctcataa acaagagagt ccacatattt actacttacc      180
ttatgagtga acaaaaaaat cacgattggg ttcgcagaac tncaaagttg caccgtgtgt      240
ggctcattag tggaaaaatg ctgctggttg cagatataaa ggctctgatc aggtggctgt      300
ggggccctaa tccagaatga gcacagttat tttgatcaat ggagtctaac ctagtcctcc      360
cccaaggttc aaaatgtcct ctggtgcttg caatttctt acagtatttt tttctaattg      420
ataccaagct gggactctcc tggtatatca tatttggaaa tgaaagtgaa acaaatgag      480 aatttttcctt ttgcgttggt gaatgcatac agtgatttaa gtttgggtgc atttctttca      540
gtctgttgat tgttctagga atcgatgctc acagatcaat gagtcatgtc caatttcata      600
aacaactgcc tgggtgagt gtggcctcat aaatgtgaac aaatagtaat ggagtggcaa      660
tcaaacctaa agtgttactg caaatcatgc catgctgaaa gaagaaacat ctcaaaaaga      720
```

```
gaataaacat ttttagggtc gggtgtggtg gttcatgcct ataatatcag cactttggga    780
ggccaaggca gaaggattgc ttgaggctag gagttggaga ccagcctgag taacatagtg    840 agacccagt cctacaaaa aaaaaaaaaa attaacaaag gattgtggtg catgcctgta     900
gtcttagcta ctcgggaggc tgaggaggga agacaacttt aacccgggag ttcaaggttr    960
cagtgctatg attgcaccat cgcgttccag ccttggtgac agagcaagac tctgtctcaa   1020
aaaaaaaaaa aaaaaactcg aa                                           1042
```

<210> SEQ ID NO 38
<211> LENGTH: 798
<212> TYPE: DNA
<213> ORGANISM: Homo sapiens

<400> SEQUENCE: 38

```
gaattcggca cgagcaggag ttcaagacca gcctgggcaa caacagtgcg accctgtctc     60
tttaaaaaat aaaaataaaa atggtaagaa aaaaactcca aattacctcg atactcagtg    120
gattaaaact atttctcttg attttgtgga ttgactggtt ggttttgcc aatcttgcgc    180 tcatacagct tcatctggtg ggtcgggtgg ggactggact tgagtaggat ggctgggtct    240
ccttccatgt agtcgctcgt cttaggcttc ttcacagcat ggtagtctta ggacaggagt    300
arcagctgta aggcccttgg ggctgtgggt tagaaattat accacgtgga ttctcgtgtt    360
caaagcaagt cacaagtcca gttcttattc aaagttttgg gtaaataggc tatatctctt    420
gattggaggt gctgtagaga ttctctggcc gtatttaatt ttcaacatca gtatagttag    480
atgaatgctg tggtgtagat gagcaaaggg tgctatagaa cagaggatgg aaacctaatt    540
cagcttgagg gaagggtcaa ggaaggcttc ttggagttgg taatgcttta cgtaagccct    600
ttaaataaaa gtattatgtg atggtgtggt tatagaaaac ataaaggtat ggccgggcgt    660
gatggctcac acctgtaatc ccagcacttg gggaggccaa agtgggagga ttggttgagc    720
tcaggagttg agaccagcct aggcaatata gtgagagcct atctctttat atattaaaaa    780
aaaaaaaaaa aactcgta                                                  798
```

<210> SEQ ID NO 39
<211> LENGTH: 1030
<212> TYPE: DNA
<213> ORGANISM: Homo sapiens
<220> FEATURE:
<221> NAME/KEY: SITE
<222> LOCATION: (431)
<223> OTHER INFORMATION: n equals a,t,g, or c

<400> SEQUENCE: 39

```
gcactggggg cactgccttc cttctcatgc ccaacctcct ccatttactg ctttcaccta     60
gaagatatcc tagtgtgtgt agggtaagtt tgggtgagtg ggccatggtg cacagagttt    120
atctgcttgg ctgttttcac tgttattctc caaataatga ctctgttgct tgtcttcata    180
ttccttcctg ttgtgggatt ccaccagttc tacactctac agcagaactc tgccattcat    240
agtcaaggac tgcagattcc ctcttcaatc tcatctttgt gtttcttaag gatttcctgg    300
ttgtcaattt tgagttctcc tttttgtttc aaacttaact atccatgttt catgtgcacc    360
tatttgttta ttatgcacaa catttctatt atttttaggg agttagcatg ggaagggaag    420
atgaacatgt natctgtctg atatttttaa acttgargyc ctgkttcatt ttcagttcat    480
gccctgctct tgctaagatt gacttgtaat ggcagtactg tgactgggta gcatgtaatc    540
actgatgaas aagaaagctg gttagatttt gggccatttg cttccacatt actgcctata    600
```

-continued

```
ctgtatgtca tcagcaatgt gttgaactgg attcagttga actggaaaag tatgggtgga      660
taaggtgggg ctgaggagtt gcttatagtg gagtaatatc tatgcacatc tgtacctgct      720 taattttct ttattcagtc attgtcttat ctgaaatatg tatgtttgcc tacacctatt       780
gcaaattcaa acatcaaagt attatatata gtaaatgaaa tttactaaga tattatcaag      840
tattaacaag tgttttagac aattgtagag ttttggggga aaattgttgg ttacaatagg      900
gaaataaaac gttactttc agtctgtatt ggattaggtt agaccagaga aaagacatg        960 atgaggtata gttaagaagg aaataagaaa tttaggaaaa tatttatgac tttgcctaac     1020
ctagtctcga                                                            1030
```

<210> SEQ ID NO 40
<211> LENGTH: 37
<212> TYPE: PRT
<213> ORGANISM: Homo sapiens
<220> FEATURE:
<221> NAME/KEY: SITE
<222> LOCATION: (37)
<223> OTHER INFORMATION: Xaa equals stop translation

<400> SEQUENCE: 40

```
Met Ser Leu Pro Ala Ser Phe Phe Lys Ile Ala Leu Val Phe Leu
 1               5                  10                  15

His Val Phe Ser Val Asn Phe Arg Ile Ser Leu Ser Val Ser Thr Ser
            20                  25                  30

Pro Leu Gly Phe Xaa
        35
```

<210> SEQ ID NO 41
<211> LENGTH: 33
<212> TYPE: PRT
<213> ORGANISM: Homo sapiens
<220> FEATURE:
<221> NAME/KEY: SITE
<222> LOCATION: (33)
<223> OTHER INFORMATION: Xaa equals stop translation

<400> SEQUENCE: 41

```
Met Ser His Phe Thr Phe Pro Leu Phe Leu Trp Gly Gln Leu Leu Phe
 1               5                  10                  15

Asn Thr Pro Cys Gly Leu Pro Ser Trp Arg Leu Cys His His Tyr Gln
            20                  25                  30

Xaa
```

<210> SEQ ID NO 42
<211> LENGTH: 92
<212> TYPE: PRT
<213> ORGANISM: Homo sapiens
<220> FEATURE:
<221> NAME/KEY: SITE
<222> LOCATION: (35)
<223> OTHER INFORMATION: Xaa equals any of the naturally occurring
      L-amino acids
<220> FEATURE:
<221> NAME/KEY: SITE
<222> LOCATION: (36)
<223> OTHER INFORMATION: Xaa equals any of the naturally occurring
      L-amino acids
<220> FEATURE:
<221> NAME/KEY: SITE
<222> LOCATION: (92)
<223> OTHER INFORMATION: Xaa equals stop translation

<400> SEQUENCE: 42

```
Met Gly Leu Pro Ser Ser Ile Pro Arg Leu Val Leu Glu Leu Ile
 1               5                  10                 15

Met Ala Gln Cys Ser Ser Leu Trp Lys Cys Pro Arg Gln Pro Arg His
            20                  25                  30

Ser Leu Xaa Xaa Leu Ser Asn Thr Thr Leu Gln Ala Ala Val Thr Asn
                35                  40                  45

His Gln Ser Ser Ala Glu Ala Ser Ser Leu Cys His Pro Cys Asn Asp
         50                  55                  60

Ser Leu Arg Pro Cys Pro Lys His Ser Gly Leu Ser Asn Thr Gln Asn
 65                  70                  75                  80

Cys Asn Val Ile Phe Cys Ser Asn Leu Asn Phe Xaa
                85                  90
```

<210> SEQ ID NO 43
<211> LENGTH: 33
<212> TYPE: PRT
<213> ORGANISM: Homo sapiens
<220> FEATURE:
<221> NAME/KEY: SITE
<222> LOCATION: (33)
<223> OTHER INFORMATION: Xaa equals stop translation

<400> SEQUENCE: 43

```
Met Val Gln Gly Ser Gly Gly Thr Cys Leu Met Met Thr Asp Leu Leu
 1               5                  10                 15

Phe Ala Val Met Leu Ala Val Met Ile Glu Ser Cys Lys Arg Leu Tyr
            20                  25                  30

Xaa
```

<210> SEQ ID NO 44
<211> LENGTH: 53
<212> TYPE: PRT
<213> ORGANISM: Homo sapiens
<220> FEATURE:
<221> NAME/KEY: SITE
<222> LOCATION: (53)
<223> OTHER INFORMATION: Xaa equals stop translation

<400> SEQUENCE: 44

```
Met Asn Phe Ile Trp Ile Leu Ser Arg Leu Ile Leu Glu Ala Ser Cys
 1               5                  10                 15

Tyr Asp Phe Leu Phe Leu Phe Leu Gly Ser Thr Thr Leu Tyr Ser Gln
            20                  25                  30

Leu Thr Ala Ala Phe Arg Pro Gly Leu Gln Leu Leu Ser Ser Arg Lys
        35                  40                  45

Cys Val Pro Val Xaa
         50
```

<210> SEQ ID NO 45
<211> LENGTH: 26
<212> TYPE: PRT
<213> ORGANISM: Homo sapiens
<220> FEATURE:
<221> NAME/KEY: SITE
<222> LOCATION: (26)
<223> OTHER INFORMATION: Xaa equals stop translation

<400> SEQUENCE: 45

```
Met Phe Leu Arg Ile Ile Ile Gln Val Gly Phe Pro Ser Ser Ile Pro
 1               5                  10                 15

Gly Gln Leu Ile Lys Phe Phe Cys Gln Xaa
```

```
                    20                  25

<210> SEQ ID NO 46
<211> LENGTH: 38
<212> TYPE: PRT
<213> ORGANISM: Homo sapiens
<220> FEATURE:
<221> NAME/KEY: SITE
<222> LOCATION: (38)
<223> OTHER INFORMATION: Xaa equals stop translation

<400> SEQUENCE: 46

Met Gln Glu Ala Arg Gln Gln Ile Thr Thr Val Val Leu Pro Thr Leu
 1               5                  10                  15

Ala Val Val Val Leu Leu Ile Val Val Phe Val Tyr Val Ala Thr Arg
                20                  25                  30

Pro Thr Ile Thr Glu Xaa
            35

<210> SEQ ID NO 47
<211> LENGTH: 71
<212> TYPE: PRT
<213> ORGANISM: Homo sapiens
<220> FEATURE:
<221> NAME/KEY: SITE
<222> LOCATION: (58)
<223> OTHER INFORMATION: Xaa equals any of the naturally occurring
      L-amino acids
<220> FEATURE:
<221> NAME/KEY: SITE
<222> LOCATION: (71)
<223> OTHER INFORMATION: Xaa equals stop translation

<400> SEQUENCE: 47

Met Cys Ser Val His Val Leu Gly Ser Gln Leu Leu Pro Gln Val Gly
 1               5                  10                  15

Ile Leu Ile Trp Leu Arg Thr Asp Pro Leu Pro Cys Tyr Leu His Leu
                20                  25                  30

Trp Val Phe Val Val Ala Val Arg Lys Phe Val Ala Gly Glu Asn Ser
            35                  40                  45

Thr Pro Leu Ala Gly Ala Leu Val Ser Xaa His Val Leu Gly Cys Phe
        50                  55                  60

Pro Pro Ser Phe Leu Ile Xaa
 65                  70

<210> SEQ ID NO 48
<211> LENGTH: 60
<212> TYPE: PRT
<213> ORGANISM: Homo sapiens

<400> SEQUENCE: 48

Met Leu Leu Leu Trp Lys Ser Leu Ile Ala Asn Asn Val Lys His Leu
 1               5                  10                  15

Phe Tyr Val Tyr Trp Ile Phe Glu Gln Ile Ala His Ser His Leu Leu
                20                  25                  30

His Thr Phe Gln Ile Asp Cys Cys Phe Leu Ile Asp Thr Trp Phe Ser
            35                  40                  45

Met Tyr Ser Lys Ser Lys Lys Lys Lys Lys Leu
        50                  55                  60

<210> SEQ ID NO 49
<211> LENGTH: 40
<212> TYPE: PRT
```

```
<213> ORGANISM: Homo sapiens
<220> FEATURE:
<221> NAME/KEY: SITE
<222> LOCATION: (14)
<223> OTHER INFORMATION: Xaa equals any of the naturally occurring
      L-amino acids
<220> FEATURE:
<221> NAME/KEY: SITE
<222> LOCATION: (40)
<223> OTHER INFORMATION: Xaa equals stop translation

<400> SEQUENCE: 49

Met Glu Tyr Ile Tyr Val Phe Phe Arg Asp Thr Phe Phe Xaa Leu Leu
 1               5                  10                  15

Leu Glu Ile Phe Gln Phe Gly Ser Arg Thr Cys Met Met Phe Ser Ser
            20                  25                  30

Phe Ala Glu Met Leu Lys Ile Xaa
        35                  40

<210> SEQ ID NO 50
<211> LENGTH: 104
<212> TYPE: PRT
<213> ORGANISM: Homo sapiens
<220> FEATURE:
<221> NAME/KEY: SITE
<222> LOCATION: (104)
<223> OTHER INFORMATION: Xaa equals stop translation

<400> SEQUENCE: 50

Met Asn Leu Ser Ser Ile Leu Ala Val Ile Phe Val Leu Thr Gly Ile
 1               5                  10                  15

Met Glu Asn Val Leu Ala Ser Gln Lys Arg Arg Leu Arg Lys Trp Met
            20                  25                  30

Cys Thr Ser Val Met Ile Val Asn Gly His Lys Arg Ala Ala Val Arg
        35                  40                  45

Asn Cys Thr Val Ser Ala Glu His Leu Met Met Ser His Asn Phe Ile
 50                  55                  60

Leu Ala Val Ile Gly Val Arg Ile Gly Thr Met Gly Ala Ala Leu Ala
 65                  70                  75                  80

Ser Cys Lys Val Arg Gln Ser Ser Leu Met Ser Met Ser Val His Ser
                85                  90                  95

Ala Ser Gln Gln Arg Met Pro Xaa
            100

<210> SEQ ID NO 51
<211> LENGTH: 23
<212> TYPE: PRT
<213> ORGANISM: Homo sapiens
<220> FEATURE:
<221> NAME/KEY: SITE
<222> LOCATION: (23)
<223> OTHER INFORMATION: Xaa equals stop translation

<400> SEQUENCE: 51

Met Ile Phe Leu Phe Leu Phe Cys Thr Leu Leu Asp Asp Cys Glu Ala
 1               5                  10                  15

Met Ser Ile Gly Leu Gly Xaa
            20

<210> SEQ ID NO 52
<211> LENGTH: 85
<212> TYPE: PRT
<213> ORGANISM: Homo sapiens
```

-continued

```
<400> SEQUENCE: 52

Met Gln Asn Gln Ser Ser Thr Asn His Pro Gly Ala Ser Ile Ala Leu
  1               5                  10                  15

Ser Arg Pro Ser Leu Asn Lys Asp Phe Arg Asp His Ala Glu Gln Gln
             20                  25                  30

His Ile Ala Ala Gln Gln Lys Ala Ala Leu Gln His Ala His Ala His
         35                  40                  45

Ser Ser Gly Tyr Phe Ile Thr Gln Asp Ser Ala Phe Gly Asn Leu Phe
     50                  55                  60

Phe Leu Phe Tyr Leu Ala Leu Thr Gln Asn Glu Glu Asn Ile Cys Asp
 65                  70                  75                  80

Gly Lys Val Thr Leu
                 85

<210> SEQ ID NO 53
<211> LENGTH: 74
<212> TYPE: PRT
<213> ORGANISM: Homo sapiens
<220> FEATURE:
<221> NAME/KEY: SITE
<222> LOCATION: (74)
<223> OTHER INFORMATION: Xaa equals stop translation

<400> SEQUENCE: 53

Met Ser Pro Ala Ala Ala Glu Pro Asp Gly Asp Gln Gln Asp Arg
  1               5                  10                  15

His Val Ser Lys Leu Ile Phe Cys Phe Val Phe Gly Ala Val Leu
             20                  25                  30

Leu Cys Val Gly Val Leu Leu Ser Ile Phe Gly Phe Gln Ala Cys Gln
         35                  40                  45

Tyr Lys Pro Leu Pro Asp Cys Pro Met Val Leu Lys Trp Arg Gly Cys
     50                  55                  60

Met Cys Arg Gly Trp Ala Trp Gly Leu Xaa
 65                  70

<210> SEQ ID NO 54
<211> LENGTH: 36
<212> TYPE: PRT
<213> ORGANISM: Homo sapiens
<220> FEATURE:
<221> NAME/KEY: SITE
<222> LOCATION: (36)
<223> OTHER INFORMATION: Xaa equals stop translation

<400> SEQUENCE: 54

Met Phe Gly Ala Phe Phe Phe Cys Leu Leu Phe Lys Ser Phe Leu Asn
  1               5                  10                  15

Gly Gly Pro Phe His Leu His Leu Ser Phe Pro Leu Lys Ser Leu Lys
             20                  25                  30

Pro Phe Leu Xaa
         35

<210> SEQ ID NO 55
<211> LENGTH: 68
<212> TYPE: PRT
<213> ORGANISM: Homo sapiens
<220> FEATURE:
<221> NAME/KEY: SITE
<222> LOCATION: (68)
<223> OTHER INFORMATION: Xaa equals stop translation

<400> SEQUENCE: 55
```

```
Met Ser Arg Asn Leu Arg Thr Ala Leu Ile Phe Gly Phe Ile Ser
  1               5                  10                 15

Leu Ile Gly Ala Ala Phe Tyr Pro Ile Tyr Phe Arg Pro Leu Met Arg
             20                  25                  30

Leu Glu Glu Tyr Lys Lys Glu Gln Ala Ile Asn Arg Ala Gly Ile Val
         35                  40                  45

Gln Glu Asp Val Gln Pro Pro Gly Leu Lys Val Trp Ser Asp Pro Phe
     50                  55                  60

Gly Arg Lys Xaa
 65
```

<210> SEQ ID NO 56
<211> LENGTH: 161
<212> TYPE: PRT
<213> ORGANISM: Homo sapiens

<400> SEQUENCE: 56

```
Met Leu Asp Ile Glu Ser Phe Ser Phe Leu Asn Arg Ala Leu Glu Ser
  1               5                  10                 15

Asp Met Ala Pro Val Leu Ile Met Ala Thr Asn Arg Gly Ile Thr Arg
             20                  25                  30

Ile Arg Gly Thr Ser Tyr Gln Ser Pro His Gly Ile Pro Ile Asp Leu
         35                  40                  45

Leu Asp Arg Leu Leu Ile Val Ser Thr Thr Pro Tyr Ser Glu Lys Asp
     50                  55                  60

Thr Lys Gln Ile Leu Arg Ile Arg Cys Glu Glu Asp Val Glu Met
 65                  70                  75                  80

Ser Glu Asp Ala Tyr Thr Val Leu Thr Arg Ile Gly Leu Glu Thr Ser
                 85                  90                  95

Leu Arg Tyr Ala Ile Gln Leu Ile Thr Ala Ala Ser Leu Val Cys Arg
                100                 105                 110

Lys Arg Lys Gly Thr Glu Val Gln Val Asp Asp Ile Lys Arg Val Tyr
            115                 120                 125

Ser Leu Phe Leu Asp Glu Ser Arg Ser Thr Gln Tyr Met Lys Glu Tyr
    130                 135                 140

Gln Asp Ala Phe Leu Phe Asn Glu Leu Lys Gly Glu Thr Met Asp Thr
145                 150                 155                 160

Ser
```

<210> SEQ ID NO 57
<211> LENGTH: 42
<212> TYPE: PRT
<213> ORGANISM: Homo sapiens
<220> FEATURE:
<221> NAME/KEY: SITE
<222> LOCATION: (42)
<223> OTHER INFORMATION: Xaa equals stop translation

<400> SEQUENCE: 57

```
Met Ala Ser Gly Pro Gly Glu Val Cys Tyr Ser Val Leu Thr Ala Glu
  1               5                  10                 15

His Pro Ala Cys Ile Arg Lys Leu Arg Ser Ser Leu Pro Cys Gln Ile
             20                  25                  30

Asn Leu Asn Gly Pro Cys Pro His Asn Xaa
         35                  40
```

<210> SEQ ID NO 58

```
<211> LENGTH: 76
<212> TYPE: PRT
<213> ORGANISM: Homo sapiens
<220> FEATURE:
<221> NAME/KEY: SITE
<222> LOCATION: (76)
<223> OTHER INFORMATION: Xaa equals stop translation

<400> SEQUENCE: 58

Met Val Leu Pro Ala Thr Gly Gly Leu Arg Val Val Ser Ala Pro Cys
 1               5                  10                  15

Ile Ser Pro Ser Leu Leu Thr Phe Leu Leu Cys Phe Pro Pro Ser Val
            20                  25                  30

Cys Gln Arg Gly Gly Thr Gly Asn Arg Thr Ala Val Ala Ala Leu Ser
        35                  40                  45

Leu Leu Ser Thr Val Tyr Ser Gly Leu Ser Gly Asp Ser Arg Glu Pro
    50                  55                  60

Gly His Leu Ala Ala Val Arg Pro Leu Asn Leu Xaa
65                  70                  75

<210> SEQ ID NO 59
<211> LENGTH: 40
<212> TYPE: PRT
<213> ORGANISM: Homo sapiens
<220> FEATURE:
<221> NAME/KEY: SITE
<222> LOCATION: (40)
<223> OTHER INFORMATION: Xaa equals stop translation

<400> SEQUENCE: 59

Met Gly Phe Leu Leu Leu Phe Phe Val Ile Ser Ser Thr Cys Tyr Thr
 1               5                  10                  15

Leu Leu Ala Gln Ser Ile Phe Leu Glu His Phe Cys Ile Ser Tyr Gly
            20                  25                  30

Asn Lys Phe Tyr Thr Leu Asp Xaa
        35                  40

<210> SEQ ID NO 60
<211> LENGTH: 33
<212> TYPE: PRT
<213> ORGANISM: Homo sapiens
<220> FEATURE:
<221> NAME/KEY: SITE
<222> LOCATION: (33)
<223> OTHER INFORMATION: Xaa equals stop translation

<400> SEQUENCE: 60

Met Leu Ile Asn Val Tyr Leu Phe Ile Ile Phe Val Phe Ile Gln Leu
 1               5                  10                  15

Leu His Ser Ser Phe Leu Arg Leu Gly His Val Asp Thr Tyr Ser Asn
            20                  25                  30

Xaa

<210> SEQ ID NO 61
<211> LENGTH: 111
<212> TYPE: PRT
<213> ORGANISM: Homo sapiens
<220> FEATURE:
<221> NAME/KEY: SITE
<222> LOCATION: (111)
<223> OTHER INFORMATION: Xaa equals stop translation

<400> SEQUENCE: 61

Met Tyr Pro Leu Tyr Cys Lys Ile Leu Leu Ser Phe Leu Phe Leu Leu
```

```
              1               5                  10                    15
Leu Ser Ser Asn His Thr Tyr Val Ala Asn His Ile Tyr Ser Phe Trp
                    20                  25              30

Leu Ile Leu Tyr Met Phe Leu Leu Ala Asn Ile Ser Lys Leu Tyr Ile
            35                  40                  45

Phe Asn Ile Leu Thr Tyr Arg Lys Cys Ser Ile Tyr Thr Pro Leu His
        50                  55                  60

Leu Val Phe Leu Phe Val Tyr Leu Arg Ile Tyr Ser Arg Asn His Ser
65                  70                  75                  80

Thr Leu Val His Arg His Leu Phe Asp Tyr Tyr Gly Gln Phe Leu
                    85                  90                  95

Lys Trp Leu His Ser Thr Leu Leu Tyr Gly Trp Ile Leu Leu Xaa
                100                 105                 110
```

<210> SEQ ID NO 62
<211> LENGTH: 76
<212> TYPE: PRT
<213> ORGANISM: Homo sapiens
<220> FEATURE:
<221> NAME/KEY: SITE
<222> LOCATION: (76)
<223> OTHER INFORMATION: Xaa equals stop translation

<400> SEQUENCE: 62

```
Met Ile Gly Asp Ile Leu Leu Phe Gly Thr Leu Leu Met Asn Ala Gly
 1               5                  10                  15

Ala Val Leu Asn Phe Lys Leu Lys Lys Asp Thr Gln Gly Phe Gly
                20                  25              30

Glu Glu Ser Arg Glu Pro Ser Thr Gly Asp Asn Ile Arg Glu Phe Leu
            35                  40                  45

Leu Ser Leu Arg Tyr Phe Arg Ile Phe Ile Ala Leu Trp Asn Ile Phe
        50                  55                  60

Met Met Phe Cys Met Ile Val Leu Phe Gly Ser Xaa
65                  70                  75
```

<210> SEQ ID NO 63
<211> LENGTH: 145
<212> TYPE: PRT
<213> ORGANISM: Homo sapiens
<220> FEATURE:
<221> NAME/KEY: SITE
<222> LOCATION: (145)
<223> OTHER INFORMATION: Xaa equals stop translation

<400> SEQUENCE: 63

```
Met Ala Phe Thr Phe Ala Ala Phe Cys Tyr Met Leu Ala Leu Leu Leu
 1               5                  10                  15

Thr Ala Ala Leu Ile Phe Phe Ala Ile Trp His Ile Ile Ala Phe Asp
                20                  25                  30

Glu Leu Lys Thr Asp Tyr Lys Asn Pro Ile Asp Gln Cys Asn Thr Leu
            35                  40                  45

Asn Pro Leu Val Leu Pro Glu Tyr Leu Ile His Ala Phe Phe Cys Val
        50                  55                  60

Met Phe Leu Cys Ala Ala Glu Trp Leu Thr Leu Gly Leu Asn Met Pro
65                  70                  75                  80

Leu Leu Ala Tyr His Ile Trp Arg Tyr Met Ser Arg Pro Val Met Ser
                85                  90                  95

Gly Pro Gly Leu Tyr Asp Pro Thr Thr Ile Met Asn Ala Asp Ile Leu
                100                 105                 110
```

```
Ala Tyr Cys Gln Lys Glu Gly Trp Cys Lys Leu Ala Phe Tyr Leu Leu
            115                 120                 125

Ala Phe Phe Tyr Tyr Leu Tyr Gly Met Ile Tyr Val Leu Val Ser Ser
        130                 135                 140

Xaa
145

<210> SEQ ID NO 64
<211> LENGTH: 45
<212> TYPE: PRT
<213> ORGANISM: Homo sapiens
<220> FEATURE:
<221> NAME/KEY: SITE
<222> LOCATION: (45)
<223> OTHER INFORMATION: Xaa equals stop translation

<400> SEQUENCE: 64

Met Leu Gln Pro Gly Thr Phe Asn Ser Ile Phe Ser Leu Phe Phe Leu
  1               5                  10                  15

Phe Val Thr Leu Val Phe His Leu Tyr Gln Leu Phe Leu Tyr Leu Leu
             20                  25                  30

Tyr Leu Gln Phe Tyr Lys Leu Pro Gln Ile Leu Phe Xaa
         35                  40                  45

<210> SEQ ID NO 65
<211> LENGTH: 47
<212> TYPE: PRT
<213> ORGANISM: Homo sapiens

<400> SEQUENCE: 65

Met Cys Glu Thr Leu Phe Ser Ser Pro Val Ala Leu Gly Thr Asn Tyr
  1               5                  10                  15

Leu Ala Arg Leu Leu Val Phe Val Leu Phe Gln Ala Ala Leu Ser Ser
             20                  25                  30

Gly Val Thr Arg Cys Gln Ser Ala Glu Val Arg Val Lys Lys Thr
         35                  40                  45

<210> SEQ ID NO 66
<211> LENGTH: 83
<212> TYPE: PRT
<213> ORGANISM: Homo sapiens
<220> FEATURE:
<221> NAME/KEY: SITE
<222> LOCATION: (51)
<223> OTHER INFORMATION: Xaa equals any of the naturally occurring
      L-amino acids
<220> FEATURE:
<221> NAME/KEY: SITE
<222> LOCATION: (83)
<223> OTHER INFORMATION: Xaa equals stop translation

<400> SEQUENCE: 66

Met Leu Ile Ala Leu Phe Cys Ile Leu Phe Gln Ile Leu Phe Ser Ile
  1               5                  10                  15

Pro Thr Arg Ile Phe Tyr Ile Phe Leu Ile Asn Lys Arg Val His Ile
             20                  25                  30

Phe Thr Thr Tyr Leu Met Ser Glu Gln Lys Asn His Asp Trp Val Arg
         35                  40                  45

Arg Thr Xaa Lys Leu His Arg Val Trp Leu Ile Ser Gly Lys Met Leu
     50                  55                  60

Leu Val Ala Asp Ile Lys Ala Leu Ile Arg Trp Leu Trp Gly Pro Asn
 65                  70                  75                  80
```

Pro Glu Xaa

<210> SEQ ID NO 67
<211> LENGTH: 49
<212> TYPE: PRT
<213> ORGANISM: Homo sapiens
<220> FEATURE:
<221> NAME/KEY: SITE
<222> LOCATION: (49)
<223> OTHER INFORMATION: Xaa equals stop translation

<400> SEQUENCE: 67

Met Val Arg Lys Lys Leu Gln Ile Thr Ser Ile Leu Ser Gly Leu Lys
 1               5                  10                  15

Leu Phe Leu Leu Ile Leu Trp Ile Asp Trp Leu Val Phe Ala Asn Leu
            20                  25                  30

Ala Leu Ile Gln Leu His Leu Val Gly Arg Val Gly Thr Gly Leu Glu
        35                  40                  45

Xaa

<210> SEQ ID NO 68
<211> LENGTH: 95
<212> TYPE: PRT
<213> ORGANISM: Homo sapiens
<220> FEATURE:
<221> NAME/KEY: SITE
<222> LOCATION: (92)
<223> OTHER INFORMATION: Xaa equals any of the naturally occurring
      L-amino acids
<220> FEATURE:
<221> NAME/KEY: SITE
<222> LOCATION: (95)
<223> OTHER INFORMATION: Xaa equals stop translation

<400> SEQUENCE: 68

Met Thr Leu Leu Leu Val Phe Ile Phe Leu Pro Val Val Gly Phe His
 1               5                  10                  15

Gln Phe Tyr Thr Leu Gln Gln Asn Ser Ala Ile His Ser Gln Gly Leu
            20                  25                  30

Gln Ile Pro Ser Ser Ile Ser Ser Leu Cys Phe Leu Arg Ile Ser Trp
        35                  40                  45

Leu Ser Ile Leu Ser Ser Pro Phe Cys Phe Lys Leu Asn Tyr Pro Cys
50                  55                  60

Phe Met Cys Thr Tyr Leu Phe Ile Met His Asn Ile Ser Ile Ile Phe
65                  70                  75                  80

Arg Glu Leu Ala Trp Glu Gly Lys Met Asn Met Xaa Ser Val Xaa
            85                  90                  95

<210> SEQ ID NO 69
<211> LENGTH: 33
<212> TYPE: PRT
<213> ORGANISM: Homo sapiens
<220> FEATURE:
<221> NAME/KEY: SITE
<222> LOCATION: (7)
<223> OTHER INFORMATION: Xaa equals any of the naturally occurring
      L-amino acids
<220> FEATURE:
<221> NAME/KEY: SITE
<222> LOCATION: (12)
<223> OTHER INFORMATION: Xaa equals any of the naturally occurring
      L-amino acids

<400> SEQUENCE: 69

```
His Val Asn Gly Asn Lys Xaa Met Asp His His Xaa Gln Val Ala Ala
 1               5                  10                  15

Ala Leu Glu Leu Val Asp Pro Pro Gly Cys Arg Asn Ser Ala Arg Gly
            20                  25                  30

Asn
```

<210> SEQ ID NO 70
<211> LENGTH: 6
<212> TYPE: PRT
<213> ORGANISM: Homo sapiens

<400> SEQUENCE: 70

```
Glu Ile Ser Asn Tyr Val
 1               5
```

<210> SEQ ID NO 71
<211> LENGTH: 40
<212> TYPE: PRT
<213> ORGANISM: Homo sapiens

<400> SEQUENCE: 71

```
Ile Arg His Glu Ser Lys Ser Met Phe Val Tyr Ser Pro Asn Leu Ser
 1               5                  10                  15

Asn Ala Lys Gly Trp His Arg Gly Gln Cys Gln Ala Val Pro Gly Tyr
            20                  25                  30

Tyr Leu Pro Leu Arg Lys Asn Ser
            35                  40
```

<210> SEQ ID NO 72
<211> LENGTH: 30
<212> TYPE: PRT
<213> ORGANISM: Homo sapiens

<400> SEQUENCE: 72

```
Glu Lys Gly Glu Gly Arg Thr Pro Ser Phe Ile Pro Thr Ala Ser Asp
 1               5                  10                  15

Pro Lys Gly Ile Leu Gly Ser Leu Val Thr Met Asp Thr Thr
            20                  25                  30
```

<210> SEQ ID NO 73
<211> LENGTH: 10
<212> TYPE: PRT
<213> ORGANISM: Homo sapiens

<400> SEQUENCE: 73

```
Lys Leu Val Ser Lys Gly Lys Val Ser Glu
 1               5                  10
```

<210> SEQ ID NO 74
<211> LENGTH: 26
<212> TYPE: PRT
<213> ORGANISM: Homo sapiens

<400> SEQUENCE: 74

```
Pro Leu Gly Lys Met Arg Gln Leu Lys Gly Lys Pro Lys Lys Glu Thr
 1               5                  10                  15

Ser Lys Asp Lys Lys Glu Arg Lys Gln Ala
            20                  25
```

<210> SEQ ID NO 75
<211> LENGTH: 16
<212> TYPE: PRT

```
<213> ORGANISM: Homo sapiens

<400> SEQUENCE: 75

Leu Leu Ile Ala Gly Thr Gly Ser Ser Leu Tyr Trp Ala Phe Thr Val
 1               5                  10                  15

<210> SEQ ID NO 76
<211> LENGTH: 42
<212> TYPE: PRT
<213> ORGANISM: Homo sapiens
<220> FEATURE:
<221> NAME/KEY: SITE
<222> LOCATION: (5)
<223> OTHER INFORMATION: Xaa equals any of the naturally occurring
      L-amino acids

<400> SEQUENCE: 76

Gly Lys Arg Val Xaa Leu Gln Val Pro Val Arg Asn Ser Arg Val Asp
 1               5                  10                  15

Pro Arg Val Arg Val Trp Gly Val Val Leu Asn Val Cys Gly Pro Gly
                20                  25                  30

Ala Trp Gly Leu Ala Glu His Ser Val Lys
            35                  40

<210> SEQ ID NO 77
<211> LENGTH: 128
<212> TYPE: PRT
<213> ORGANISM: Homo sapiens
<220> FEATURE:
<221> NAME/KEY: SITE
<222> LOCATION: (24)
<223> OTHER INFORMATION: Xaa equals any of the naturally occurring
      L-amino acids
<220> FEATURE:
<221> NAME/KEY: SITE
<222> LOCATION: (36)
<223> OTHER INFORMATION: Xaa equals any of the naturally occurring
      L-amino acids
<220> FEATURE:
<221> NAME/KEY: SITE
<222> LOCATION: (43)
<223> OTHER INFORMATION: Xaa equals any of the naturally occurring
      L-amino acids

<400> SEQUENCE: 77

Lys Gln Cys Pro Ala Leu Asn Gly Ser Phe Lys Gly Val Gly Thr Asn
 1               5                  10                  15

Cys Lys Met Met Tyr Leu Glu Xaa Trp Gly Leu Arg Asp Ile Leu Leu
                20                  25                  30

Pro Pro Arg Xaa Phe Val Ala Asp Gly Ser Xaa Gln Gly Gly Glu Arg
                35                  40                  45

Glu Ala Ser Val Leu Phe Gly Lys Leu Ala Ile Lys Thr Gly Lys Gly
     50                  55                  60

Val Leu Phe Ser Arg Lys Leu Asp Leu Phe Arg Thr Leu Ser Ala Pro
65                  70                  75                  80

Asn Arg Cys Gly Gln Leu Pro Ala Ala Gln Arg Asp Glu Gly Gln Arg
                85                  90                  95

Gln Asp Ala Ala Gly Lys Val Asn Ile Val Phe Val Ser Thr Val Glu
                100                 105                 110

Asp Lys Lys Gly Met Lys Ser Thr Val Arg Thr Ile Met Val Gly Glu
                115                 120                 125

<210> SEQ ID NO 78
<211> LENGTH: 28
```

```
<212> TYPE: PRT
<213> ORGANISM: Homo sapiens
<220> FEATURE:
<221> NAME/KEY: SITE
<222> LOCATION: (9)
<223> OTHER INFORMATION: Xaa equals any of the naturally occurring
      L-amino acids
<220> FEATURE:
<221> NAME/KEY: SITE
<222> LOCATION: (16)
<223> OTHER INFORMATION: Xaa equals any of the naturally occurring
      L-amino acids

<400> SEQUENCE: 78

Arg Asp Ile Leu Leu Pro Pro Arg Xaa Phe Val Ala Asp Gly Ser Xaa
 1               5                  10                  15

Gln Gly Gly Glu Arg Glu Ala Ser Val Leu Phe Gly
            20                  25

<210> SEQ ID NO 79
<211> LENGTH: 38
<212> TYPE: PRT
<213> ORGANISM: Homo sapiens

<400> SEQUENCE: 79

Leu Phe Arg Thr Leu Ser Ala Pro Asn Arg Cys Gly Gln Leu Pro Ala
 1               5                  10                  15

Ala Gln Arg Asp Glu Gly Gln Arg Gln Asp Ala Ala Gly Lys Val Asn
            20                  25                  30

Ile Val Phe Val Ser Thr
            35

<210> SEQ ID NO 80
<211> LENGTH: 238
<212> TYPE: PRT
<213> ORGANISM: Homo sapiens

<400> SEQUENCE: 80

Gly Arg Pro Thr Arg Pro Lys Thr Pro Tyr Asp Glu Ser Lys Phe Tyr
 1               5                  10                  15

Ile Gly Cys Asp Leu Cys Thr Asn Trp Tyr His Gly Glu Cys Val Gly
            20                  25                  30

Ile Thr Glu Lys Glu Ala Lys Lys Met Asp Val Tyr Ile Cys Asn Asp
        35                  40                  45

Cys Lys Arg Ala Gln Glu Gly Ser Ser Glu Glu Leu Tyr Cys Ile Cys
    50                  55                  60

Arg Thr Pro Tyr Asp Glu Ser Gln Phe Tyr Ile Gly Cys Asp Arg Cys
65                  70                  75                  80

Gln Asn Trp Tyr His Gly Arg Cys Val Gly Ile Leu Gln Ser Glu Ala
                85                  90                  95

Glu Leu Ile Asp Glu Tyr Val Cys Pro Gln Cys Gln Ser Thr Glu Asp
            100                 105                 110

Ala Met Thr Val Leu Thr Pro Leu Thr Glu Lys Asp Tyr Glu Gly Leu
        115                 120                 125

Lys Arg Val Leu Arg Ser Leu Gln Ala His Lys Met Ala Trp Pro Phe
    130                 135                 140

Leu Glu Pro Val Asp Pro Asn Asp Ala Pro Asp Tyr Tyr Gly Val Ile
145                 150                 155                 160

Lys Glu Pro Met Asp Leu Ala Thr Met Glu Glu Arg Val Gln Arg Arg
                165                 170                 175
```

```
Tyr Tyr Glu Lys Leu Thr Glu Phe Val Ala Asp Met Thr Lys Ile Phe
            180                 185                 190

Asp Asn Cys Arg Tyr Tyr Asn Pro Ser Asp Ser Pro Phe Tyr Gln Cys
            195                 200                 205

Ala Glu Val Leu Glu Ser Phe Phe Val Gln Lys Leu Lys Gly Phe Lys
            210                 215                 220

Ala Ser Arg Ser His Asn Asn Lys Leu Gln Ser Thr Ala Ser
225                 230                 235

<210> SEQ ID NO 81
<211> LENGTH: 20
<212> TYPE: PRT
<213> ORGANISM: Homo sapiens

<400> SEQUENCE: 81

Thr Pro Tyr Asp Glu Ser Lys Phe Tyr Ile Gly Cys Asp Leu Cys Thr
  1               5                  10                  15

Asn Trp Tyr His
            20

<210> SEQ ID NO 82
<211> LENGTH: 24
<212> TYPE: PRT
<213> ORGANISM: Homo sapiens

<400> SEQUENCE: 82

Glu Ala Lys Lys Met Asp Val Tyr Ile Cys Asn Asp Cys Lys Arg Ala
  1               5                  10                  15

Gln Glu Gly Ser Ser Glu Glu Leu
            20

<210> SEQ ID NO 83
<211> LENGTH: 25
<212> TYPE: PRT
<213> ORGANISM: Homo sapiens

<400> SEQUENCE: 83

Arg Cys Gln Asn Trp Tyr His Gly Arg Cys Val Gly Ile Leu Gln Ser
  1               5                  10                  15

Glu Ala Glu Leu Ile Asp Glu Tyr Val
            20                  25

<210> SEQ ID NO 84
<211> LENGTH: 22
<212> TYPE: PRT
<213> ORGANISM: Homo sapiens

<400> SEQUENCE: 84

Ser Thr Glu Asp Ala Met Thr Val Leu Thr Pro Leu Thr Glu Lys Asp
  1               5                  10                  15

Tyr Glu Gly Leu Lys Arg
            20

<210> SEQ ID NO 85
<211> LENGTH: 21
<212> TYPE: PRT
<213> ORGANISM: Homo sapiens

<400> SEQUENCE: 85

Asp Pro Asn Asp Ala Pro Asp Tyr Tyr Gly Val Ile Lys Glu Pro Met
  1               5                  10                  15
```

Asp Leu Ala Thr Met
            20

<210> SEQ ID NO 86
<211> LENGTH: 22
<212> TYPE: PRT
<213> ORGANISM: Homo sapiens

<400> SEQUENCE: 86

Glu Lys Leu Thr Glu Phe Val Ala Asp Met Thr Lys Ile Phe Asp Asn
  1               5                  10                  15

Cys Arg Tyr Tyr Asn Pro
            20

<210> SEQ ID NO 87
<211> LENGTH: 10
<212> TYPE: PRT
<213> ORGANISM: Homo sapiens

<400> SEQUENCE: 87

Val Asp Pro Arg Val Arg Lys Arg Leu Met
  1               5                  10

<210> SEQ ID NO 88
<211> LENGTH: 53
<212> TYPE: PRT
<213> ORGANISM: Homo sapiens

<400> SEQUENCE: 88

Cys Arg Glu Leu Ser Ser Ser Cys Leu Ser Gly Arg Ala Pro Phe Lys
  1               5                  10                  15

Ser Ser Asp Cys Lys Glu Arg Arg Ser Arg Cys Pro Arg Val Pro Gly
                20                  25                  30

Phe Gln Asn Lys Asn Arg Val Ala Ile Leu Ala Glu Leu Asp Lys Glu
            35                  40                  45

Lys Arg Lys Leu Leu
      50

<210> SEQ ID NO 89
<211> LENGTH: 25
<212> TYPE: PRT
<213> ORGANISM: Homo sapiens

<400> SEQUENCE: 89

Ile Arg His Glu Leu Lys Ser Trp Arg Glu Glu Asn Thr Ser His Pro
  1               5                  10                  15

Ala Ser Gly Lys Gly Pro Leu Leu Asp
                20                  25

<210> SEQ ID NO 90
<211> LENGTH: 202
<212> TYPE: PRT
<213> ORGANISM: Homo sapiens

<400> SEQUENCE: 90

Asn Leu Gly Gly Lys Lys Thr His Pro Thr Leu Pro Pro Gly Arg Gly
  1               5                  10                  15

Leu Ser Trp Thr Cys Leu Leu Gln Leu Leu Ser Gln Met Gly Thr
                20                  25                  30

Ser Arg Thr Asp Thr Ser Ala Asn Ser Ser Ser Ala Ser Leu Ser Ser
            35                  40                  45

```
Ala Pro Ser Cys Cys Val Trp Glu Ser Cys Pro Ser Leu Gly Ser
        50                  55                  60

Arg His Ala Asn Ile Ser Pro Ser Gln Thr Ala Pro Trp Cys Ser Ser
 65                  70                  75                  80

Gly Gly Ala Ala Cys Ala Val Val Gly Leu Gly Gly Cys Asp Pro Gly
                85                  90                  95

Pro Leu Pro Gly Ala Thr Ser Ala Pro Cys Lys Ala Ala Glu Arg Ser
            100                 105                 110

Ala Asp Gly Pro Arg Pro Ser Leu His Leu Trp Arg Glu Pro Pro Val
            115                 120                 125

Cys Pro Val Pro Tyr Leu Trp Val Ser Val Leu Asp Lys Arg His Ala
            130                 135                 140

His Gln Arg Pro Gly His Leu Gly Pro Trp Met Trp Leu Gln Leu Gly
145                 150                 155                 160

Ala Gly Thr Ala Lys Arg Asp Arg His Trp Arg Leu Arg Ala Pro Asp
                165                 170                 175

Val Trp Val Pro Phe Ser Ala Asp His Gly Ala Leu Asp Cys Ala Cys
            180                 185                 190

Gly Ile Val Phe Leu Arg Gly Cys Pro Cys
            195                 200

<210> SEQ ID NO 91
<211> LENGTH: 21
<212> TYPE: PRT
<213> ORGANISM: Homo sapiens

<400> SEQUENCE: 91

Thr Leu Pro Pro Gly Arg Gly Leu Ser Trp Thr Cys Leu Leu Gln Leu
 1               5                  10                  15

Leu Leu Ser Gln Met
            20

<210> SEQ ID NO 92
<211> LENGTH: 20
<212> TYPE: PRT
<213> ORGANISM: Homo sapiens

<400> SEQUENCE: 92

Ser Ala Asn Ser Ser Ala Ser Leu Ser Ser Ala Pro Ser Cys Cys
 1               5                  10                  15

Val Trp Glu Ser
            20

<210> SEQ ID NO 93
<211> LENGTH: 25
<212> TYPE: PRT
<213> ORGANISM: Homo sapiens

<400> SEQUENCE: 93

Pro Ser Gln Thr Ala Pro Trp Cys Ser Ser Gly Gly Ala Ala Cys Ala
 1               5                  10                  15

Val Val Gly Leu Gly Gly Cys Asp Pro
            20                  25

<210> SEQ ID NO 94
<211> LENGTH: 21
<212> TYPE: PRT
<213> ORGANISM: Homo sapiens

<400> SEQUENCE: 94
```

-continued

Ala Pro Cys Lys Ala Ala Glu Arg Ser Ala Asp Gly Pro Arg Pro Ser
 1               5                  10                  15

Leu His Leu Trp Arg
            20

<210> SEQ ID NO 95
<211> LENGTH: 29
<212> TYPE: PRT
<213> ORGANISM: Homo sapiens

<400> SEQUENCE: 95

Gln Arg Pro Gly His Leu Gly Pro Trp Met Trp Leu Gln Leu Gly Ala
 1               5                  10                  15

Gly Thr Ala Lys Arg Asp Arg His Trp Arg Leu Arg Ala
            20                  25

<210> SEQ ID NO 96
<211> LENGTH: 25
<212> TYPE: PRT
<213> ORGANISM: Homo sapiens

<400> SEQUENCE: 96

Leu Arg Ala Pro Asp Val Trp Val Pro Phe Ser Ala Asp His Gly Ala
 1               5                  10                  15

Leu Asp Cys Ala Cys Gly Ile Val Phe
            20                  25

<210> SEQ ID NO 97
<211> LENGTH: 254
<212> TYPE: PRT
<213> ORGANISM: Homo sapiens

<400> SEQUENCE: 97

Ala Pro Pro Arg Leu Pro His Gly Ala Gln Val Ala Gly Leu His Val
 1               5                  10                  15

Pro Trp Leu Gly Leu Gly Ala Val Ile Leu Ala Arg Ser Arg Ala Gln
            20                  25                  30

Leu Gln Leu Arg Ala Arg Leu Gln Arg Gly Gln Gln Met Asp Pro Asp
        35                  40                  45

Arg Ala Phe Ile Cys Gly Glu Ser Arg Gln Phe Ala Gln Cys Leu Ile
    50                  55                  60

Phe Gly Phe Leu Phe Leu Thr Ser Gly Met Leu Ile Ser Val Leu Gly
65                  70                  75                  80

Ile Trp Val Pro Gly Cys Gly Ser Asn Trp Ala Gln Glu Pro Leu Asn
                85                  90                  95

Glu Thr Asp Thr Gly Asp Ser Glu Pro Arg Met Cys Gly Phe Leu Ser
            100                 105                 110

Leu Gln Ile Met Gly Pro Leu Ile Val Leu Gly Leu Cys Phe Phe
        115                 120                 125

Val Val Ala His Val Lys Lys Arg Asn Thr Leu Asn Ala Gly Gln Asp
    130                 135                 140

Ala Ser Glu Arg Glu Glu Gly Gln Ile Gln Ile Met Glu Pro Val Gln
145                 150                 155                 160

Val Thr Val Ala Ser Ala Val Ala Glu Ser Pro Gly Thr Asn Ser Leu
                165                 170                 175

Leu Pro Asn Glu Asn Pro Pro Ser Tyr Tyr Ser Ile Phe Asn Tyr Gly
            180                 185                 190

-continued

```
Thr Pro Thr Ser Glu Gly Ala Ala Ser Glu Arg Asp Cys Glu Ser Ile
        195                 200                 205

Tyr Thr Ile Ser Gly Thr Asn Ser Ser Glu Ala Ser His Thr Pro
    210                 215                 220

His Leu Pro Ser Glu Leu Pro Pro Arg Tyr Glu Leu Lys Glu Asn Ala
225                 230                 235                 240

Ala Ala Thr Phe Leu Pro Leu Ser Ser Glu Pro Ser Pro Pro
                245                 250

<210> SEQ ID NO 98
<211> LENGTH: 23
<212> TYPE: PRT
<213> ORGANISM: Homo sapiens

<400> SEQUENCE: 98

Ala Gln Val Ala Gly Leu His Val Pro Trp Leu Gly Leu Gly Ala Val
1               5                   10                  15

Ile Leu Ala Arg Ser Arg Ala
            20

<210> SEQ ID NO 99
<211> LENGTH: 20
<212> TYPE: PRT
<213> ORGANISM: Homo sapiens

<400> SEQUENCE: 99

Arg Gly Gln Gln Met Asp Pro Asp Arg Ala Phe Ile Cys Gly Glu Ser
1               5                   10                  15

Arg Gln Phe Ala
            20

<210> SEQ ID NO 100
<211> LENGTH: 26
<212> TYPE: PRT
<213> ORGANISM: Homo sapiens

<400> SEQUENCE: 100

Leu Ile Ser Val Leu Gly Ile Trp Val Pro Gly Cys Gly Ser Asn Trp
1               5                   10                  15

Ala Gln Glu Pro Leu Asn Glu Thr Asp Thr
            20                  25

<210> SEQ ID NO 101
<211> LENGTH: 26
<212> TYPE: PRT
<213> ORGANISM: Homo sapiens

<400> SEQUENCE: 101

Thr Gly Asp Ser Glu Pro Arg Met Cys Gly Phe Leu Ser Leu Gln Ile
1               5                   10                  15

Met Gly Pro Leu Ile Val Leu Val Gly Leu
            20                  25

<210> SEQ ID NO 102
<211> LENGTH: 26
<212> TYPE: PRT
<213> ORGANISM: Homo sapiens

<400> SEQUENCE: 102

Asp Ala Ser Glu Arg Glu Glu Gly Gln Ile Gln Ile Met Glu Pro Val
1               5                   10                  15
```

-continued

Gln Val Thr Val Ala Ser Ala Val Ala Glu
                20                  25

<210> SEQ ID NO 103
<211> LENGTH: 29
<212> TYPE: PRT
<213> ORGANISM: Homo sapiens

<400> SEQUENCE: 103

Glu Arg Glu Glu Gly Gln Ile Gln Ile Met Glu Pro Val Gln Val Thr
 1               5                  10                  15

Val Ala Ser Ala Val Ala Glu Ser Pro Gly Thr Asn Ser
                20                  25

<210> SEQ ID NO 104
<211> LENGTH: 28
<212> TYPE: PRT
<213> ORGANISM: Homo sapiens

<400> SEQUENCE: 104

Ser Glu Ala Ser His Thr Pro His Leu Pro Ser Glu Leu Pro Pro Arg
 1               5                  10                  15

Tyr Glu Glu Lys Glu Asn Ala Ala Ala Thr Phe Leu
                20                  25

<210> SEQ ID NO 105
<211> LENGTH: 116
<212> TYPE: PRT
<213> ORGANISM: Homo sapiens
<220> FEATURE:
<221> NAME/KEY: SITE
<222> LOCATION: (79)
<223> OTHER INFORMATION: Xaa equals any of the naturally occurring
      L-amino acids
<220> FEATURE:
<221> NAME/KEY: SITE
<222> LOCATION: (91)
<223> OTHER INFORMATION: Xaa equals any of the naturally occurring
      L-amino acids
<220> FEATURE:
<221> NAME/KEY: SITE
<222> LOCATION: (95)
<223> OTHER INFORMATION: Xaa equals any of the naturally occurring
      L-amino acids

<400> SEQUENCE: 105

Gly Ser Arg Ser Arg Thr Phe Leu Ser Ser Arg Pro Arg Val Arg
 1               5                  10                  15

Pro Arg Val Ala Arg Arg Gln Lys Gly Thr Ala Ala Arg Arg
                20                  25                  30

Gln Lys Gly Thr Ala Ala Arg Arg Gln Lys Gly Thr Ala Ala Arg
            35                  40                  45

Arg Arg Gln Lys Gly Thr Ala Ala Arg Arg Gln Lys Gly Thr Ala
        50                  55                  60

Leu Ser Pro Leu Arg Pro Ser Ser Ser Leu Pro Gln Gly Xaa Glu
 65                      70                  75              80

Ala Lys Pro Leu His Leu Phe Arg Ala Gly Xaa Arg Pro Gly Xaa Gly
                85                  90                  95

Asn Leu Val Ser Glu Ser Ala Gly Arg Ser Ala Gly Gln Gly Ser Pro
                100                 105                 110

Gly Pro Asp Ala
            115

```
<210> SEQ ID NO 106
<211> LENGTH: 29
<212> TYPE: PRT
<213> ORGANISM: Homo sapiens

<400> SEQUENCE: 106

Arg Gln Lys Gly Thr Ala Ala Arg Arg Gln Lys Gly Thr Ala Ala
 1               5                  10                  15

Arg Arg Arg Gln Lys Gly Thr Ala Ala Arg Arg Arg Gln
                20                  25

<210> SEQ ID NO 107
<211> LENGTH: 25
<212> TYPE: PRT
<213> ORGANISM: Homo sapiens
<220> FEATURE:
<221> NAME/KEY: SITE
<222> LOCATION: (11)
<223> OTHER INFORMATION: Xaa equals any of the naturally occurring
      L-amino acids
<220> FEATURE:
<221> NAME/KEY: SITE
<222> LOCATION: (15)
<223> OTHER INFORMATION: Xaa equals any of the naturally occurring
      L-amino acids

<400> SEQUENCE: 107

Ala Lys Pro Leu His Leu Phe Arg Ala Gly Xaa Arg Pro Gly Xaa Gly
 1               5                  10                  15

Asn Leu Val Ser Glu Ser Ala Gly Arg
                20                  25

<210> SEQ ID NO 108
<211> LENGTH: 242
<212> TYPE: PRT
<213> ORGANISM: Homo sapiens

<400> SEQUENCE: 108

Thr Lys Phe Val Gln Cys Pro Asp Gly Glu Leu Gln Lys Arg Lys Glu
 1               5                  10                  15

Val Val His Thr Val Ser Leu His Glu Ile Asp Val Ile Asn Ser Arg
                20                  25                  30

Thr Gln Gly Phe Leu Ala Leu Phe Ser Gly Asp Thr Gly Glu Ile Lys
            35                  40                  45

Ser Glu Val Arg Glu Gln Ile Asn Ala Lys Val Ala Glu Trp Arg Glu
         50                  55                  60

Glu Gly Lys Ala Glu Ile Ile Pro Gly Val Leu Phe Ile Asp Glu Val
 65                  70                  75                  80

His Met Leu Asp Ile Glu Ser Phe Ser Phe Leu Asn Arg Ala Leu Glu
                 85                  90                  95

Ser Asp Met Ala Pro Val Leu Ile Met Ala Thr Asn Arg Gly Ile Thr
            100                 105                 110

Arg Ile Arg Gly Thr Ser Tyr Gln Ser Pro His Gly Ile Pro Ile Asp
        115                 120                 125

Leu Leu Asp Arg Leu Leu Ile Val Ser Thr Thr Pro Tyr Ser Glu Lys
130                 135                 140

Asp Thr Lys Gln Ile Leu Arg Ile Arg Cys Glu Glu Asp Val Glu
145                 150                 155                 160

Met Ser Glu Asp Ala Tyr Thr Val Leu Thr Arg Ile Gly Leu Glu Thr
                165                 170                 175

Ser Leu Arg Tyr Ala Ile Gln Leu Ile Thr Ala Ala Ser Leu Val Cys
```

-continued

```
              180               185               190
Arg Lys Arg Lys Gly Thr Glu Val Gln Val Asp Asp Ile Lys Arg Val
              195               200               205

Tyr Ser Leu Phe Leu Asp Glu Ser Arg Ser Thr Gln Tyr Met Lys Glu
              210               215               220

Tyr Gln Asp Ala Phe Leu Phe Asn Glu Leu Lys Gly Glu Thr Met Asp
225               230               235               240

Thr Ser
```

<210> SEQ ID NO 109
<211> LENGTH: 24
<212> TYPE: PRT
<213> ORGANISM: Homo sapiens

<400> SEQUENCE: 109

```
Val Val His Thr Val Ser Leu His Glu Ile Asp Val Ile Asn Ser Arg
  1               5                  10                  15

Thr Gln Gly Phe Leu Ala Leu Phe
                20
```

<210> SEQ ID NO 110
<211> LENGTH: 15
<212> TYPE: PRT
<213> ORGANISM: Homo sapiens

<400> SEQUENCE: 110

```
Pro Gly Val Leu Phe Ile Asp Glu Val His Met Leu Asp Ile Glu
  1               5                  10                  15
```

<210> SEQ ID NO 111
<211> LENGTH: 7
<212> TYPE: PRT
<213> ORGANISM: Homo sapiens

<400> SEQUENCE: 111

```
Glu Glu Gly Lys Ala Glu Ile
  1               5
```

<210> SEQ ID NO 112
<211> LENGTH: 9
<212> TYPE: PRT
<213> ORGANISM: Homo sapiens

<400> SEQUENCE: 112

```
Leu Ser Gln Asp Leu Lys Gly Ala Arg
  1               5
```

<210> SEQ ID NO 113
<211> LENGTH: 66
<212> TYPE: PRT
<213> ORGANISM: Homo sapiens

<400> SEQUENCE: 113

```
Leu Ile Thr His Gly Cys Leu Ser Tyr Tyr Leu Leu Ser Leu Lys Leu
  1               5                  10                  15

Ser Ser Leu Leu Phe Phe Phe Phe Leu Glu Leu Leu Arg Ile Phe
                20                  25                  30

Pro Val Trp Asp Pro Cys Thr Trp Phe Gly Phe Ser Leu Pro Cys Asp
              35                  40                  45

Asn Tyr Asn Pro Asp Ala Ser Ser Phe Cys Leu Asn Tyr Gly Ser Ala
50                  55                  60
```

Leu Pro
65

<210> SEQ ID NO 114
<211> LENGTH: 82
<212> TYPE: PRT
<213> ORGANISM: Homo sapiens

<400> SEQUENCE: 114

Ile Val Leu Leu Phe Phe Phe Trp Met Lys Thr Pro Ala Phe Pro Asp
1               5                   10                  15

Ser Pro Pro Ser Ser Val Leu Gln Phe Ser Glu Lys Ser Trp Asp Met
            20                  25                  30

Trp Glu Gly Ala Trp Glu Leu Gly Ser Leu Arg Leu Pro Gly Arg Gln
        35                  40                  45

Phe Arg Leu Cys Arg Lys Glu Gln Ser Pro Trp Glu Ala Leu Gly Glu
    50                  55                  60

Gly Gly Ala Ala Ala Gln His Ala Trp Tyr Cys Gln Pro Arg Gly Ala
65                  70                  75                  80

Cys Val

<210> SEQ ID NO 115
<211> LENGTH: 44
<212> TYPE: PRT
<213> ORGANISM: Homo sapiens

<400> SEQUENCE: 115

Met Leu Ile His Thr Val Ile Lys Leu Leu Asp Ser Ile Ser Ser Asn
1               5                   10                  15

Ser Phe Thr Thr Cys Val Tyr Leu Ile Leu Phe Ser Ile Phe Leu Leu
            20                  25                  30

Phe His Ser Thr Ile Cys Ser Glu Ile Glu Ser Cys
        35                  40

<210> SEQ ID NO 116
<211> LENGTH: 15
<212> TYPE: PRT
<213> ORGANISM: Homo sapiens

<400> SEQUENCE: 116

Lys Ile Asn Asn Cys Phe Phe Lys Pro His Lys Lys Cys Ile Asn
1               5                   10                  15

<210> SEQ ID NO 117
<211> LENGTH: 10
<212> TYPE: PRT
<213> ORGANISM: Homo sapiens

<400> SEQUENCE: 117

Ile Arg His Glu Asp Ala Ser Ala Val Thr
1               5                   10

<210> SEQ ID NO 118
<211> LENGTH: 30
<212> TYPE: PRT
<213> ORGANISM: Homo sapiens

<400> SEQUENCE: 118

Ser Arg Pro Val Met Ser Gly Pro Gly Leu Tyr Asp Pro Thr Thr Ile
1               5                   10                  15

Met Asn Ala Asp Ile Leu Ala Tyr Cys Gln Lys Glu Gly Trp
            20                  25                  30

<210> SEQ ID NO 119
<211> LENGTH: 30
<212> TYPE: PRT
<213> ORGANISM: Homo sapiens

<400> SEQUENCE: 119

Phe Phe Cys Val Met Phe Leu Cys Ala Ala Glu Trp Leu Thr Leu Gly
 1               5                  10                  15

Leu Asn Met Pro Leu Leu Ala Tyr His Ile Trp Arg Tyr Met
            20                  25                  30

<210> SEQ ID NO 120
<211> LENGTH: 35
<212> TYPE: PRT
<213> ORGANISM: Homo sapiens

<400> SEQUENCE: 120

Trp His Ile Ile Ala Phe Asp Glu Leu Lys Thr Asp Tyr Lys Asn Pro
 1               5                  10                  15

Ile Asp Gln Cys Asn Thr Leu Asn Pro Leu Val Leu Pro Glu Tyr Leu
            20                  25                  30

Ile His Ala
        35

<210> SEQ ID NO 121
<211> LENGTH: 20
<212> TYPE: PRT
<213> ORGANISM: Homo sapiens
<220> FEATURE:
<221> NAME/KEY: SITE
<222> LOCATION: (12)
<223> OTHER INFORMATION: Xaa equals any of the naturally occurring
      L-amino acids

<400> SEQUENCE: 121

Gly Ser Pro Gly Cys Arg Asn Ser Ala Thr Ala Xaa Ala Pro Arg Ser
 1               5                  10                  15

Ser Ser Pro Ala
        20

<210> SEQ ID NO 122
<211> LENGTH: 11
<212> TYPE: PRT
<213> ORGANISM: Homo sapiens

<400> SEQUENCE: 122

Met Ala Phe Thr Phe Ala Ala Phe Cys Tyr Met
 1               5                  10

<210> SEQ ID NO 123
<211> LENGTH: 9
<212> TYPE: PRT
<213> ORGANISM: Homo sapiens

<400> SEQUENCE: 123

Gly Met Ile Tyr Val Leu Val Ser Ser
 1               5

<210> SEQ ID NO 124
<211> LENGTH: 34
<212> TYPE: PRT

<213> ORGANISM: Homo sapiens

<400> SEQUENCE: 124

```
Leu Pro Thr Ser Arg Gln Ser Cys Gln Ile Thr Tyr Met Ala Thr Ser
 1               5                  10                  15
Leu Pro Gln Leu Leu Gly Ser Ser Lys Leu Ser Phe Met Phe Asn Cys
            20                  25                  30
Phe Ser
```

<210> SEQ ID NO 125
<211> LENGTH: 41
<212> TYPE: PRT
<213> ORGANISM: Homo sapiens
<220> FEATURE:
<221> NAME/KEY: SITE
<222> LOCATION: (34)
<223> OTHER INFORMATION: Xaa equals any of the naturally occurring
      L-amino acids

<400> SEQUENCE: 125

```
Asn Ser Phe Phe Phe Pro Cys Cys Phe Arg Tyr Lys Leu Phe Gly Ser
 1               5                  10                  15
Thr Ser Ser Phe Cys Leu Ile Ser Gly Ser Ser Val Gln Trp Ser Asp
            20                  25                  30
Pro Xaa Pro Glu Cys Arg Gly Lys Ser
        35                  40
```

<210> SEQ ID NO 126
<211> LENGTH: 23
<212> TYPE: PRT
<213> ORGANISM: Homo sapiens

<400> SEQUENCE: 126

```
Val Trp Val Ser Gly Pro Trp Cys Thr Glu Phe Ile Cys Leu Ala Val
 1               5                  10                  15
Phe Thr Val Ile Leu Gln Ile
            20
```

<210> SEQ ID NO 127
<211> LENGTH: 79
<212> TYPE: PRT
<213> ORGANISM: Homo sapiens

<400> SEQUENCE: 127

```
Thr Gly Gly Thr Ala Phe Leu Leu Met Pro Asn Leu His Leu Leu
 1               5                  10                  15
Leu Ser Pro Arg Arg Tyr Pro Ser Val Cys Arg Val Ser Leu Gly Glu
            20                  25                  30
Trp Ala Met Val His Arg Val Tyr Leu Leu Gly Cys Phe His Cys Tyr
        35                  40                  45
Ser Pro Asn Asn Asp Ser Val Ala Cys Leu His Ile Pro Ser Cys Cys
    50                  55                  60
Gly Ile Pro Pro Val Leu His Ser Thr Ala Glu Leu Cys His Ser
65                  70                  75
```

<210> SEQ ID NO 128
<211> LENGTH: 33
<212> TYPE: PRT
<213> ORGANISM: Homo sapiens

<400> SEQUENCE: 128

```
                                  -continued

Arg Tyr Pro Ser Val Cys Arg Val Ser Leu Gly Glu Trp Ala Met Val
 1               5                  10                  15

His Arg Val Tyr Leu Leu Gly Cys Phe His Cys Tyr Ser Pro Asn Asn
                 20                  25                  30

Asp
```

CORNICHON-LIKE PROTEIN

This application is a continuation-in-part of, and claims benefit under 35 U.S.C. §120 of copending U.S. patent application Ser. No: PCT/US98/17709 filed Aug. 27, 1998, which is hereby incorporated by reference, which claims benefit under 35 U.S.C. §119(e) based on U.S. Provisional Applications:

|    | Filing Date | Appln No. |
|----|-------------|-----------|
| 1. | 29-Aug-1997 | 60/056,270 |
| 2. | 29-Aug-1997 | 60/056,271 |
| 3. | 29-Aug-1997 | 60/056,247 |
| 4. | 29-Aug-1997 | 60/056,073 |

FIELD OF THE INVENTION

This invention relates to newly identified polynucleotides and the polypeptides encoded by these polynucleotides, uses of such polynucleotides and polypeptides, and their production.

BACKGROUND OF THE INVENTION

Unlike bacterium, which exist as a single compartment surrounded by a membrane, human cells and other eucaryotes are subdivided by membranes into many functionally distinct compartments. Each membrane-bounded compartment, or organelle, contains different proteins essential for the function of the organelle. The cell uses "sorting signals," which are amino acid motifs located within the protein, to target proteins to particular cellular organelles.

One type of sorting signal, called a signal sequence, a signal peptide, or a leader sequence, directs a class of proteins to an organelle called the endoplasmic reticulum (ER). The ER separates the membrane-bounded proteins from all other types of proteins. Once localized to the ER, both groups of proteins can be further directed to another organelle called the Golgi apparatus. Here, the Golgi distributes the proteins to vesicles, including secretory vesicles, the cell membrane, lysosomes, and the other organelles.

Proteins targeted to the ER by a signal sequence can be released into the extracellular space as a secreted protein. For example, vesicles containing secreted proteins can fuse with the cell membrane and release their contents into the extracellular space—a process called exocytosis. Exocytosis can occur constitutively or after receipt of a triggering signal. In the latter case, the proteins are stored in secretory vesicles (or secretory granules) until exocytosis is triggered. Similarly, proteins residing on the cell membrane can also be secreted into the extracellular space by proteolytic cleavage of a "linker" holding the protein to the membrane.

Despite the great progress made in recent years, only a small number of genes encoding human secreted proteins have been identified. These secreted proteins include the commercially valuable human insulin, interferon, Factor VIII, human growth hormone, tissue plasminogen activator, and erythropoeitin. Thus, in light of the pervasive role of secreted proteins in human physiology, a need exists for identifying and characterizing novel human secreted proteins and the genes that encode them. This knowledge will allow one to detect, to treat, and to prevent medical disorders by using secreted proteins or the genes that encode them.

SUMMARY OF THE INVENTION

The present invention relates to novel polynucleotides and the encoded polypeptides. Moreover, the present invention relates to vectors, host cells, antibodies, and recombinant methods for producing the polypeptides and polynucleotides. Also provided are diagnostic methods for detecting disorders related to the polypeptides, and therapeutic methods for treating such disorders. The invention further relates to screening methods for identifying binding partners of the polypeptides.

DETAILED DESCRIPTION

Definitions

The following definitions are provided to facilitate understanding of certain terms used throughout this specification.

In the present invention, "isolated" refers to material removed from its original environment (e.g., the natural environment if it is naturally occurring), and thus is altered "by the hand of man" from its natural state. For example, an isolated polynucleotide could be part of a vector or a composition of matter, or could be contained within a cell, and still be "isolated" because that vector, composition of matter, or particular cell is not the original environment of the polynucleotide.

In the present invention, a "secreted" protein refers to those proteins capable of being directed to the ER, secretory vesicles, or the extracellular space as a result of a signal sequence, as well as those proteins released into the extracellular space without necessarily containing a signal sequence. If the secreted protein is released into the extracellular space, the secreted protein can undergo extracellular processing to produce a "mature" protein. Release into the extracellular space can occur by many mechanisms, including exocytosis and proteolytic cleavage.

In specific embodiments, the polynucleotides of the invention are less than 300 kb, 200 kb, 100 kb, 50 kb, 15 kb, 10 kb, or 7.5 kb in length. In a further embodiment, polynucleotides of the invention comprise at least 15 contiguous nucleotides of the coding sequence, but do not comprise all or a portion of any intron. In another embodiment, the nucleic acid comprising the coding sequence does not contain coding sequences of a genomic flanking gene (i.e., 5' or 3' to the gene in the genome).

As used herein, a "polynucleotide" refers to a molecule having a nucleic acid sequence contained in SEQ ID NO:X or the cDNA contained within the clone deposited with the ATCC. For example, the polynucleotide can contain the nucleotide sequence of the full length cDNA sequence, including the 5' and 3' untranslated sequences, the coding region, with or without the signal sequence, the secreted protein coding region, as well as fragments, epitopes, domains, and variants of the nucleic acid sequence. Moreover, as used herein, a "polypeptide" refers to a molecule having the translated amino acid sequence generated from the polynucleotide as broadly defined.

In the present invention, the full length sequence identified as SEQ ID NO:X was often generated by overlapping sequences contained in multiple clones (contig analysis). A representative clone containing all or most of the sequence for SEQ ID NO:X was deposited with the American Type Culture Collection ("ATCC"). As shown in Table 1, each clone is identified by a cDNA Clone ID (Identifier) and the ATCC Deposit Number. The ATCC is located at 10801 University Boulevard, Manassas, Va. 20110-2209, USA. The ATCC deposit was made pursuant to the terms of the Budapest Treaty on the international recognition of the deposit of microorganisms for purposes of patent procedure.

A "polynucleotide" of the present invention also includes those polynucleotides capable of hybridizing, under stringent hybridization conditions, to sequences contained in SEQ ID NO:X, the complement thereof, or the cDNA within the clone deposited with the ATCC. "Stringent hybridization conditions" refers to an overnight incubation at 42° C. in a solution comprising 50% formamide, 5×SSC (750 mM NaCl, 75 mM sodium citrate), 50 mM sodium phosphate (pH 7.6), 5×Denhardt's solution, 10% dextran sulfate, and 20 μg/ml denatured, sheared salmon sperm DNA, followed by washing the filters in 0.1×SSC at about 65° C.

Also contemplated are nucleic acid molecules that hybridize to the polynucleotides of the present invention at lower stringency hybridization conditions. Changes in the stringency of hybridization and signal detection are primarily accomplished through the manipulation of formamide concentration (lower percentages of formamide result in lowered stringency); salt conditions, or temperature. For example, lower stringency conditions include an overnight incubation at 37° C. in a solution comprising 6×SSPE (20×SSPE=3M NaCl; 0.2M $NaH_2PO_4$; 0.02M EDTA, pH 7.4), 0.5% SDS, 30% formamide, 100 ug/ml salmon sperm blocking DNA; followed by washes at 50° C. with 1×SSPE, 0.1% SDS. In addition, to achieve even lower stringency, washes performed following stringent hybridization can be done at higher salt concentrations (e.g. 5×SSC).

Note that variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility.

Of course, a polynucleotide which hybridizes only to polyA+ sequences (such as any 3' terminal polyA+ tract of a cDNA shown in the sequence listing), or to a complementary stretch of T (or U) residues, would not be included in the definition of "polynucleotide," since such a polynucleotide would hybridize to any nucleic acid molecule containing a poly (A) stretch or the complement thereof (e.g., practically any double-stranded cDNA clone).

The polynucleotide of the present invention can be composed of any polyribonucleotide or polydeoxribonucleotide, which may be unmodified RNA or DNA or modified RNA or DNA. For example, polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, the polynucleotide can be composed of triple-stranded regions comprising RNA or DNA or both RNA and DNA. A polynucleotide may also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

The polypeptide of the present invention can be composed of amino acids joined to each other by peptide bonds or modified peptide bonds, i.e., peptide isosteres, and may contain amino acids other than the 20 gene-encoded amino acids. The polypeptides may be modified by either natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched, for example, as a result of ubiquitination, and they may be cyclic, with or without branching. Cyclic, branched, and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, PROTEINS—STRUCTURE AND MOLECULAR PROPERTIES, 2nd Ed., T. E. Creighton, W. H. Freeman and Company, New York (1993); POSTTRANSLATIONAL COVALENT MODIFICATION OF PROTEINS, B. C. Johnson, Ed., Academic Press, New York, pgs. 1–12 (1983); Seifter et al., Meth Enzymol 182:626–646 (1990); Rattan et al., Ann NY Acad Sci 663:48–62 (1992).)

"SEQ ID NO:X" refers to a polynucleotide sequence while "SEQ ID NO:Y" refers to a polypeptide sequence, both sequences identified by an integer specified in Table 1.

"A polypeptide having biological activity" refers to polypeptides exhibiting activity similar, but not necessarily identical to, an activity of a polypeptide of the present invention, including mature forms, as measured in a particular biological assay, with or without dose dependency. In the case where dose dependency does exist, it need not be identical to that of the polypeptide, but rather substantially similar to the dose-dependence in a given activity as compared to the polypeptide of the present invention (i.e., the candidate polypeptide will exhibit greater activity or not more than about 25-fold less and, preferably, not more than about tenfold less activity, and most preferably, not more than about three-fold less activity relative to the polypeptide of the present invention.)

Polynucleotides and Polypeptides of the Invention
Features of Protein Encoded by Gene No: 1

In specific embodiments, polypeptides of the invention comprise the following amino acid sequence: HVNGNKXMDHHXQVAAALELVDPPGCRNSARGN (SEQ ID NO:69). Polynucleotides encoding these polypeptides are also encompassed by the invention. The gene encoding the disclosed cDNA is believed to reside on chromosome 8. Accordingly, polynucleotides related to this invention are useful as a marker in linkage analysis for chromosome 8.

This gene is expressed primarily in anergic T-cells.

Therefore, polynucleotides and polypeptides of the invention are useful as reagents for differential identification of the tissue(s) or cell type(s) present in a biological sample and for diagnosis of diseases and conditions which include, but are not limited to, immune or hematopoietic disorders, particularly inflammatory disorders. Similarly, polypeptides and antibodies directed to these polypeptides are useful in providing immunological probes for differential identification of the tissue(s) or cell type(s). For a number of disorders of the above tissues or cells, particularly of the immune or hematopoietic system, expression of this gene at significantly higher or lower levels may be routinely detected in certain tissues or cells (e.g., immune, hematopoietic, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in anergic T-cells indicates that polynucleotides and polypeptides corresponding to this gene are useful for the diagnosis and treatment of a variety of immune system disorders. Expression of this gene product indicates a role in the regulation of the proliferation; survival; differentiation; and/or activation of potentially all hematopoietic cell lineages, including blood stem cells. This gene product may be involved in the regulation of cytokine production, antigen presentation, or other processes that may also suggest a usefulness in the treatment of cancer (e.g., by boosting immune responses).

Moreover, since the gene is expressed in cells of lymphoid origin, the natural gene product may be involved in immune functions. Therefore it may be also used as an agent for immunological disorders including arthritis, asthma, immune deficiency diseases such as AIDS, leukemia, rheumatoid arthritis, inflammatory bowel disease, sepsis, acne, and psoriasis. and tissues. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:11 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 852 of SEQ ID NO:11, b is an integer of 15 to 866, where both a and b correspond to the positions of nucleotide residues shown in SEQ ID NO:11, and where b is greater than or equal to a+14.

Features of Protein Encoded by Gene No: 2

In specific embodiments, polypeptides of the invention comprise the following amino acid sequence: EISNYV (SEQ ID NO:70). Polynucleotides encoding these polypeptides are also encompassed by the invention.

This gene is expressed primarily in anergic T-cells.

Therefore, polynucleotides and polypeptides of the invention are useful as reagents for differential identification of the tissue(s) or cell type(s) present in a biological sample and for diagnosis of diseases and conditions which include, but are not limited to, immune or hematopoietic diseases and disorders, particularly inflammatory conditions. Similarly, polypeptides and antibodies directed to these polypeptides are useful in providing immunological probes for differential identification of the tissue(s) or cell type(s). For a number of disorders of the above tissues or cells, particularly of the immune or hematopoietic system, expression of this gene at significantly higher or lower levels may be routinely detected in certain tissues or cell types (e.g., immune, hematopoietic, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 41 as residues: Arg-26 to Gln-32.

The tissue distribution in anergic T-cells indicates that polynucleotides and polypeptides corresponding to this gene are useful for the diagnosis and treatment of a variety of immune system disorders. Expression of this gene product indicates a role in the regulation of the proliferation; survival; differentiation; and/or activation of potentially all hematopoietic cell lineages, including blood stem cells. This gene product may be involved in the regulation of cytokine production, antigen presentation, or other processes that may also suggest a usefulness in the treatment of cancer (e.g., by boosting immune responses).

Moreover, since the gene is expressed in cells of lymphoid origin, the natural gene product may be involved in immune functions. Therefore it may be also used as an agent for immunological disorders including arthritis, asthma, immune deficiency diseases such as AIDS, leukemia, rheumatoid arthritis, inflammatory bowel disease, sepsis, acne, and psoriasis. and tissues. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:12 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 637 of SEQ ID NO:12, b is an integer of 15 to 651, where both a and b correspond to the positions of nucleotide residues shown in SEQ ID NO:12, and where b is greater than or equal to a+14.

Features of Protein Encoded by Gene No: 3

In specific embodiments, polypeptides of the invention comprise the following amino acid sequence: IRHESKSM-FVYSPNLSNAKGWHRGQCQAVPGYYLPLRK NS (SEQ ID NO:71). Polynucleotides encoding these polypeptides are also encompassed by the invention. The gene encoding the disclosed cDNA is believed to reside on chromosome 13. Accordingly, polynucleotides related to this invention are useful as a marker in linkage analysis for chromosome 13.

This gene is expressed primarily in spinal cord.

Therefore, polynucleotides and polypeptides of the invention are useful as reagents for differential identification of the tissue(s) or cell type(s) present in a biological sample and for diagnosis of diseases and conditions which include, but are not limited to, neural or central nervous system diseases and disorders, particularly neurodegenerative conditions. Similarly, polypeptides and antibodies directed to these polypeptides are useful in providing immunological probes for differential identification of the tissue(s) or cell type(s). For a number of disorders of the above tissues or cells, particularly of the neural system, expression of this gene at significantly higher or lower levels may be routinely detected in certain tissues or cell types (e.g., neural, spinal cord, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 42 as residues: Lys-25 to Ser-33.

The tissue distribution in spinal cord indicates the protein product of this gene is useful for the detection, treatment, and/or prevention of neurodegenerative disease states, behavioral disorders, or inflammatory conditions which include, but are not limited to Alzheimer's Disease, Parkinson's Disease, Huntington's Disease, Tourette Syndrome, meningitis, encephalitis, demyelinating diseases, peripheral neuropathies, neoplasia, trauma, congenital malformations, spinal cord injuries, ischemia and infarction, aneurysms, hemorrhages, schizophrenia, mania, dementia, paranoia, obsessive compulsive disorder, depression, panic disorder, learning disabilities, ALS, psychoses, autism, and altered behaviors, including disorders in feeding, sleep patterns, balance, and perception.

In addition, elevated expression of this gene product in regions of the brain indicates it plays a role in normal neural function. Potentially, this gene product is involved in synapse formation, neurotransmission, learning, cognition, homeostasis, or neuronal differentiation or survival. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:13 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1322 of SEQ ID NO:13, b is an integer of 15 to 1336, where both a and b correspond to the positions of nucleotide residues shown in SEQ ID NO:13, and where b is greater than or equal to a+14.
Features of Protein Encoded by Gene No: 4

This gene is expressed primarily in fibrosarcoma.

Therefore, polynucleotides and polypeptides of the invention are useful as reagents for differential identification of the tissue(s) or cell type(s) present in a biological sample and for diagnosis of diseases and conditions which include, but are not limited to, musculoskeletal disorders, particularly proliferative disorders such as fibrosarcoma. Similarly, polypeptides and antibodies directed to these polypeptides are useful in providing immunological probes for differential identification of the tissue(s) or cell type(s). For a number of disorders of the above tissues or cells, particularly of the musculoskeletal system, expression of this gene at significantly higher or lower levels may be routinely detected in certain tissues or cell types (e.g., musculoskeletal, proliferative, fibroids, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in fibrosarcoma indicates that polynucleotides and polypeptides corresponding to this gene are useful for the detection, treatment, and/or prevention of various muscle disorders, such as muscular dystrophy, cardiomyopathy, fibroids, myomas, and rhabdomyosarcomas. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:14 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 571 of SEQ ID NO:14, b is an integer of 15 to 585, where both a and b correspond to the positions of nucleotide residues shown in SEQ ID NO:14, and where b is greater than or equal to a+14.
Features of Protein Encoded by Gene No: 5

In specific embodiments, polypeptides of the invention comprise the following amino acid sequence: EKGEGRTPSFIPASDPKGILGSLVTMDTT (SEQ ID NO:72). Polynucleotides encoding these polypeptides are also encompassed by the invention. The gene encoding the disclosed cDNA is believed to reside on chromosome 1. Accordingly, polynucleotides related to this invention are useful as a marker in linkage analysis for chromosome 1.

This gene is expressed primarily in fast growing tissues such as human whole embryo, fetal brain, and cancer tissues.

Therefore, polynucleotides and polypeptides of the invention are useful as reagents for differential identification of the tissue(s) or cell type(s) present in a biological sample and for diagnosis of diseases and conditions which include, but are not limited to, developmental or proliferative disorders, such as growth deficiencies or tumorgenesis. Similarly, polypeptides and antibodies directed to these polypeptides are useful in providing immunological probes for differential identification of the tissue(s) or cell type(s). For a number of disorders of the above tissues or cells, particularly of the fast growing tissues such as fetal tissues and cancer tissues, expression of this gene at significantly higher or lower levels may be routinely detected in certain tissues or cell types (e.g., proliferative, developmental, and cancerous and wounded tissues) or bodily fluids (e.g., amniotic fluid, lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution within fetal tissue and other cellular sources marked by proliferating cells indicates this protein may play a role in the regulation of cellular division, and may show utility in the diagnosis and treatment of cancer and other proliferative disorders. Similarly, developmental tissues rely on decisions involving cell differentiation and/or apoptosis in pattern formation. Dysregulation of apoptosis can result in inappropriate suppression of cell death, as occurs in the development of some cancers, or in failure to control the extent of cell death, as is believed to occur in acquired immunodeficiency and certain neurodegenerative disorders, such as spinal muscular atrophy (SMA). Therefore, the polynucleotides and polypeptides of the present invention are useful in treating, detecting, and/or preventing said disorders and conditions, in addition to other types of degenerative conditions. Thus this protein may modulate apoptosis or tissue differentiation and is useful in the detection, treatment, and/or prevention of degenerative or proliferative conditions and diseases.

Alternatively, expression within human fetal brain indicates that polynucleotides and polypeptides corresponding to this gene are useful for the detection/treatment of neurodegenerative disease states and behavioural disorders such as Alzheimers Disease, Parkinsons Disease, Huntingtons Disease, Tourette Syndrome, schizophrenia, mania, dementia, paranoia, obsessive compulsive disorder, panic disorder, learning disabilities, ALS, psychoses , autism, and altered bahaviors, including disorders in feeding, sleep patterns, balance, and perception. In addition, the gene or gene product may also play a role in the treatment and/or detection of developmental disorders associated with the developing embryo, sexually-linked disorders, or disorders of the cardiovascular system. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:15 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1130 of SEQ ID NO:15, b is an integer of 15 to 1144, where both a and b correspond to the positions of nucleotide residues shown in SEQ ID NO:15, and where b is greater than or equal to a+14.

Features of Protein Encoded by Gene No: 6

In specific embodiments, polypeptides of the invention comprise the following amino acid sequence: KLVSKGKVSE (SEQ ID NO:73). Polynucleotides encoding these polypeptides are also encompassed by the invention.

This gene is expressed primarily in stromal cells.

Therefore, polynucleotides and polypeptides of the invention are useful as reagents for differential identification of the tissue(s) or cell type(s) present in a biological sample and for diagnosis of diseases and conditions which include, but are not limited to, immune or hematopoietic diseases and/or disorders, particularly defects of stromal cell development. Similarly, polypeptides and antibodies directed to these polypeptides are useful in providing immunological probes for differential identification of the tissue(s) or cell type(s). For a number of disorders of the above tissues or cells, particularly of stromal cells, expression of this gene at significantly higher or lower levels may be routinely detected in certain tissues or cell types (e.g., immune, hematopoietic, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in stromal cells indicates that polynucleotides and polypeptides corresponding to this gene are useful for the diagnosis and treatment of a variety of immune system disorders. Expression of this gene product indicates a role in the regulation of the proliferation; survival; differentiation; and/or activation of potentially all hematopoietic cell lineages, including blood stem cells. This gene product may be involved in the regulation of cytokine production, antigen presentation, or other processes that may also suggest a usefulness in the treatment of cancer (e.g., by boosting immune responses).

Moreover, since the gene is expressed in cells of lymphoid origin, the natural gene product may be involved in immune functions. Therefore it may be also used as an agent for immunological disorders including arthritis, asthma, immune deficiency diseases such as AIDS, leukemia, rheumatoid arthritis, inflammatory bowel disease, sepsis, acne, and psoriasis. and tissues. In addition, this gene product may have commercial utility in the expansion of stem cells and committed progenitors of various blood lineages, and in the differentiation and/or proliferation of various cell types. The uses include bone marrow cell ex- vivo culture, bone marrow transplantation, bone marrow reconstitution, radiotherapy or chemotherapy of neoplasia. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:16 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1023 of SEQ ID NO:16, b is an integer of 15 to 1037, where both a and b correspond to the positions of nucleotide residues shown in SEQ ID NO:16, and where b is greater than or equal to a+14.

Features of Protein Encoded by Gene No: 7

In specific embodiments, polypeptides of the invention comprise the following amino acid sequence: PLGKM-RQLKGKPKKETSKDKKERKQA (SEQ ID NO:74). Polynucleotides encoding these polypeptides are also encompassed by the invention.

This gene is expressed primarily in in cancer tissues, as well as, thyroid, and to a lesser extent in prostate cancer, testes, and macrophage.

Therefore, polynucleotides and polypeptides of the invention are useful as reagents for differential identification of the tissue(s) or cell type(s) present in a biological sample and for diagnosis of diseases and conditions which include, but are not limited to, reproductive, endocrine, or immune disorders, particularly tumorgenesis, immuneodeficiencies, bacterial infections, or inflammatory disorders. Similarly, polypeptides and antibodies directed to these polypeptides are useful in providing immunological probes for differential identification of the tissue(s) or cell type(s). For a number of disorders of the above tissues or cells, particularly of the cancers and thyroid, expression of this gene at significantly higher or lower levels may be routinely detected in certain tissues or cell types (e.g., reproductive, endocrine, immune, and cancerous and wounded tissues) or bodily fluids (e.g., lymph, seminal fluid, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 46 as residues: Met-1 to Gln-7.

The tissue distribution in cancer tissues indicates that polynucleotides and polypeptides corresponding to this gene are useful for the diagnosis and treatment of cancer and other proliferative disorders. Expression within tumor tissue and other cellular sources marked by proliferating cells indicates this protein may play a role in the regulation of cellular division, and may show utility in the diagnosis and treatment of cancer and other proliferative disorders. Similarly, developmental tissues rely on decisions involving cell differentiation and/or apoptosis in pattern formation. Dysregulation of apoptosis can result in inappropriate suppression of cell death, as occurs in the development of some cancers, or in failure to control the extent of cell death, as is believed to occur in acquired immunodeficiency and certain neurodegenerative disorders, such as spinal muscular atrophy (SMA). Therefore, the polynucleotides and polypeptides of the present invention are useful in treating, detecting, and/or preventing said disorders and conditions, in addition to other types of degenerative conditions. Thus this protein may modulate apoptosis or tissue differentiation and is useful in the detection, treatment, and/or prevention of degenerative or proliferative conditions and diseases.

Additionally, the expression in hematopoietic cells and tissues indicates that this protein may play a role in the proliferation, differentiation, and/or survival of hematopoietic cell lineages. In such an event, this gene may be useful in the treatment of lymphoproliferative disorders, and in the maintenance and differentiation of various hematopoietic lineages from early hematopoietic stem and committed progenitor cells. Similarly, embryonic development also involves decisions involving cell differentiation and/or apoptosis in pattern formation. Thus this protein may also be involved in apoptosis or tissue differentiation and could again be useful in cancer therapy.

Alternatively, the tissue distribution within various endocrine tissues indicates that polynucleotides and polypeptides corresponding to this gene are useful for the detection, treatment, and/or prevention of various endocrine disorders and cancers, particularly Addison's disease, Cushing's Syndrome, and disorders and/or cancers of the pancreas (e.g., diabetes mellitus), adrenal cortex, ovaries, pituitary (e.g., hyper-, hypopituitarism), thyroid (e.g., hyper-, hypothyroidism), parathyroid (e.g., hyper-, hypoparathyroidism), hypothallamus, and testes.

Moreover, the expression within various reproductive organs indicates that the protein product of this gene may show utility in the detection, treatment, and/or prevention of a variety of reproductive disorders, particularly male infertility. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:17 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 911 of SEQ ID NO:17, b is an integer of 15 to 925, where both a and b correspond to the positions of nucleotide residues shown in SEQ ID NO:17, and where b is greater than or equal to a+14.

Features of Protein Encoded by Gene No: 8

In specific embodiments, polypeptides of the invention comprise the following amino acid sequence: LLIAGTGSS-LYWAFTV (SEQ ID NO:75). Polynucleotides encoding these polypeptides are also encompassed by the invention. The gene encoding the disclosed cDNA is believed to reside on chromosome 12. Accordingly, polynucleotides related to this invention are useful as a marker in linkage analysis for chromosome 12.

This gene is expressed primarily in brain, reproductive organs, and immune cell/tissues, and to a lesser extent, in other tissues.

Therefore, polynucleotides and polypeptides of the invention are useful as reagents for differential identification of the tissue(s) or cell type(s) present in a biological sample and for diagnosis of diseases and conditions which include, but are not limited to, neuronal, reproductive, or immune and inflammatory diseases. Similarly, polypeptides and antibodies directed to these polypeptides are useful in providing immunological probes for differential identification of the tissue(s) or cell type(s). For a number of disorders of the above tissues or cells, particularly of the brain, reproductive organs, and immune cell/tissues, expression of this gene at significantly higher or lower levels may be routinely detected in certain tissues of cell types (e.g., neural, reproductive, immune, and cancerous and wounded tissues) or bodily fluids (e.g., lymph, seminal fluid, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in brain indicates that polynucleotides and polypeptides corresponding to this gene are useful for the detection/treatment of neurodegenerative disease states and behavioural disorders such as Alzheimers Disease, Parkinsons Disease, Huntingtons Disease, Tourette Syndrome, schizophrenia, mania, dementia, paranoia, obsessive compulsive disorder, panic disorder, learning disabilities, ALS, psychoses, autism, and altered bahaviors, including disorders in feeding, sleep patterns, balance, and perception. In addition, the gene or gene product may also play a role in the treatment and/or detection of developmental disorders associated with the developing embryo, sexually-linked disorders, or disorders of the cardiovascular system.

Alternatively, the secreted protein can also be used to determine biological activity, to raise antibodies, as tissue markers, to isolate cognate ligands or receptors, to identify agents that modulate their interactions and as nutritional supplements. It may also have a very wide range of biological acitivities. Typical of these are cytokine, cell proliferation/differentiation modulating activity or induction of other cytokines; immunostimulating/immunosuppressant activities (e.g., for treating human immunodeficiency virus infection, cancer, autoimmune diseases and allergy); regulation of hematopoiesis (e.g., for treating anaemia or as adjunct to chemotherapy); stimulation or growth of bone, cartilage, tendons, ligaments and/or nerves (e.g., for treating wounds, stimulation of follicle stimulating hormone (for control of fertility); chemotactic and chemokinetic activities (e.g., for treating infections, tumors); hemostatic or thrombolytic activity (e.g., for treating haemophilia, cardiac infarction etc.); anti-inflammatory activity (e.g., for treating septic shock, Crohn's disease); as antimicrobials; for treating psoriasis or other hyperproliferative diseases; for regulation of metabolism, and behaviour. Also contemplated is the use of the corresponding nucleic acid in gene therapy procedures. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:18 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1183 of SEQ ID NO:18, b is an integer of 15 to 1197, where both a and b correspond to the positions of nucleotide residues shown in SEQ ID NO:18, and where b is greater than or equal to a+14.
Features of Protein Encoded by Gene No: 9

This gene is expressed primarily in human tonsils and B-cells from lymphoma patients.

Therefore, polynucleotides and polypeptides of the invention are useful as reagents for differential identification of the tissue(s) or cell type(s) present in a biological sample and for diagnosis of diseases and conditions which include, but are not limited to, disorders related to immune or hematopoietic system, particularly B-cell lymphoma. Similarly, polypeptides and antibodies directed to these polypeptides are useful in providing immunological probes for differential identification of the tissue(s) or cell type(s). For a number of disorders of the above tissues or cells, particularly of the immune or hematopoietic system, expression of this gene at significantly higher or lower levels may be routinely detected in certain tissues or cell types (e.g., immune, hematopoietic, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 48 as residues: Ser-51 to Leu-60.

The tissue distribution in human tonsils and B-cells indicates that polynucleotides and polypeptides corresponding to this gene are useful for the diagnosis and treatment of a variety of immune system disorders. Expression of this gene product indicates a role in the regulation of the proliferation; survival; differentiation; and/or activation of potentially all hematopoietic cell lineages, including blood stem cells. This gene product may be involved in the regulation of cytokine production, antigen presentation, or other processes that may also suggest a usefulness in the treatment of cancer (e.g., by boosting immune responses).

Moreover, since the gene is expressed in cells of lymphoid origin, the natural gene product may be involved in immune functions. Therefore it may be also used as an agent for immunological disorders including arthritis, asthma, immune deficiency diseases such as AIDS, leukemia, rheumatoid arthritis, inflammatory bowel disease, sepsis, acne, and psoriasis. and tissues. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:19 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1092 of SEQ ID NO:19, b is an integer of 15 to 1106, where both a and b correspond to the positions of nucleotide residues shown in SEQ ID NO:19, and where b is greater than or equal to a+14.
Features of Protein Encoded by Gene No: 10

In specific embodiments, polypeptides of the invention comprise the following amino acid sequence: GKRVXLQVPVRNSRVDPRVRVWGVVLNVCGPGAWG LAEHSVK (SEQ ID NO:76), KQCPALNGSFKGVGTNCKM-M Y L E X W G L R D I L L P P R X F V A D G S X Q G G E R E A S V L F G K L A I K-TGKGVLFSRKLDLFRTLSAPNRCG QLPAAQRDE-GQRQDAAGKVNIFVSTVEDKKGMKSTVRTIMVGE (SEQ ID NO:77), RDILLPPRXFVADGSXQGGEREASV-LFG (SEQ ID NO:78), and/or LFRTLSAPN RCGQL-PAAQRDEGQRQDAAGKVNIVFVST (SEQ ID NO:79). Polynucleotides encoding these polypeptides are also encompassed by the invention. The gene encoding the disclosed cDNA is believed to reside on chromosome 9. Accordingly, polynucleotides related to this invention are useful as a marker in linkage analysis for chromosome 9.

This gene is expressed primarily in resting T-cells, fetal liver and spleen.

Therefore, polynucleotides and polypeptides of the invention are useful as reagents for differential identification of the tissue(s) or cell type(s) present in a biological sample and for diagnosis of diseases and conditions which include, but are not limited to, developmental disorders, or disorders related to immune system, particularly immunodeficiencies and inflammatory disorders. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., developmental, differentiating, immune, and cancerous and wounded tissues) or bodily fluids (e.g., amniotic fluid, lymph, bile, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in resting T-cells, fetal liver and spleen indicates that polynucleotides and polypeptides corresponding to this gene are useful for the diagnosis and treatment of a variety of immune or hematopoietic system disorders. Expression of this gene product indicates a role in the regulation of the proliferation; survival; differentiation;

and/or activation of potentially all hematopoietic cell lineages, including blood stem cells. This gene product may be involved in the regulation of cytokine production, antigen presentation, or other processes that may also suggest a usefulness in the treatment of cancer (e.g., by boosting immune responses).

Moreover, since the gene is expressed in cells of lymphoid origin, the natural gene product may be involved in immune functions. Therefore it may be also used as an agent for immunological disorders including arthritis, asthma, immune deficiency diseases such as AIDS, leukemia, rheumatoid arthritis, inflammatory bowel disease, sepsis, acne, and psoriasis. and tissues. In addition, this gene product may have commercial utility in the expansion of stem cells and committed progenitors of various blood lineages, and in the differentiation and/or proliferation of various cell types. The uses include bone marrow cell ex- vivo culture, bone marrow transplantation, bone marrow reconstitution, radiotherapy or chemotherapy of neoplasia.

Alternatively, expression within fetal tissue and other cellular sources marked by proliferating cells indicates that this protein may play a role in the regulation of cellular division, and may show utility in the diagnosis and treatment of cancer and other proliferative disorders. Similarly, embryonic development also involves decisions involving cell differentiation and/or apoptosis in pattern formation. Thus this protein may also be involved in apoptosis or tissue differentiation and could again be useful in cancer therapy. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:20 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 918 of SEQ ID NO:20, b is an integer of 15 to 932, where both a and b correspond to the positions of nucleotide residues shown in SEQ ID NO:20, and where b is greater than or equal to a+14.

Features of Protein Encoded by Gene No: 11

The translation product of this gene shares sequence homology with the human TATA-binding protein-associated factor dTAFII250 which is thought to be a general transcriptional activator of RNA polymerase II (See Genbank Accession no.R56493). In specific embodiments, polypeptides of the invention comprise the following amino acid sequence: GRPTRPKTPYDESKFYIGCDLCTNWYH-GECVGITEKEAKKMD VYICNDCKRAQEGSSEELYCI-CRTPYDESQFYIGCDRCQNWYHGRCVGILQS EAELIDEYVCPQCQSTEDAMTVLT-PLTEKDYEGLKRVLRSLQAHKMAWPFL EPVDP-NDAPDYYGVIKEPMDLATMEERVQR-RYYEKLTEFVADMTKIFDNCRYY NPSDSPFYQCAE VLESFFVQKLKGFKASRSHNNKLQSTAS (SEQ ID NO:80), TPYDESKFYIGCDLCTNWYH (SEQ ID NO:81), EAKKMDVYICNDCKRAQE GSSEEL (SEQ ID NO:82), RCQNWYHGRCVGILQSEAELIDEYV (SEQ ID NO:83), STEDAMTVLTPLTEKDYEGLKR (SEQ ID NO:84), DPNDAPDYYGVIKEPMD LATM (SEQ ID NO:85), VDPRVRKRLM (SEQ ID NO:87), and/or EKLTEF-VADMT KIFDNCRYYNP (SEQ ID NO:86). Polynucleotides encoding these polypeptides are also encompassed by the invention.

This gene is expressed primarily in Jurkat T-cells and human striatum.

Therefore, polynucleotides and polypeptides of the invention are useful as reagents for differential identification of the tissue(s) or cell type(s) present in a biological sample and for diagnosis of diseases and conditions which include, but are not limited to, disorders of immune or nervous system. Similarly, polypeptides and antibodies directed to these polypeptides are useful in providing immunological probes for differential identification of the tissue(s) or cell type(s). For a number of disorders of the above tissues or cells, particularly of the immune and nervous system, expression of this gene at significantly higher or lower levels may be routinely detected in certain tissues or cell types (e.g., immune, hematopoietic, neural, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 50 as residues: Gln-24 to Lys-30, Gly-41 to Ala-46, Ala-97 to Pro-103.

The tissue distribution in human striatum indicates that polynucleotides and polypeptides corresponding to this gene are useful for the detection/treatment of neurodegenerative disease states and behavioural disorders such as Alzheimers Disease, Parkinsons Disease, Huntingtons Disease, Tourette Syndrome, schizophrenia, mania, dementia, paranoia, obsessive compulsive disorder, panic disorder, learning disabilities, ALS, psychoses, autism, and altered bahaviors, including disorders in feeding, sleep patterns, balance, and preception. In addition, the gene or gene product may also play a role in the treatment and/or detection of developmental disorders associated with the developing embryo, sexually-linked disorders, or disorders of the cardiovascular system.

Alternatively, the tissue distribution indicates that polynucleotides and polypeptides corresponding to this gene are useful for the diagnosis and treatment of a variety of immune system disorders. Expression of this gene product indicates a role in the regulation of the proliferation; survival; differentiation; and/or activation of potentially all hematopoietic cell lineages, including blood stem cells. This gene product may be involved in the regulation of cytokine production, antigen presentation, or other processes that may also suggest a usefulness in the treatment of cancer (e.g., by boosting immune responses).

Moreover, since the gene is expressed in cells of lymphoid origin, the natural gene product may be involved in immune functions. Therefore it may be also used as an agent for immunological disorders including arthritis, asthma, immune deficiency diseases such as AIDS, leukemia, rheumatoid arthritis, inflammatory bowel disease, sepsis, acne, and psoriasis, and tissues. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:21 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1018 of SEQ ID NO:21, b is an integer of 15 to 1032, where both a and b correspond to the positions of nucleotide residues shown in SEQ ID NO:21, and where b is greater than or equal to a+14.

Features of Protein Encoded by Gene No: 12

The gene encoding the disclosed cDNA is believed to reside on chromosome 14. Accordingly, polynucleotides related to this invention are useful as a marker in linkage analysis for chromosome 14.

This gene is expressed primarily in human umbilical vein endothelial cells, breast, and to a lesser extent in placenta.

Therefore, polynucleotides and polypeptides of the invention are useful as reagents for differential identification of the tissue(s) or cell type(s) present in a biological sample and for diagnosis of diseases and conditions which include, but are not limited to, vascular or developmental disorders, particularly those involving the umbilical cord or placenta, in addition to reproductive disorders. Similarly, polypeptides and antibodies directed to these polypeptides are useful in providing immunological probes for differential identification of the tissue(s) or cell type(s). For a number of disorders of the above tissues or cells, particularly of the endothelial system, expression of this gene at significantly higher or lower levels may be routinely detected in certain tissues or cell types (e.g., endothelial, vascular, reproductive, breast, developmental, and cancerous and wounded tissues) or bodily fluids (e.g., amniotic fluid, breast milk, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in umbilical cord endothelial cells indicates that polynucleotides and polypeptides corresponding to this gene are useful for the diagnosis and treatment of cardiovascular disorders, such as atherosclerosis, vasculitis, microvascular disease, vascular leak syndrome, embolism, stroke, aneurysm, and other related blood vessel disorders. Moreover, expression within embryonic tissue and other cellular sources marked by proliferating cells indicates that this protein may play a role in the regulation of cellular division, and may show utility in the diagnosis and treatment of cancer and other proliferative disorders. Similarly, embryonic development also involves decisions involving cell differentiation and/or apoptosis in pattern formation. Dysregulation of apoptosis can result in inappropriate suppression of cell death, as occurs in the development of some cancers, or in failure to control the extent of cell death, as is believed to occur in acquired immunodeficiency and certain neurodegenerative disorders, such as spinal muscular atrophy (SMA).

Therefore, the polynucleotides and polypeptides of the present invention are useful in treating, detecting, and/or preventing said disorders and conditions, in addition to other types of degenerative conditions. Thus this protein may modulate apoptosis or tissue differentiation and is useful in the detection, treatment, and/or prevention of degenerative or proliferative conditions and diseases, in addition to cancer therapy. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:22 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 473 of SEQ ID NO:22, b is an integer of 15 to 487, where both a and b correspond to the positions of nucleotide residues shown in SEQ ID NO:22, and where b is greater than or equal to a+14.

Features of Protein Encoded by Gene No: 13

In specific embodiments, polypeptides of the invention comprise the following amino acid sequence: CRELSSS-CLSGRAPFKSSDCKERRSRCPRVPGFQNKNRV AIL-AELDKEKRKLL (SEQ ID NO:88). Polynucleotides encoding these polypeptides are also encompassed by the invention. The gene encoding the disclosed cDNA is believed to reside on chromosome 9. Accordingly, polynucleotides related to this invention are useful as a marker in linkage analysis for chromosome 9.

This gene is expressed primarily in human brain, fetal liver spleen, dendritic cells, and to a lesser extent in human B-cell lymphoma.

Therefore, polynucleotides and polypeptides of the invention are useful as reagents for differential identification of the tissue(s) or cell type(s) present in a biological sample and for diagnosis of diseases and conditions which include, but are not limited to, neural, developmental, immune, or hematopoietic disorders. Similarly, polypeptides and antibodies directed to these polypeptides are useful in providing immunological probes for differential identification of the tissue(s) or cell type(s). For a number of disorders of the above tissues or cells, particularly of the nervous or immune system, expression of this gene at significantly higher or lower levels may be routinely detected in certain tissues or cell types (e.g., neural, immune, hematopoietic, hepatic, developmental, reproductive, and cancerous and wounded tissues) or bodily fluids (e.g., lymph, amniotic fluid, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 52 as residues: Met-1 to Pro-10, Pro-19 to Gln-32, Gln-73 to Asp-80.

The tissue distribution in brain indicates that polynucleotides and polypeptides corresponding to this gene are useful for the detection/treatment of neurodegenerative disease states and behavioural disorders such as Alzheimers Disease, Parkinsons Disease, Huntingtons Disease, Tourette Syndrome, schizophrenia, mania, dementia, paranoia, obsessive compulsive disorder, panic disorder, learning disabilities, ALS, psychoses, autism, and altered behaviors, including disorders in feeding, sleep patterns, balance, and perception. In addition, the gene or gene product may also play a role in the treatment and/or detection of developmental disorders associated with the developing embryo, sexually-linked disorders, or disorders of the cardiovascular system.

Alternatively, the expression within various immune cells, in addition to fetal liver/spleen indicates that polynucleotides and polypeptides corresponding to this gene are useful for the diagnosis and treatment of a variety of immune system disorders. Expression of this gene product in B-cell lymphoma and dendritic cells indicates a role in the regulation of the proliferation; survival; differentiation; and/or activation of potentially all hematopoietic cell lineages, including blood stem cells. This gene product may be involved in the regulation of cytokine production, antigen presentation, or other processes that may also suggest a usefulness in the treatment of cancer (e.g., by boosting immune responses).

Moreover, since the gene is expressed in cells of lymphoid origin, the natural gene product may be involved in immune functions. Therefore it may be also used as an agent for immunological disorders including arthritis, asthma, immune deficiency diseases such as AIDS, leukemia, rheumatoid arthritis, inflammatory bowel disease, sepsis, acne, and psoriasis. and tissues. In addition, this gene product may have commercial utility in the expansion of stem cells and committed progenitors of various blood lineages, and in the differentiation and/or proliferation of various cell types.

Moreover, expression within fetal tissue and other cellular sources marked by proliferating cells indicates this protein may play a role in the regulation of cellular division, and may show utility in the diagnosis and treatment of cancer and other proliferative disorders. Similarly, developmental tissues rely on decisions involving cell differentiation and/or apoptosis in pattern formation. Dysregulation of apoptosis can result in inappropriate suppression of cell death, as occurs in the development of some cancers, or in failure to control the extent of cell death, as is believed to occur in acquired immunodeficiency and certain neurodegenerative disorders, such as spinal muscular atrophy (SMA). Therefore, the polynucleotides and polypeptides of the present invention are useful in treating, detecting, and/or preventing said disorders and conditions, in addition to other types of degenerative conditions. Thus this protein may modulate apoptosis or tissue differentiation and is useful in the detection, treatment, and/or prevention of degenerative or proliferative conditions and diseases. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:23 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1446 of SEQ ID NO:23, b is an integer of 15 to 1460, where both a and b correspond to the positions of nucleotide residues shown in SEQ ID NO:23, and where b is greater than or equal to a+14.

Features of Protein Encoded by Gene No: 14

In specific embodiments, polypeptides of the invention comprise the following amino acid sequence: IRHELKSWREENTSHPASGKGPLLD (SEQ ID NO:89), NLGGKKTHPTLPPGRGLSWTCLLQLLLSQMGTSRTDTSANSSSASLSSAPSCCVWESCSPSLGSRHANISPSQTAPWCSSGGAACAVVGLGGCDPGPLPGATSAP CKAAERSADGPRPSLHLWREPPVCPVPYLWVSVLDKRHAHQRPGHLGPWMWLQLGAGTAKRDRHWRLRAPDVWVPFSADHGALDCACGIVFLRGCPC (SEQ ID NO:90), TLPPGRGLSWTCLLQLLLSQM (SEQ ID NO:91), SANSSSASLSSAP SCCVWES (SEQ ID NO:92), PSQTAPWCSSGGAACAVVGLGGCDP (SEQ ID NO:93), APCKAAERSADGPRPSLHLWR (SEQ ID NO:94), QRPGHLGPWMW LQLGAGTAKRDRHWRLRA (SEQ ID NO:95), LRAPDVWVPFSADHGALDCAC GIVF (SEQ ID NO:96), APPRLPHGAQVAGLHVPWLGLGAVILARSRAQLQLRA RLQRGQQMDPDRAFICGESRQFAQCLIFGFLFLTSGMLISVLGIWVPGCGSNWAQEPLNETDTGDSEPRMCGFLSLQIMGPLIVLVGLCFFVVAHVKKRNTLN AGQDASEREEGQIQIMEPVQVTVASAVAESPGTNSLLPNENPPSYYSIFNYGTPTSEGAASERDCESIYTISGTNSSSEASHTPHLPSELPPRYEEKENAAATFLPLSSE PSPP (SEQ ID NO:97), AQVAGLHVPWLGLGAVILARSRA (SEQ ID NO:98), RGQQMDPDRAFICGESRQFA (SEQ ID NO:99), LISVLGIWVPGCGSNWAQEP LNETDT (SEQ ID NO:100), TGDSEPRMCGFLSLQIMGPLIVLVGL (SEQ ID NO:101), DASEREEGQIQIMEPVQVTVASAVAE (SEQ ID NO:102), EREEG QIQIMEPVQVTVASAVAESPGTNS (SEQ ID NO:103), and/or SEASHTPHLPS ELPPRYEEKENAAATFL (SEQ ID NO:104). Polynucleotides encoding these polypeptides are also encompassed by the invention.

This gene is expressed primarily in human adult pulmonary tissue, and to a lesser extent in human kidney and messangial cell.

Therefore, polynucleotides and polypeptides of the invention are useful as reagents for differential identification of the tissue(s) or cell type(s) present in a biological sample and for diagnosis of diseases and conditions which include, but are not limited to, cardiopulmonary disorders, particularly respiratory system disorders, such as emphysema, or kidney disorders. Similarly, polypeptides and antibodies directed to these polypeptides are useful in providing immunological probes for differential identification of the tissue(s) or cell type(s). For a number of disorders of the above tissues or cells, particularly of the respiratory or renal system, expression of this gene at significantly higher or lower levels may be routinely detected in certain tissues or cell types (e.g., pulmonary, cardiovascular, endothelil, kidney, and cancerous and wounded tissues) or bodily fluids (e.g., lymph, pulmonary surfactant, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 53 as residues: Glu-8 to Val-18.

The tissue distribution in pulmonary tissue indicates that polynucleotides and polypeptides corresponding to this gene are useful for the diagnosis and treatment of a variety of respiratory disorders, including emphysema, asthma, or bronchitis. Alternatively, expression in human kidney indicates that this gene or gene product could be used in the treatment and/or detection of kidney diseases including renal failure, nephritus, renal tubular acidosis, proteinuria, pyuria, edema, pyelonephritis, hydronephritis, nephrotic syndrome, crush syndrome, glomerulonephritis, hematuria, renal colic and kidney stones, in addition to Wilms Tumor Disease, and congenital kidney abnormalities such as horseshoe kidney, polycystic kidney, and Falconi's syndrome. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:24 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1084 of SEQ ID NO:24, b is an integer of 15 to 1098, where both a and b correspond to the positions of nucleotide residues shown in SEQ ID NO:24, and where b is greater than or equal to a+14.

Features of Protein Encoded by Gene No: 15

This gene is expressed primarily in human cerebellum.

Therefore, polynucleotides and polypeptides of the invention are useful as reagents for differential identification of the tissue(s) or cell type(s) present in a biological sample and for diagnosis of diseases and conditions which include, but are not limited to, neural or central nervous system disorders, particularly neurodegenerative disorders such as Alzheimers. Similarly, polypeptides and antibodies directed to these polypeptides are useful in providing immunological probes for differential identification of the tissue(s) or cell type(s). For a number of disorders of the above tissues or cells, particularly of the nervous system, expression of this gene at significantly higher or lower levels may be routinely detected in certain tissues or cell types (e.g., neural, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in human cerebrum indicates that polynucleotides and polypeptides corresponding to this gene are useful for the detection/treatment of neurodegenerative disease states and behavioural disorders such as Alzheimers Disease, Parkinsons Disease, Huntingtons Disease, Tourette Syndrome, schizophrenia, mania, dementia, paranoia, obsessive compulsive disorder, panic disorder, learning disabilities, ALS, psychoses, autism, and altered behaviors, including disorders in feeding, sleep patterns, balance, and perception. In addition, the gene or gene product may also play a role in the treatment and/or detection of developmental disorders associated with the developing embryo, sexually-linked disorders, or disorders of the cardiovascular system. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:25 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1001 of SEQ ID NO:25, b is an integer of 15 to 1015, where both a and b correspond to the positions of nucleotide residues shown in SEQ ID NO:25, and where b is greater than or equal to a+14.

Features of Protein Encoded by Gene No: 16

When tested against K562 cell lines, supernatants removed from cells containing this gene activated the ISRE (interferon-sensitive responsive element) promoter element. Thus, it is likely that this gene activates leukmia cells, and to a lesser extent, immune or hematopoietic cells, through the Jaks-STAT signal transduction pathway. ISRE is a promoter element found upstream in many genes which are involved in the Jaks-STAT pathway. The Jaks-STAT pathway is a large, signal transduction pathway involved in the differentiation and proliferation of cells. Therefore, activation of the Jaks-STATs pathway, reflected by the binding of the ISRE element, can be used to indicate proteins involved in the proliferation and differentiation of cells.

In specific embodiments, polypeptides of the invention comprise the following amino acid sequence; GSRSRT-FLSSSRPRVRPRVARRRQKGTAARRRQKGTAA RRRQKGTAARRRQKGTAARRRQKGTAL-SPLRPSSSSLPQGXEAKPLHLFRAG XRPGXGNLVS-ESAGRSAGQGSPGPDA (SEQ ID NO:105), RQKG-TAARRRQK GTAARRRQKGTAARRRQ (SEQ ID NO:106), and/or AKPLHLFRAGXRPGXG NLVSESAGR (SEQ ID NO:107). Polynucleotides encoding these polypeptides are also encompassed by the invention.

This gene is expressed primarily in human endothelial cells and human stromal endometrial fibroblasts.

Therefore, polynucleotides and polypeptides of the invention are useful as reagents for differential identification of the tissue(s) or cell type(s) present in a biological sample and for diagnosis of diseases and conditions which include, but are not limited to, integumentary or vascular diseases and/or disorders, particularly endothelial or fibroblast related disorders. Similarly, polypeptides and antibodies directed to these polypeptides are useful in providing immunological probes for differential identification of the tissue(s) or cell type(s). For a number of disorders of the above tissues or cells, particularly of the integumentary system, expression of this gene at significantly higher or lower levels may be routinely detected in certain tissues or cell types (e.g., integumentary, endothelial, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 55 as residues: Glu-35 to Gln-40.

The tissue distribution in endothelial tissues and fibroblasts, combined with the observed ISRE biological activity indicates that polynucleotides and polypeptides corresponding to this gene are useful for the treatment, diagnosis, and/or prevention of various skin disorders including congenital disorders (i.e. nevi, moles, freckles, Mongolian spots, hemangiomas, port-wine syndrome), integumentary tumors (i.e. keratoses, Bowen's disease, basal cell carcinoma, squamous cell carcinoma, malignant melanoma, Paget's disease, mycosis fungoides, and Kaposi's sarcoma), injuries and inflammation of the skin (i.e.wounds, rashes, prickly heat disorder, psoriasis, dermatitis), atherosclerosis, uticaria, eczema, photosensitivity, autoimmune disorders (i.e. lupus erythematosus, vitiligo, dermatomyositis, morphea, scleroderma, pemphigoid, and pemphigus), keloids, striae, erythema, petechiae, purpura, and xanthelasma.

Moreover, such disorders may predispose an individual (i.e. increased susceptibility) to viral and bacterial infections of the skin (i.e. cold sores, warts, chickenpox, molluscum contagiosum, herpes zoster, boils, cellulitis, erysipelas, impetigo, tinea, althletes foot, and ringworm). Moreover, the protein is useful in the detection, treatment, and/or prevention of a variety of vascular disorders and condtions, which include, but are not limited to miscrovascular disease, vascular leak syndrome, aneurysm, stroke, embolism, thrombosis, coronary artery disease, arteriosclerosis, and/or atherosclerosis. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:26 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1183 of SEQ ID NO:26, b is an integer of 15 to 1197, where both a and b correspond to the positions of nucleotide residues shown in SEQ ID NO:26, and where b is greater than or equal to a+14.

Features of Protein Encoded by Gene No: 17

The translation product of this gene shares sequence homology with ATP/GTP binding site motif A of Saccharomyces cerevisiae (See Genbank Accession No.gnl|PID|e217937) which is thought to be important in the regulation of various cellular processes, including transcription of important genes, in addition to signal transduction pathways.

In specific embodiments, polypeptides of the invention comprise the following amino acid sequence: TKFVQCPDGELQKRKEVVHTVSLHEIDVINSR TQGFLALFSGDTGEIKSEVREQINAKVAEWREEGKAEIIPGVLFIDEVHMLDIE SFSFLNRALESDMAPVLIMATNRGITRIRGTSYQSPHGIPIDLLDRLLIVSTTPYS EKDTKQILRIRCEEEDVEMSEDAYTVLTRIGLETSL-RYAIQLITAASLVCRKRKG TEVQVDDIKRVYS-LFLDESRSTQYMKEYQDAFLFNELKGETMDTS (SEQ ID NO:108), VVHTVSLHEIDVINSRTQGFLALF (SEQ ID NO:109), PGVLFIDEVH MLDIE (SEQ ID NO:110), or EEGKAEI (SEQ ID NO:111). Polynucleotides encoding these polypeptides are also encompassed by the invention. The gene encoding the disclosed cDNA is believed to reside on chromosome 19. Accordingly, polynucleotides related to this invention are useful as a marker in linkage analysis for chromosome 19.

This gene is expressed primarily in human adult testis, and to a lesser extent, in activated T-cells.

Therefore, polynucleotides and polypeptides of the invention are useful as reagents for differential identification of the tissue(s) or cell type(s) present in a biological sample and for diagnosis of diseases and conditions which include, but are not limited to, male reproductive, endocrine, or immune diseases and/or disorders, particularly male infertility resulting from autoimmunity. Similarly, polypeptides and antibodies directed to these polypeptides are useful in providing immunological probes for differential identification of the tissue(s) or cell type(s). For a number of disorders of the above tissues or cells, particularly of the male reproductive system, expression of this gene at significantly higher or lower levels may be routinely detected in certain tissues or cell types (e.g., reproductive, endocrine, immune, and cancerous and wounded tissues) or bodily fluids (e.g., lymph, seminal fluid, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 56 as residues: Arg-34 to His-42, Pro-59 to Gln-67, Arg-112 to Thr-117, Glu-134 to Gln-139, Glu-156 to Ser-161.

The tissue distribution in human adult testis indicates that polynucleotides and polypeptides corresponding to this gene are useful for diagnosis and treatment of a variety of male reproductive disorders, particularly male infertility. Similarly, the tissue distribution in testes indicates that polynucleotides and polypeptides corresponding to this gene are useful for the detection, treatment, and/or prevention of various endocrine disorders and cancers, particularly Addison's disease, Cushing's Syndrome, and disorders and/or cancers of the pancrease (e.g., diabetes mellitus), adrenal cortex, ovaries, pituitary (e.g., hyper-, hypopituitarism), thyroid (e.g., hyper-, hypothyroidism), parathyroid (e.g., hyper-,hypoparathyroidism), hypothallamus, and testes.

Moreover, this gene product is also useful in assays designed to identify binding agents, as such agents (antagonists) are useful as male contraceptive agents. Similarly, the protein is believed to be useful in the treatment and/or diagnosis of testicular cancer. The testes are also a site of active gene expression of transcripts that may be expressed, particularly at low levels, in other tissues of the body. Therefore, this gene product may be expressed in other specific tissues or organs where it may play related functional roles in other processes, such as hematopoiesis, inflammation, bone formation, and kidney function, to name a few possible target indications. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:27 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 988 of SEQ ID NO:27, b is an integer of 15 to 1002, where both a and b correspond to the positions of nucleotide residues shown in SEQ ID NO:27, and where b is greater than or equal to a+14.

Features of Protein Encoded by Gene No: 18

The gene encoding the disclosed cDNA is believed to reside on chromosome 1. Accordingly, polynucleotides related to this invention are useful as a marker in linkage analysis for chromosome 1. In specific embodiments, polypeptides of the invention comprise the following amino acid sequence: LSQDLKGAR (SEQ ID NO:112), and/or LITHGCLSYYLLSLKLSSLLFFFF-FLELLRIFPVWDPCTWFGFSLPCDNYNPDAS SFCLNYGSALP (SEQ ID NO:113). Polynucleotides encoding these polypeptides are also encompassed by the invention.

This gene is expressed primarily in human placental tissues.

Therefore, polynucleotides and polypeptides of the invention are useful as reagents for differential identification of the tissue(s) or cell type(s) present in a biological sample and for diagnosis of diseases and conditions which include, but are not limited to, reproductive or developmental disorders. Similarly, polypeptides and antibodies directed to these polypeptides are useful in providing immunological probes for differential identification of the tissue(s) or cell type(s). For a number of disorders of the above tissues or cells, particularly reproductive and developmental disorders, expression of this gene at significantly higher or lower levels may be routinely detected in certain tissues or cell types (e.g., reproductive, developmental, and cancerous and wounded tissues) or bodily fluids (e.g., lymph, amniotic fluid, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in placental tissues indicates that the protein product of this gene is useful for the diagnosis, treatment, and/or prevention of various reproductive, developmental, or congenital disorders, particularly Tay-Sachs disease, phenylkenonuria, galactosemia, hyperlipidemias, porphyrias, and Hurler's syndrome.

Alternatively, expression within placental tissue and other cellular sources marked by proliferating cells indicates that this protein may play a role in the regulation of cellular division, and may show utility in the diagnosis and treatment of cancer and other proliferative disorders. Similarly, embryonic development also involves decisions involving cell differentiation and/or apoptosis in pattern formation. Thus this protein may also be involved in apoptosis or tissue differentiation and could again be useful in cancer therapy. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:28 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1313 of SEQ ID NO:28, b is an integer of 15 to 1327, where both a and b correspond to the positions of nucleotide residues shown in SEQ ID NO:28, and where b is greater than or equal to a+14.

Features of Protein Encoded by Gene No: 19

The gene encoding the disclosed cDNA is believed to reside on chromosome 15. Accordingly, polynucleotides related to this invention are useful as a marker in linkage analysis for chromosome 15. In specific embodiments, polypeptides of the invention comprise the following amino acid sequence: IVLLFFFWMKTPAFPDSPPS SVLQFSEK-SWDMWEGAWELGSLRLPGRQFRL-CRKEQSPWEALGEGGAAAQH AWYCQPRGACV (SEQ ID NO:114). Polynucleotides encoding these polypeptides are also encompassed by the invention.

This gene is expressed primarily in human fetal brain tissue, and to a lesser extent in pineal gland, prostate, and thyroid tissues.

Therefore, polynucleotides and polypeptides of the invention are useful as reagents for differential identification of the tissue(s) or cell type(s) present in a biological sample and for diagnosis of diseases and conditions which include, but are not limited to, endocrine, reproductive, neural, or developmental disorders. Similarly, polypeptides and antibodies directed to these polypeptides are useful in providing immunological probes for differential identification of the tissue(s) or cell type(s). For a number of disorders of the above tissues or cells, particularly of the central nervous system, expression of this gene at significantly higher or lower levels may be routinely detected in certain tissues or cell types (e.g., endocrine, reproductive, neural, developmental, and cancerous and wounded tissues) or bodily fluids (e.g., lymph, amniotic fluid, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 58 as residues: Val-32 to Asn-40, Gly-59 to Gly-65.

The tissue distribution amongst various endocrine tissues indicates that the protein product of this gene is useful for the detection, treatment, and/or prevention of various endocrine disorders and cancers, particularly Addison's disease, Cushing's Syndrome, and disorders and/or cancers of the pancrease (e.g., diabetes mellitus), adrenal cortex, ovaries, pituitary (e.g., hyper-, hypopituitarism), thyroid (e.g., hyper-, hypothyroidism), parathyroid (e.g., hyper-, hypoparathyroidism), hypothallamus, and testes.

Alternatively, the tissue distribution in fetal brain tissue indicates that the protein product of this gene is useful for the detection and/or treatment of neurodegenerative disease states and behavioural disorders such as Alzheimers Disease, Parkinsons Disease, Huntingtons Disease, Tourette Syndrome, schizophrenia, mania, dementia, paranoia, obsessive compulsive disorder, panic disorder, learning disabilities, ALS, psychoses, autism, and altered behaviors, including disorders in feeding, sleep patterns, balance, and perception. In addition, the gene or gene product may also play a role in the treatment and/or detection of developmental disorders associated with the developing embryo, sexually-linked disorders, or disorders of the cardiovascular system. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:29 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 654 of SEQ ID NO:29, b is an integer of 15 to 668, where both a and b correspond to the positions of nucleotide residues shown in SEQ ID NO:29, and where b is greater than or equal to a+14.

Features of Protein Encoded by Gene No: 20

This gene is expressed primarily in Merkel cells.

Therefore, polynucleotides and polypeptides of the invention are useful as reagents for differential identification of the tissue(s) or cell type(s) present in a biological sample and for diagnosis of diseases and conditions which include, but are not limited to, integumentary disorders or diseases. Similarly, polypeptides and antibodies directed to these polypeptides are useful in providing immunological probes for differential identification of the tissue(s) or cell type(s). For a number of disorders of the above tissues or cells, particularly of the immune or integumentary system, expression of this gene at significantly higher or lower levels may be routinely detected in certain tissues or cell types (e.g., integumentary, immune, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in Merkel cells indicates that the protein product of this gene is useful for the treatment, diagnosis, and/or prevention of various skin disorders including congenital disorders (i.e. nevi, moles, freckles, Mongolian spots, hemangiomas, port-wine syndrome), integumentary tumors (i.e. keratoses, Bowen's disease, basal cell carcinoma, squamous cell carcinoma, malignant melanoma. Paget's disease, mycosis fungoides, and Kaposi's sarcoma), injuries and inflammation of the skin (i.e.wounds, rashes, prickly heat disorder, psoriasis, dermatitis), atherosclerosis, uticaria, eczema, photosensitivity, autoimmune disorders (i.e. lupus erythematosus, vitiligo, dermatomyositis, morphea, scleroderma, pemphigoid, and pemphigus), keloids, striae, erythema, petechiae, purpura, and xanthelasma.

Moreover, such disorders may predispose increased susceptibility to viral and bacterial infections of the skin (i.e. cold sores, warts, chickenpox, molluscum contagiosum, herpes zoster, boils, cellulitis, erysipelas, impetigo, tinea, althletes foot, and ringworm). Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:30 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1229 of SEQ ID NO:30, b is an integer of 15 to 1243, where both a and b correspond to the positions of nucleotide residues shown in SEQ ID NO:30, and where b is greater than or equal to a+14.

Features of Protein Encoded by Gene No: 21

In specific embodiments, polypeptides of the invention comprise the following amino acid sequence: MLIHTVIKLLDSISSNSFTTCVYLILFSIFLLFHSTICSEIESC (SEQ ID NO:115). Polynucleotides encoding these polypeptides are also encompassed by the invention.

This gene is expressed primarily in Merkel cells.

Therefore, polynucleotides and polypeptides of the invention are useful as reagents for differential identification of the tissue(s) or cell type(s) present in a biological sample and for diagnosis of diseases and conditions which include, but are not limited to, integumentary disorders, particularly in the diagnosis, treatment, or prevention of melanoma. Similarly, polypeptides and antibodies directed to these polypeptides are useful in providing immunological probes for differential identification of the tissue(s) or cell type(s). For a number of disorders of the above tissues or cells, particularly of the immune and integumentary systems, expression of this gene at significantly higher or lower levels may be routinely detected in certain tissues or cell types (e.g., integumentary, immune, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in Merkel cells indicates that the protein product of this gene is useful for the treatment, diagnosis, and/or prevention of various skin disorders including congenital disorders (i.e. nevi, moles, freckles, Mongolian spots, hemangiomas, port-wine syndrome), integumentary tumors (i.e. keratoses, Bowen's disease, basal cell carcinoma, squamous cell carcinoma, malignant melanoma, Paget's disease, mycosis fungoides, and Kaposi's sarcoma), injuries and inflammation of the skin (i.e.wounds, rashes, prickly heat disorder, psoriasis, dermatitis), atherosclerosis, uticaria, eczema, photosensitivity, autoimmune disorders (i.e. lupus erythematosus, vitiligo, dermatomyositis. morphea, scieroderma, pemphigoid, and pemphigus), keloids, striae, erythema, petechiae, purpura, and xanthelasma. Moreover, such disorders may predispose increased susceptibility to viral and bacterial infections of the skin (i.e. cold sores, warts, chickenpox, molluscum contagiosum, herpes zoster, boils, cellulitis, erysipelas, impetigo, tinea, althletes foot, and ringworm).

Many polynucleotide sequences, such as EST sequences, are publicly available and accessible through sequence databases. Some of these sequences are related to SEQ ID NO:31 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1039 of SEQ ID NO:31, b is an integer of 15 to 1053, where both a and b correspond to the positions of nucleotide residues shown in SEQ ID NO:31, and where b is greater than or equal to a+14.

Features of Protein Encoded by Gene No: 22

In specific embodiments, polypeptides of the invention comprise the following amino acid sequence: KINNCFFKPHKKCIN (SEQ ID NO:116). Polynucleotides encoding these polypeptides are also encompassed by the invention.

This gene is expressed primarily in Merkel cells.

Therefore, polynucleotides and polypeptides of the invention are useful as reagents for differential identification of the tissue(s) or cell type(s) present in a biological sample and for diagnosis of diseases and conditions which include, but are not limited to, integumentary or immune system diseases and disorders. Similarly, polypeptides and antibodies directed to these polypeptides are useful in providing immunological probes for differential identification of the tissue(s) or cell type(s). For a number of disorders of the above tissues or cells, particularly of the immune and integumentary systems, expression of this gene at significantly higher or lower levels may be routinely detected in certain tissues or cell types (e.g., immune, integumentary, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 61 as residues: Ile-74 to His-79.

The tissue distribution in Merkel cells indicates that the protein product of this gene is useful for the treatment, diagnosis, and/or prevention of various skin disorders including congenital disorders (i.e. nevi, moles, freckles, Mongolian spots, hemangiomas, port-wine syndrome), integumentary tumors (i.e. keratoses, Bowen's disease, basal cell carcinoma, squamous cell carcinoma, malignant melanoma, Paget's disease, mycosis fungoides, and Kaposi's sarcoma), injuries and inflammation of the skin (i.e.wounds, rashes, prickly heat disorder, psoriasis, dermatitis), atherosclerosis, uticaria, eczema, photosensitivity, autoimmune disorders (i.e. lupus erythematosus, vitiligo, dermatomyositis, morphea, scleroderma, pemphigoid, and pemphigus), keloids, striae, erythema, petechiae, purpura, and xanthelasma.

Moreover, such disorders may predispose increased susceptibility to viral and bacterial infections of the skin (i.e. cold sores, warts, chickenpox, molluscum contagiosum, herpes zoster, boils, cellulitis, erysipelas, impetigo, tinea, althletes foot, and ringworm). Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:32 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1000 of SEQ ID NO:32, b is an integer of 15 to 1014, where both a and b correspond to the positions of nucleotide residues shown in SEQ ID NO:32, and where b is greater than or equal to a+14.

Features of Protein Encoded by Gene No: 23

In specific embodiments, polypeptides of the invention comprise the following amino acid sequence: IRHE-DASAVT (SEQ ID NO:117). Polynucleotides encoding these polypeptides are also encompassed by the invention. The gene encoding the disclosed cDNA is thought to reside on chromosome 19. Accordingly, polynucleotides related to this invention are useful as a marker in linkage analysis for chromosome 19.

This gene is expressed primarily in fetal liver spleen and in vascular tissues such as fetal heart, embryonic and placental tissues, and to a lesser extent in, bone marrow stromal cells and Jurket membrane bound polysomes.

Therefore, polynucleotides and polypeptides of the invention are useful as reagents for differential identification of the tissue(s) or cell type(s) present in a biological sample and for diagnosis of diseases and conditions which include, but are not limited to, developmental, vascular, or immune disorders, particularly immunodeficiencies or inflammatory disorders. Similarly, polypeptides and antibodies directed to these polypeptides are useful in providing immunological probes for differential identification of the tissue(s) or cell type(s). For a number of disorders of the above tissues or cells, particularly of the immune and vascular systems, expression of this gene at significantly higher or lower levels may be routinely detected in certain tissues or cell types (e.g., immune, hematopoietic, vascular, and cancerous and wounded tissues) or bodily fluids (e.g., lymph, amniotic fluid, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 62 as residues: Leu-23 to Gln-29, Glu-33 to Ile-44.

The tissue distribution in fetal liver/spleen tissue indicates that the protein product of this gene is useful for the treatment and/or diagnosis of hematopoietic related disorders such as anemia, pancytopenia, leukopenia, thrombocytopenia or leukemia since stromal cells are important in the production of cells of hematopoietic lineages. The uses include bone marrow cell ex vivo culture, bone marrow transplantation, bone marrow reconstitution, radiotherapy or chemotherapy of neoplasia. The gene product may also be involved in lymphopoiesis, therefore, it can be used in immune disorders such as infection, inflammation, allergy, immunodeficiency etc. In addition, this gene product may have commercial utility in the expansion of stem cells and committed progenitors of various blood lineages, and in the differentiation and/or proliferation of various cell types.

Similarly, expression within fetal tissues and other cellular sources marked by proliferating cells indicates that this protein may play a role in the regulation of cellular division, and may show utility in the diagnosis and treatment of cancer and other proliferative disorders. Similarly, embryonic development also involves decisions involving cell differentiation and/or apoptosis in pattern formation. Thus this protein may also be involved in apoptosis or tissue differentiation and could again be useful in cancer therapy. Furthermore, the tissue distribution indicates that the protein product of this gene is useful for the diagnosis and/or treatment of disorders of the placenta. Specific expression within the placenta indicates that this gene product may play a role in the proper establishment and maintenance of placental function.

Alternatively, this gene product may be produced by the placenta and then transported to the embryo, where it may play a crucial role in the development and/or survival of the developing embryo or fetus. Expression of this gene product in a vascular-rich tissue such as the placenta also indicates that this gene product may be produced more generally in endothelial cells or within the circulation. In such instances, it may play more generalized roles in vascular function, such as in angiogenesis. It may also be produced in the vasculature and have effects on other cells within the circulation, such as hematopoietic cells. It may serve to promote the proliferation, survival, activation, and/or differentiation of hematopoietic cells, as well as other cells throughout the body.

The tissue distribution in fetal heart tissue indicates that the protein product of this gene is useful for the diagnosis and treatment of conditions and pathologies of the cardiovascular system, such as heart disease, restenosis, atherosclerosis, stoke, angina, thrombosis, and wound healing. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:33 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1359 of SEQ ID NO:33, b is an integer of 15 to 1373, where both a and b correspond to the positions of nucleotide residues shown in SEQ ID NO:33, and where b is greater than or equal to a+14.

Features of Protein Encoded by Gene No: 24

The translation product of this gene shares sequence homology with cni gene product (Cornichon protein) of Drosophila melanogaster which is involved in signal processing during development (See Genbank Accession No.gi|2460430).

In specific embodiments, polypeptides of the invention comprise the following amino acid sequence: SRPVMSG-PGLYDPTTIMNADILAYCQKEGW (SEQ ID NO:118), FFCV MFLCAAEWLTLGLNMPLLAYHIWRYM (SEQ ID NO:119), WHIIAFDELKTDYKNPIDQCNTLNPLV-LPEYLIHA (SEQ ID NO:120), GSPGC RNSATAX-APRSSSPA (SEQ ID NO:121), MAFTFAAFCYM (SEQ ID NO:122), and/or GMIYVLVSS (SEQ ID NO:123). Polynucleotides encoding these polypeptides are also encompassed by the invention.

This gene is expressed primarily in melanocytes.

Therefore, polynucleotides and polypeptides of the invention are useful as reagents for differential identification of the tissue(s) or cell type(s) present in a biological sample and for diagnosis of diseases and conditions which include, but are not limited to, integumentary disorders, particularly melanocytoma and other cancers. Similarly, polypeptides and antibodies directed to these polypeptides are useful in providing immunological probes for differential identification of the tissue(s) or cell type(s). For a number of disorders of the above tissues or cells, particularly of the immune and integumentary systems, expression of this gene at significantly higher or lower levels may be routinely detected in certain tissues or cell types (e.g., immune, integumentary, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 63 as residues: Leu-34 to Gln-44.

The tissue distribution in melanocytes indicates that the protein product of this gene is useful for the treatment, diagnosis, and/or prevention of various skin disorders including congenital disorders (i.e. nevi, moles, freckles, Mongolian spots, hemangiomas, port-wine syndrome), integumentary tumors (i.e. keratoses, Bowen's disease, basal cell carcinoma, squamous cell carcinoma, malignant melanoma, Paget's disease, mycosis fungoides, and Kaposi's sarcoma), injuries and inflammation of the skin (i.e.wounds, rashes, prickly heat disorder, psoriasis, dermatitis), atherosclerosis, uticaria, eczema, photosensitivity, autoimmune disorders (i.e. lupus erythematosus, vitiligo, dermatomyositis, morphea, scleroderma, pemphigoid, and pemphigus), keloids, striae, erythema, petechiae, purpura, and xanthelasma.

Moreover, such disorders may predispose increased susceptibility to viral and bacterial infections of the skin (i.e. cold sores, warts, chickenpox, molluscum contagiosum, herpes zoster, boils, cellulitis, erysipelas, impetigo, tinea, althletes foot, and ringworm). Based upon the homology to the Cornichon protein, it may be inferred that the protein product of this gene is useful for the detection, treatment, and/or prevention of a variety of proliferative disorders, particularly cancers, ulcers, or tumors. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:34 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1390 of SEQ ID NO:34, b is an integer of 15 to 1404, where both a and b correspond to the positions of nucleotide residues shown in SEQ ID NO:34, and where b is greater than or equal to a+14.

Features of Protein Encoded by Gene No: 25

When tested against K562 cell lines, supernatants removed from cells containing this gene activated the ISRE (interferon-sensitive responsive element) promoter element. Thus, it is likely that this gene activates leukemia cells, and to a lesser extent other cells, through the Jak-STAT signal transduction pathway. ISRE is a promoter element found upstream in many genes which are involved in the Jaks-STAT pathway. The Jaks-STAT pathway is a large, signal transduction pathway involved in the differentiation and proliferation of cells. Therefore, activation of the Jaks-STATs pathway, reflected by the binding of the ISRE element, can be used to indicate proteins involved in the proliferation and differentiation of cells.

In specific embodiments, polypeptides of the invention comprise the following amino acid sequence: LPTSRQSC-QITYMATSLPQLLGSSKLSFMFNCFS (SEQ ID NO:124). Polynucleotides encoding these polypeptides are also encompassed by the invention.

This gene is expressed primarily in fetal liver/spleen tissue, and to a lesser extent, in human B cell lymphoma.

Therefore, polynucleotides and polypeptides of the invention are useful as reagents for differential identification of the tissue(s) or cell type(s) present in a biological sample and for diagnosis of diseases and conditions which include, but are not limited to, developmental or immune disorders, particularly B cell diseases, such as lymphomas. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., developmental, immune, hematopoietic, and cancerous and wounded tissues) or bodily fluids (e.g., lymph, amniotic fluid, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in fetal liver/spleen tissue and B cell lymphoma indicates that the protein product of this gene is useful for the diagnosis and/or treatment of a variety of immune system disorders. Expression of this gene product in fetal liver/spleen tissue indicates a role in the regulation of the proliferation; survival; differentiation; and/or activation of potentially all hematopoietic cell lineages, including blood stem cells. This gene product may be involved in the regulation of cytokine production, antigen presentation, or other processes that may also suggest a usefulness in the treatment of cancer (e.g., by boosting immune responses).

Moreover, since the gene is expressed in cells of lymphoid origin, the natural gene product may be involved in immune functions. Therefore it may be also used as an agent for immunological disorders including arthritis, asthma, immune deficiency diseases such as AIDS, leukemia, rheumatoid arthritis, inflammatory bowel disease, sepsis, acne, and psoriasis. and tissues. In addition, this gene product may have commercial utility in the expansion of stem cells and committed progenitors of various blood lineages, and in the differentiation and/or proliferation of various cell types.

Similarly, expression within fetal tissue and other cellular sources marked by proliferating cells, combined with the detected ISRE biological activity, indicates that this protein may play a role in the regulation of cellular division, and may show utility in the diagnosis and treatment of cancer and other proliferative disorders. Similarly, embryonic development also involves decisions involving cell differentiation and/or apoptosis in pattern formation. Thus this protein may also be involved in apoptosis or tissue differentiation and could again be useful in cancer therapy. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:35 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1079 of SEQ ID NO:35, b is an integer of 15 to 1093, where both a and b correspond to the positions of nucleotide residues shown in SEQ ID NO:35, and where b is greater than or equal to a+14.

Features of Protein Encoded by Gene No: 26

The translation product of this gene shares sequence homology with human complement decay-accelerating factor (DAF) (See Genbank Accession No. gi|1857867). DAF is believed to play an important role in the regulation of the complement cascade, specifically this protein recognizes c4b and c3b fragments that condense with cell-surface hydroxyl or amino groups when nascent c4b and c3b are locally generated during c4 and c3 activation. interaction of daf with cell-associated c4b and c3b polypeptides interferes with their ability to catalyze the conversion of c2 and factor b to enzymatically active c2a and bb and thereby prevents the formation of c4b2a and c3bbb, the amplification convertases of the complement cascade. In addition, mutation of DAF has been found to lead to the Cromer blood group system which consists of at least seven high-incidence (cr(a), tc(a), dr(a), es(a), wes(b), umc, and ifc) and low-incidence (tc(b), tc(c), and wes(a)) antigens that reside on DAF. In the cromer phenotypes dr(a–) and inab there is reduced or absent expression of DAF, respectively.

In specific embodiments, polypeptides of the invention comprise the following amino acid sequence: NSFFFPC-CFRYKLFGSTSSFCLISGSSVQWSDPXPECRGKS (SEQ ID NO:125). Polynucleotides encoding these polypeptides are also encompassed by the invention. The gene encoding the disclosed cDNA is believed to reside on chromosome 1. Accordingly, polynucleotides related to this invention are useful as a marker in linkage analysis for chromosome 1.

This gene is expressed primarily in activated human neutrophils.

Therefore, polynucleotides and polypeptides of the invention are useful as reagents for differential identification of the tissue(s) or cell type(s) present in a biological sample and for diagnosis of diseases and conditions which include, but are not limited to, immune or hematopoietic disorders, particularly neutropenia, in addition to disorders related to the complement or neural system. Similarly, polypeptides and antibodies directed to these polypeptides are useful in providing immunological probes for differential identification of the tissue(s) or cell type(s). For a number of disorders of the above tissues or cells, particularly of the hematopoietic, complement, or neural system, expression of this gene at significantly higher or lower levels may be routinely detected in certain tissues or cell types (e.g., immune, hematopoietic, neural and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in neutrophils indicates that the protein product of this gene is useful for the diagnosis and/or treatment of a variety of immune system disorders. Expression of this gene product in neutrophils indicates a role in the regulation of the proliferation; survival; differentiation; and/or activation of potentially all hematopoietic cell lineages, including blood stem cells. This gene product may be involved in the regulation of cytokine production, antigen presentation, or other processes that may also suggest a usefulness in the treatment of cancer (e.g., by boosting immune responses).

Moreover, since the gene is expressed in cells of lymphoid origin, the natural gene product may be involved in immune functions. Therefore it may be also used as an agent for immunological disorders including arthritis, asthma, immune deficiency diseases such as AIDS, leukemia, rheumatoid arthritis, inflammatory bowel disease, sepsis, acne, and psoriasis. and tissues. In addition, this gene product may have commercial utility in the expansion of stem cells and committed progenitors of various blood lineages, and in the differentiation and/or proliferation of various cell types.

Similarly, the tissue distribution in neutrophils, combined with the homology to the DAF protein, indicates that the protein product of this gene is useful for the detection, treatment, and/or prevention of a variety of blood disorders, particularly complement disorders, or disorders related to blood group antigens, such as the Cromer blood group system (i.e. transfusions,etc.) Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:36 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 404 of SEQ ID NO:36, b is an integer of 15 to 418, where both a and b correspond to the positions of nucleotide residues shown in SEQ ID NO:36, and where b is greater than or equal to a+14.

Features of Protein Encoded by Gene No: 27

When tested against K562 cell lines, supernatants removed from cells containing this gene activated the ISRE (interferon- sensitive responsive element) pathway. Thus, it is likely that this gene activates leukemia cells, and to a lesser extent in other cells, through the Jaks-STAT signal transduction pathway. ISRE is a promoter element found upstream in many genes which are involved in the Jaks-STAT pathway. The Jaks-STAT pathway is a large, signal transduction pathway involved in the differentiation and proliferation of cells. Therefore, activation of the Jaks-STATs pathway, reflected by the binding of the ISRE element, can be used to indicate proteins involved in the proliferation and differentiation of cells.

This gene is expressed primarily in neutrophils.

Therefore, polynucleotides and polypeptides of the invention are useful as reagents for differential identification of the tissue(s) or cell type(s) present in a biological sample and for diagnosis of diseases and conditions which include, but are not limited to, immune disorders, particularly neutropenia. Similarly, polypeptides and antibodies directed to these polypeptides are useful in providing immunological probes for differential identification of the tissue(s) or cell type(s). For a number of disorders of the above tissues or cells, particularly of the immune or hematopoietic system, expression of this gene at significantly higher or lower levels may be routinely detected in certain tissues or cell types (e.g., immune, hematopoietic, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

Preferred epitopes include those comprising a sequence shown in SEQ ID NO. 66 as residues: Asp-45 to Thr-50.

The tissue distribution in neutrophils, combined with the detected ISRE biological activity, indicates that the protein product of this gene is useful for the diagnosis and/or treatment of a variety of immune system disorders. Expression of this gene product in neutrophils indicates a role in the regulation of the proliferation; survival; differentiation; and/or activation of potentially all hematopoietic cell lineages, including blood stem cells. This gene product may be involved in the regulation of cytokine production, antigen presentation, or other processes that may also suggest a usefulness in the treatment of cancer (e.g., by boosting immune responses).

Moreover, since the gene is expressed in cells of lymphoid origin, the natural gene product may be involved in immune functions. Therefore it may be also used as an agent for immunological disorders including arthritis, asthma, immune deficiency diseases such as AIDS, leukemia, rheumatoid arthritis, inflammatory bowel disease, sepsis, acne, and psoriasis. and tissues. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:37 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1028 of SEQ ID NO:37, b is an integer of 15 to 1042, where both a and b correspond to the positions of nucleotide residues shown in SEQ ID NO:37, and where b is greater than or equal to a+14.

Features of Protein Encoded by Gene No: 28

When tested against K-562 cell lines, supernatants removed from cells containing this gene activated the ISRE (interferon- sensitive responsive element) promoter element. Thus, it is likely that this gene activates leukemia cells, and to a lesser extent, immune or hematopoietic cells, through the Jaks-STAT signal transduction pathway ISRE is a promoter element found upstream in many genes which are involved in the Jaks-STAT pathway. The Jaks-STAT pathway is a large, signal transduction pathway involved in the differentiation and proliferation of cells. Therefore, activation of the Jaks-STATs pathway, reflected by the binding of the ISRE element, can be used to indicate proteins involved in the proliferation and differentiation of cells.

This gene is expressed primarily in activated T-cells.

Therefore, polynucleotides and polypeptides of the invention are useful as reagents for differential identification of the tissue(s) or cell type(s) present in a biological sample and for diagnosis of diseases and conditions which include, but are not limited to, immune or hematopoietic disorders, particularly immunodeficencies such as AIDs, or inflammatory disorders. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, hematopoietic, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in activated T-cells indicates that polynucleotides and polypeptides corresponding to this gene are useful for the diagnosis and treatment of a variety of immune system disorders. Expression of this gene product in indicates a role in the regulation of the proliferation; survival; differentiation; and/or activation of potentially all hematopoietic cell lineages, including blood stem cells. This gene product may be involved in the regulation of cytokine production, antigen presentation, or other processes that may also suggest a usefulness in the treatment of cancer (e.g., by boosting immune responses).

Moreover, since the gene is expressed in cells of lymphoid origin, the natural gene product may be involved in immune functions. Therefore it may be also used as an agent for immunological disorders including arthritis, asthma, immune deficiency diseases such as AIDS, leukemia, rheumatoid arthritis, inflammatory bowel disease, sepsis, acne, and psoriasis. and tissues. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:38 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 784 of SEQ ID NO:38, b is an integer of 15 to 798, where both a and b correspond to the positions of nucleotide residues shown in SEQ ID NO:38, and where b is greater than or equal to a+14.

Features of Protein Encoded by Gene No: 29

In specific embodiments, polypeptides of the invention comprise the following amino acid sequence: VWVSGP-WCTEFICLAVFTVILQI (SEQ ID NO:126), TGG TAFLL-MPNLLHLLLSPRRYPSVCRVS-LGEWAMVHRVYLLGCFHCYSPNNDSV ACLHIPSCCGIPPVLHSTAELCHS (SEQ ID NO:127), and/or RYPSVCRVSLGE WAMVHRVYLLGCFHCYSP-NND (SEQ ID NO:128). Polynucleotides encoding these polypeptides are also encompassed by the invention.

This gene is expressed primarily in neutrophils.

Therefore, polynucleotides and polypeptides of the invention are useful as reagents for differential identification of the tissue(s) or cell type(s) present in a biological sample and for diagnosis of diseases and conditions which include, but are not limited to, immune or hematopoietic disorders, particularly neutropenia. Similarly, polypeptides and antibodies directed to these polypeptides are useful in providing immunological probes for differential identification of the tissue(s) or cell type(s). For a number of disorders of the above tissues or cells, particularly of the immune or hemopoietic system, expression of this gene at significantly higher or lower levels may be routinely detected in certain tissues or cell types (e.g., immune, hematopoietic, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in neutrophils indicates that polynucleotides and polypeptides corresponding to this gene are useful for the diagnosis and treatment of a variety of immune system disorders. Expression of this gene product indicates a role in the regulation of the proliferation; survival; differentiation; and/or activation of potentially all hematopoietic cell lineages, including blood stem cells. This gene product may be involved in the regulation of cytokine production, antigen presentation, or other processes that may also suggest a usefulness in the treatment of cancer (e.g., by boosting immune responses).

Moreover, since the gene is expressed in cells of lymphoid origin, the natural gene product may be involved in immune functions. Therefore it may be also used as an agent for immunological disorders including arthritis, asthma, immune deficiency diseases such as AIDS, leukemia, rheumatoid arthritis, inflammatory bowel disease, sepsis, acne, and psoriasis. and tissues. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:39 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1016 of SEQ ID NO:39, b is an integer of 15 to 1030, where both a and b correspond to the positions of nucleotide residues shown in SEQ ID NO:39, and where b is greater than or equal to a+14.

TABLE 1

| Gene No. | cDNA Clone ID | ATCC Deposit Nr and Date | Vector | NT SEQ ID NO: X | Total NT Seq. | 5' NT of Clone Seq. | 3' NT of Clone Seq. | 5' NT of Start Codon | 5' NT of First AA of Signal Pep | AA SEQ ID NO: Y | First AA of Sig Pep | Last AA of Sig Pep | First AA of Secreted Portion | Last AA of ORF |
|---|---|---|---|---|---|---|---|---|---|---|---|---|---|---|
| 1 | HSAXS66 | 209197 08/08/97 | Uni-ZAP XR | 11 | 866 | 1 | 866 | 102 | 102 | 40 | 1 | 24 | 25 | 36 |
| 2 | HSAYL90 | 209197 08/08/97 | Uni-ZAP XR | 12 | 651 | 1 | 651 | 188 | 188 | 41 | 1 | 21 | 22 | 32 |
| 3 | HSDIT06 | 209197 08/08/97 | Uni-ZAP XR | 13 | 1336 | 1 | 1336 | 123 | 123 | 42 | 1 | 18 | 19 | 91 |
| 4 | HSFAL43 | 209197 08/08/97 | Uni-ZAP XR | 14 | 585 | 1 | 585 | 123 | 123 | 43 | 1 | 30 | 31 | 32 |
| 5 | HSKEI54 | 209197 08/08/97 | Uni-ZAP XR | 15 | 1144 | 175 | 1144 | 316 | 316 | 44 | 1 | 36 | 37 | 52 |
| 6 | HSQBE28 | 209197 08/08/97 | Uni-ZAP XR | 16 | 1037 | 229 | 1037 | 317 | 317 | 45 | 1 | 17 | 18 | 25 |
| 7 | HTEAN76 | 209197 08/08/97 | Uni-ZAP XR | 17 | 925 | 156 | 925 | 260 | 260 | 46 | 1 | 31 | 32 | 37 |
| 8 | HTNAG39 | 209197 08/08/97 | pBluescript SK- | 18 | 1197 | 403 | 1191 | 468 | 468 | 47 | 1 | 45 | 46 | 70 |
| 9 | HTODL90 | 209197 08/08/97 | Uni-ZAP XR | 19 | 1106 | 1 | 1106 | 925 | 925 | 48 | 1 | 39 | 40 | 60 |
| 10 | HTWDC20 | 209297 08/08/97 | pSport1 | 20 | 932 | 1 | 932 | 156 | 156 | 49 | 1 | 26 | 27 | 39 |

TABLE 1-continued

| Gene No. | cDNA Clone ID | ATCC Deposit Nr and Date | Vector | NT SEQ ID NO: X | Total NT Seq. | 5' NT of Clone Seq. | 3' NT of Clone Seq. | 5' NT of Start Codon | 5' NT of First AA of Signal Pep | AA SEQ ID NO: Y | First AA of Sig Pep | Last AA of Sig Pep | First AA of Secreted Portion | Last AA of ORF |
|---|---|---|---|---|---|---|---|---|---|---|---|---|---|---|
| 11 | HUFAT34 | 209197 08/08/97 | pSport1 | 21 | 1032 | 1 | 1032 | 32 | 32 | 50 | 1 | 22 | 23 | 103 |
| 12 | HUSGX69 | 209197 08/08/97 | pSport1 | 22 | 487 | 1 | 487 | 243 | 243 | 51 | 1 | 16 | 17 | 22 |
| 13 | HAICJ23 | 209197 08/08/97 | Uni-ZAP XR | 23 | 1460 | 1 | 1460 | 189 | 189 | 52 | 1 | 47 | 48 | 85 |
| 14 | HAPOF67 | 209197 08/08/97 | Uni-ZAP XR | 24 | 1098 | 1 | 1098 | 78 | 78 | 53 | 1 | 47 | 48 | 73 |
| 15 | HCEBR71 | 209197 08/08/97 | Uni-ZAP XR | 25 | 1015 | 1 | 1015 | 102 | 102 | 54 | 1 | 17 | 18 | 35 |
| 16 | HE8DG53 | 209197 08/08/97 | Uni-ZAP XR | 26 | 1197 | 307 | 1197 | 350 | 350 | 55 | 1 | 20 | 21 | 67 |
| 17 | HFSAY85 | 209197 08/08/97 | Uni-ZAP XR | 27 | 1002 | 457 | 1002 | 295 | 295 | 56 | 1 | 58 | 59 | 161 |
| 18 | HHEDD41 | 209197 08/08/97 | pCMVSport 3.0 | 28 | 1327 | 154 | 1327 | 442 | 442 | 57 | 1 | 22 | 23 | 41 |
| 19 | HKCSO46 | 209197 08/08/97 | pBluescript | 29 | 668 | 20 | 668 | 217 | 217 | 58 | 1 | 37 | 38 | 75 |
| 20 | HKGAV60 | 209197 08/08/97 | pSport1 | 30 | 1243 | 1 | 1243 | 192 | 192 | 59 | 1 | 20 | 21 | 39 |
| 21 | HKGDJ35 | 209197 08/08/97 | pSport1 | 31 | 1053 | 1 | 1053 | 238 | 238 | 60 | 1 | 19 | 20 | 32 |
| 22 | HKGDJ66 | 209197 08/08/97 | pSport1 | 32 | 1014 | 1 | 1014 | 215 | 215 | 61 | 1 | 24 | 25 | 110 |
| 23 | HMCDK27 | 209197 08/08/97 | Uni-ZAP XR | 33 | 1373 | 1 | 969 | 33 | 33 | 62 | 1 | 17 | 18 | 75 |
| 24 | HMCDX48 | 209197 08/08/97 | Uni-ZAP XR | 34 | 1404 | 1 | 1403 | 63 | 63 | 63 | 1 | 30 | 31 | 144 |
| 25 | HMIAS24 | 209197 08/08/97 | Uni-ZAP XR | 35 | 1093 | 1 | 1093 | 178 | 178 | 64 | 1 | 42 | 43 | 44 |
| 26 | HNFEG11 | 209197 08/08/97 | Uni-ZAP XR | 36 | 418 | 1 | 418 | 251 | 251 | 65 | 1 | 31 | 32 | 47 |
| 27 | HNGEP09 | 209197 08/08/97 | Uni-ZAP XR | 37 | 1042 | 1 | 1042 | 72 | 72 | 66 | 1 | 15 | 16 | 82 |
| 28 | HTXKK52 | 209197 08/08/97 | Uni-ZAP XR | 38 | 798 | 1 | 798 | 81 | 81 | 67 | 1 | 30 | 31 | 48 |
| 29 | HNGJP90 | 209197 08/08/97 | Uni-ZAP XR | 39 | 1030 | 1 | 1030 | 157 | 157 | 68 | 1 | 14 | 15 | 94 |

Table 1 summarizes the information corresponding to each "Gene No." described above. The nucleotide sequence identified as "NT SEQ ID NO:X" was assembled from partially homologous ("overlapping") sequences obtained from the "cDNA clone ID" identified in Table 1 and, in some cases, from additional related DNA clones. The overlapping sequences were assembled into a single contiguous sequence of high redundancy (usually three to five overlapping sequences at each nucleotide position), resulting in a final sequence identified as SEQ ID NO:X.

The cDNA Clone ID was deposited on the date and given the corresponding deposit number listed in "ATCC Deposit No:Z and Date." Some of the deposits contain multiple different clones corresponding to the same gene. "Vector" refers to the type of vector contained in the cDNA Clone ID.

"Total NT Seq." refers to the total number of nucleotides in the contig identified by "Gene No." The deposited clone may contain all or most of these sequences, reflected by the nucleotide position indicated as "5' NT of Clone Seq." and the "3' NT of Clone Seq." of SEQ ID NO:X. The nucleotide position of SEQ ID NO:X of the putative start codon (methionine) is identified as "5' NT of Start Codon." Similarly, the nucleotide position of SEQ ID NO:X of the predicted signal sequence is identified as "5' NT of First AA of Signal Pep."

The translated amino acid sequence, beginning with the methionine, is identified as "AA SEQ ID NO:Y," although other reading frames can also be easily translated using known molecular biology techniques. The polypeptides produced by these alternative open reading frames are specifically contemplated by the present invention.

The first and last amino acid position of SEQ ID NO:Y of the predicted signal peptide is identified as "First AA of Sig Pep" and "Last AA of Sig Pep." The predicted first amino acid position of SEQ ID NO:Y of the secreted portion is identified as "Predicted First AA of Secreted Portion." Finally, the amino acid position of SEQ ID NO:Y of the last amino acid in the open reading frame is identified as "Last AA of ORF."

SEQ ID NO:X and the translated SEQ ID NO:Y are sufficiently accurate and otherwise suitable for a variety of uses well known in the art and described further below. For instance, SEQ ID NO:X is useful for designing nucleic acid hybridization probes that will detect nucleic acid sequences contained in SEQ ID NO:X or the cDNA contained in the deposited clone. These probes will also hybridize to nucleic acid molecules in biological samples, thereby enabling a variety of forensic and diagnostic methods of the invention. Similarly, polypeptides identified from SEQ ID NO:Y may be used to generate antibodies which bind specifically to the secreted proteins encoded by the cDNA clones identified in Table 1.

Nevertheless, DNA sequences generated by sequencing reactions can contain sequencing errors. The errors exist as misidentified nucleotides, or as insertions or deletions of nucleotides in the generated DNA sequence. The erroneously inserted or deleted nucleotides cause frame shifts in the reading frames of the predicted amino acid sequence. In these cases, the predicted amino acid sequence diverges from the actual amino acid sequence, even though the generated DNA sequence may be greater than 99.9% identical to the actual DNA sequence (for example, one base insertion or deletion in an open reading frame of over 1000 bases).

Accordingly, for those applications requiring precision in the nucleotide sequence or the amino acid sequence, the present invention provides not only the generated nucleotide sequence identified as SEQ ID NO:X and the predicted translated amino acid sequence identified as SEQ ID NO:Y, but also a sample of plasmid DNA containing a human cDNA of the invention deposited with the ATCC, as set forth in Table 1. The nucleotide sequence of each deposited clone can readily be determined by sequencing the deposited clone in accordance with known methods. The predicted amino acid sequence can then be verified from such deposits. Moreover, the amino acid sequence of the protein encoded by a particular clone can also be directly determined by peptide sequencing or by expressing the protein in a suitable host cell containing the deposited human cDNA, collecting the protein, and determining its sequence.

The present invention also relates to the genes corresponding to SEQ ID NO:X, SEQ ID NO:Y, or the deposited clone. The corresponding gene can be isolated in accordance with known methods using the sequence information disclosed herein. Such methods include preparing probes or primers from the disclosed sequence and identifying or amplifying the corresponding gene from appropriate sources of genomic material.

Also provided in the present invention are species homologs. Species homologs may be isolated and identified by making suitable probes or primers from the sequences provided herein and screening a suitable nucleic acid source for the desired homologue.

The polypeptides of the invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

The polypeptides may be in the form of the secreted protein, including the mature form, or may be a part of a larger protein, such as a fusion protein (see below). It is often advantageous to include an additional amino acid sequence which contains secretory or leader sequences, prosequences, sequences which aid in purification, such as multiple histidine residues, or an additional sequence for stability during recombinant production.

The polypeptides of the present invention are preferably provided in an isolated form, and preferably are substantially purified. A recombinantly produced version of a polypeptide, including the secreted polypeptide, can be substantially purified by the one-step method described in Smith and Johnson, Gene 67:31–40 (1988). Polypeptides of the invention also can be purified from natural or recombinant sources using antibodies of the invention raised against the secreted protein in methods which are well known in the art.

Signal Sequences

Methods for predicting whether a protein has a signal sequence, as well as the cleavage point for that sequence, are available. For instance, the method of McGeoch, Virus Res. 3:271–286 (1985), uses the information from a short N-terminal charged region and a subsequent uncharged region of the complete (uncleaved) protein. The method of von Heinje, Nucleic Acids Res. 14:4683–4690 (1986) uses the information from the residues surrounding the cleavage site, typically residues −13 to +2, where +1 indicates the amino terminus of the secreted protein. The accuracy of predicting the cleavage points of known mammalian secretory proteins for each of these methods is in the range of 75–80%. (von Heinje, supra.) However, the two methods do not always produce the same predicted cleavage point(s) for a given protein.

In the present case, the deduced amino acid sequence of the secreted polypeptide was analyzed by a computer program called SignalP (Henrik Nielsen et al., Protein Engineering 10:1–6 (1997)), which predicts the cellular location of a protein based on the amino acid sequence. As part of this computational prediction of localization, the methods of McGeoch and von Heinje are incorporated. The analysis of the amino acid sequences of the secreted proteins described herein by this program provided the results shown in Table 1.

As one of ordinary skill would appreciate, however, cleavage sites sometimes vary from organism to organism and cannot be predicted with absolute certainty. Accordingly, the present invention provides secreted polypeptides having a sequence shown in SEQ ID NO:Y which have an N-terminus beginning within 5 residues (i.e., + or −5 residues) of the predicted cleavage point. Similarly, it is also recognized that in some cases, cleavage of the signal sequence from a secreted protein is not entirely uniform, resulting in more than one secreted species. These polypeptides, and the polynucleotides encoding such polypeptides, are contemplated by the present invention.

Moreover, the signal sequence identified by the above analysis may not necessarily predict the naturally occurring signal sequence. For example, the naturally occurring signal sequence may be further upstream from the predicted signal sequence. However, it is likely that the predicted signal sequence will be capable of directing the secreted protein to the ER. These polypeptides, and the polynucleotides encoding such polypeptides, are contemplated by the present invention.

Polynucleotide and Polypeptide Variants

"Variant" refers to a polynucleotide or polypeptide differing from the polynucleotide or polypeptide of the present invention, but retaining essential properties thereof. Generally, variants are overall closely similar, and, in many regions, identical to the polynucleotide or polypeptide of the present invention.

By a polynucleotide having a nucleotide sequence at least, for example, 95% "identical" to a reference nucleotide sequence of the present invention, it is intended that the nucleotide sequence of the polynucleotide is identical to the reference sequence except that the polynucleotide sequence may include up to five point mutations per each 100 nucleotides of the reference nucleotide sequence encoding the polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. The query sequence may be an entire sequence shown in Table 1, the ORF (open reading frame), or any fragment specified as described herein.

As a practical matter, whether any particular nucleic acid molecule or polypeptide is at least 90%, 95%, 96%, 97%, 98% or 99% identical to a nucleotide sequence of the presence invention can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al. (Comp. App. Biosci. (1990) 6:237–245). In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identiy are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the lenght of the subject nucleotide sequence, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the FASTDB alignment does not show a matched/alignement of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequnce are manually corrected for. No other manual corrections are to made for the purposes of the present invention.

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted, (indels) or substituted with another amino acid. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 90%, 95%, 96%, 97%, 98% or 99% identical to, for instance, the amino acid sequences shown in Table 1 or to the amino acid sequence encoded by deposited DNA clone can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al. (Comp. App. Biosci. (1990) 6:237–245). In a sequence alignment the query and subject sequences are either both nucleotide sequences or both amino acid sequences. The result of said global sequence alignment is in percent identity. Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter.

If the subject sequence is shorter than the query sequence due to N- or C-terminal deletions, not because of internal deletions, a manual correction must be made to the results. This is becuase the FASTDB program does not account for N- and C-terminal truncations of the subject sequence when calculating global percent identity. For subject sequences truncated at the N- and C-termini, relative to the the query sequence, the percent identity is corrected by calculating the number of residues of the query sequence that are N- and C-terminal of the subject sequence, which are not matched/aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence.

For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequnce are manually corrected for. No other manual corrections are to made for the purposes of the present invention.

The variants may contain alterations in the coding regions, non-coding regions, or both. Especially preferred are polynucleotide variants containing alterations which produce silent substitutions, additions, or deletions, but do not alter the properties or activities of the encoded polypeptide. Nucleotide variants produced by silent substitutions due to the degeneracy of the genetic code are preferred. Moreover, variants in which 5–10, 1–5, or 1–2 amino acids are substituted, deleted, or added in any combination are also preferred. Polynucleotide variants can be produced for a variety of reasons, e.g., to optimize codon expression for a particular host (change codons in the human mRNA to those preferred by a bacterial host such as E. coli).

Naturally occurring variants are called "allelic variants," and refer to one of several alternate forms of a gene occupying a given locus on a chromosome of an organism. (Genes II, Lewin, B., ed., John Wiley & Sons, New York (1985).) These allelic variants can vary at either the polynucleotide and/or polypeptide level. Alternatively, non-naturally occurring variants may be produced by mutagenesis techniques or by direct synthesis.

Using known methods of protein engineering and recombinant DNA technology, variants may be generated to improve or alter the characteristics of the polypeptides of the present invention. For instance, one or more amino acids can be deleted from the N-terminus or C-terminus of the secreted protein without substantial loss of biological function. The authors of Ron et al., J. Biol. Chem. 268: 2984–2988 (1993), reported variant KGF proteins having heparin binding activity even after deleting 3, 8, or 27 amino-terminal amino acid residues. Similarly, Interferon gamma exhibited up to ten times higher activity after deleting 8–10 amino acid residues from the carboxy terminus of this protein. (Dobeli et al., J. Biotechnology 7:199–216 (1988).)

Moreover, ample evidence demonstrates that variants often retain a biological activity similar to that of the naturally occurring protein. For example, Gayle and coworkers (J. Biol. Chem 268:22105–22111 (1993)) conducted extensive mutational analysis of human cytokine IL-1a. They used random mutagenesis to generate over 3,500 individual IL-1a mutants that averaged 2.5 amino acid changes per variant over the entire length of the molecule. Multiple mutations were examined at every possible amino acid position. The investigators found that "[m]ost of the molecule could be altered with little effect on either [binding or biological activity]." (See, Abstract.) In fact, only 23 unique amino acid sequences, out of more than 3,500 nucleotide sequences examined, produced a protein that significantly differed in activity from wild-type.

Furthermore, even if deleting one or more amino acids from the N-terminus or C-terminus of a polypeptide results in modification or loss of one or more biological functions, other biological activities may still be retained. For example, the ability of a deletion variant to induce and/or to bind antibodies which recognize the secreted form will likely be retained when less than the majority of the residues of the secreted form are removed from the N-terminus or C-terminus. Whether a particular polypeptide lacking N- or C-terminal residues of a protein retains such immunogenic activities can readily be determined by routine methods described herein and otherwise known in the art.

Thus, the invention further includes polypeptide variants which show substantial biological activity. Such variants include deletions, insertions, inversions, repeats, and substitutions selected according to general rules known in the art so as have little effect on activity. For example, guidance concerning how to make phenotypically silent amino acid substitutions is provided in Bowie, J. U. et al., Science 247:1306–1310 (1990), wherein the authors indicate that there are two main strategies for studying the tolerance of an amino acid sequence to change.

The first strategy exploits the tolerance of amino acid substitutions by natural selection during the process of evolution. By comparing amino acid sequences in different species, conserved amino acids can be identified. These conserved amino acids are likely important for protein function. In contrast, the amino acid positions where substitutions have been tolerated by natural selection indicates that these positions are not critical for protein function. Thus, positions tolerating amino acid substitution could be modified while still maintaining biological activity of the protein.

The second strategy uses genetic engineering to introduce amino acid changes at specific positions of a cloned gene to identify regions critical for protein function. For example, site directed mutagenesis or alanine-scanning mutagenesis (introduction of single alanine mutations at every residue in the molecule) can be used. (Cunningham and Wells, Science 244:1081–1085 (1989).) The resulting mutant molecules can then be tested for biological activity.

As the authors state, these two strategies have revealed that proteins are surprisingly tolerant of amino acid substitutions. The authors further indicate which amino acid changes are likely to be permissive at certain amino acid positions in the protein. For example, most buried (within the tertiary structure of the protein) amino acid residues require nonpolar side chains, whereas few features of surface side chains are generally conserved. Moreover, tolerated conservative amino acid substitutions involve replacement of the aliphatic or hydrophobic amino acids Ala, Val, Leu and Ile; replacement of the hydroxyl residues Ser and Thr; replacement of the acidic residues Asp and Glu; replacement of the amide residues Asn and Gln, replacement of the basic residues Lys, Arg, and His; replacement of the aromatic residues Phe, Tyr, and Trp, and replacement of the small-sized amino acids Ala, Ser, Thr, Met, and Gly.

Besides conservative amino acid substitution, variants of the present invention include (i) substitutions with one or more of the non-conserved amino acid residues, where the substituted amino acid residues may or may not be one encoded by the genetic code, or (ii) substitution with one or more of amino acid residues having a substituent group, or (iii) fusion of the mature polypeptide with another compound, such as a compound to increase the stability and/or solubility of the polypeptide (for example, polyethylene glycol), or (iv) fusion of the polypeptide with additional amino acids, such as an IgG Fc fusion region peptide, or leader or secretory sequence, or a sequence facilitating purification. Such variant polypeptides are deemed to be within the scope of those skilled in the art from the teachings herein.

For example, polypeptide variants containing amino acid substitutions of charged amino acids with other charged or neutral amino acids may produce proteins with improved characteristics, such as less aggregation. Aggregation of pharmaceutical formulations both reduces activity and increases clearance due to the aggregate's immunogenic activity. (Pinckard et al., Clin. Exp. Immunol. 2:331–340 (1967); Robbins et al., Diabetes 36: 838–845 (1987); Cleland et al., Crit. Rev. Therapeutic Drug Carrier Systems 10:307–377 (1993).)

A further embodiment of the invention relates to a polypeptide which comprises the amino acid sequence of the present invention having an amino acid sequence which contains at least one amino acid substitution, but not more than 50 amino acid substitutions, even more preferably, not more than 40 amino acid substitutions, still more preferably, not more than 30 amino acid substitutions, and still even more preferably, not more than 20 amino acid substitutions. Of course, in order of ever-increasing preference, it is highly preferable for a polypeptide to have an amino acid sequence which comprises the amino acid sequence of the present invention, which contains at least one, but not more than 10, 9, 8, 7, 6, 5, 4, 3, 2 or 1 amino acid substitutions. In specific embodiments, the number of additions, substitutions, and/or deletions in the amino acid sequence of the present invention or fragments thereof (e.g., the mature form and/or other fragments described herein), is 1–5, 5–10, 5–25, 5–50, 10–50 or 50–150, conservative amino acid substitutions are preferable.

Polynucleotide and Polypeptide Fragments

In the present invention, a "polynucleotide fragment" refers to a short polynucleotide having a nucleic acid sequence contained in the deposited clone or shown in SEQ ID NO:X. The short nucleotide fragments are preferably at least about 15 nt, and more preferably at least about 20 nt, still more preferably at least about 30 nt, and even more preferably, at least about 40 nt in length. A fragment "at least 20 nt in length," for example, is intended to include 20 or more contiguous bases from the cDNA sequence contained in the deposited clone or the nucleotide sequence shown in SEQ ID NO:X. These nucleotide fragments are useful as diagnostic probes and primers as discussed herein. Of course, larger fragments (e.g., 50, 150, 500, 600, 2000 nucleotides) are preferred.

Moreover, representative examples of polynucleotide fragments of the invention, include, for example, fragments having a sequence from about nucleotide number 1–50, 51–100, 101–150, 151–200, 201–250, 251–300, 301–350, 351–400, 401–450, 451–500, 501–550, 551–600, 651–700, 701–750, 751–800, 800–850, 851–900, 901–950, 951–1000, 1001–1050, 1051–1100, 1101–1150, 1151–1200, 1201–1250, 1251–1300, 1301–1350, 1351–1400, 1401–1450, 1451–1500, 1501–1550, 1551–1600, 1601–1650, 1651–1700, 1701–1750, 1751–1800, 1801–1850, 1851–1900, 1901–1950, 1951–2000, or 2001 to the end of SEQ ID NO:X or the cDNA contained in the deposited clone. In this context "about" includes the particularly recited ranges, larger or smaller by several (5, 4, 3, 2, or 1) nucleotides, at either terminus or at both termini. Preferably, these fragments encode a polypeptide which has biological activity. More preferably, these polynucleotides can be used as probes or primers as discussed herein.

In the present invention, a "polypeptide fragment" refers to a short amino acid sequence contained in SEQ ID NO:Y or encoded by the cDNA contained in the deposited clone. Protein fragments may be "free-standing," or comprised within a larger polypeptide of which the fragment forms a part or region, most preferably as a single continuous region. Representative examples of polypeptide fragments of the invention, include, for example, fragments from about amino acid number 1–20, 21–40, 41–60, 61–80, 81–100, 102–120, 121–140, 141–160, or 161 to the end of the coding region. Moreover, polypeptide fragments can be about 20, 30, 40, 50, 60, 70, 80, 90, 100, 110, 120, 130, 140, or 150 amino acids in length. In this context "about" includes the particularly recited ranges, larger or smaller by several (5, 4, 3, 2, or 1) amino acids, at either extreme or at both extremes.

Preferred polypeptide fragments include the secreted protein as well as the mature form. Further preferred polypeptide fragments include the secreted protein or the mature form having a continuous series of deleted residues from the amino or the carboxy terminus, or both. For example, any number of amino acids, ranging from 1–60, can be deleted from the amino terminus of either the secreted polypeptide or the mature form. Similarly, any number of amino acids, ranging from 1–30, can be deleted from the carboxy terminus of the secreted protein or mature form. Furthermore, any combination of the above amino and carboxy terminus deletions are preferred. Similarly, polynucleotide fragments encoding these polypeptide fragments are also preferred.

Also preferred are polypeptide and polynucleotide fragments characterized by structural or functional domains, such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions. Polypeptide fragments of SEQ ID NO:Y falling within conserved domains are specifically contemplated by the present invention. Moreover, polynucleotide fragments encoding these domains are also contemplated.

Other preferred fragments are biologically active fragments. Biologically active fragments are those exhibiting activity similar, but not necessarily identical, to an activity of the polypeptide of the present invention. The biological activity of the fragments may include an improved desired activity, or a decreased undesirable activity.

Epitopes & Antibodies

In the present invention, "epitopes" refer to polypeptide fragments having antigenic or immunogenic activity in an animal, especially in a human. A preferred embodiment of the present invention relates to a polypeptide fragment comprising an epitope, as well as the polynucleotide encoding this fragment. A region of a protein molecule to which an antibody can bind is defined as an "antigenic epitope." In contrast, an "immunogenic epitope" is defined as a part of a protein that elicits an antibody response. (See, for instance, Geysen et al., Proc. Natl. Acad. Sci. USA 81:3998–4002 (1983).)

Fragments which function as epitopes may be produced by any conventional means. (See, e.g., Houghten, R. A., Proc. Natl. Acad. Sci. USA 82:5131–5135 (1985) further described in U.S. Pat. No. 4,631,211.)

In the present invention, antigenic epitopes preferably contain a sequence of at least seven, more preferably at least nine, and most preferably between about 15 to about 30 amino acids. Antigenic epitopes are useful to raise antibodies, including monoclonal antibodies, that specifically bind the epitope. (See, for instance, Wilson et al., Cell 37:767–778 (1984); Sutcliffe, J. G. et al., Science 219:660–666 (1983).)

Similarly, immunogenic epitopes can be used to induce antibodies according to methods well known in the art. (See, for instance, Sutcliffe et al., supra; Wilson et al., supra; Chow, M. et al., Proc. Natl. Acad. Sci. USA 82:910–914; and Bittle, F. J. et al., J. Gen. Virol. 66:2347–2354 (1985).) A preferred immunogenic epitope includes the secreted protein. The immunogenic epitopes may be presented together with a carrier protein, such as an albumin, to an animal system (such as rabbit or mouse) or, if it is long enough (at least about 25 amino acids), without a carrier. However, immunogenic epitopes comprising as few as 8 to 10 amino acids have been shown to be sufficient to raise antibodies capable of binding to, at the very least, linear epitopes in a denatured polypeptide (e.g., in Western blotting.)

As used herein, the term "antibody" (Ab) or "monoclonal antibody" (Mab) is meant to include intact molecules as well as antibody fragments (such as, for example, Fab and F(ab')2 fragments) which are capable of specifically binding to protein. Fab and F(ab')2 fragments lack the Fc fragment of intact antibody, clear more rapidly from the circulation, and may have less non-specific tissue binding than an intact antibody. (Wahl et al., J. Nucl. Med. 24:316–325 (1983).) Thus, these fragments are preferred, as well as the products of a FAB or other immunoglobulin expression library. Moreover, antibodies of the present invention include chimeric, single chain, and humanized antibodies.

Fusion Proteins

Any polypeptide of the present invention can be used to generate fusion proteins. For example, the polypeptide of the present invention, when fused to a second protein, can be used as an antigenic tag. Antibodies raised against the polypeptide of the present invention can be used to indirectly detect the second protein by binding to the polypeptide. Moreover, because secreted proteins target cellular locations based on trafficking signals, the polypeptides of the present invention can be used as targeting molecules once fused to other proteins.

Examples of domains that can be fused to polypeptides of the present invention include not only heterologous signal sequences, but also other heterologous functional regions. The fusion does not necessarily need to be direct, but may occur through linker sequences.

Moreover, fusion proteins may also be engineered to improve characteristics of the polypeptide of the present invention. For instance, a region of additional amino acids, particularly charged amino acids, may be added to the N-terminus of the polypeptide to improve stability and persistence during purification from the host cell or subsequent handling and storage. Also, peptide moieties may be added to the polypeptide to facilitate purification. Such regions may be removed prior to final preparation of the polypeptide. The addition of peptide moieties to facilitate handling of polypeptides are familiar and routine techniques in the art.

Moreover, polypeptides of the present invention, including fragments, and specifically epitopes, can be combined with parts of the constant domain of immunoglobulins (IgG), resulting in chimeric polypeptides. These fusion proteins facilitate purification and show an increased half-life in vivo. One reported example describes chimeric proteins consisting of the first two domains of the human CD4-polypeptide and various domains of the constant regions of the heavy or light chains of mammalian immunoglobulins. (EP A 394,827; Traunecker et al., Nature 331:84–86 (1988).) Fusion proteins having disulfide-linked dimeric structures (due to the IgG) can also be more efficient in binding and neutralizing other molecules, than the monomeric secreted protein or protein fragment alone. (Fountoulakis et al., J. Biochem. 270:3958–3964 (1995).)

Similarly, EP-A-O 464 533 (Canadian counterpart 2045869) discloses fusion proteins comprising various portions of constant region of immunoglobulin molecules together with another human protein or part thereof. In many cases, the Fc part in a fusion protein is beneficial in therapy and diagnosis, and thus can result in, for example, improved pharmacokinetic properties. (EP-A 0232 262.) Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, D. Bennett et al., J. Molecular Recognition 8:52–58 (1995); K. Johanson et al., J. Biol. Chem. 270:9459–9471 (1995).)

Moreover, the polypeptides of the present invention can be fused to marker sequences, such as a peptide which facilitates purification of the fused polypeptide. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821–824 (1989), for instance, hexa-histidine provides for convenient purification of the fusion protein. Another peptide tag useful for purification, the "HA" tag, corresponds to an epitope derived from the influenza hemagglutinin protein. (Wilson et al., Cell 37:767 (1984).)

Thus, any of these above fusions can be engineered using the polynucleotides or the polypeptides of the present invention.

Vectors, Host Cells, and Protein Production

The present invention also relates to vectors containing the polynucleotide of the present invention, host cells, and the production of polypeptides by recombinant techniques. The vector may be, for example, a phage, plasmid, viral, or retroviral vector. Retroviral vectors may be replication competent or replication defective. In the latter case, viral propagation generally will occur only in complementing host cells.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The polynucleotide insert should be operatively linked to an appropriate promoter, such as the phage lambda PL promoter, the E. coli lac, trp, phoA and tac promoters, the SV40 early and late promoters and promoters of retroviral LTRs, to name a few. Other suitable promoters will be known to the skilled artisan. The expression constructs will further contain sites for transcription initiation, termination, and, in the transcribed region, a ribosome binding site for translation. The coding portion of the transcripts expressed by the constructs will preferably include a translation initiating codon at the beginning and a termination codon (UAA, UGA or UAG) appropriately positioned at the end of the polypeptide to be translated.

As indicated, the expression vectors will preferably include at least one selectable marker. Such markers include dihydrofolate reductase, G418 or neomycin resistance for eukaryotic cell culture and tetracycline, kanamycin or ampicillin resistance genes for culturing in E. coli and other bacteria. Representative examples of appropriate hosts include, but are not limited to, bacterial cells, such as *E. coli*, Streptomyces and Salmonella typhimurium cells; fungal cells, such as yeast cells; insect cells such as Drosophila S2 and Spodoptera Sf9 cells; animal cells such as CHO, COS, 293, and Bowes melanoma cells; and plant cells. Appropriate culture mediums and conditions for the above-described host cells are known in the art.

Among vectors preferred for use in bacteria include pQE70, pQE60 and pQE-9, available from QIAGEN, Inc.; pBluescript vectors, Phagescript vectors, pNH8A, pNH16a, pNH18A, pNH46A, available from Stratagene Cloning Systems, Inc.; and ptrc99a, pKK223-3, pKK233-3, pDR540, pRIT5 available from Pharmacia Biotech, Inc. Among preferred eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

Introduction of the construct into the host cell can be effected by calcium phosphate transfection, DEAE-dextran mediated transfection, cationic lipid-mediated transfection, electroporation, transduction, infection, or other methods. Such methods are described in many standard laboratory manuals, such as Davis et al., Basic Methods In Molecular Biology (1986). It is specifically contemplated that the polypeptides of the present invention may in fact be expressed by a host cell lacking a recombinant vector.

A polypeptide of this invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

Polypeptides of the present invention, and preferably the secreted form, can also be recovered from: products purified from natural sources, including bodily fluids, tissues and cells, whether directly isolated or cultured; products of chemical synthetic procedures; and products produced by recombinant techniques from a prokaryotic or eukaryotic host, including, for example, bacterial, yeast, higher plant, insect, and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes. Thus, it is well known in the art that the N-terminal methionine encoded by the translation initiation codon generally is removed with high efficiency from any protein after translation in all eukaryotic cells. While the N-terminal methionine on most proteins also is efficiently removed in most prokaryotes, for some proteins, this prokaryotic removal process is inefficient, depending on the nature of the amino acid to which the N-terminal methionine is covalently linked.

In addition to encompassing host cells containing the vector constructs discussed herein, the invention also encompasses primary, secondary, and immortalized host cells of vertebrate origin, particularly mammalian origin, that have been engineered to delete or replace endogenous genetic material (e.g., coding sequence), and/or to include genetic material (e.g., heterologous polynucleotide sequences) that is operably associated with the polynucleotides of the invention, and which activates, alters, and/or amplifies endogenous polynucleotides. For example, techniques known in the art may be used to operably associate heterologous control regions (e.g., promoter and/or enhancer) and endogenous polynucleotide sequences via homologous recombination (see, e.g., U.S. Pat. No. 5,641, 670, issued Jun. 24, 1997; International Publication No. WO 96/29411, published Sep. 26, 1996; International Publication No. WO 94/12650, published Aug. 4, 1994; Koller et al., Proc. Natl. Acad. Sci. USA 86:8932–8935 (1989); and Zijlstra et al., Nature 342:435–438 (1989), the disclosures of each of which are incorporated by reference in their entireties).

Uses of the Polynucleotides

Each of the polynucleotides identified herein can be used in numerous ways as reagents. The following description should be considered exemplary and utilizes known techniques.

The polynucleotides of the present invention are useful for chromosome identification. There exists an ongoing need to identify new chromosome markers, since few chromosome marking reagents, based on actual sequence data (repeat polymorphisms), are presently available. Each polynucleotide of the present invention can be used as a chromosome marker.

Briefly, sequences can be mapped to chromosomes by preparing PCR primers (preferably 15–25 bp) from the sequences shown in SEQ ID NO:X. Primers can be selected using computer analysis so that primers do not span more than one predicted exon in the genomic DNA. These primers are then used for PCR screening of somatic cell hybrids containing individual human chromosomes. Only those hybrids containing the human gene corresponding to the SEQ ID NO:X will yield an amplified fragment.

Similarly, somatic hybrids provide a rapid method of PCR mapping the polynucleotides to particular chromosomes. Three or more clones can be assigned per day using a single thermal cycler. Moreover, sublocalization of the polynucleotides can be achieved with panels of specific chromosome fragments. Other gene mapping strategies that can be used include in situ hybridization, prescreening with labeled flow-sorted chromosomes, and preselection by hybridization to construct chromosome specific-cDNA libraries.

Precise chromosomal location of the polynucleotides can also be achieved using fluorescence in situ hybridization (FISH) of a metaphase chromosomal spread. This technique uses polynucleotides as short as 500 or 600 bases; however, polynucleotides 2,000–4,000 bp are preferred. For a review of this technique, see Verma et al., "Human Chromosomes: a Manual of Basic Techniques," Pergamon Press, New York (1988).

For chromosome mapping, the polynucleotides can be used individually (to mark a single chromosome or a single site on that chromosome) or in panels (for marking multiple sites and/or multiple chromosomes). Preferred polynucleotides correspond to the noncoding regions of the cDNAs because the coding sequences are more likely conserved within gene families, thus increasing the chance of cross hybridization during chromosomal mapping.

Once a polynucleotide has been mapped to a precise chromosomal location, the physical position of the polynucleotide can be used in linkage analysis. Linkage analysis establishes coinheritance between a chromosomal location and presentation of a particular disease. (Disease mapping data are found, for example, in V. McKusick, Mendelian Inheritance in Man (available on line through Johns Hopkins University Welch Medical Library).) Assuming 1 megabase mapping resolution and one gene per 20 kb, a cDNA precisely localized to a chromosomal region associated with the disease could be one of 50–500 potential causative genes.

Thus, once coinheritance is established, differences in the polynucleotide and the corresponding gene between affected and unaffected individuals can be examined. First, visible structural alterations in the chromosomes, such as deletions or translocations, are examined in chromosome spreads or by PCR. If no structural alterations exist, the presence of point mutations are ascertained. Mutations observed in some or all affected individuals, but not in normal individuals, indicates that the mutation may cause the disease. However, complete sequencing of the polypeptide and the corresponding gene from several normal individuals is required to distinguish the mutation from a polymorphism. If a new polymorphism is identified, this polymorphic polypeptide can be used for further linkage analysis.

Furthermore, increased or decreased expression of the gene in affected individuals as compared to unaffected individuals can be assessed using polynucleotides of the present invention. Any of these alterations (altered expression, chromosomal rearrangement, or mutation) can be used as a diagnostic or prognostic marker.

In addition to the foregoing, a polynucleotide can be used to control gene expression through triple helix formation or antisense DNA or RNA. Both methods rely on binding of the polynucleotide to DNA or RNA. For these techniques, preferred polynucleotides are usually 20 to 40 bases in length and complementary to either the region of the gene involved in transcription (triple helix—see Lee et al., Nucl. Acids Res. 6:3073 (1979); Cooney et al., Science 241:456 (1988); and Dervan et al., Science 251:1360 (1991)) or to the mRNA itself (antisense—Okano, J. Neurochem. 56:560 (1991); Oligodeoxy-nucleotides as Antisense Inhibitors of Gene Expression, CRC Press, Boca Raton, Fla. (1988).) Triple helix formation optimally results in a shut-off of RNA transcription from DNA, while antisense RNA hybridization blocks translation of an mRNA molecule into polypeptide. Both techniques are effective in model systems, and the information disclosed herein can be used to design antisense or triple helix polynucleotides in an effort to treat disease.

Polynucleotides of the present invention are also useful in gene therapy. One goal of gene therapy is to insert a normal gene into an organism having a defective gene, in an effort to correct the genetic defect. The polynucleotides disclosed in the present invention offer a means of targeting such genetic defects in a highly accurate manner. Another goal is to insert a new gene that was not present in the host genome, thereby producing a new trait in the host cell.

The polynucleotides are also useful for identifying individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identifying personnel. This method does not suffer from the current limitations of "Dog Tags" which can be lost, switched, or stolen, making positive identification difficult. The polynucleotides of the present invention can be used as additional DNA markers for RFLP.

The polynucleotides of the present invention can also be used as an alternative to RFLP, by determining the actual base-by-base DNA sequence of selected portions of an individual's genome. These sequences can be used to prepare PCR primers for amplifying and isolating such selected DNA, which can then be sequenced. Using this technique, individuals can be identified because each individual will have a unique set of DNA sequences. Once an unique ID database is established for an individual, positive identification of that individual, living or dead, can be made from extremely small tissue samples.

Forensic biology also benefits from using DNA-based identification techniques as disclosed herein. DNA sequences taken from very small biological samples such as tissues, e.g., hair or skin, or body fluids, e.g., blood, saliva, semen, etc., can be amplified using PCR. In one prior art technique, gene sequences amplified from polymorphic loci, such as DQa class II HLA gene, are used in forensic biology to identify individuals. (Erlich, H., PCR Technology, Freeman and Co. (1992).) Once these specific polymorphic loci are amplified, they are digested with one or more restriction enzymes, yielding an identifying set of bands on a Southern blot probed with DNA corresponding to the DQa class II HLA gene. Similarly, polynucleotides of the present invention can be used as polymorphic markers for forensic purposes.

There is also a need for reagents capable of identifying the source of a particular tissue. Such need arises, for example, in forensics when presented with tissue of unknown origin. Appropriate reagents can comprise, for example, DNA probes or primers specific to particular tissue prepared from the sequences of the present invention. Panels of such reagents can identify tissue by species and/or by organ type. In a similar fashion, these reagents can be used to screen tissue cultures for contamination.

In the very least, the polynucleotides of the present invention can be used as molecular weight markers on Southern gels, as diagnostic probes for the presence of a specific mRNA in a particular cell type, as a probe to "subtract-out" known sequences in the process of discovering novel polynucleotides, for selecting and making oligomers for attachment to a "gene chip" or other support, to raise anti-DNA antibodies using DNA immunization techniques, and as an antigen to elicit an immune response.

Uses of the Polypeptides

Each of the polypeptides identified herein can be used in numerous ways. The following description should be considered exemplary and utilizes known techniques.

A polypeptide of the present invention can be used to assay protein levels in a biological sample using antibody-based techniques. For example, protein expression in tissues can be studied with classical immunohistological methods. (Jalkanen, M., et al., J. Cell. Biol. 101:976–985 (1985); Jalkanen, M., et al., J. Cell . Biol. 105:3087–3096 (1987).) Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase, and radioisotopes, such as iodine ($125I$, $121I$), carbon ($14C$), sulfur ($35S$), tritium ($3H$), indium ($112In$), and technetium ($99mTc$), and fluorescent labels, such as fluorescein and rhodamine, and biotin.

In addition to assaying secreted protein levels in a biological sample, proteins can also be detected in vivo by imaging. Antibody labels or markers for in vivo imaging of protein include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma.

A protein-specific antibody or antibody fragment which has been labeled with an appropriate detectable imaging moiety, such as a radioisotope (for example, 131I, 112In, 99mTc), a radio-opaque substance, or a material detectable by nuclear magnetic resonance, is introduced (for example, parenterally, subcutaneously, or intraperitoneally) into the mammal. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of 99mTc. The labeled antibody or antibody fragment will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).)

Thus, the invention provides a diagnostic method of a disorder, which involves (a) assaying the expression of a polypeptide of the present invention in cells or body fluid of an individual; (b) comparing the level of gene expression with a standard gene expression level, whereby an increase or decrease in the assayed polypeptide gene expression level compared to the standard expression level is indicative of a disorder.

Moreover, polypeptides of the present invention can be used to treat disease. For example, patients can be administered a polypeptide of the present invention in an effort to replace absent or decreased levels of the polypeptide (e.g., insulin), to supplement absent or decreased levels of a different polypeptide (e.g., hemoglobin S for hemoglobin B), to inhibit the activity of a polypeptide (e.g., an oncogene), to activate the activity of a polypeptide (e.g., by binding to a receptor), to reduce the activity of a membrane bound receptor by competing with it for free ligand (e.g., soluble TNF receptors used in reducing inflammation), or to bring about a desired response (e.g., blood vessel growth).

Similarly, antibodies directed to a polypeptide of the present invention can also be used to treat disease. For example, administration of an antibody directed to a polypeptide of the present invention can bind and reduce overproduction of the polypeptide. Similarly, administration of an antibody can activate the polypeptide, such as by binding to a polypeptide bound to a membrane (receptor).

At the very least, the polypeptides of the present invention can be used as molecular weight markers on SDS-PAGE gels or on molecular sieve gel filtration columns using methods well known to those of skill in the art. Polypeptides can also be used to raise antibodies, which in turn are used to measure protein expression from a recombinant cell, as a way of assessing transformation of the host cell. Moreover, the polypeptides of the present invention can be used to test the following biological activities.

Biological Activities

The polynucleotides and polypeptides of the present invention can be used in assays to test for one or more biological activities. If these polynucleotides and polypeptides do exhibit activity in a particular assay, it is likely that these molecules may be involved in the diseases associated with the biological activity. Thus, the polynucleotides and polypeptides could be used to treat the associated disease.

Immune Activity

A polypeptide or polynucleotide of the present invention may be useful in treating deficiencies or disorders of the immune system, by activating or inhibiting the proliferation, differentiation, or mobilization (chemotaxis) of immune cells. Immune cells develop through a process called hematopoiesis, producing myeloid (platelets, red blood cells, neutrophils, and macrophages) and lymphoid (B and T lymphocytes) cells from pluripotent stem cells. The etiology of these immune deficiencies or disorders may be genetic, somatic, such as cancer or some autoimmune disorders, acquired (e.g., by chemotherapy or toxins), or infectious. Moreover, a polynucleotide or polypeptide of the present invention can be used as a marker or detector of a particular immune system disease or disorder.

A polynucleotide or polypeptide of the present invention may be useful in treating or detecting deficiencies or disorders of hematopoietic cells. A polypeptide or polynucleotide of the present invention could be used to increase differentiation and proliferation of hematopoietic cells, including the pluripotent stem cells, in an effort to treat those disorders associated with a decrease in certain (or many) types hematopoietic cells. Examples of immunologic deficiency syndromes include, but are not limited to: blood protein disorders (e.g. agammaglobulinemia, dysgammaglobulinemia), ataxia telangiectasia, common variable immunodeficiency, Digeorge Syndrome, HIV infection, HTLV-BLV infection, leukocyte adhesion deficiency syndrome, lymphopenia, phagocyte bactericidal dysfunction, severe combined immunodeficiency (SCIDs), Wiskott-Aldrich Disorder, anemia, thrombocytopenia, or hemoglobinuria.

Moreover, a polypeptide or polynucleotide of the present invention could also be used to modulate hemostatic (the stopping of bleeding) or thrombolytic activity (clot formation). For example, by increasing hemostatic or thrombolytic activity, a polynucleotide or polypeptide of the present invention could be used to treat blood coagulation disorders (e.g., afibrinogenemia, factor deficiencies), blood platelet disorders (e.g. thrombocytopenia), or wounds resulting from trauma, surgery, or other causes. Alternatively, a polynucleotide or polypeptide of the present invention that can decrease hemostatic or thrombolytic activity could be used to inhibit or dissolve clotting. These molecules could be important in the treatment of heart attacks (infarction), strokes, or scarring.

A polynucleotide or polypeptide of the present invention may also be useful in treating or detecting autoimmune disorders. Many autoimmune disorders result from inappropriate recognition of self as foreign material by immune cells. This inappropriate recognition results in an immune response leading to the destruction of the host tissue. Therefore, the administration of a polypeptide or polynucleotide of the present invention that inhibits an immune response, particularly the proliferation, differentiation, or chemotaxis of T-cells, may be an effective therapy in preventing autoimmune disorders.

Examples of autoimmune disorders that can be treated or detected by the present invention include, but are not limited to: Addison's Disease, hemolytic anemia, antiphospholipid syndrome, rheumatoid arthritis, dermatitis, allergic encephalomyelitis, glomerulonephritis, Goodpasture's Syndrome, Graves' Disease, Multiple Sclerosis, Myasthenia Gravis, Neuritis, Ophthalmia, Bullous Pemphigoid, Pemphigus, Polyendocrinopathies, Purpura, Reiter's Disease, Stiff-Man Syndrome, Autoimmune Thyroiditis, Systemic Lupus Erythematosus, Autoimmune Pulmonary Inflammation, Guillain-Barre Syndrome, insulin dependent diabetes mellitis, and autoimmune inflammatory eye disease.

Similarly, allergic reactions and conditions, such as asthma (particularly allergic asthma) or other respiratory problems, may also be treated by a polypeptide or polynucleotide of the present invention. Moreover, these molecules can be used to treat anaphylaxis, hypersensitivity to an antigenic molecule, or blood group incompatibility.

A polynucleotide or polypeptide of the present invention may also be used to treat and/or prevent organ rejection or graft-versus-host disease (GVHD). Organ rejection occurs by host immune cell destruction of the transplanted tissue through an immune response. Similarly, an immune response is also involved in GVHD, but, in this case, the foreign transplanted immune cells destroy the host tissues. The administration of a polypeptide or polynucleotide of the present invention that inhibits an immune response, particularly the proliferation, differentiation, or chemotaxis of T-cells, may be an effective therapy in preventing organ rejection or GVHD.

Similarly, a polypeptide or polynucleotide of the present invention may also be used to modulate inflammation. For example, the polypeptide or polynucleotide may inhibit the proliferation and differentiation of cells involved in an inflammatory response. These molecules can be used to treat inflammatory conditions, both chronic and acute conditions, including inflammation associated with infection (e.g., septic shock, sepsis, or systemic inflammatory response syndrome (SIRS)), ischemia-reperfusion injury, endotoxin lethality, arthritis, complement-mediated hyperacute rejection, nephritis, cytokine or chemokine induced lung injury, inflammatory bowel disease, Crohn's disease, or resulting from over production of cytokines (e.g., TNF or IL-1.)

Hyperproliferative Disorders

A polypeptide or polynucleotide can be used to treat or detect hyperproliferative disorders, including neoplasms. A polypeptide or polynucleotide of the present invention may inhibit the proliferation of the disorder through direct or indirect interactions. Alternatively, a polypeptide or polynucleotide of the present invention may proliferate other cells which can inhibit the hyperproliferative disorder.

For example, by increasing an immune response, particularly increasing antigenic qualities of the hyperproliferative disorder or by proliferating, differentiating, or mobilizing T-cells, hyperproliferative disorders can be treated. This immune response may be increased by either enhancing an existing immune response, or by initiating a new immune response. Alternatively, decreasing an immune response may also be a method of treating hyperproliferative disorders, such as a chemotherapeutic agent.

Examples of hyperproliferative disorders that can be treated or detected by a polynucleotide or polypeptide of the present invention include, but are not limited to neoplasms located in the: abdomen, bone, breast, digestive system, liver, pancreas, peritoneum, endocrine glands (adrenal, parathyroid, pituitary, testicles, ovary, thymus, thyroid), eye, head and neck, nervous (central and peripheral), lymphatic system, pelvic, skin, soft tissue, spleen, thoracic, and urogenital.

Similarly, other hyperproliferative disorders can also be treated or detected by a polynucleotide or polypeptide of the present invention. Examples of such hyperproliferative disorders include, but are not limited to: hypergammaglobulinemia, lymphoproliferative disorders, paraproteinemias, purpura, sarcoidosis, Sezary Syndrome, Waldenstron's Macroglobulinemia, Gaucher's Disease, histiocytosis, and any other hyperproliferative disease, besides neoplasia, located in an organ system listed above.

Infectious Disease

A polypeptide or polynucleotide of the present invention can be used to treat or detect infectious agents. For example, by increasing the immune response, particularly increasing the proliferation and differentiation of B and/or T cells, infectious diseases may be treated. The immune response may be increased by either enhancing an existing immune response, or by initiating a new immune response. Alternatively, the polypeptide or polynucleotide of the present invention may also directly inhibit the infectious agent, without necessarily eliciting an immune response.

Viruses are one example of an infectious agent that can cause disease or symptoms that can be treated or detected by a polynucleotide or polypeptide of the present invention. Examples of viruses, include, but are not limited to the following DNA and RNA viral families: Arbovirus, Adenoviridae, Arenaviridae, Arterivirus, Birnaviridae, Bunyaviridae, Caliciviridae, Circoviridae, Coronaviridae, Flaviviridae, Hepadnaviridae (Hepatitis), Herpesviridae (such as, Cytomegalovirus, Herpes Simplex, Herpes Zoster), Mononegavirus (e.g., Paramyxoviridae, Morbillivirus, Rhabdoviridae), Orthomyxoviridae (e.g., Influenza), Papovaviridae, Parvoviridae, Picornaviridae, Poxviridae (such as Smallpox or Vaccinia), Reoviridae (e.g., Rotavirus), Retroviridae (HTLV-I, HTLV-II, Lentivirus), and Togaviridae (e.g., Rubivirus). Viruses falling within these families can cause a variety of diseases or symptoms, including, but not limited to: arthritis, bronchiollitis, encephalitis, eye infections (e.g., conjunctivitis, keratitis), chronic fatigue syndrome, hepatitis (A, B, C, E, Chronic Active, Delta), meningitis, opportunistic infections (e.g., AIDS), pneumonia, Burkitt's Lymphoma, chickenpox, hemorrhagic fever, Measles, Mumps, Parainfluenza, Rabies, the common cold, Polio, leukemia, Rubella, sexually transmitted diseases, skin diseases (e.g., Kaposi's, warts), and viremia. A polypeptide or polynucleotide of the present invention can be used to treat or detect any of these symptoms or diseases.

Similarly, bacterial or fungal agents that can cause disease or symptoms and that can be treated or detected by a polynucleotide or polypeptide of the present invention include, but not limited to, the following Gram-Negative and Gram-positive bacterial families and fungi: Actinomycetales (e.g., Corynebacterium, Mycobacterium, Norcardia), Aspergillosis, Bacillaceae (e.g., Anthrax, Clostridium), Bacteroidaceae, Blastomycosis, Bordetella, Borrelia, Brucellosis, Candidiasis, Campylobacter, Coccidioidomycosis, Cryptococcosis, Dermatocycoses, Enterobacteriaceae (Klebsiella, Salmonella, Serratia, Yersinia), Erysipelothrix, Helicobacter, Legionellosis, Leptospirosis, Listeria, Mycoplasmatales, Neisseriaceae (e.g., Acinetobacter, Gonorrhea, Menigococcal), Pasteurellacea Infections (e.g., Actinobacillus, Heamophilus, Pasteurella), Pseudomonas, Rickettsiaceae, Chlamydiaceae, Syphilis, and Staphylococcal. These bacterial or fungal families can cause the following diseases or symptoms, including, but not limited to: bacteremia, endocarditis, eye infections (conjunctivitis, tuberculosis, uveitis), gingivitis, opportunistic infections (e.g., AIDS related infections), paronychia, prosthesis-related infections, Reiter's Disease, respiratory tract infections, such as Whooping Cough or Empyema, sepsis, Lyme Disease, Cat-Scratch Disease, Dysentery, Paratyphoid Fever, food poisoning, Typhoid, pneumonia, Gonorrhea, meningitis, Chlamydia, Syphilis, Diphtheria, Leprosy, Paratuberculosis, Tuberculosis, Lupus, Botulism, gangrene, tetanus, impetigo, Rheumatic Fever, Scarlet Fever, sexually transmitted diseases, skin diseases (e.g., cellulitis, dermatocycoses), toxemia, urinary tract infections, wound infections. A polypeptide or polynucleotide of the present invention can be used to treat or detect any of these symptoms or diseases.

Moreover, parasitic agents causing disease or symptoms that can be treated or detected by a polynucleotide or polypeptide of the present invention include, but not limited to, the following families: Amebiasis, Babesiosis, Coccidiosis, Cryptosporidiosis, Dientamoebiasis, Dourine, Ectoparasitic, Giardiasis, Helminthiasis, Leishmaniasis, Theileriasis, Toxoplasmosis, Trypanosomiasis, and Trichomonas. These parasites can cause a variety of diseases or symptoms, including, but not limited to: Scabies, Trombiculiasis, eye infections, intestinal disease (e.g., dysentery, giardiasis), liver disease, lung disease, opportunistic infections (e.g., AIDS related), Malaria, pregnancy complications, and toxoplasmosis. A polypeptide or polynucleotide of the present invention can be used to treat or detect any of these symptoms or diseases.

Preferably, treatment using a polypeptide or polynucleotide of the present invention could either be by administering an effective amount of a polypeptide to the patient, or by removing cells from the patient, supplying the cells with a polynucleotide of the present invention, and returning the engineered cells to the patient (ex vivo therapy). Moreover, the polypeptide or polynucleotide of the present invention can be used as an antigen in a vaccine to raise an immune response against infectious disease.

Regeneration

A polynucleotide or polypeptide of the present invention can be used to differentiate, proliferate, and attract cells, leading to the regeneration of tissues. (See, Science 276:59–87 (1997).) The regeneration of tissues could be used to repair, replace, or protect tissue damaged by congenital defects, trauma (wounds, burns, incisions, or ulcers), age, disease (e.g. osteoporosis, osteocarthritis, periodontal disease, liver failure), surgery, including cosmetic plastic surgery, fibrosis, reperfusion injury, or systemic cytokine damage.

Tissues that could be regenerated using the present invention include organs (e.g., pancreas, liver, intestine, kidney, skin, endothelium), muscle (smooth, skeletal or cardiac), vasculature (including vascular and lymphatics), nervous, hematopoietic, and skeletal (bone, cartilage, tendon, and ligament) tissue. Preferably, regeneration occurs without or decreased scarring. Regeneration also may include angiogenesis.

Moreover, a polynucleotide or polypeptide of the present invention may increase regeneration of tissues difficult to heal. For example, increased tendon/ligament regeneration would quicken recovery time after damage. A polynucleotide or polypeptide of the present invention could also be used prophylactically in an effort to avoid damage. Specific diseases that could be treated include of tendinitis, carpal tunnel syndrome, and other tendon or ligament defects. A further example of tissue regeneration of non-healing wounds includes pressure ulcers, ulcers associated with vascular insufficiency, surgical, and traumatic wounds.

Similarly, nerve and brain tissue could also be regenerated by using a polynucleotide or polypeptide of the present invention to proliferate and differentiate nerve cells. Diseases that could be treated using this method include central and peripheral nervous system diseases, neuropathies, or mechanical and traumatic disorders (e.g., spinal cord disorders, head trauma, cerebrovascular disease, and stoke). Specifically, diseases associated with peripheral nerve injuries, peripheral neuropathy (e.g., resulting from chemotherapy or other medical therapies), localized neuropathies, and central nervous system diseases (e.g., Alzheimer's disease, Parkinson's disease, Huntington's disease, amyotrophic lateral sclerosis, and ShyDrager syndrome), could all be treated using the polynucleotide or polypeptide of the present invention.

Chemotaxis

A polynucleotide or polypeptide of the present invention may have chemotaxis activity. A chemotaxic molecule attracts or mobilizes cells (e.g., monocytes, fibroblasts, neutrophils, T-cells, mast cells, eosinophils, epithelial and/or endothelial cells) to a particular site in the body, such as inflammation, infection, or site of hyperproliferation. The mobilized cells can then fight off and/or heal the particular trauma or abnormality.

A polynucleotide or polypeptide of the present invention may increase chemotaxic activity of particular cells. These chemotactic molecules can then be used to treat inflammation, infection, hyperproliferative disorders, or any immune system disorder by increasing the number of cells targeted to a particular location in the body. For example, chemotaxic molecules can be used to treat wounds and other trauma to tissues by attracting immune cells to the injured location. Chemotactic molecules of the present invention can also attract fibroblasts, which can be used to treat wounds.

It is also contemplated that a polynucleotide or polypeptide of the present invention may inhibit chemotactic activity. These molecules could also be used to treat disorders. Thus, a polynucleotide or polypeptide of the present invention could be used as an inhibitor of chemotaxis.

Binding Activity

A polypeptide of the present invention may be used to screen for molecules that bind to the polypeptide or for molecules to which the polypeptide binds. The binding of the polypeptide and the molecule may activate (agonist), increase, inhibit (antagonist), or decrease activity of the polypeptide or the molecule bound. Examples of such molecules include antibodies, oligonucleotides, proteins (e.g., receptors), or small molecules.

Preferably, the molecule is closely related to the natural ligand of the polypeptide, e.g., a fragment of the ligand, or a natural substrate, a ligand, a structural or functional mimetic. (See, Coligan et al., Current Protocols in Immunology 1(2):Chapter 5 (1991).) Similarly, the molecule can be closely related to the natural receptor to which the polypeptide binds, or at least, a fragment of the receptor capable of being bound by the polypeptide (e.g., active site). In either case, the molecule can be rationally designed using known techniques.

Preferably, the screening for these molecules involves producing appropriate cells which express the polypeptide, either as a secreted protein or on the cell membrane. Preferred cells include cells from mammals, yeast, Drosophila, or *E. coli*. Cells expressing the polypeptide (or cell membrane containing the expressed polypeptide) are then preferably contacted with a test compound potentially containing the molecule to observe binding, stimulation, or inhibition of activity of either the polypeptide or the molecule.

The assay may simply test binding of a candidate compound to the polypeptide, wherein binding is detected by a label, or in an assay involving competition with a labeled competitor. Further, the assay may test whether the candidate compound results in a signal generated by binding to the polypeptide.

Alternatively, the assay can be carried out using cell-free preparations, polypeptide/molecule affixed to a solid support, chemical libraries, or natural product mixtures. The assay may also simply comprise the steps of mixing a candidate compound with a solution containing a polypeptide, measuring polypeptide/molecule activity or binding, and comparing the polypeptide/molecule activity or binding to a standard.

Preferably, an ELISA assay can measure polypeptide level or activity in a sample (e.g., biological sample) using a monoclonal or polyclonal antibody. The antibody can measure polypeptide level or activity by either binding, directly or indirectly, to the polypeptide or by competing with the polypeptide for a substrate.

All of these above assays can be used as diagnostic or prognostic markers. The molecules discovered using these assays can be used to treat disease or to bring about a particular result in a patient (e.g., blood vessel growth) by activating or inhibiting the polypeptide/molecule. Moreover, the assays can discover agents which may inhibit or enhance the production of the polypeptide from suitably manipulated cells or tissues.

Therefore, the invention includes a method of identifying compounds which bind to a polypeptide of the invention comprising the steps of: (a) incubating a candidate binding compound with a polypeptide of the invention; and (b) determining if binding has occurred. Moreover, the invention includes a method of identifying agonists/antagonists comprising the steps of: (a) incubating a candidate compound with a polypeptide of the invention, (b) assaying a biological activity, and (b) determining if a biological activity of the polypeptide has been altered.

Other Activities

A polypeptide or polynucleotide of the present invention may also increase or decrease the differentiation or proliferation of embryonic stem cells, besides, as discussed above, hematopoietic lineage.

A polypeptide or polynucleotide of the present invention may also be used to modulate mammalian characteristics, such as body height, weight, hair color, eye color, skin, percentage of adipose tissue, pigmentation, size, and shape (e.g., cosmetic surgery). Similarly, a polypeptide or polynucleotide of the present invention may be used to modulate mammalian metabolism affecting catabolism, anabolism, processing, utilization, and storage of energy.

A polypeptide or polynucleotide of the present invention may be used to change a mammal's mental state or physical state by influencing biorhythms, caricadic rhythms, depression (including depressive disorders), tendency for violence, tolerance for pain, reproductive capabilities (preferably by Activin or Inhibin-like activity), hormonal or endocrine levels, appetite, libido, memory, stress, or other cognitive qualities.

A polypeptide or polynucleotide of the present invention may also be used as a food additive or preservative, such as to increase or decrease storage capabilities, fat content, lipid, protein, carbohydrate, vitamins, minerals, cofactors or other nutritional components.

Other Preferred Embodiments

Other preferred embodiments of the claimed invention include an isolated nucleic acid molecule comprising a nucleotide sequence which is at least 95% identical to a sequence of at least about 50 contiguous nucleotides in the nucleotide sequence of SEQ ID NO:X wherein X is any integer as defined in Table 1.

Also preferred is a nucleic acid molecule wherein said sequence of contiguous nucleotides is included in the nucleotide sequence of SEQ ID NO:X in the range of positions beginning with the nucleotide at about the position of the 5' Nucleotide of the Clone Sequence and ending with the nucleotide at about the position of the 3' Nucleotide of the Clone Sequence as defined for SEQ ID NO:X in Table 1.

Also preferred is a nucleic acid molecule wherein said sequence of contiguous nucleotides is included in the nucleotide sequence of SEQ ID NO:X in the range of positions beginning with the nucleotide at about the position of the 5' Nucleotide of the Start Codon and ending with the nucleotide at about the position of the 3' Nucleotide of the Clone Sequence as defined for SEQ ID NO:X in Table 1.

Similarly preferred is a nucleic acid molecule wherein said sequence of contiguous nucleotides is included in the nucleotide sequence of SEQ ID NO:X in the range of positions beginning with the nucleotide at about the position of the 5' Nucleotide of the First Amino Acid of the Signal Peptide and ending with the nucleotide at about the position of the 3' Nucleotide of the Clone Sequence as defined for SEQ ID NO:X in Table 1.

Also preferred is an isolated nucleic acid molecule comprising a nucleotide sequence which is at least 95% identical to a sequence of at least about 150 contiguous nucleotides in the nucleotide sequence of SEQ ID NO:X.

Further preferred is an isolated nucleic acid molecule comprising a nucleotide sequence which is at least 95% identical to a sequence of at least about 500 contiguous nucleotides in the nucleotide sequence of SEQ ID NO:X.

A further preferred embodiment is a nucleic acid molecule comprising a nucleotide sequence which is at least 95% identical to the nucleotide sequence of SEQ ID NO:X beginning with the nucleotide at about the position of the 5' Nucleotide of the First Amino Acid of the Signal Peptide and ending with the nucleotide at about the position of the 3' Nucleotide of the Clone Sequence as defined for SEQ ID NO:X in Table 1.

A further preferred embodiment is an isolated nucleic acid molecule comprising a nucleotide sequence which is at least 95% identical to the complete nucleotide sequence of SEQ ID NO:X.

Also preferred is an isolated nucleic acid molecule which hybridizes under stringent hybridization conditions to a nucleic acid molecule, wherein said nucleic acid molecule which hybridizes does not hybridize under stringent hybridization conditions to a nucleic acid molecule having a nucleotide sequence consisting of only A residues or of only T residues.

Also preferred is a composition of matter comprising a DNA molecule which comprises a human cDNA clone identified by a cDNA Clone Identifier in Table 1, which DNA molecule is contained in the material deposited with the American Type Culture Collection and given the ATCC Deposit Number shown in Table 1 for said cDNA Clone Identifier.

Also preferred is an isolated nucleic acid molecule comprising a nucleotide sequence which is at least 95% identical to a sequence of at least 50 contiguous nucleotides in the nucleotide sequence of a human cDNA clone identified by a cDNA Clone Identifier in Table 1, which DNA molecule is contained in the deposit given the ATCC Deposit Number shown in Table 1.

Also preferred is an isolated nucleic acid molecule, wherein said sequence of at least 50 contiguous nucleotides is included in the nucleotide sequence of the complete open reading frame sequence encoded by said human cDNA clone.

Also preferred is an isolated nucleic acid molecule comprising a nucleotide sequence which is at least 95% identical to sequence of at least 150 contiguous nucleotides in the nucleotide sequence encoded by said human cDNA clone.

A further preferred embodiment is an isolated nucleic acid molecule comprising a nucleotide sequence which is at least 95% identical to sequence of at least 500 contiguous nucleotides in the nucleotide sequence encoded by said human cDNA clone.

A further preferred embodiment is an isolated nucleic acid molecule comprising a nucleotide sequence which is at least 95% identical to the complete nucleotide sequence encoded by said human cDNA clone.

A further preferred embodiment is a method for detecting in a biological sample a nucleic acid molecule comprising a nucleotide sequence which is at least 95% identical to a sequence of at least 50 contiguous nucleotides in a sequence selected from the group consisting of: a nucleotide sequence of SEQ ID NO:X wherein X is any integer as defined in Table 1; and a nucleotide sequence encoded by a human cDNA clone identified by a cDNA Clone Identifier in Table 1 and contained in the deposit with the ATCC Deposit Number shown for said cDNA clone in Table 1; which method comprises a step of comparing a nucleotide sequence of at least one nucleic acid molecule in said sample with a sequence selected from said group and determining whether the sequence of said nucleic acid molecule in said sample is at least 95% identical to said selected sequence.

Also preferred is the above method wherein said step of comparing sequences comprises determining the extent of nucleic acid hybridization between nucleic acid molecules in said sample and a nucleic acid molecule comprising said sequence selected from said group. Similarly, also preferred is the above method wherein said step of comparing sequences is performed by comparing the nucleotide sequence determined from a nucleic acid molecule in said sample with said sequence selected from said group. The nucleic acid molecules can comprise DNA molecules or RNA molecules.

A further preferred embodiment is a method for identifying the species, tissue or cell type of a biological sample which method comprises a step of detecting nucleic acid molecules in said sample, if any, comprising a nucleotide sequence that is at least 95% identical to a sequence of at least 50 contiguous nucleotides in a sequence selected from the group consisting of: a nucleotide sequence of SEQ ID NO:X wherein X is any integer as defined in Table 1; and a nucleotide sequence encoded by a human cDNA clone identified by a cDNA Clone Identifier in Table 1 and contained in the deposit with the ATCC Deposit Number shown for said cDNA clone in Table 1.

The method for identifying the species, tissue or cell type of a biological sample can comprise a step of detecting nucleic acid molecules comprising a nucleotide sequence in a panel of at least two nucleotide sequences, wherein at least one sequence in said panel is at least 95% identical to a sequence of at least 50 contiguous nucleotides in a sequence selected from said group.

Also preferred is a method for diagnosing in a subject a pathological condition associated with abnormal structure or expression of a gene encoding a secreted protein identified in Table 1, which method comprises a step of detecting in a biological sample obtained from said subject nucleic acid molecules, if any, comprising a nucleotide sequence that is at least 95% identical to a sequence of at least 50 contiguous nucleotides in a sequence selected from the group consisting of: a nucleotide sequence of SEQ ID NO:X wherein X is any integer as defined in Table 1; and a nucleotide sequence encoded by a human cDNA clone identified by a cDNA Clone Identifier in Table 1 and contained in the deposit with the ATCC Deposit Number shown for said cDNA clone in Table 1.

The method for diagnosing a pathological condition can comprise a step of detecting nucleic acid molecules comprising a nucleotide sequence in a panel of at least two nucleotide sequences, wherein at least one sequence in said panel is at least 95% identical to a sequence of at least 50 contiguous nucleotides in a sequence selected from said group.

Also preferred is a composition of matter comprising isolated nucleic acid molecules wherein the nucleotide sequences of said nucleic acid molecules comprise a panel of at least two nucleotide sequences, wherein at least one sequence in said panel is at least 95% identical to a sequence of at least 50 contiguous nucleotides in a sequence selected from the group consisting of: a nucleotide sequence of SEQ ID NO:X wherein X is any integer as defined in Table 1; and a nucleotide sequence encoded by a human cDNA clone identified by a cDNA Clone Identifier in Table 1 and contained in the deposit with the ATCC Deposit Number shown for said cDNA clone in Table 1. The nucleic acid molecules can comprise DNA molecules or RNA molecules.

Also preferred is an isolated polypeptide comprising an amino acid sequence at least 90% identical to a sequence of at least about 10 contiguous amino acids in the amino acid sequence of SEQ ID NO:Y wherein Y is any integer as defined in Table 1.

Also preferred is a polypeptide, wherein said sequence of contiguous amino acids is included in the amino acid sequence of SEQ ID NO:Y in the range of positions beginning with the residue at about the position of the First Amino Acid of the Secreted Portion and ending with the residue at about the Last Amino Acid of the Open Reading Frame as set forth for SEQ ID NO:Y in Table 1.

Also preferred is an isolated polypeptide comprising an amino acid sequence at least 95% identical to a sequence of at least about 30 contiguous amino acids in the amino acid sequence of SEQ ID NO:Y.

Further preferred is an isolated polypeptide comprising an amino acid sequence at least 95% identical to a sequence of at least about 100 contiguous amino acids in the amino acid sequence of SEQ ID NO:Y.

Further preferred is an isolated polypeptide comprising an amino acid sequence at least 95% identical to the complete amino acid sequence of SEQ ID NO:Y.

Further preferred is an isolated polypeptide comprising an amino acid sequence at least 90% identical to a sequence of at least about 10 contiguous amino acids in the complete amino acid sequence of a secreted protein encoded by a human cDNA clone identified by a cDNA Clone Identifier in Table 1 and contained in the deposit with the ATCC Deposit Number shown for said cDNA clone in Table 1.

Also preferred is a polypeptide wherein said sequence of contiguous amino acids is included in the amino acid sequence of a secreted portion of the secreted protein encoded by a human cDNA clone identified by a cDNA Clone Identifier in Table 1 and contained in the deposit with the ATCC Deposit Number shown for said cDNA clone in Table 1.

Also preferred is an isolated polypeptide comprising an amino acid sequence at least 95% identical to a sequence of at least about 30 contiguous amino acids in the amino acid sequence of the secreted portion of the protein encoded by a human cDNA clone identified by a cDNA Clone Identifier in Table 1 and contained in the deposit with the ATCC Deposit Number shown for said cDNA clone in Table 1.

Also preferred is an isolated polypeptide comprising an amino acid sequence at least 95% identical to a sequence of at least about 100 contiguous amino acids in the amino acid sequence of the secreted portion of the protein encoded by a human cDNA clone identified by a cDNA Clone Identifier in Table 1 and contained in the deposit with the ATCC Deposit Number shown for said cDNA clone in Table 1.

Also preferred is an isolated polypeptide comprising an amino acid sequence at least 95% identical to the amino acid sequence of the secreted portion of the protein encoded by a human cDNA clone identified by a cDNA Clone Identifier in Table 1 and contained in the deposit with the ATCC Deposit Number shown for said cDNA clone in Table 1.

Further preferred is an isolated antibody which binds specifically to a polypeptide comprising an amino acid sequence that is at least 90% identical to a sequence of at least 10 contiguous amino acids in a sequence selected from the group consisting of: an amino acid sequence of SEQ ID NO:Y wherein Y is any integer as defined in Table 1; and a complete amino acid sequence of a protein encoded by a human cDNA clone identified by a cDNA Clone Identifier in Table 1 and contained in the deposit with the ATCC Deposit Number shown for said cDNA clone in Table 1.

Further preferred is a method for detecting in a biological sample a polypeptide comprising an amino acid sequence which is at least 90% identical to a sequence of at least 10 contiguous amino acids in a sequence selected from the group consisting of: an amino acid sequence of SEQ ID NO:Y wherein Y is any integer as defined in Table 1; and a complete amino acid sequence of a protein encoded by a human cDNA clone identified by a cDNA Clone Identifier in Table 1 and contained in the deposit with the ATCC Deposit Number shown for said cDNA clone in Table 1; which method comprises a step of comparing an amino acid sequence of at least one polypeptide molecule in said sample with a sequence selected from said group and determining whether the sequence of said polypeptide molecule in said sample is at least 90% identical to said sequence of at least 10 contiguous amino acids.

Also preferred is the above method wherein said step of comparing an amino acid sequence of at least one polypeptide molecule in said sample with a sequence selected from said group comprises determining the extent of specific binding of polypeptides in said sample to an antibody which binds specifically to a polypeptide comprising an amino acid sequence that is at least 90% identical to a sequence of at least 10 contiguous amino acids in a sequence selected from the group consisting of: an amino acid sequence of SEQ ID NO:Y wherein Y is any integer as defined in Table 1; and a complete amino acid sequence of a protein encoded by a human cDNA clone identified by a cDNA Clone Identifier in Table 1 and contained in the deposit with the ATCC Deposit Number shown for said cDNA clone in Table 1.

Also preferred is the above method wherein said step of comparing sequences is performed by comparing the amino acid sequence determined from a polypeptide molecule in said sample with said sequence selected from said group.

Also preferred is a method for identifying the species, tissue or cell type of a biological sample which method comprises a step of detecting polypeptide molecules in said sample, if any, comprising an amino acid sequence that is at least 90% identical to a sequence of at least 10 contiguous amino acids in a sequence selected from the group consisting of: an amino acid sequence of SEQ ID NO:Y wherein Y is any integer as defined in Table 1; and a complete amino acid sequence of a secreted protein encoded by a human cDNA clone identified by a cDNA Clone Identifier in Table 1 and contained in the deposit with the ATCC Deposit Number shown for said cDNA clone in Table 1.

Also preferred is the above method for identifying the species, tissue or cell type of a biological sample, which method comprises a step of detecting polypeptide molecules comprising an amino acid sequence in a panel of at least two amino acid sequences, wherein at least one sequence in said panel is at least 90% identical to a sequence of at least 10 contiguous amino acids in a sequence selected from the above group.

Also preferred is a method for diagnosing in a subject a pathological condition associated with abnormal structure or expression of a gene encoding a secreted protein identified in Table 1, which method comprises a step of detecting in a biological sample obtained from said subject polypeptide molecules comprising an amino acid sequence in a panel of at least two amino acid sequences, wherein at least one sequence in said panel is at least 90% identical to a sequence of at least 10 contiguous amino acids in a sequence selected from the group consisting of: an amino acid sequence of SEQ ID NO:Y wherein Y is any integer as defined in Table 1; and a complete amino acid sequence of a secreted protein encoded by a human cDNA clone identified by a cDNA Clone Identifier in Table 1 and contained in the deposit with the ATCC Deposit Number shown for said cDNA clone in Table 1.

In any of these methods, the step of detecting said polypeptide molecules includes using an antibody.

Also preferred is an isolated nucleic acid molecule comprising a nucleotide sequence which is at least 95% identical to a nucleotide sequence encoding a polypeptide wherein said polypeptide comprises an amino acid sequence that is at least 90% identical to a sequence of at least 10 contiguous amino acids in a sequence selected from the group consisting of: an amino acid sequence of SEQ ID NO:Y wherein Y is any integer as defined in Table 1; and a complete amino acid sequence of a secreted protein encoded by a human cDNA clone identified by a cDNA Clone Identifier in Table 1 and contained in the deposit with the ATCC Deposit Number shown for said cDNA clone in Table 1.

Also preferred is an isolated nucleic acid molecule, wherein said nucleotide sequence encoding a polypeptide has been optimized for expression of said polypeptide in a prokaryotic host.

Also preferred is an isolated nucleic acid molecule, wherein said polypeptide comprises an amino acid sequence selected from the group consisting of: an amino acid sequence of SEQ ID NO:Y wherein Y is any integer as defined in Table 1; and a complete amino acid sequence of a secreted protein encoded by a human cDNA clone identified by a cDNA Clone Identifier in Table 1 and contained in the deposit with the ATCC Deposit Number shown for said cDNA clone in Table 1.

Further preferred is a method of making a recombinant vector comprising inserting any of the above isolated nucleic acid molecule into a vector. Also preferred is the recombinant vector produced by this method. Also preferred is a method of making a recombinant host cell comprising introducing the vector into a host cell, as well as the recombinant host cell produced by this method.

Also preferred is a method of making an isolated polypeptide comprising culturing this recombinant host cell under conditions such that said polypeptide is expressed and recovering said polypeptide. Also preferred is this method of making an isolated polypeptide, wherein said recombinant host cell is a eukaryotic cell and said polypeptide is a secreted portion of a human secreted protein comprising an amino acid sequence selected from the group consisting of: an amino acid sequence of SEQ ID NO:Y beginning with the residue at the position of the First Amino Acid of the Secreted Portion of SEQ ID NO:Y wherein Y is an integer set forth in Table 1 and said position of the First Amino Acid of the Secreted Portion of SEQ ID NO:Y is defined in Table 1; and an amino acid sequence of a secreted portion of a protein encoded by a human cDNA clone identified by a cDNA Clone Identifier in Table 1 and contained in the deposit with the ATCC Deposit Number shown for said cDNA clone in Table 1. The isolated polypeptide produced by this method is also preferred.

Also preferred is a method of treatment of an individual in need of an increased level of a secreted protein activity, which method comprises administering to such an individual a pharmaceutical composition comprising an amount of an isolated polypeptide, polynucleotide, or antibody of the claimed invention effective to increase the level of said protein activity in said individual.

Having generally described the invention, the same will be more readily understood by reference to the following examples, which are provided by way of illustration and are not intended as limiting.

EXAMPLES

Example 1
Isolation of a Selected cDNA Clone from the Deposited Sample

Each cDNA clone in a cited ATCC deposit is contained in a plasmid vector. Table 1 identifies the vectors used to construct the cDNA library from which each clone was isolated. In many cases, the vector used to construct the library is a phage vector from which a plasmid has been excised. The table immediately below correlates the related plasmid for each phage vector used in constructing the cDNA library. For example, where a particular clone is identified in Table 1 as being isolated in the vector "Lambda Zap," the corresponding deposited clone is in "pBluescript."

| Vector Used to Construct Library | Corresponding Deposited Plamid |
|---|---|
| Lambda Zap | pBluescript (pBS) |
| Uni-Zap XR | pBluescript (pBS) |
| Zap Express | pBK |
| lafmid BA | plafmid BA |
| pSport1 | pSport1 |
| pCMVSport 2.0 | pCMVSport 2.0 |
| pCMVSport 3.0 | pCMVSport 3.0 |
| pCR ® 2.1 | pCR ® 2.1 |

Vectors Lambda Zap (U.S. Pat. Nos. 5,128,256 and 5,286,636), Uni-Zap XR (U.S. Pat. Nos. 5,128,256 and 5,286,636), Zap Express (U.S. Pat. Nos. 5,128,256 and 5,286,636), pBluescript (pBS) (Short, J. M. et al., Nucleic Acids Res. 16:7583–7600 (1988); Alting-Mees, M. A. and Short, J. M., Nucleic Acids Res. 17:9494 (1989)) and pBK (Alting-Mees, M. A. et al., Strategies 5:58–61 (1992)) are commercially available from Stratagene Cloning Systems, Inc., 11011 N. Torrey Pines Road, La Jolla, Calif., 92037. pBS contains an ampicillin resistance gene and pBK contains a neomycin resistance gene. Both can be transformed into E. coli strain XL-1 Blue, also available from Stratagene. pBS comes in 4 forms SK+, SK−, KS+ and KS. The S and K refers to the orientation of the polylinker to the T7 and T3 primer sequences which flank the polylinker region ("S" is for SacI and "K" is for KpnI which are the first sites on each respective end of the linker). "+" or "−" refer to the orientation of the f1 origin of replication ("ori"), such that in one orientation, single stranded rescue initiated from the f1 ori generates sense strand DNA and in the other, antisense.

Vectors pSport1, pCMVSport 2.0 and pCMVSport 3.0, were obtained from Life Technologies, Inc., P. O. Box 6009, Gaithersburg, Md. 20897. All Sport vectors contain an ampicillin resistance gene and may be transformed into E. coli strain DH10B, also available from Life Technologies. (See, for instance, Gruber, C. E., et al., Focus 15:59 (1993).) Vector lafmid BA (Bento Soares, Columbia University, NY) contains an ampicillin resistance gene and can be transformed into E. coli strain XL-1 Blue. Vector pCR®2.1, which is available from Invitrogen, 1600 Faraday Avenue, Carlsbad, Calif. 92008, contains an ampicillin resistance gene and may be transformed into E. coli strain DH10B, available from Life Technologies. (See, for instance, Clark, J. M., Nuc. Acids Res. 16:9677–9686 (1988) and Mead, D. et al., Bio/Technology 9: (1991).) Preferably, a polynucleotide of the present invention does not comprise the phage vector sequences identified for the particular clone in Table 1, as well as the corresponding plasmid vector sequences designated above.

The deposited material in the sample assigned the ATCC Deposit Number cited in Table 1 for any given cDNA clone also may contain one or more additional plasmids, each comprising a cDNA clone different from that given clone. Thus, deposits sharing the same ATCC Deposit Number contain at least a plasmid for each cDNA clone identified in Table 1. Typically, each ATCC deposit sample cited in Table 1 comprises a mixture of approximately equal amounts (by weight) of about 50 plasmid DNAs, each containing a different cDNA clone; but such a deposit sample may include plasmids for more or less than 50 cDNA clones, up to about 500 cDNA clones.

Two approaches can be used to isolate a particular clone from the deposited sample of plasmid DNAs cited for that clone in Table 1. First, a plasmid is directly isolated by screening the clones using a polynucleotide probe corresponding to SEQ ID NO:X.

Particularly, a specific polynucleotide with 30–40 nucleotides is synthesized using an Applied Biosystems DNA synthesizer according to the sequence reported. The oligonucleotide is labeled, for instance, with $^{32}$P-γ-ATP using T4 polynucleotide kinase and purified according to routine methods. (E.g., Maniatis et al., Molecular Cloning: A Laboratory Manual, Cold Spring Harbor Press, Cold Spring, N.Y. (1982).) The plasmid mixture is transformed into a suitable host, as indicated above (such as XL-1 Blue (Stratagene)) using techniques known to those of skill in the art, such as those provided by the vector supplier or in related publications or patents cited above. The transformants are plated on 1.5% agar plates (containing the appropriate selection agent, e.g., ampicillin) to a density of about 150 transformants (colonies) per plate. These plates are screened using Nylon membranes according to routine methods for bacterial colony screening (e.g., Sambrook et al., Molecular Cloning: A Laboratory Manual, 2nd Edit., (1989), Cold Spring Harbor Laboratory Press, pages 1.93 to 1.104), or other techniques known to those of skill in the art.

Alternatively, two primers of 17–20 nucleotides derived from both ends of the SEQ ID NO:X (i.e., within the region of SEQ ID NO:X bounded by the 5' NT and the 3' NT of the clone defined in Table 1) are synthesized and used to amplify the desired cDNA using the deposited cDNA plasmid as a template. The polymerase chain reaction is carried out under routine conditions, for instance, in 25 μl of reaction mixture with 0.5 ug of the above cDNA template. A convenient reaction mixture is 1.5–5 mM $MgCl_2$, 0.01% (w/v) gelatin, 20 μM each of dATP, dCTP, dGTP, dTTP, 25 pmol of each primer and 0.25 Unit of Taq polymerase. Thirty five cycles of PCR (denaturation at 94° C. for 1 min; annealing at 55° C. for 1 min; elongation at 72° C. for 1 min) are performed with a Perkin-Elmer Cetus automated thermal cycler. The amplified product is analyzed by agarose gel electrophoresis and the DNA band with expected molecular weight is excised and purified. The PCR product is verified to be the selected sequence by subcloning and sequencing the DNA product.

Several methods are available for the identification of the 5' or 3' non-coding portions of a gene which may not be present in the deposited clone. These methods include but are not limited to, filter probing, clone enrichment using specific probes, and protocols similar or identical to 5' and 3' "RACE" protocols which are well known in the art. For instance, a method similar to 5' RACE is available for generating the missing 5' end of a desired full-length transcript. (Fromont-Racine et al., Nucleic Acids Res. 21(7):1683–1684 (1993).)

Briefly, a specific RNA oligonucleotide is ligated to the 5' ends of a population of RNA presumably containing full-length gene RNA transcripts. A primer set containing a primer specific to the ligated RNA oligonucleotide and a primer specific to a known sequence of the gene of interest is used to PCR amplify the 5' portion of the desired full-length gene. This amplified product may then be sequenced and used to generate the full length gene.

This above method starts with total RNA isolated from the desired source, although poly-A+ RNA can be used. The RNA preparation can then be treated with phosphatase if necessary to eliminate 5' phosphate groups on degraded or damaged RNA which may interfere with the later RNA ligase step. The phosphatase should then be inactivated and the RNA treated with tobacco acid pyrophosphatase in order to remove the cap structure present at the 5' ends of messenger RNAs. This reaction leaves a 5' phosphate group at the 5' end of the cap cleaved RNA which can then be ligated to an RNA oligonucleotide using T4 RNA ligase.

This modified RNA preparation is used as a template for first strand cDNA synthesis using a gene specific oligonucleotide. The first strand synthesis reaction is used as a template for PCR amplification of the desired 5' end using a primer specific to the ligated RNA oligonucleotide and a primer specific to the known sequence of the gene of interest. The resultant product is then sequenced and analyzed to confirm that the 5' end sequence belongs to the desired gene.

Example 2

Isolation of Genomic Clones Corresponding to a Polynucleotide

A human genomic P1 library (Genomic Systems, Inc.) is screened by PCR using primers selected for the cDNA sequence corresponding to SEQ ID NO:X., according to the method described in Example 1. (See also, Sambrook.)

Example 3

Tissue Distribution of Polypeptide

Tissue distribution of mRNA expression of polynucleotides of the present invention is determined using protocols for Northern blot analysis, described by, among others, Sambrook et al. For example, a cDNA probe produced by the method described in Example 1 is labeled with $p^{32}$ using the rediprime™ DNA labeling system (Amersham Life Science), according to manufacturer's instructions. After labeling, the probe is purified using CHROMA SPIN-100™ column (Clontech Laboratories, Inc.), according to manufacturer's protocol number PT 1200-1. The purified labeled probe is then used to examine various human tissues for mRNA expression.

Multiple Tissue Northern (MTN) blots containing various human tissues (H) or human immune system tissues (IM) (Clontech) are examined with the labeled probe using ExpressHyb™ hybridization solution (Clontech) according to manufacturer's protocol number PT 1190-1. Following hybridization and washing, the blots are mounted and exposed to film at −70° C. overnight, and the films developed according to standard procedures.

Example 4

Chromosomal Mapping of the Polynucleotides

An oligonucleotide primer set is designed according to the sequence at the 5' end of SEQ ID NO:X. This primer preferably spans about 100 nucleotides. This primer set is then used in a polymerase chain reaction under the following set of conditions: 30 seconds, 95° C.; 1 minute, 56° C.; 1 minute, 70° C. This cycle is repeated 32 times followed by one 5 minute cycle at 70° C. Human, mouse, and hamster DNA is used as template in addition to a somatic cell hybrid panel containing individual chromosomes or chromosome fragments (Bios, Inc). The reactions is analyzed on either 8% polyacrylamide gels or 3.5% agarose gels. Chromosome mapping is determined by the presence of an approximately 100 bp PCR fragment in the particular somatic cell hybrid.

Example 5

Bacterial Expression of a Polypeptide

A polynucleotide encoding a polypeptide of the present invention is amplified using PCR oligonucleotide primers corresponding to the 5' and 3' ends of the DNA sequence, as outlined in Example 1, to synthesize insertion fragments. The primers used to amplify the cDNA insert should preferably contain restriction sites, such as BamHI and XbaI, at the 5' end of the primers in order to clone the amplified product into the expression vector. For example, BamHI and XbaI correspond to the restriction enzyme sites on the bacterial expression vector pQE-9. (Qiagen, Inc., Chatsworth, Calif.). This plasmid vector encodes antibiotic resistance (Amp$^r$), a bacterial origin of replication (ori), an IPTG-regulatable promoter/operator (P/O), a ribosome binding site (RBS), a 6-histidine tag (6-His), and restriction enzyme cloning sites.

The pQE-9 vector is digested with BamHI and XbaI and the amplified fragment is ligated into the pQE-9 vector maintaining the reading frame initiated at the bacterial RBS. The ligation mixture is then used to transform the E. coli strain M15/rep4 (Qiagen, Inc.) which contains multiple copies of the plasmid pREP4, which expresses the lacI repressor and also confers kanamycin resistance (Kan$^r$). Transformants are identified by their ability to grow on LB plates and ampicillin/kanamycin resistant colonies are selected. Plasmid DNA is isolated and confirmed by restriction analysis.

Clones containing the desired constructs are grown overnight (O/N) in liquid culture in LB media supplemented with both Amp (100 ug/ml) and Kan (25 ug/ml). The O/N culture is used to inoculate a large culture at a ratio of 1:100 to 1:250. The cells are grown to an optical density 600 (O.D.$^{600}$) of between 0.4 and 0.6. IPTG (Isopropyl-B-D-thiogalacto pyranoside) is then added to a final concentration of 1 mM. IPTG induces by inactivating the lacI repressor, clearing the P/O leading to increased gene expression.

Cells are grown for an extra 3 to 4 hours. Cells are then harvested by centrifugation (20 mins at 6000×g). The cell pellet is solubilized in the chaotropic agent 6 Molar Guanidine HCl by stirring for 3–4 hours at 4° C. The cell debris is removed by centrifugation, and the supernatant containing the polypeptide is loaded onto a nickel-nitrilo-tri-acetic acid ("Ni-NTA") affinity resin column (available from QIAGEN, Inc., supra). Proteins with a 6×His tag bind to the Ni-NTA resin with high affinity and can be purified in a simple one-step procedure (for details see: The QIAexpressionist (1995) QIAGEN, Inc., supra).

Briefly, the supernatant is loaded onto the column in 6 M guanidine-HCl, pH 8, the column is first washed with 10 volumes of 6 M guanidine-HCl, pH 8, then washed with 10 volumes of 6 M guanidine-HCl pH 6, and finally the polypeptide is eluted with 6 M guanidine-HCl, pH 5.

The purified protein is then renatured by dialyzing it against phosphate-buffered saline (PBS) or 50 mM Na-acetate, pH 6 buffer plus 200 mM NaCl. Alternatively, the protein can be successfully refolded while immobilized on the Ni-NTA column. The recommended conditions are as follows: renature using a linear 6M-1M urea gradient in 500 mM NaCl, 20% glycerol, 20 mM Tris/HCl pH 7.4, containing protease inhibitors. The renaturation should be performed over a period of 1.5 hours or more. After renaturation the proteins are eluted by the addition of 250 mM immidazole. Immidazole is removed by a final dialyzing step against PBS or 50 mM sodium acetate pH 6 buffer plus 200 mM NaCl. The purified protein is stored at 4° C. or frozen at −80° C.

In addition to the above expression vector, the present invention further includes an expression vector comprising phage operator and promoter elements operatively linked to a polynucleotide of the present invention, called pHE4a. (ATCC Accession Number 209645, deposited on Feb. 25, 1998.) This vector contains: 1) a neomycinphosphotransferase gene as a selection marker, 2) an E. coli origin of replication, 3) a T5 phage promoter sequence, 4) two lac operator sequences, 5) a Shine-Delgarno sequence, and 6) the lactose operon repressor gene (lacIq). The origin of replication (oriC) is derived from pUC19 (LTI, Gaithersburg, Md.). The promoter sequence and operator sequences are made synthetically.

DNA can be inserted into the pHEa by restricting the vector with NdeI and XbaI, BamHI, XhoI, or Asp718, running the restricted product on a gel, and isolating the larger fragment (the stuffer fragment should be about 310 base pairs). The DNA insert is generated according to the PCR protocol described in Example 1, using PCR primers having restriction sites for NdeI (5' primer) and XbaI, BamHI, XhoI, or Asp718 (3' primer). The PCR insert is gel purified and restricted with compatible enzymes. The insert and vector are ligated according to standard protocols.

The engineered vector could easily be substituted in the above protocol to express protein in a bacterial system.

Example 6

Purification of a Polypeptide from an Inclusion Body

The following alternative method can be used to purify a polypeptide expressed in E coli when it is present in the form of inclusion bodies. Unless otherwise specified, all of the following steps are conducted at 4–10° C.

Upon completion of the production phase of the E. coli fermentation, the cell culture is cooled to 4–10° C. and the cells harvested by continuous centrifugation at 15,000 rpm (Heraeus Sepatech). On the basis of the expected yield of protein per unit weight of cell paste and the amount of purified protein required, an appropriate amount of cell paste, by weight, is suspended in a buffer solution containing 100 mM Tris, 50 mM EDTA, pH 7.4. The cells are dispersed to a homogeneous suspension using a high shear mixer.

The cells are then lysed by passing the solution through a microfluidizer (Microfuidics, Corp. or APV Gaulin, Inc.) twice at 4000–6000 psi. The homogenate is then mixed with NaCl solution to a final concentration of 0.5 M NaCl, followed by centrifugation at 7000×g for 15 min. The resultant pellet is washed again using 0.5M NaCl, 100 mM Tris, 50 mM EDTA, pH 7.4.

The resulting washed inclusion bodies are solubilized with 1.5 M guanidine hydrochloride (GuHCl) for 2–4 hours. After 7000×g centrifugation for 15 min., the pellet is discarded and the polypeptide containing supernatant is incubated at 4° C. overnight to allow further GuHCl extraction.

Following high speed centrifugation (30,000×g) to remove insoluble particles, the GuHCl solubilized protein is refolded by quickly mixing the GuHCl extract with 20 volumes of buffer containing 50 mM sodium, pH 4.5, 150 mM NaCl, 2 mM EDTA by vigorous stirring. The refolded diluted protein solution is kept at 4° C. without mixing for 12 hours prior to further purification steps.

To clarify the refolded polypeptide solution, a previously prepared tangential filtration unit equipped with 0.16 μm membrane filter with appropriate surface area (e.g., Filtron), equilibrated with 40 mM sodium acetate, pH 6.0 is employed. The filtered sample is loaded onto a cation exchange resin (e.g., Poros HS-50, Perseptive Biosystems). The column is washed with 40 mM sodium acetate, pH 6.0 and eluted with 250 mM, 500 mM, 1000 mM, and 1500 mM NaCl in the same buffer, in a stepwise manner. The absorbance at 280 nm of the effluent is continuously monitored. Fractions are collected and further analyzed by SDS-PAGE.

Fractions containing the polypeptide are then pooled and mixed with 4 volumes of water. The diluted sample is then loaded onto a previously prepared set of tandem columns of strong anion (Poros HQ-50, Perseptive Biosystems) and weak anion (Poros CM-20, Perseptive Biosystems) exchange resins. The columns are equilibrated with 40 mM sodium acetate, pH 6.0. Both columns are washed with 40 mM sodium acetate, pH 6.0, 200 mM NaCl. The CM-20 column is then eluted using a 10 column volume linear gradient ranging from 0.2 M NaCl, 50 mM sodium acetate, pH 6.0 to 1.0 M NaCl, 50 mM sodium acetate, pH 6.5. Fractions are collected under constant $A_{280}$ monitoring of the effluent. Fractions containing the polypeptide (determined, for instance, by 16% SDS-PAGE) are then pooled.

The resultant polypeptide should exhibit greater than 95% purity after the above refolding and purification steps. No major contaminant bands should be observed from Commassie blue stained 16% SDS-PAGE gel when 5 μg of purified protein is loaded. The purified protein can also be tested for endotoxin/LPS contamination, and typically the LPS content is less than 0.1 ng/ml according to LAL assays.

Example 7

Cloning and Expression of a Polypeptide in a Baculovirus Expression System

In this example, the plasmid shuttle vector pA2 is used to insert a polynucleotide into a baculovirus to express a polypeptide. This expression vector contains the strong polyhedrin promoter of the *Autographa californica* nuclear polyhedrosis virus (AcMNPV) followed by convenient restriction sites such as BamHI, Xba I and Asp718. The polyadenylation site of the simian virus 40 ("SV40") is used for efficient polyadenylation. For easy selection of recombinant virus, the plasmid contains the beta-galactosidase gene from E. coli under control of a weak Drosophila promoter in the same orientation, followed by the polyadenylation signal of the polyhedrin gene. The inserted genes are flanked on both sides by viral sequences for cell-mediated homologous recombination with wild-type viral DNA to generate a viable virus that express the cloned polynucleotide.

Many other baculovirus vectors can be used in place of the vector above, such as pAc373, pVL941, and pAcIM1, as one skilled in the art would readily appreciate, as long as the construct provides appropriately located signals for transcription, translation, secretion and the like, including a signal peptide and an in-frame AUG as required. Such vectors are described, for instance, in Luckow et al., Virology 170:31–39 (1989).

Specifically, the cDNA sequence contained in the deposited clone, including the AUG initiation codon and the naturally associated leader sequence identified in Table 1, is amplified using the PCR protocol described in Example 1. If the naturally occurring signal sequence is used to produce the secreted protein, the pA2 vector does not need a second signal peptide. Alternatively, the vector can be modified (pA2 GP) to include a baculovirus leader sequence, using the standard methods described in Summers et al., "A Manual of Methods for Baculovirus Vectors and Insect Cell Culture Procedures," Texas Agricultural Experimental Station Bulletin No. 1555 (1987).

The amplified fragment is isolated from a 1% agarose gel using a commercially available kit ("Geneclean," BIO 101 Inc., La Jolla, Calif.). The fragment then is digested with appropriate restriction enzymes and again purified on a 1% agarose gel.

The plasmid is digested with the corresponding restriction enzymes and optionally, can be dephosphorylated using calf intestinal phosphatase, using routine procedures known in the art. The DNA is then isolated from a 1% agarose gel using a commercially available kit ("Geneclean" BIO 101 Inc., La Jolla, Calif.).

The fragment and the dephosphorylated plasmid are ligated together with T4 DNA ligase. E. coli HB 101 or other suitable E. coli hosts such as XL-1 Blue (Stratagene Cloning Systems, La Jolla, Calif.) cells are transformed with the ligation mixture and spread on culture plates. Bacteria containing the plasmid are identified by digesting DNA from individual colonies and analyzing the digestion product by gel electrophoresis. The sequence of the cloned fragment is confirmed by DNA sequencing.

Five $\mu$g of a plasmid containing the polynucleotide is co-transfected with 1.0 $\mu$g of a commercially available linearized baculovirus DNA ("BaculoGold™ baculovirus DNA", Pharmingen, San Diego, Calif.), using the lipofection method described by Felgner et al., Proc. Natl. Acad. Sci. USA 84:7413–7417 (1987). One $\mu$g of BaculoGold™ virus DNA and 5 $\mu$g of the plasmid are mixed in a sterile well of a microtiter plate containing 50 $\mu$l of serum-free Grace's medium (Life Technologies Inc., Gaithersburg, Md.). Afterwards, 10 $\mu$l Lipofectin plus 90 $\mu$l Grace's medium are added, mixed and incubated for 15 minutes at room temperature. Then the transfection mixture is added drop-wise to Sf9 insect cells (ATCC CRL 1711) seeded in a 35 mm tissue culture plate with 1 ml Grace's medium without serum. The plate is then incubated for 5 hours at 27° C. The transfection solution is then removed from the plate and 1 ml of Grace's insect medium supplemented with 10% fetal calf serum is added. Cultivation is then continued at 27° C. for four days.

After four days the supernatant is collected and a plaque assay is performed, as described by Summers and Smith, supra. An agarose gel with "Blue Gal" (Life Technologies Inc., Gaithersburg) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, page 9–10.) After appropriate incubation, blue stained plaques are picked with the tip of a micropipettor (e.g., Eppendorf). The agar containing the recombinant viruses is then resuspended in a microcentrifuge tube containing 200 $\mu$l of Grace's medium and the suspension containing the recombinant baculovirus is used to infect Sf9 cells seeded in 35 mm dishes. Four days later the supernatants of these culture dishes are harvested and then they are stored at 4° C.

To verify the expression of the polypeptide, Sf9 cells are grown in Grace's medium supplemented with 10% heat-inactivated FBS. The cells are infected with the recombinant baculovirus containing the polynucleotide at a multiplicity of infection ("MOI") of about 2. If radiolabeled proteins are desired, 6 hours later the medium is removed and is replaced with SF900 II medium minus methionine and cysteine (available from Life Technologies Inc., Rockville, Md.). After 42 hours, 5 $\mu$Ci of $^{35}$S-methionine and 5 $\mu$Ci $^{35}$S-cysteine (available from Amersham) are added. The cells are further incubated for 16 hours and then are harvested by centrifugation. The proteins in the supernatant as well as the intracellular proteins are analyzed by SDS-PAGE followed by autoradiography (if radiolabeled).

Microsequencing of the amino acid sequence of the amino terminus of purified protein may be used to determine the amino terminal sequence of the produced protein.

Example 8
Expression of a Polypeptide in Mammalian Cells

The polypeptide of the present invention can be expressed in a mammalian cell. A typical mammalian expression vector contains a promoter element, which mediates the initiation of transcription of mRNA, a protein coding sequence, and signals required for the termination of transcription and polyadenylation of the transcript. Additional elements include enhancers, Kozak sequences and intervening sequences flanked by donor and acceptor sites for RNA splicing. Highly efficient transcription is achieved with the early and late promoters from SV40, the long terminal repeats (LTRs) from Retroviruses, e.g., RSV, HTLVI, HIVI and the early promoter of the cytomegalovirus (CMV). However, cellular elements can also be used (e.g., the human actin promoter).

Suitable expression vectors for use in practicing the present invention include, for example, vectors such as pSVL and pMSG (Pharmacia, Uppsala, Sweden), pRSVcat (ATCC 37152), pSV2dhfr (ATCC 37146), pBC12MI (ATCC 67109), pCMVSport 2.0, and pCMVSport 3.0. Mammalian host cells that could be used include, human Hela, 293, H9 and Jurkat cells, mouse NIH3T3 and C127 cells, Cos 1, Cos 7 and CV1, quail QC1-3 cells, mouse L cells and Chinese hamster ovary (CHO) cells.

Alternatively, the polypeptide can be expressed in stable cell lines containing the polynucleotide integrated into a chromosome. The co-transfection with a selectable marker such as dhfr, gpt, neomycin, hygromycin allows the identification and isolation of the transfected cells.

The transfected gene can also be amplified to express large amounts of the encoded protein. The DHFR (dihydrofolate reductase) marker is useful in developing cell lines that carry several hundred or even several thousand copies of the gene of interest. (See, e.g., Alt, F. W., et al., J. Biol. Chem. 253:1357–1370 (1978); Hamlin, J. L. and Ma, C., Biochem. et Biophys. Acta, 1097:107–143 (1990); Page, M. J. and Sydenham, M. A., Biotechnology 9:64–68 (1991).) Another useful selection marker is the enzyme glutamine synthase (GS) (Murphy et al., Biochem J. 227:277–279 (1991); Bebbington et al., Bio/Technology 10:169–175

(1992). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of proteins.

Derivatives of the plasmid pSV2-dhfr (ATCC Accession No. 37146), the expression vectors pC4 (ATCC Accession No. 209646) and pC6 (ATCC Accession No.209647) contain the strong promoter (LTR) of the Rous Sarcoma Virus (Cullen et al., Molecular and Cellular Biology, 438–447 (March, 1985)) plus a fragment of the CMV-enhancer (Boshart et al., Cell 41:521–530 (1985).) Multiple cloning sites, e.g., with the restriction enzyme cleavage sites BamHI, XbaI and Asp718, facilitate the cloning of the gene of interest. The vectors also contain the 3' intron, the polyadenylation and termination signal of the rat preproinsulin gene, and the mouse DHFR gene under control of the SV40 early promoter.

Specifically, the plasmid pC6, for example, is digested with appropriate restriction enzymes and then dephosphorylated using calf intestinal phosphates by procedures known in the art. The vector is then isolated from a 1% agarose gel.

A polynucleotide of the present invention is amplified according to the protocol outlined in Example 1. If the naturally occurring signal sequence is used to produce the secreted protein, the vector does not need a second signal peptide. Alternatively, if the naturally occurring signal sequence is not used, the vector can be modified to include a heterologous signal sequence. (See, e.g., WO 96/34891.)

The amplified fragment is isolated from a 1% agarose gel using a commercially available kit ("Geneclean," BIO 101 Inc., La Jolla, Calif.). The fragment then is digested with appropriate restriction enzymes and again purified on a 1% agarose gel.

The amplified fragment is then digested with the same restriction enzyme and purified on a 1% agarose gel. The isolated fragment and the dephosphorylated vector are then ligated with T4 DNA ligase. E. coli HB101 or XL-1 Blue cells are then transformed and bacteria are identified that contain the fragment inserted into plasmid pC6 using, for instance, restriction enzyme analysis.

Chinese hamster ovary cells lacking an active DHFR gene is used for transfection. Five µg of the expression plasmid pC6 is cotransfected with 0.5 µg of the plasmid pSVneo using lipofectin (Felgner et al., supra). The plasmid pSV2-neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/mil of metothrexate plus 1 mg/ml G418. After about 10–14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 µM, 2 µM, 5 µM, 10 mM, 20 mM). The same procedure is repeated until clones are obtained which grow at a concentration of 100–200 µM. Expression of the desired gene product is analyzed, for instance, by SDS-PAGE and Western blot or by reversed phase HPLC analysis.

Example 9

Protein Fusions

The polypeptides of the present invention are preferably fused to other proteins. These fusion proteins can be used for a variety of applications. For example, fusion of the present polypeptides to His-tag, HA-tag, protein A, IgG domains, and maltose binding protein facilitates purification. (See Example 5; see also EPA 394,827; Traunecker, et al., Nature 331:84–86 (1988).) Similarly, fusion to IgG-1, IgG-3, and albumin increases the halflife time in vivo. Nuclear localization signals fused to the polypeptides of the present invention can target the protein to a specific subcellular localization, while covalent heterodimer or homodimers can increase or decrease the activity of a fusion protein. Fusion proteins can also create chimeric molecules having more than one function. Finally, fusion proteins can increase solubility and/or stability of the fused protein compared to the non-fused protein. All of the types of fusion proteins described above can be made by modifying the following protocol, which outlines the fusion of a polypeptide to an IgG molecule, or the protocol described in Example 5.

Briefly, the human Fc portion of the IgG molecule can be PCR amplified, using primers that span the 5' and 3' ends of the sequence described below. These primers also should have convenient restriction enzyme sites that will facilitate cloning into an expression vector, preferably a mammalian expression vector.

For example, if pC4 (Accession No. 209646) is used, the human Fc portion can be ligated into the BamHI cloning site. Note that the 3' BamHI site should be destroyed. Next, the vector containing the human Fc portion is re-restricted with BamHI, linearizing the vector, and a polynucleotide of the present invention, isolated by the PCR protocol described in Example 1, is ligated into this BamHI site. Note that the polynucleotide is cloned without a stop codon, otherwise a fusion protein will not be produced.

If the naturally occurring signal sequence is used to produce the secreted protein, pC4 does not need a second signal peptide. Alternatively, if the naturally occurring signal sequence is not used, the vector can be modified to include a heterologous signal sequence. (See, e.g., WO 96/34891.)

Human IgG Fc region:

```
GGGATCCGGAGCCCAAATCTTCTGACAAAACTCACACATGCCCACCGTGCC    (SEQ ID NO:1)

CAGCACCTGAATTCGAGGGTGCACCGTCAGTCTTCCTCTTCCCCCCAAAACC

CAAGGACACCCTCATGATCTCCCGGACTCCTGAGGTCACATGCGTGGTGGT

GGACGTAAGCCACGAAGACCCTGAGGTCAAGTTCAACTGGTACGTGGACG

GCGTGGAGGTGCATAATGCCAAGACAAAGCCGCGGGAGGAGCAGTACAAC

AGCACGTACCGTGTGGTCAGCGTCCTCACCGTCCTGCACCAGGACTGGCTG
```

```
-continued
AATGGCAAGGAGTACAAGTGCAAGGTCTCCAACAAAGCCCTCCCAACCCCC

ATCGAGAAAACCATCTCCAAAGCCAAAGGGCAGCCCCGAGAACCACAGGT

GTACACCCTGCCCCCATCCCGGGATGAGCTGACCAAGAACCAGGTCAGCCT

GACCTGCCTGGTCAAAGGCTTCTATCCAAGCGACATCGCCGTGGAGTGGGA

GAGCAATGGGCAGCCGGAGAACAACTACAAGACCACGCCTCCCGTGCTGG

ACTCCGACGGCTCCTTCTTCCTCTACAGCAAGCTCACCGTGGACAAGAGCA

GGTGGCAGCAGGGGAACGTCTTCTCATGCTCCGTGATGCATGAGGCTCTGC

ACAACCACTACACGCAGAAGAGCCTCTCCCTGTCTCCGGGTAAATGAGTGC

GACGGCCGCGACTCTAGAGGAT
```

Example 10
Production of an Antibody from a Polypeptide

The antibodies of the present invention can be prepared by a variety of methods. (See, Current Protocols, Chapter 2.) For example, cells expressing a polypeptide of the present invention is administered to an animal to induce the production of sera containing polyclonal antibodies. In a preferred method, a preparation of the secreted protein is prepared and purified to render it substantially free of natural contaminants. Such a preparation is then introduced into an animal in order to produce polyclonal antisera of greater specific activity.

In the most preferred method, the antibodies of the present invention are monoclonal antibodies (or protein binding fragments thereof). Such monoclonal antibodies can be prepared using hybridoma technology. (Köhler et al., Nature 256:495 (1975); Köhler et al., Eur. J. Immunol. 6:511 (1976); Köhler et al., Eur. J. Immunol. 6:292 (1976); Hammerling et al., in: Monoclonal Antibodies and T-Cell Hybridomas, Elsevier, N.Y., pp. 563–681 (1981).) In general, such procedures involve immunizing an animal (preferably a mouse) with polypeptide or, more preferably, with a secreted polypeptide-expressing cell. Such cells may be cultured in any suitable tissue culture medium; however, it is preferable to culture cells in Earle's modified Eagle's medium supplemented with 10% fetal bovine serum (inactivated at about 56° C.), and supplemented with about 10 g/l of nonessential amino acids, about 1,000 U/ml of penicillin, and about 100 μg/ml of streptomycin.

The splenocytes of such mice are extracted and fused with a suitable myeloma cell line. Any suitable myeloma cell line may be employed in accordance with the present invention; however, it is preferable to employ the parent myeloma cell line (SP2O), available from the ATCC. After fusion, the resulting hybridoma cells are selectively maintained in HAT medium, and then cloned by limiting dilution as described by Wands et al. (Gastroenterology 80:225–232 (1981).) The hybridoma cells obtained through such a selection are then assayed to identify clones which secrete antibodies capable of binding the polypeptide.

Alternatively, additional antibodies capable of binding to the polypeptide can be produced in a two-step procedure using anti-idiotypic antibodies. Such a method makes use of the fact that antibodies are themselves antigens, and therefore, it is possible to obtain an antibody which binds to a second antibody. In accordance with this method, protein specific antibodies are used to immunize an animal, preferably a mouse. The splenocytes of such an animal are then used to produce hybridoma cells, and the hybridoma cells are screened to identify clones which produce an antibody whose ability to bind to the protein-specific antibody can be blocked by the polypeptide. Such antibodies comprise anti-idiotypic antibodies to the protein-specific antibody and can be used to immunize an animal to induce formation of further protein-specific antibodies.

It will be appreciated that Fab and F(ab')2 and other fragments of the antibodies of the present invention may be used according to the methods disclosed herein. Such fragments are typically produced by proteolytic cleavage, using enzymes such as papain (to produce Fab fragments) or pepsin (to produce F(ab')2 fragments). Alternatively, secreted protein-binding fragments can be produced through the application of recombinant DNA technology or through synthetic chemistry.

For in vivo use of antibodies in humans, it may be preferable to use "humanized" chimeric monoclonal antibodies. Such antibodies can be produced using genetic constructs derived from hybridoma cells producing the monoclonal antibodies described above. Methods for producing chimeric antibodies are known in the art. (See, for review, Morrison, Science 229:1202 (1985); Oi et al., Bio-Techniques 4:214 (1986); Cabilly et al., U.S. Pat. No. 4,816,567; Taniguchi et al. EP 171496; Morrison et al., EP 173494; Neuberger et al., WO 8601533; Robinson et al., WO 8702671; Boulianne et al., Nature 312:643 (1984); Neuberger et al., Nature 314:268 (1985).)

Example 11
Production of Secreted Protein for High-Throughput Screening Assays

The following protocol produces a supernatant containing a polypeptide to be tested. This supernatant can then be used in the Screening Assays described in Examples 13–20.

First, dilute Poly-D-Lysine (644 587 Boehringer-Mannheim) stock solution (1 mg/ml in PBS) 1:20 in PBS (w/o calcium or magnesium 17-516F Biowhittaker) for a working solution of 50 ug/ml. Add 200 ul of this solution to each well (24 well plates) and incubate at RT for 20 minutes. Be sure to distribute the solution over each well (note: a 12-channel pipetter may be used with tips on every other channel). Aspirate off the Poly-D-Lysine solution and rinse with 1 ml PBS (Phosphate Buffered Saline). The PBS should remain in the well until just prior to plating the cells and plates may be poly-lysine coated in advance for up to two weeks.

Plate 293T cells (do not carry cells past P+20) at $2 \times 10^5$ cells/well in 0.5 ml DMEM(Dulbecco's Modified Eagle Medium)(with 4.5 G/L glucose and L-glutamine (12-604F Biowhittaker))/10% heat inactivated FBS(14-503F Biowhittaker)/1×Penstrep(17-602E Biowhittaker). Let the cells grow overnight.

The next day, mix together in a sterile solution basin: 300 ul Lipofectamine (18324-012 Gibco/BRL) and 5mil Optimem I (31985070 Gibco/BRL)/96-well plate.

With a small volume multi-channel pipetter, aliquot approximately 2 ug of an expression vector containing a polynucleotide insert, produced by the methods described in Examples 8 or 9, into an appropriately labeled 96-well round bottom plate. With a multi-channel pipetter, add 50 ul of the Lipofectamine/Optimem 1 mixture to each well.

Pipette up and down gently to mix. Incubate at RT 15–45 minutes. After about 20 minutes, use a multi-channel pipetter to add 150 ul Optimem I to each well. As a control, one plate of vector DNA lacking an insert should be transfected with each set of transfections.

Preferably, the transfection should be performed by tag-teaming the following tasks. By tag-teaming, hands on time is cut in half, and the cells do not spend too much time on PBS. First, person A aspirates off the media from four 24-well plates of cells, and then person B rinses each well with 0.5–1 ml PBS. Person A then aspirates off PBS rinse, and person B, using a 12-channel pipetter with tips on every other channel, adds the 200 ul of DNA/Lipofectamine/Optimem I complex to the odd wells first, then to the even wells, to each row on the 24-well plates. Incubate at 37° C. for 6 hours.

While cells are incubating, prepare appropriate media, either 1% BSA in DMEM with 1×penstrep, or CHO-5 media (116.6 mg/L of CaCl2 (anhyd); 0.00130 mg/L $CuSO_4$—$5H_2O$; 0.050 mg/L of $Fe(NO_3)_3$—$9H_2O$; 0.417 mg/L of $FeSO_4$—$7H_2O$; 311.80 mg/L of Kcl; 28.64 mg/L of $MgCl_2$; 48.84 mg/L of $MgSO_4$; 6995.50 mg/L of NaCl; 2400.0 mg/L of $NaHCO_3$; 62.50 mg/L of $NaH_2PO_4$—$H_2O$; 71.02 mg/L of $Na_2HPO4$; 0.4320 mg/L of $ZnSO_4$—$7H_2O$; 0.002 mg/L of Arachidonic Acid; 1.022 mg/L of Cholesterol; 0.070 mg/L of DL-alpha-Tocopherol-Acetate; 0.0520 mg/L of Linoleic Acid; 0.010 mg/L of Linolenic Acid; 0.010 mg/L of Myristic Acid; 0.010 mg/L of Oleic Acid; 0.010 mg/L of Palmitric Acid; 0.010 mg/L of Palmitic Acid; 100 mg/L of Pluronic F-68; 0.010 mg/L of Stearic Acid; 2.20 mg/L of Tween 80; 4551 mg/L of D-Glucose; 130.85 mg/ml of L-Alanine; 147.50 mg/ml of L-Arginine-HCL; 7.50 mg/ml of L-Asparagine-$H_2O$; 6.65 mg/ml of L-Aspartic Acid; 29.56 mg/ml of L-Cystine-2HCL-$H_2O$; 31.29 mg/ml of L-Cystine-2HCL; 7.35 mg/ml of L-Glutamic Acid; 365.0 mg/ml of L-Glutamine; 18.75 mg/ml of Glycine; 52.48 mg/ml of L-Histidine-HCL-$H_2O$; 106.97 mg/ml of L-Isoleucine; 111.45 mg/ml of L-Leucine; 163.75 mg/ml of L-Lysine HCL; 32.34 mg/ml of L-Methionine; 68.48 mg/ml of L-Phenylalainine; 40.0 mg/ml of L-Proline; 26.25 mg/ml of L-Serine; 101.05 mg/ml of L-Threonine; 19.22 mg/ml of L-Tryptophan; 91.79 mg/ml of L-Tryrosine-2Na-$2H_2O$; 99.65 mg/ml of L-Valine; 0.0035 mg/L of Biotin; 3.24 mg/L of D—Ca Pantothenate; 11.78 mg/L of Choline Chloride; 4.65 mg/L of Folic Acid; 15.60 mg/L of i-Inositol; 3.02 mg/L of Niacinamide; 3.00 mg/L of Pyridoxal HCL; 0.031 mg/L of Pyridoxine HCL; 0.319 mg/L of Riboflavin; 3.17 mg/L of Thiamine HCL; 0.365 mg/L of Thymidine; and 0.680 mg/L of Vitamin $B_{12}$; 25 mM of HEPES Buffer; 2.39 mg/L of Na Hypoxanthine; 0.105 mg/L of Lipoic Acid; 0.081 mg/L of Sodium Putrescine-2HCL; 55.0 mg/L of Sodium Pyruvate; 0.0067 mg/L of Sodium Selenite; 20 uM of Ethanolamine; 0.122 mg/L of Ferric Citrate; 41.70 mg/L of Methyl-B-Cyclodextrin complexed with Linoleic Acid; 33.33 mg/L of Methyl-B-Cyclodextrin complexed with Oleic Acid; and 10 mg/L of Methyl-B-Cyclodextrin complexed with Retinal) with 2 mm glutamine and 1×penstrep. (BSA (81-068-3 Bayer) 100 gm dissolved in 1L DMEM for a 10% BSA stock solution). Filter the media and collect 50 ul for endotoxin assay in 15 ml polystyrene conical.

The transfection reaction is terminated, preferably by tag-teaming, at the end of the incubation period. Person A aspirates off the transfection media, while person B dds 1.5 ml appropriate media to each well. Incubate at 37° C. for 45 or 72 hours depending on the media used: 1% BSA for 45 hours or CHO-5 for 72 hours.

On day four, using a 300 ul multichannel pipetter, aliquot 600 ul in one 1 ml deep well plate and the remaining supernatant into a 2 ml deep well. The supernatants from each well can then be used in the assays described in Examples 13–20.

It is specifically understood that when activity is obtained in any of the assays described below using a supernatant, the activity originates from either the polypeptide directly (e.g., as a secreted protein) or by the polypeptide inducing expression of other proteins, which are then secreted into the supernatant. Thus, the invention further provides a method of identifying the protein in the supernatant characterized by an activity in a particular assay.

Example 12

Construction of GAS Reporter Construct

One signal transduction pathway involved in the differentiation and proliferation of cells is called the Jaks-STATs pathway. Activated proteins in the Jaks-STATs pathway bind to gamma activation site "GAS" elements or interferon-sensitive responsive element ("ISRE"), located in the promoter of many genes. The binding of a protein to these elements alter the expression of the associated gene.

GAS and ISRE elements are recognized by a class of transcription factors called Signal Transducers and Activators of Transcription, or "STATs." There are six members of the STATs family. Stat1 and Stat3 are present in many cell types, as is Stat2 (as response to IFN-alpha is widespread). Stat4 is more restricted and is not in many cell types though it has been found in T helper class I, cells after treatment with IL-12. Stat5 was originally called mammary growth factor, but has been found at higher concentrations in other cells including myeloid cells. It can be activated in tissue culture cells by many cytokines.

The STATs are activated to translocate from the cytoplasm to the nucleus upon tyrosine phosphorylation by a set of kinases known as the Janus Kinase ("Jaks") family. Jaks represent a distinct family of soluble tyrosine kinases and include Tyk2, Jak1, Jak2, and Jak3. These kinases display significant sequence similarity and are generally catalytically inactive in resting cells.

The Jaks are activated by a wide range of receptors summarized in the Table below. (Adapted from review by Schidler and Darnell, Ann. Rev. Biochem. 64:621–51 (1995).) A cytokine receptor family, capable of activating Jaks, is divided into two groups: (a) Class 1 includes receptors for IL-2, IL-3, IL-4, IL-6, IL-7, IL-9, IL-11, IL-12, IL-15, Epo, PRL, GH, G-CSF, GM-CSF, LIF, CNTF, and thrombopoietin; and (b) Class 2 includes IFN-a, IFN-g, and IL-10. The Class 1 receptors share a conserved cysteine motif (a set of four conserved cysteines and one tryptophan) and a WSXWS motif (a membrane proximal region encoding Trp-Ser-Xxx-Trp-Ser (SEQ ID NO:2)).

Thus, on binding of a ligand to a receptor, Jaks are activated, which in turn activate STATs, which then translocate and bind to GAS elements. This entire process is encompassed in the Jaks-STATs signal transduction pathway.

Therefore, activation of the Jaks-STATs pathway, reflected by the binding of the GAS or the ISRE element, can be used to indicate proteins involved in the proliferation and differentiation of cells. For example, growth factors and cytokines are known to activate the Jaks-STATs pathway. (See Table below.) Thus, by using GAS elements linked to reporter molecules, activators of the Jaks-STATs pathway can be identified.

| Ligand | JAKs | | | | STATS | Gas (elements) or ISRE |
|---|---|---|---|---|---|---|
| | tyk2 | Jak1 | Jak2 | Jak3 | | |
| IFN family | | | | | | |
| IFN-a/B | + | + | − | − | 1, 2, 3 | ISRE |
| IFN-g | | + | + | − | 1 | GAS (IRF1 > Lys6 > IFP) |
| Il-10 | + | ? | ? | − | 1, 3 | |
| gp130 family | | | | | | |
| IL-6 (Pleiotrophic) | + | + | + | ? | 1, 3 | GAS (IRF1 > Lys6 > IFP) |
| Il-11 (Pleiotrophic) | ? | + | ? | ? | 1, 3 | |
| OnM (Pleiotrophic) | ? | + | + | ? | 1, 3 | |
| LIF (Pleiotrophic) | ? | + | + | ? | 1, 3 | |
| CNTF (Pleiotrphic) | −/+ | + | + | ? | 1, 3 | |
| G-CSF (Pleiotrophic) | ? | + | ? | ? | 1, 3 | |
| IL-12 (PLeiotrophic) | + | − | + | + | 1, 3 | |
| g-C family | | | | | | |
| IL-2 (lymphocytes) | − | + | − | + | 1, 3, 5 | GAS |
| IL-4 (lymphocytes) | − | + | − | + | 6 | GAS (IRF1 = IFP >> Ly6) (IgH) |
| IL-7 (lymphocytes) | − | + | − | + | 5 | GAS |
| IL-9 (lymphocytes) | − | + | − | + | 5 | GAS |
| IL-13 (lymphocytes) | − | + | ? | ? | 6 | GAS |
| IL-15 | ? | + | ? | + | 5 | GAS |
| gp140 family | | | | | | |
| IL-3 (myeloid) | − | − | + | − | 5 | GAS (IRF1 > IFP >> Ly6) |
| IL-5 (myeloid) | − | − | + | − | 5 | GAS |
| GM-CSF (myeloid) | − | − | + | − | 5 | GAS |
| Growth hormone family | | | | | | |
| GH | ? | − | + | − | 5 | |
| PRL | ? | +/− | + | − | 1, 3, 5 | |
| EPO | ? | − | + | − | 5 | GAS (B-CAS > IRF1 = IFP >> Ly6) |
| Receptor Tyrosine Kinases | | | | | | |
| EGF | ? | + | + | − | 1, 3 | GAS (IRF1) |
| PDGF | ? | + | + | − | 1, 3 | |
| CSF-1 | ? | + | + | − | 1, 3 | GAS (not IRF1) |

To construct a synthetic GAS containing promoter element, which is used in the Biological Assays described in Examples 13–14, a PCR based strategy is employed to generate a GAS-SV40 promoter sequence. The 5' primer contains four tandem copies of the GAS binding site found in the IRFI promoter and previously demonstrated to bind STATs upon induction with a range of cytokines (Rothman et al., Immunity 1:457–468 (1994).), although other GAS or ISRE elements can be used instead. The 5' primer also contains 18 bp of sequence complementary to the SV40 early promoter sequence and is flanked with an XhoI site. The sequence of the 5' primer is:

5':GCGCCTCGAGATTTCCCCGAAATCTAGATTTCCCCGAAATGATTTCCCCG (SEQ ID NO:3)

AAATGATTTCCCCGAAATATCTGCCATCTCAATTAG:3'

The downstream primer is complementary to the SV40 promoter and is flanked with a Hind III site: 5':GCG-GCAAGCTTTTTGCAAAGCCTAGGC:3' (SEQ ID NO:4)

PCR amplification is performed using the SV40 promoter template present in the B-gal :promoter plasmid obtained from Clontech. The resulting PCR fragment is digested with XhoI/Hind III and subcloned into BLSK2-. (Stratagene.) Sequencing with forward and reverse primers confirms that the insert contains the following sequence:

5':<u>CTCGAG</u>ATTTCCCCGAAATCTAGATTTCCCCGAAATGATTTCCCCGAAATG (SEQ ID NO:5)

ATTTCCCCGAAATATCTGCCATCTCAATTAGTCAGCAACCATAGTCCCGCCC

CTAACTCCGCCCATCCCGCCCCTAACTCCGCCCAGTTCCGCCCATTCTCCGC

CCCATGGCTGACTAATTTTTTTTATTTATGCAGAGGCCGAGGCCGCCTCGGC

CTCTGAGCTATTCCAGAAGTAGTGAGGAGGCTTTTTTGGAGGCCTAGGCTTT

TGCAAA<u>AAGCTT</u>:3'

With this GAS promoter element linked to the SV40 promoter, a GAS:SEAP2 reporter construct is next engineered. Here, the reporter molecule is a secreted alkaline phosphatase, or "SEAP." Clearly, however, any reporter molecule can be instead of SEAP, in this or in any of the other Examples. Well known reporter molecules that can be used instead of SEAP include chloramphenicol acetyltransferase (CAT), luciferase, alkaline phosphatase, B-galactosidase, green fluorescent protein (GFP), or any protein detectable by an antibody.

The above sequence confirmed synthetic GAS-SV40 promoter element is subcloned into the pSEAP-Promoter vector obtained from Clontech using HindIII and XhoI, effectively replacing the SV40 promoter with the amplified GAS:SV40 promoter element, to create the GAS-SEAP vector. However, this vector does not contain a neomycin resistance gene, and therefore, is not preferred for mammalian expression systems.

Thus, in order to generate mammalian stable cell lines expressing the GAS-SEAP reporter, the GAS-SEAP cassette is removed from the GAS-SEAP vector using SalI and NotI, and inserted into a backbone vector containing the neomycin resistance gene, such as pGFP-1 (Clontech), using these restriction sites in the multiple cloning site, to create the GAS-SEAP/Neo vector. Once this vector is transfected into mammalian cells, this vector can then be used as a reporter molecule for GAS binding as described in Examples 13–14.

Other constructs can be made using the above description and replacing GAS with a different promoter sequence. For example, construction of reporter molecules containing NFK-B and EGR promoter sequences are described in Examples 15 and 16. However, many other promoters can be substituted using the protocols described in these Examples. For instance, SRE, IL-2, NFAT, or Osteocalcin promoters can be substituted, alone or in combination (e.g., GAS/NF-KB/EGR, GAS/NF-KB, Il-2/NFAT, or NF-KB/GAS). Similarly, other cell lines can be used to test reporter construct activity, such as HELA (epithelial), HUVEC (endothelial), Reh (B-cell), Saos-2 (osteoblast), HUVAC (aortic), or Cardiomyocyte.

Example 13
High-Throughput Screening Assay for T-cell Activity

The following protocol is used to assess T-cell activity by identifying factors, such as growth factors and cytokines, that may proliferate or differentiate T-cells. T-cell activity is assessed using the GAS/SEAP/Neo construct produced in Example 12. Thus, factors that increase SEAP activity indicate the ability to activate the Jaks-STATS signal transduction pathway. The T-cell used in this assay is Jurkat T-cells (ATCC Accession No. TIB-152), although Molt-3 cells (ATCC Accession No. CRL-1552) and Molt-4 cells (ATCC Accession No. CRL-1582) cells can also be used.

Jurkat T-cells are lymphoblastic CD4+ Th1 helper cells. In order to generate stable cell lines, approximately 2 million Jurkat cells are transfected with the GASSEAP/neo vector using DMRIE-C (Life Technologies)(transfection procedure described below). The transfected cells are seeded to a density of approximately 20,000 cells per well and transfectants resistant to 1 mg/ml genticin selected. Resistant colonies are expanded and then tested for their response to increasing concentrations of interferon gamma. The dose response of a selected clone is demonstrated.

Specifically, the following protocol will yield sufficient cells for 75 wells containing 200 ul of cells. Thus, it is either scaled up, or performed in multiple to generate sufficient cells for multiple 96 well plates. Jurkat cells are maintained in RPMI+10% serum with 1% Pen-Strep. Combine 2.5 mls of OPTI-MEM (Life Technologies) with 10 ug of plasmid DNA in a T25 flask. Add 2.5 ml OPTI-MEM containing 50 ul of DMRIE-C and incubate at room temperature for 15–45 mins.

During the incubation period, count cell concentration, spin down the required number of cells ($10^7$ per transfection), and resuspend in OPTI-MEM to a final concentration of $10^7$ cells/ml. Then add 1 ml of $1\times10^7$ cells in OPTI-MEM to T25 flask and incubate at 37° C. for 6 hrs. After the incubation, add 10 ml of RPMI+15% serum.

The Jurkat:GAS-SEAP stable reporter lines are maintained in RPMI+10% serum, 1 mg/ml Genticin, and 1% Pen-Strep. These cells are treated with supernatants containing a polypeptide as produced by the protocol described in Example 11.

On the day of treatment with the supernatant, the cells should be washed and resuspended in fresh RPMI+10% serum to a density of 500,000 cells per ml. The exact number of cells required will depend on the number of supernatants being screened. For one 96 well plate, approximately 10 million cells (for 10 plates, 100 million cells) are required.

Transfer the cells to a triangular reservoir boat, in order to dispense the cells into a 96 well dish, using a 12 channel pipette. Using a 12 channel pipette, transfer 200 ul of cells into each well (therefore adding 100,000 cells per well).

After all the plates have been seeded, 50 ul of the supernatants are transferred directly from the 96 well plate containing the supernatants into each well using a 12 channel pipette. In addition, a dose of exogenous interferon gamma (0.1, 1.0, 10 ng) is added to wells H9, H10, and H11 to serve as additional positive controls for the assay.

The 96 well dishes containing Jurkat cells treated with supernatants are placed in an incubator for 48 hrs (note: this time is variable between 48–72 hrs). 35 ul samples from each well are then transferred to an opaque 96 well plate using a 12 channel pipette. The opaque plates should be covered (using sellophene covers) and stored at −20° C. until SEAP assays are performed according to Example 17. The plates containing the remaining treated cells are placed at 4° C. and serve as a source of material for repeating the assay on a specific well if desired.

As a positive control, 100 Unit/ml interferon gamma can be used which is known to activate Jurkat T cells. Over 30 fold induction is typically observed in the positive control wells.

The above protocol may be used in the generation of both transient, as well as, stable transfected cells, which would be apparent to those of skill in the art.

Example 14
High-Throughput Screening Assay Identifying Myeloid Activity

The following protocol is used to assess myeloid activity by identifying factors, such as growth factors and cytokines, that may proliferate or differentiate myeloid cells. Myeloid cell activity is assessed using the GAS/SEAP/Neo construct produced in Example 12. Thus, factors that increase SEAP activity indicate the ability to activate the Jaks-STATS signal transduction pathway. The myeloid cell used in this assay is U937, a pre-monocyte cell line, although TF-1, HL60, or KG1 can be used.

To transiently transfect U937 cells with the GAS/SEAP/Neo construct produced in Example 12, a DEAE-Dextran method (Kharbanda et. al., 1994, Cell Growth & Differentiation, 5:259–265) is used. First, harvest 2×10e$^7$ U937 cells and wash with PBS. The U937 cells are usually grown in RPMI 1640 medium containing 10% heat-inactivated fetal bovine serum (FBS) supplemented with 100 units/ml penicillin and 100 mg/ml streptomycin.

Next, suspend the cells in 1 ml of 20 mM Tris-HCl (pH 7.4) buffer containing 0.5 mg/ml DEAE-Dextran, 8 ug GAS-SEAP2 plasmid DNA, 140 mM NaCl, 5 mM KCl, 375 uM $Na_2HPO_4.7H_2O$, 1 mM $MgCl_2$, and 675 uM $CaCl_2$. Incubate at 37° C. for 45 min.

Wash the cells with RPMI 1640 medium containing 10% FBS and then resuspend in 10 ml complete medium and incubate at 37° C. for 36 hr.

The GAS-SEAP/U937 stable cells are obtained by growing the cells in 400 ug/ml G418. The G418-free medium is used for routine growth but every one to two months, the cells should be re-grown in 400 ug/ml G418 for couple of passages.

These cells are tested by harvesting 1×10$^8$ cells (this is enough for ten 96-well plates assay) and wash with PBS. Suspend the cells in 200 ml above described growth medium, with a final density of 5×10$^5$ cells/ml. Plate 200 ul cells per well in the 96-well plate (or 1×10$^5$ cells/well).

Add 50 ul of the supernatant prepared by the protocol described in Example 11. Incubate at 37° C. for 48 to 72 hr. As a positive control, 100 Unit/ml interferon gamma can be used which is known to activate U937 cells. Over 30 fold induction is typically observed in the positive control wells. SEAP assay the supernatant according to the protocol described in Example 17.

Example 15
High-Throughput Screening Assay Identifying Neuronal Activity

When cells undergo differentiation and proliferation, a group of genes are activated through many different signal transduction pathways. One of these genes, EGR1 (early growth response gene 1), is induced in various tissues and cell types upon activation. The promoter of EGR1 is responsible for such induction. Using the EGR1 promoter linked to reporter molecules, activation of cells can be assessed.

Particularly, the following protocol is used to assess neuronal activity in PC12 cell lines. PC12 cells (rat phenochromocytoma cells) are known to proliferate and/or differentiate by activation with a number of mitogens, such as TPA (tetradecanoyl phorbol acetate), NGF (nerve growth factor), and EGF (epidermal growth factor). The EGR1 gene expression is activated during this treatment. Thus, by stably transfecting PC12 cells with a construct containing an EGR promoter linked to SEAP reporter, activation of PC12 cells can be assessed.

The EGR/SEAP reporter construct can be assembled by the following protocol. The EGR-1 promoter sequence (−633 to +1)(Sakamoto K et al., Oncogene 6:867–871 (1991)) can be PCR amplified from human genomic DNA using the following primers:

```
                                  (SEQ ID NO:6)
5'GCGCTCGAGGGATGACAGCGATAGAACCCCGG-3'

(SEQ ID NO:7)
5'GCGAAGCTTCGCGACTCCCCGGATCCGCCTC-3'
```

Using the GAS:SEAP/Neo vector produced in Example 12, EGR1 amplified product can then be inserted into this vector. Linearize the GAS:SEAP/Neo vector using restriction enzymes XhoI/HindIII, removing the GAS/SV40 stuffer. Restrict the EGR1 amplified product with these same enzymes. Ligate the vector and the EGR1 promoter.

To prepare 96 well-plates for cell culture, two mls of a coating solution (1:30 dilution of collagen type I (Upstate Biotech Inc. Cat#08-115) in 30% ethanol (filter sterilized)) is added per one 10 cm plate or 50 ml per well of the 96-well plate, and allowed to air dry for 2 hr.

PC12 cells are routinely grown in RPMI-1640 medium (Bio Whittaker) containing 10% horse serum (JRH BIOSCIENCES, Cat. # 12449-78P), 5% heat-inactivated fetal bovine serum (FBS) supplemented with 100 units/ml penicillin and 100 ug/ml streptomycin on a precoated 10 cm tissue culture dish. One to four split is done every three to four days. Cells are removed from the plates by scraping and resuspended with pipetting up and down for more than 15 times.

Transfect the EGR/SEAP/Neo construct into PC12 using the Lipofectamine protocol described in Example 11. EGR-SEAP/PC12 stable cells are obtained by growing the cells in 300 ug/ml G418. The G418-free medium is used for routine growth but every one to two months, the cells should be re-grown in 300 ug/ml G418 for couple of passages.

To assay for neuronal activity, a 10 cm plate with cells around 70 to 80% confluent is screened by removing the old medium. Wash the cells once with PBS Phosphate buffered saline). Then starve the cells in low serum medium (RPMI-1640 containing 1% horse serum and 0.5% FBS with antibiotics) overnight.

The next morning, remove the medium and wash the cells with PBS. Scrape off the cells from the plate, suspend the cells well in 2 ml low serum medium. Count the cell number and add more low serum medium to reach final cell density as $5 \times 10^5$ cells/ml.

Add 200 ul of the cell suspension to each well of 96-well plate (equivalent to $1 \times 10^5$ cells/well). Add 50 ul supernatant produced by Example 11, 37° C. for 48 to 72 hr. As a positive control, a growth factor known to activate PC12 cells through EGR can be used, such as 50 ng/ul of Neuronal Growth Factor (NGF). Over fifty-fold induction of SEAP is typically seen in the positive control wells. SEAP assay the supernatant according to Example 17.

Example 16
High-Throughput Screening Assay for T-cell Activity

NF-κB (Nuclear Factor κB) is a transcription factor activated by a wide variety of agents including the inflammatory cytokines IL-1 and TNF, CD30 and CD40, lymphotoxin-alpha and lymphotoxin-beta, by exposure to LPS or thrombin, and by expression of certain viral gene products. As a transcription factor, NF-κB regulates the expression of genes involved in immune cell activation, control of apoptosis (NF-κB appears to shield cells from apoptosis), B and T-cell development, anti-viral and antimicrobial responses, and multiple stress responses.

In non-stimulated conditions, NF-κB is retained in the cytoplasm with I-κB (Inhibitor κB). However, upon stimulation, I-κB is phosphorylated and degraded, causing NF-κB to shuttle to the nucleus, thereby activating transcription of target genes. Target genes activated by NF-κB include IL-2, IL-6, GM-CSF, ICAM-1 and class 1 MHC.

Due to its central role and ability to respond to a range of stimuli, reporter constructs utilizing the NF-κB promoter element are used to screen the supernatants produced in Example 11. Activators or inhibitors of NF-kB would be useful in treating diseases. For example, inhibitors of NF-κB could be used to treat those diseases related to the acute or chronic activation of NF-kB, such as rheumatoid arthritis.

To construct a vector containing the NF-κB promoter element, a PCR based strategy is employed. The upstream primer contains four tandem copies of the NF-κB binding site (GGGGACTTTCCC) (SEQ ID NO:8), 18 bp of sequence complementary to the 5' end of the SV40 early promoter sequence, and is flanked with an XhoI site:
5' :GCGGCCTCGAGGGGACTTTCCCGGG-GACTTTCCGGGGACTTTCCGGGAC TTTCCATC-CTGCCATCTCAATTAG:3' (SEQ ID NO:9)

The downstream primer is complementary to the 3' end of the SV40 promoter and is flanked with a Hind III site:
5':GCGGCAAGCTTTTTGCAAAGCCTAGGC:3' (SEQ ID NO:4)

PCR amplification is performed using the SV40 promoter template present in the pB-gal:promoter plasmid obtained from Clontech. The resulting PCR fragment is digested with XhoI and Hind III and subcloned into BLSK2-. (Stratagene) Sequencing with the T7 and T3 primers confirms the insert contains the following sequence:

5':CTCGAGGGGACTTTCCCGGGGACTTTCCGGGGACTTTCCGGGACTTTCC (SEQ ID NO:10)
ATCTGCCATCTCAATTAGTCAGCAACCATAGTCCCGCCCCTAACTCCGCCCA
TCCCGCCCCTAACTCCGCCCAGTTCCGCCCATTCTCCGCCCCATGGCTGACT
AATTTTTTTTATTTATGCAGAGGCCGAGGCCGCCTCGGCCTCTGAGCTATTC
CAGAAGTAGTGAGGAGGCTTTTTTGGAGGCCTAGGCTTTTGCAAAAAGCTT:
3'

Next, replace the SV40 minimal promoter element present in the pSEAP2-promoter plasmid (Clontech) with this NF-κB/SV40 fragment using XhoI and HindIII. However, this vector does not contain a neomycin resistance gene, and therefore, is not preferred for mammalian expression systems.

In order to generate stable mammalian cell lines, the NF-κB/SV40 /SEAP cassette is removed from the above NF-κB/SEAP vector using restriction enzymes SalI and NotI, and inserted into a vector containing neomycin resistance. Particularly, the NF-κB/SV40 /SEAP cassette was inserted into pGFP-1 (Clontecb), replacing the GFP gene, after restricting pGFP-1 with SalI and NotI.

Once NF-κB/SV40 /SEAP/Neo vector is created, stable Jurkat T-cells are created and maintained according to the protocol described in Example 13. Similarly, the method for assaying supernatants with these stable Jurkat T-cells is also described in Example 13. As a positive control, exogenous TNF alpha (0.1,1, 10 ng) is added to wells H9, H10, and H11, with a 5–10 fold activation typically observed.

Example 17
Assay for SEAP Activity

As a reporter molecule for the assays described in Examples 13–16, SEAP activity is assayed using the Tropix Phospho-light Kit (Cat. BP-400) according to the following general procedure. The Tropix Phospho-light Kit supplies the Dilution, Assay, and Reaction Buffers used below.

Prime a dispenser with the 2.5×Dilution Buffer and dispense 15 μl of 2.5×dilution buffer into Optiplates containing 35 μl of a supernatant. Seal the plates with a plastic sealer and incubate at 65° C. for 30 min. Separate the Optiplates to avoid uneven heating.

Cool the samples to room temperature for 15 minutes. Empty the dispenser and prime with the Assay Buffer. Add 50 μl Assay Buffer and incubate at room temperature 5 min. Empty the dispenser and prime with the Reaction Buffer (see the table below). Add 50 μl Reaction Buffer and incubate at room temperature for 20 minutes. Since the intensity of the chemiluminescent signal is time dependent, and it takes about 10 minutes to read 5 plates on luminometer, one should treat 5 plates at each time and start the second set 10 minutes later.

Read the relative light unit in the luminometer. Set H12 as blank, and print the results. An increase in chemiluminescence indicates reporter activity.

Reaction Buffer Formulation:

| # of plates | Rxn buffer diluent (ml) | CSPD (ml) |
|---|---|---|
| 10 | 60 | 3 |
| 11 | 65 | 3.25 |
| 12 | 70 | 3.5 |
| 13 | 75 | 3.75 |
| 14 | 80 | 4 |
| 15 | 85 | 4.25 |
| 16 | 90 | 4.5 |
| 17 | 95 | 4.75 |
| 18 | 100 | 5 |
| 19 | 105 | 5.25 |
| 20 | 110 | 5.5 |
| 21 | 115 | 5.75 |
| 22 | 120 | 6 |
| 23 | 125 | 6.25 |
| 24 | 130 | 6.5 |
| 25 | 135 | 6.75 |
| 26 | 140 | 7 |
| 27 | 145 | 7.25 |
| 28 | 150 | 7.5 |
| 29 | 155 | 7.75 |
| 30 | 160 | 8 |
| 31 | 165 | 8.25 |
| 32 | 170 | 8.5 |
| 33 | 175 | 8.75 |
| 34 | 180 | 9 |
| 35 | 185 | 9.25 |
| 36 | 190 | 9.5 |
| 37 | 195 | 9.75 |
| 38 | 200 | 10 |
| 39 | 205 | 10.25 |
| 40 | 210 | 10.5 |
| 41 | 215 | 10.75 |
| 42 | 220 | 11 |
| 43 | 225 | 11.25 |
| 44 | 230 | 11.5 |
| 45 | 235 | 11.75 |
| 46 | 240 | 12 |
| 47 | 245 | 12.25 |
| 48 | 250 | 12.5 |
| 49 | 255 | 12.75 |
| 50 | 260 | 13 |

Example 18
High-Throughput Screening Assay Identifying Changes in Small Molecule Concentration and Membrane Permeability Binding of a ligand to a receptor is known to alter intracellular levels of small molecules, such as calcium, potassium, sodium, and pH, as well as alter membrane potential. These alterations can be measured in an assay to identify supernatants which bind to receptors of a particular cell. Although the following protocol describes an assay for calcium, this protocol can easily be modified to detect changes in potassium, sodium, pH, membrane potential, or any other small molecule which is detectable by a fluorescent probe.

The following assay uses Fluorometric Imaging Plate Reader ("FLIPR") to measure changes in fluorescent molecules (Molecular Probes) that bind small molecules. Clearly, any fluorescent molecule detecting a small molecule can be used instead of the calcium fluorescent molecule, fluo-4 (Molecular Probes, Inc.; catalog no. F-14202), used here.

For adherent cells, seed the cells at 10,000–20,000 cells/well in a Co-star black 96-well plate with clear bottom. The plate is incubated in a $CO_2$ incubator for 20 hours. The adherent cells are washed two times in Biotek washer with 200 ul of HBSS (Hank's Balanced Salt Solution) leaving 100 ul of buffer after the final wash.

A stock solution of 1 mg/ml fluo-4 is made in 10% pluronic acid DMSO. To load the cells with fluo-4, 50 ul of 12 ug/ml fluo-4 is added to each well. The plate is incubated at 37° C. in a $CO_2$ incubator for 60 min. The plate is washed four times in the Biotek washer with HBSS leaving 100 ul of buffer.

For non-adherent cells, the cells are spun down from culture media. Cells are re-suspended to $2-5\times10^6$ cells/ml with HBSS in a 50-ml conical tube. 4 ul of 1 mg/ml fluo-4 solution in 10% pluronic acid DMSO is added to each ml of cell suspension. The tube is then placed in a 37° C. water bath for 30–60 min. The cells are washed twice with HBSS, resuspended to $1\times10^6$ cells/ml, and dispensed into a microplate, 100 ul/well. The plate is centrifuged at 1000 rpm for 5 min. The plate is then washed once in Denley CellWash with 200 ul, followed by an aspiration step to 100 ul final volume.

For a non-cell based assay, each well contains a fluorescent molecule, such as fluo-4. The supernatant is added to the well, and a change in fluorescence is detected.

To measure the fluorescence of intracellular calcium, the FLIPR is set for the following parameters: (1) System gain is 300–800 mW; (2) Exposure time is 0.4 second; (3) Camera F/stop is F/2; (4) Excitation is 488 nm; (5) Emission is 530 nm; and (6) Sample addition is 50 ul. Increased emission at 530 nm indicates an extracellular signaling event which has resulted in an increase in the intracellular $Ca++$ concentration.

Example 19
High-Throughput Screening Assay Identifying Tyrosine Kinase Activity

The Protein Tyrosine Kinases (PTK) represent a diverse group of transmembrane and cytoplasmic kinases. Within the Receptor Protein Tyrosine Kinase RPTK) group are receptors for a range of mitogenic and metabolic growth factors including the PDGF, FGF, EGF, NGF, HGF and Insulin receptor subfamilies. In addition there are a large family of RPTKs for which the corresponding ligand is unknown. Ligands for RPTKs include mainly secreted small proteins, but also membrane-bound and extracellular matrix proteins.

Activation of RPTK by ligands involves ligand-mediated receptor dimerization, resulting in transphosphorylation of the receptor subunits and activation of the cytoplasmic tyrosine kinases. The cytoplasmic tyrosine kinases include receptor associated tyrosine kinases of the src-family (e.g., src, yes, lck, lyn, fyn) and non-receptor linked and cytosolic protein tyrosine kinases, such as the Jak family, members of which mediate signal transduction triggered by the cytokine superfamily of receptors (e.g., the Interleukins, Interferons, GM-CSF, and Leptin).

Because of the wide range of known factors capable of stimulating tyrosine kinase activity, the identification of novel human secreted proteins capable of activating tyrosine kinase signal transduction pathways are of interest. Therefore, the following protocol is designed to identify those novel human secreted proteins capable of activating the tyrosine kinase signal transduction pathways.

Seed target cells (e.g., primary keratinocytes) at a density of approximately 25,000 cells per well in a 96 well Loprodyne Silent Screen Plates purchased from Nalge Nunc (Naperville, Ill.). The plates are sterilized with two 30 minute rinses with 100% ethanol, rinsed with water and dried overnight. Some plates are coated for 2 hr with 100 ml of cell culture grade type I collagen (50 mg/ml), gelatin (2%) or polylysine (50 mg/ml), all of which can be purchased from Sigma Chemicals (St. Louis, Mo.) or 10% Matrigel purchased from Becton Dickinson (Bedford, Mass.), or calf serum, rinsed with PBS and stored at 4° C. Cell growth on these plates is assayed by seeding 5,000 cells/well in growth medium and indirect quantitation of cell number through use of alamarBlue as described by the manufacturer Alamar Biosciences, Inc. (Sacramento, Calif.) after 48 hr. Falcon plate covers #3071 from Becton Dickinson (Bedford, Mass.) are used to cover the Loprodyne Silent Screen Plates. Falcon Microtest III cell culture plates can also be used in some proliferation experiments.

To prepare extracts, A431 cells are seeded onto the nylon membranes of Loprodyne plates (20,000/200 ml/well) and cultured overnight in complete medium. Cells are quiesced by incubation in serum-free basal medium for 24 hr. After 5–20 minutes treatment with EGF (60 ng/ml) or 50 ul of the supernatant produced in Example 11, the medium was removed and 100 ml of extraction buffer ((20 mM HEPES pH 7.5, 0.15 M NaCl, 1% Triton X-100, 0.1% SDS, 2 mM Na3VO4, 2 mM Na4P2O7 and a cocktail of protease inhibitors (# 1836170) obtained from Boeheringer Mannheim (Indianapolis, Ind.) is added to each well and the plate is shaken on a rotating shaker for 5 minutes at 4° C. The plate is then placed in a vacuum transfer manifold and the extract filtered through the 0.45 mm membrane bottoms of each well using house vacuum. Extracts are collected in a 96-well catch/assay plate in the bottom of the vacuum manifold and immediately placed on ice. To obtain extracts clarified by centrifugation, the content of each well, after detergent solubilization for 5 minutes, is removed and centrifuged for 15 minutes at 4° C. at 16,000×g.

Test the filtered extracts for levels of tyrosine kinase activity. Although many methods of detecting tyrosine kinase activity are known, one method is described here.

Generally, the tyrosine kinase activity of a supernatant is evaluated by determining its ability to phosphorylate a tyrosine residue on a specific substrate (a biotinylated peptide). Biotinylated peptides that can be used for this purpose include PSK1 (corresponding to amino acids 6–20 of the cell division kinase cdc2-p34) and PSK2 (corresponding to amino acids 1–17 of gastrin). Both peptides are substrates for a range of tyrosine kinases and are available from Boehringer Mannheim.

The tyrosine kinase reaction is set up by adding the following components in order. First, add 10 ul of 5 uM Biotinylated Peptide, then 10 ul ATP/Mg$_{2+}$ (5 mM ATP/50 mM MgCl$_2$), then 10 ul of 5×Assay Buffer (40 mM imidazole hydrochloride, pH7.3, 40 mM beta-glycerophosphate, 1 mM EGTA, 100 mM MgCl$_2$, 5 mM MnCl$_2$, 0.5 mg/ml BSA), then 5 ul of Sodium Vanadate(1 mM), and then 5 ul of water. Mix the components gently and preincubate the reaction mix at 30° C. for 2 min. Initial the reaction by adding 10 ul of the control enzyme or the filtered supernatant.

The tyrosine kinase assay reaction is then terminated by adding 10 ul of 120 mm EDTA and place the reactions on ice.

Tyrosine kinase activity is determined by transferring 50 ul aliquot of reaction mixture to a microtiter plate (MTP) module and incubating at 37° C. for 20 min. This allows the streptavadin coated 96 well plate to associate with the biotinylated peptide. Wash the MTP module with 300 ul/well of PBS four times. Next add 75 ul of anti-phospotyrosine antibody conjugated to horse radish peroxidase(anti-P-Tyr-POD(0.5 u/ml)) to each well and incubate at 37° C. for one hour. Wash the well as above.

Next add 100 ul of peroxidase substrate solution (Boehringer Mannheim) and incubate at room temperature for at least 5 mins (up to 30 min). Measure the absorbance of the sample at 405 nm by using ELISA reader. The level of bound peroxidase activity is quantitated using an ELISA reader and reflects the level of tyrosine kinase activity.

Example 20

High-Throughput Screening Assay Identifying Phosphorylation Activity

As a potential alternative and/or compliment to the assay of protein tyrosine kinase activity described in Example 19, an assay which detects activation (phosphorylation) of major intracellular signal transduction intermediates can also be used. For example, as described below one particular assay can detect tyrosine phosphorylation of the Erk-1 and Erk-2 kinases. However, phosphorylation of other molecules, such as Raf, JNK, p38 MAP, Map kinase kinase (MEK), MEK kinase, Src, Muscle specific kinase (MuSK), IRAK, Tec, and Janus, as well as any other phosphoserine, phosphotyrosine, or phosphothreonine molecule, can be detected by substituting these molecules for Erk-1 or Erk-2 in the following assay.

Specifically, assay plates are made by coating the wells of a 96-well ELISA plate with 0.1 ml of protein G (1 ug/ml) for 2 hr at room temp, (RT). The plates are then rinsed with PBS and blocked with 3% BSA/PBS for 1 hr at RT. The protein G plates are then treated with 2 commercial monoclonal antibodies (100 ng/well) against Erk-1 and Erk-2 (1 hr at RT) (Santa Cruz Biotechnology). (To detect other molecules, this step can easily be modified by substituting a monoclonal antibody detecting any of the above described molecules.) After 3–5 rinses with PBS, the plates are stored at 4° C. until use.

A431 cells are seeded at 20,000/well in a 96-well Loprodyne filterplate and cultured overnight in growth medium. The cells are then starved for 48 hr in basal medium (DMEM) and then treated with EGF (6 ng/well) or 50 ul of the supernatants obtained in Example 11 for 5–20 minutes. The cells are then solubilized and extracts filtered directly into the assay plate.

After incubation with the extract for 1 hr at RT, the wells are again rinsed. As a positive control, a commercial preparation of MAP kinase (10 ng/well) is used in place of A431 extract. Plates are then treated with a commercial polyclonal (rabbit) antibody (1 ug/ml) which specifically recognizes the phosphorylated epitope of the Erk-1 and Erk-2 kinases (1 hr at RT). This antibody is biotinylated by standard procedures. The bound polyclonal antibody is then quantitated by successive incubations with Europium-streptavidin and Europium fluorescence enhancing reagent in the Wallac DELFIA instrument (time-resolved fluorescence). An increased fluorescent signal over background indicates a phosphorylation.

Example 21

Method of Determining Alterations in a Gene Corresponding to a Polynucleotide

RNA isolated from entire families or individual patients presenting with a phenotype of interest (such as a disease) is be isolated. cDNA is then generated from these RNA samples using protocols known in the art. (See, Sambrook.) The cDNA is then used as a template for PCR, employing primers surrounding regions of interest in SEQ ID NO:X. Suggested PCR conditions consist of 35 cycles at 95° C. for 30 seconds; 60–120 seconds at 52–58° C.; and 60–120 seconds at 70° C., using buffer solutions described in Sidransky, D., et al., Science 252:706 (1991).

PCR products are then sequenced using primers labeled at their 5' end with T4 polynucleotide kinase, employing SequiTherm Polymerase. (Epicentre Technologies). The intron-exon borders of selected exons is also determined and genomic PCR products analyzed to confirm the results. PCR products harboring suspected mutations is then cloned and sequenced to validate the results of the direct sequencing.

PCR products is cloned into T-tailed vectors as described in Holton, T. A. and Graham, M. W., Nucleic Acids Research, 19:1156 (1991) and sequenced with T7 polymerase (United States Biochemical). Affected individuals are identified by mutations not present in unaffected individuals.

Genomic rearrangements are also observed as a method of determining alterations in a gene corresponding to a polynucleotide. Genomic clones isolated according to Example 2 are nick-translated with digoxigenindeoxy-uridine 5'-triphosphate (Boehringer Manheim), and FISH performed as described in Johnson, Cg. et al., Methods Cell Biol. 35:73–99 (1991). Hybridization with the labeled probe is carried out using a vast excess of human cot-1 DNA for specific hybridization to the corresponding genomic locus.

Chromosomes are counterstained with 4,6-diamino-2-phenylidole and propidium iodide, producing a combination of C- and R-bands. Aligned images for precise mapping are obtained using a triple-band filter set (Chroma Technology, Brattleboro, Vt.) in combination with a cooled charge-coupled device camera (Photometrics, Tucson, Ariz.) and variable excitation wavelength filters. (Johnson, Cv. et al., Genet. Anal. Tech. Appl., 8:75 (1991).) Image collection, analysis and chromosomal fractional length measurements are performed using the ISee Graphical Program System. (Inovision Corporation, Durham, N.C.) Chromosome alterations of the genomic region hybridized by the probe are identified as insertions, deletions, and translocations. These alterations are used as a diagnostic marker for an associated disease.

Example 22
Method of Detecting Abnormal Levels of a Polypeptide in a Biological Sample A polypeptide of the present invention can be detected in a biological sample, and if an increased or decreased level of the polypeptide is detected, this polypeptide is a marker for a particular phenotype. Methods of detection are numerous, and thus, it is understood that one skilled in the art can modify the following assay to fit their particular needs.

For example, antibody-sandwich ELISAs are used to detect polypeptides in a sample, preferably a biological sample. Wells of a microtiter plate are coated with specific antibodies, at a final concentration of 0.2 to 10 ug/ml. The antibodies are either monoclonal or polyclonal and are produced by the method described in Example 10. The wells are blocked so that non-specific binding of the polypeptide to the well is reduced.

The coated wells are then incubated for >2 hours at RT with a sample containing the polypeptide. Preferably, serial dilutions of the sample should be used to validate results. The plates are then washed three times with deionized or distilled water to remove unbounded polypeptide.

Next, 50 ul of specific antibody-alkaline phosphatase conjugate, at a concentration of 25–400 ng, is added and incubated for 2 hours at room temperature. The plates are again washed three times with deionized or distilled water to remove unbounded conjugate.

Add 75 ul of 4-methylumbelliferyl phosphate (MUP) or p-nitrophenyl phosphate (NPP) substrate solution to each well and incubate 1 hour at room temperature. Measure the reaction by a microtiter plate reader. Prepare a standard curve, using serial dilutions of a control sample, and plot polypeptide concentration on the X-axis (log scale) and fluorescence or absorbance of the Y-axis (linear scale). Interpolate the concentration of the polypeptide in the sample using the standard curve.

Example 23
Formulating a Polypeptide

The secreted polypeptide composition will be formulated and dosed in a fashion consistent with good medical practice, taking into account the clinical condition of the individual patient (especially the side effects of treatment with the secreted polypeptide alone), the site of delivery, the method of administration, the scheduling of administration, and other factors known to practitioners. The "effective amount" for purposes herein is thus determined by such considerations.

As a general proposition, the total pharmaceutically effective amount of secreted polypeptide administered parenterally per dose will be in the range of about 1 $\mu$g/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the secreted polypeptide is typically administered at a dose rate of about 1 $\mu$g/kg/hour to about 50 $\mu$g/kg/hour, either by 1–4 injections per day or by continuous subcutaneous infusions, for example, using a mini-pump. An intravenous bag solution may also be employed. The length of treatment needed to observe changes and the interval following treatment for responses to occur appears to vary depending on the desired effect.

Pharmaceutical compositions containing the secreted protein of the invention are administered orally, rectally, parenterally, intracistemally, intravaginally, intraperitoneally, topically (as by powders, ointments, gels, drops or transdermal patch), bucally, or as an oral or nasal spray. "Pharmaceutically acceptable carrier" refers to a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

The secreted polypeptide is also suitably administered by sustained-release systems. Suitable examples of sustained-release compositions include semi-permeable polymer matrices in the form of shaped articles, e.g., films, or mirocapsules. Sustained-release matrices include polylactides (U.S. Pat. No. 3,773,919, EP 58,481), copolymers of L-glutamic acid and gamma-ethyl-L-glutamate (Sidman, U. et al., Biopolymers 22:547–556 (1983)), poly (2-hydroxyethyl methacrylate) (R. Langer et al., J. Biomed. Mater. Res. 15:167–277 (1981), and R. Langer, Chem. Tech. 12:98–105 (1982)), ethylene vinyl acetate (R. Langer et al.) or poly-D-(-)-3-hydroxybutyric acid (EP 133,988). Sustained-release compositions also include liposomally entrapped polypeptides. Liposomes containing the secreted polypeptide are prepared by methods known per se: DE 3,218,121; Epstein et al., Proc. Natl. Acad. Sci. USA 82:3688–3692 (1985); Hwang et al., Proc. Natl. Acad. Sci. USA 77:4030–4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200–800 Angstroms) unilamellar type in which the lipid content is greater than about 30 mol. percent cholesterol, the selected proportion being adjusted for the optimal secreted polypeptide therapy.

For parenteral administration, in one embodiment, the secreted polypeptide is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting the polypeptide uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, or dextrins; chelating agents such as EDTA; sugar alcohols such as mannitol or sorbitol; counterions such as sodium; and/or nonionic surfactants such as polysorbates, poloxamers, or PEG.

The secreted polypeptide is typically formulated in such vehicles at a concentration of about 0.1 mg/ml to 100 mg/ml, preferably 1–10 mg/ml, at a pH of about 3 to 8. It will be understood that the use of certain of the foregoing excipients, carriers, or stabilizers will result in the formation of polypeptide salts.

Any polypeptide to be used for therapeutic administration can be sterile. Sterility is readily accomplished by filtration through sterile filtration membranes (e.g., 0.2 micron membranes). Therapeutic polypeptide compositions generally are placed into a container having a sterile access port, for example, an intravenous solution bag or vial having a stopper pierceable by a hypodermic injection needle.

Polypeptides ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous polypeptide solution, and the resulting mixture is lyophilized. The infusion solution is prepared by reconstituting the lyophilized polypeptide using bacteriostatic Water-for-Injection.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides of the present invention may be employed in conjunction with other therapeutic compounds.

Example 24

Method of Treating Decreased Levels of the Polypeptide

It will be appreciated that conditions caused by a decrease in the standard or normal expression level of a secreted protein in an individual can be treated by administering the polypeptide of the present invention, preferably in the secreted form. Thus, the invention also provides a method of treatment of an individual in need of an increased level of the polypeptide comprising administering to such an individual a pharmaceutical composition comprising an amount of the polypeptide to increase the activity level of the polypeptide in such an individual.

For example, a patient with decreased levels of a polypeptide receives a daily dose 0.1–100 ug/kg of the polypeptide for six consecutive days. Preferably, the polypeptide is in the secreted form. The exact details of the dosing scheme, based on administration and formulation, are provided in Example 23.

Example 25

Method of Treating Increased Levels of the Polypeptide

Antisense technology is used to inhibit production of a polypeptide of the present invention. This technology is one example of a method of decreasing levels of a polypeptide, preferably a secreted form, due to a variety of etiologies, such as cancer.

For example, a patient diagnosed with abnormally increased levels of a polypeptide is administered intravenously antisense polynucleotides at 0.5, 1.0, 1.5, 2.0 and 3.0 mg/kg day for 21 days. This treatment is repeated after a 7-day rest period if the treatment was well tolerated. The formulation of the antisense polynucleotide is provided in Example 23.

Example 26

Method of Treatment Using Gene Therapy

One method of gene therapy transplants fibroblasts, which are capable of expressing a polypeptide, onto a patient. Generally, fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin) is added. The flasks are then incubated at 37° C. for approximately one week.

At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al., DNA, 7:219–25 (1988)), flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention can be amplified using PCR primers which correspond to the 5' and 3' end sequences respectively as set forth in Example 1. Preferably, the 5' primer contains an EcoRI site and the 3' primer includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is then used to transform bacteria HB101, which are then plated onto agar containing kanamycin for the purpose of confirming that the vector has the gene of interest properly inserted.

The amphotropic pA317 or GP+am12 packaging cells are grown in tissue culture to confluent density in Dulbecco's Modified Eagles Medium (DMFEM) with 10% calf serum (CS), penicillin and streptomycin. The MSV vector containing the gene is then added to the media and the packaging cells transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his. Once the fibroblasts have been efficiently infected, the fibroblasts are analyzed to determine whether protein is produced.

The engineered fibroblasts are then transplanted onto the host, either alone or after having been grown to confluence on cytodex 3 microcarrier beads.

Example 27
Method of Treatment Using Gene Therapy—In Vivo

Another aspect of the present invention is using in vivo gene therapy methods to treat disorders, diseases and conditions. The gene therapy method relates to the introduction of naked nucleic acid (DNA, RNA, and antisense DNA or RNA) sequences into an animal to increase or decrease the expression of the polypeptide. The polynucleotide of the present invention may be operatively linked to a promoter or any other genetic elements necessary for the expression of the polypeptide by the target tissue. Such gene therapy and delivery techniques and methods are known in the art, see, for example, WO90/11092, WO98/11779; U.S. Pat. No. 5,693,622, 5,705,151, 5,580,859; Tabata H. et al. (1997) Cardiovasc. Res. 35(3):470–479, Chao J et al. (1997) Pharmacol. Res. 35(6):517–522, Wolff J. A. (1997) Neuromuscul. Disord. 7(5):314–318, Schwartz B. et al. (1996) Gene Ther. 3(5):405–411, Tsurumi Y. et al. (1996) Circulation 94(12):3281–3290 (incorporated herein by reference).

The polynucleotide constructs may be delivered by any method that delivers injectable materials to the cells of an animal, such as, injection into the interstitial space of tissues (heart, muscle, skin, lung, liver, intestine and the like). The polynucleotide constructs can be delivered in a pharmaceutically acceptable liquid or aqueous carrier.

The term "naked" polynucleotide, DNA or RNA, refers to sequences that are free from any delivery vehicle that acts to assist, promote, or facilitate entry into the cell, including viral sequences, viral particles, liposome formulations, lipofectin or precipitating agents and the like. However, the polynucleotides of the present invention may also be delivered in liposome formulations (such as those taught in Felgner P. L. et al. (1995) Ann. NY Acad. Sci. 772:126–139 and Abdallah B. et al. (1995) Biol. Cell 85(1):1–7) which can be prepared by methods well known to those skilled in the art.

The polynucleotide vector constructs used in the gene therapy method are preferably constructs that will not integrate into the host genome nor will they contain sequences that allow for replication. Any strong promoter known to those skilled in the art can be used for driving the expression of DNA. Unlike other gene therapies techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The polynucleotide construct can be delivered to the interstitial space of tissues within the an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. In vivo muscle cells are particularly competent in their ability to take up and express polynucleotides.

For the naked polynucleotide injection, an effective dosage amount of DNA or RNA will be in the range of from about 0.05 g/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration. The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked polynucleotide constructs can be delivered to arteries during angioplasty by the catheter used in the procedure.

The dose response effects of injected polynucleotide in muscle in vivo is determined as follows. Suitable template DNA for production of mRNA coding for polypeptide of the present invention is prepared in accordance with a standard recombinant DNA methodology. The template DNA, which may be either circular or linear, is either used as naked DNA or complexed with liposomes. The quadriceps muscles of mice are then injected with various amounts of the template DNA.

Five to six week old female and male Balb/C mice are anesthetized by intraperitoneal injection with 0.3 ml of 2.5% Avertin. A 1.5 cm incision is made on the anterior thigh, and the quadriceps muscle is directly visualized. The template DNA is injected in 0.1 ml of carrier in a 1 cc syringe through a 27 gauge needle over one minute, approximately 0.5 cm from the distal insertion site of the muscle into the knee and about 0.2 cm deep. A suture is placed over the injection site for future localization, and the skin is closed with stainless steel clips.

After an appropriate incubation time (e.g., 7 days) muscle extracts are prepared by excising the entire quadriceps. Every fifth 15 um cross-section of the individual quadriceps muscles is histochemically stained for protein expression. A time course for protein expression may be done in a similar fashion except that quadriceps from different mice are harvested at different times. Persistence of DNA in muscle following injection may be determined by Southern blot analysis after preparing total cellular DNA and HIRT supernatants from injected and control mice. The results of the above experimentation in mice can be use to extrapolate proper dosages and other treatment parameters in humans and other animals using naked DNA.

Example 28

Transgenic Animals

The polypeptides of the invention can also be expressed in transgenic animals. Animals of any species, including, but not limited to, mice, rats, rabbits, hamsters, guinea pigs, pigs, micro-pigs, goats, sheep, cows and non-human primates, e.g., baboons, monkeys, and chimpanzees may be used to generate transgenic animals. In a specific embodiment, techniques described herein or otherwise known in the art, are used to express polypeptides of the invention in humans, as part of a gene therapy protocol.

Any technique known in the art may be used to introduce the transgene (i.e., polynucleotides of the invention) into animals to produce the founder lines of transgenic animals. Such techniques include, but are not limited to, pronuclear microinjection (Paterson et al., Appl. Microbiol. Biotechnol. 40:691–698 (1994); Carver et al., Biotechnology (NY) 11:1263–1270 (1993); Wright et al., Biotechnology (NY) 9:830–834 (1991); and Hoppe et al., U.S. Pat. No. 4,873,191 (1989)); retrovirus mediated gene transfer into germ lines (Van der Putten et al., Proc. Natl. Acad. Sci., USA 82:614–6152 (1985)), blastocysts or embryos; gene targeting in embryonic stem cells (Thompson et al., Cell 56:313–321 (1989)); electroporation of cells or embryos (Lo, 1983, Mol Cell. Biol. 3:1803–1814 (1983)); introduction of the polynucleotides of the invention using a gene gun (see, e.g., Ulmer et al., Science 259:1745 (1993); introducing nucleic acid constructs into embryonic pleuripotent stem cells and transferring the stem cells back into the blastocyst; and sperm-mediated gene transfer (Lavitrano et al., Cell 57:717–723 (1989); etc. For a review of such techniques, see Gordon, "Transgenic Animals," Intl. Rev. Cytol. 115:171–229 (1989), which is incorporated by reference herein in its entirety.

Any technique known in the art may be used to produce transgenic clones containing polynucleotides of the invention, for example, nuclear transfer into enucleated oocytes of nuclei from cultured embryonic, fetal, or adult cells induced to quiescence (Campell et al., Nature 380:64–66 (1996); Wilmut et al., Nature 385:810–813 (1997)).

The present invention provides for transgenic animals that carry the transgene in all their cells, as well as animals which carry the transgene in some, but not all their cells, i.e., mosaic animals or chimeric. The transgene may be integrated as a single transgene or as multiple copies such as in concatamers, e.g., head-to-head tandems or head-to-tail tandems. The transgene may also be selectively introduced into and activated in a particular cell type by following, for example, the teaching of Lasko et al. (Lasko et al., Proc. Natl. Acad. Sci. USA 89:6232–6236 (1992)). The regulatory sequences required for such a cell-type specific activation will depend upon the particular cell type of interest, and will be apparent to those of skill in the art. When it is desired that the polynucleotide transgene be integrated into the chromosomal site of the endogenous gene, gene targeting is preferred. Briefly, when such a technique is to be utilized, vectors containing some nucleotide sequences homologous to the endogenous gene are designed for the purpose of integrating, via homologous recombination with chromosomal sequences, into and disrupting the function of the nucleotide sequence of the endogenous gene. The transgene may also be selectively introduced into a particular cell type, thus inactivating the endogenous gene in only that cell type, by following, for example, the teaching of Gu et al. (Gu et al., Science 265:103–106 (1994)). The regulatory sequences required for such a cell-type specific inactivation will depend upon the particular cell type of interest, and will be apparent to those of skill in the art.

Once transgenic animals have been generated, the expression of the recombinant gene may be assayed utilizing standard techniques. Initial screening may be accomplished by Southern blot analysis or PCR techniques to analyze animal tissues to verify that integration of the transgene has taken place. The level of mRNA expression of the transgene in the tissues of the transgenic animals may also be assessed using techniques which include, but are not limited to, Northern blot analysis of tissue samples obtained from the animal, in situ hybridization analysis, and reverse transcriptase-PCR (rt-PCR). Samples of transgenic gene-expressing tissue may also be evaluated immunocytochemically or immunohistochemically using antibodies specific for the transgene product.

Once the founder animals are produced, they may be bred, inbred, outbred, or crossbred to produce colonies of the particular animal. Examples of such breeding strategies include, but are not limited to: outbreeding of founder animals with more than one integration site in order to establish separate lines; inbreeding of separate lines in order to produce compound transgenics that express the transgene at higher levels because of the effects of additive expression of each transgene; crossing of heterozygous transgenic animals to produce animals homozygous for a given integration site in order to both augment expression and eliminate the need for screening of animals by DNA analysis; crossing of separate homozygous lines to produce compound heterozygous or homozygous lines; and breeding to place the transgene on a distinct background that is appropriate for an experimental model of interest.

Transgenic animals of the invention have uses which include, but are not limited to, animal model systems useful in elaborating the biological function of polypeptides of the present invention, studying conditions and/or disorders associated with aberrant expression, and in screening for compounds effective in ameliorating such conditions and/or disorders.

Example 29

Knock-Out Animals

Endogenous gene expression can also be reduced by inactivating or "knocking out" the gene and/or its promoter using targeted homologous recombination. (E.g., see Smithies et al., Nature 317:230–234 (1985); Thomas & Capecchi, Cell 51:503–512 (1987); Thompson et al., Cell 5:313–321 (1989); each of which is incorporated by reference herein in its entirety). For example, a mutant, non-functional polynucleotide of the invention (or a completely unrelated DNA sequence) flanked by DNA homologous to the endogenous polynucleotide sequence (either the coding regions or regulatory regions of the gene) can be used, with or without a selectable marker and/or a negative selectable marker, to transfect cells that express polypeptides of the invention in vivo. In another embodiment, techniques known in the art are used to generate knockouts in cells that contain, but do not express the gene of interest. Insertion of the DNA construct, via targeted homologous recombination, results in inactivation of the targeted gene. Such approaches are particularly suited in research and agricultural fields where modifications to embryonic stem cells can be used to generate animal offspring with an inactive targeted gene (e.g., see Thomas & Capecchi 1987 and Thompson 1989, supra). However this approach can be routinely adapted for use in humans provided the recombinant DNA constructs are directly administered or targeted to the required site in vivo using appropriate viral vectors that will be apparent to those of skill in the art.

In further embodiments of the invention, cells that are genetically engineered to express the polypeptides of the invention, or alternatively, that are genetically engineered not to express the polypeptides of the invention (e.g., knockouts) are administered to a patient in vivo. Such cells may be obtained from the patient (i.e., animal, including human) or an MHC compatible donor and can include, but are not limited to fibroblasts, bone marrow cells, blood cells (e.g., lymphocytes), adipocytes, muscle cells, endothelial cells etc. The cells are genetically engineered in vitro using recombinant DNA techniques to introduce the coding sequence of polypeptides of the invention into the cells, or alternatively, to disrupt the coding sequence and/or endogenous regulatory sequence associated with the polypeptides of the invention, e.g., by transduction (using viral vectors, and preferably vectors that integrate the transgene into the cell genome) or transfection procedures, including, but not limited to, the use of plasmids, cosmids, YACs, naked DNA, electroporation, liposomes, etc. The coding sequence of the polypeptides of the invention can be placed under the control of a strong constitutive or inducible promoter or promoter/enhancer to achieve expression, and preferably secretion, of the polypeptides of the invention. The engineered cells which express and preferably secrete the polypeptides of the invention can be introduced into the patient systemically, e.g., in the circulation, or intraperitoneally.

Alternatively, the cells can be incorporated into a matrix and implanted in the body, e.g., genetically engineered fibroblasts can be implanted as part of a skin graft; genetically engineered endothelial cells can be implanted as part of a lymphatic or vascular graft. (See, for example, Anderson et al. U.S. Pat. No. 5,399,349; and Mulligan & Wilson, U.S. Pat. No. 5,460,959 each of which is incorporated by reference herein in its entirety).

When the cells to be administered are non-autologous or non-MHC compatible cells, they can be administered using well known techniques which prevent the development of a host immune response against the introduced cells. For example, the cells may be introduced in an encapsulated form which, while allowing for an exchange of components with the immediate extracellular environment, does not allow the introduced cells to be recognized by the host immune system.

Transgenic and "knock-out" animals of the invention have uses which include, but are not limited to, animal model systems useful in elaborating the biological function of polypeptides of the present invention, studying conditions and/or disorders associated with aberrant expression, and in screening for compounds effective in ameliorating such conditions and/or disorders.

It will be clear that the invention may be practiced otherwise than as particularly described in the foregoing description and examples. Numerous modifications and variations of the present invention are possible in light of the above teachings and, therefore, are within the scope of the appended claims.

The entire disclosure of each document cited (including patents, patent applications, journal articles, abstracts, laboratory manuals, books, or other disclosures) in the Background of the Invention, Detailed Description, and Examples is hereby incorporated herein by reference. Further, the hard copy of the sequence listing submitted herewith and the corresponding computer readable form are both incorporated herein by reference in their entireties.

What is claimed is:

1. An isolated protein comprising amino acid residues 31 to 144 of SEQ ID NO:63.

2. The isolated protein of claim 1 which comprises amino acid residues 2 to 144 of SEQ ID NO:63.

3. The isolated protein of claim 1 which comprises amino acid residues 1 to 144 of SEQ ID NO:63.

4. The protein of claim 1 which comprises a heterologous polypeptide sequence.

5. A composition comprising the protein of claim 1 and a pharmaceutically acceptable carrier.

6. An isolated protein produced by the method comprising:
 (a) expressing the protein of claim 1 by a cell; and
 (b) recovering said protein.

7. An isolated protein comprising the amino acid sequence of the secreted portion of the polypeptide encoded by the HMCDX48 cDNA contained in ATCC Deposit No. 209197.

8. The isolated protein of claim 7 which comprises the amino acid sequence of the complete polypeptide encoded by the HMCDX48 cDNA contained in ATCC Deposit No. 209197, excepting the N-terminal methionine.

9. The isolated protein of claim 7 which comprises the amino acid sequence of the complete polypeptide encoded by the HMCDX48 cDNA contained in ATCC Deposit No. 209197.

10. The protein of claim 7 which comprises a heterologous polypeptide sequence.

11. A composition comprising the protein of claim 7 and a pharmaceutically acceptable carrier.

12. An isolated protein produced by the method comprising:
 (a) expressing the protein of claim 7 by a cell; and
 (b) recovering said protein.

13. An isolated protein comprising a polypeptide sequence which is at least 90% identical to amino acid residues 31 to 144 of SEQ ID NO:63, wherein said isolated protein is capable of specifically binding an antibody that also specifically binds to a protein whose sequence consists of amino acid residues 31 to 144 of SEQ ID NO:63.

14. The isolated protein of claim 13 wherein said polypeptide sequence is at least 90% identical to amino acid residues 1 to 144 of SEQ ID NO:63.

15. The isolated protein of claim 13 wherein said polypeptide sequence is at least 95% identical to amino acid residues 31 to 144 of SEQ ID NO:63.

16. The isolated protein of claim 13 wherein said polypeptide sequence is at least 95% identical to amino acid residues 1 to 144 of SEQ ID NO:63.

17. The protein of claim 13 which comprises a heterologous polypeptide sequence.

18. A composition comprising the protein of claim 13 and a pharmaceutically acceptable carrier.

19. An isolated protein produced by the method comprising:
 (a) expressing the protein of claim 13 by a cell; and
 (b) recovering said protein.

20. An isolated protein comprising a polypeptide sequence which is at least 90% identical to the secreted portion of the polypeptide encoded by the HMCDX48 cDNA contained in ATCC Deposit No. 209197, wherein said isolated protein is capable of specifically binding an antibody that also specifically binds to a protein whose sequence consists of the secreted portion of the polypeptide encoded by HMCDX48 cDNA contained in ATCC Deposit No. 209197.

21. The isolated protein of claim 20 wherein said polypeptide sequence is at least 90% identical to the complete polypeptide encoded by the HMCDX48 cDNA contained in ATCC Deposit No. 209197.

22. The isolated protein of claim 20 wherein said polypeptide sequence is at least 95% identical to the secreted portion of the polypeptide encoded by the HMCDX48 cDNA contained in ATCC Deposit No. 209197.

23. The isolated protein of claim 20 wherein said polypeptide sequence is at least 95% identical to the complete polypeptide encoded by the HMCDX48 cDNA contained in ATCC Deposit No. 209197.

24. The protein of claim 20 which comprises a heterologous polypeptide sequence.

25. A composition comprising the protein of claim 20 and a pharmaceutically acceptable carrier.

26. An isolated protein produced by the method comprising:
 (a) expressing the protein of claim 20 by a cell; and
 (b) recovering said protein.

27. An isolated protein comprising at least 30 contiguous amino acid residues of amino acid residues 31 to 144 of SEQ ID NO:63, wherein said isolated protein is capable of specifically binding an antibody that also specifically binds to a protein whose sequence consists of residues 31 to 144 of SEQ ID NO:63.

28. The isolated protein of claim 27 which comprises at least 50 contiguous amino acid residues of amino acid residues 31 to 144 of SEQ ID NO:63.

29. The protein of claim 27 which comprises a heterologous polypeptide sequence.

30. A composition comprising the protein of claim 27 and a pharmaceutically acceptable carrier.

31. An isolated protein produced by the method comprising:
 (a) expressing the protein of claim 27 by a cell; and
 (b) recovering said protein.

32. An isolated protein comprising at least 30 contiguous amino acid residues of the secreted portion of the polypeptide encoded by the HMCDX48 cDNA contained in ATCC Deposit No. 209197, wherein said isolated protein is capable of specifically binding an antibody that also specifically binds to a protein whose sequence consists of the secreted portion of the polypeptide encoded by HMCDX48 cDNA contained in ATCC Deposit No. 209197.

33. The isolated protein of claim 32 which comprises at least 50 contiguous amino acid residues of the secreted portion of the polypeptide encoded by the HMCDX48 cDNA contained in ATCC Deposit No. 209197.

34. The protein of claim 32 which comprises a heterologous polypeptide sequence.

35. A composition comprising the protein of claim 32 and pharmaceutically acceptable carrier.

36. An isolated protein produced by the method comprising:

(a) expressing the protein of claim 32 by a cell; and (b) recovering said protein.

37. An isolated protein comprising at least 30 contiguous amino acid residues of amino acid residues 1 to 144 of SEQ ID NO:63, wherein said isolated protein is capable of specifically binding an antibody that also specifically binds to a protein whose sequence consists of SEQ ID NO:63.

38. The isolated protein of claim 37 which comprises at least 50 contiguous amino acid residues of amino acid residues 1 to 144 of SEQ ID NO:63.

39. The protein of claim 37 which comprises a heterologous polypeptide sequence.

40. A composition comprising the protein of claim 37 and a pharmaceutically acceptable carrier.

41. An isolated protein produced by the method comprising:

(a) expressing the protein of claim 37 by a cell; and (b) recovering said protein.

42. An isolated protein comprising at least 30 contiguous amino acid residues of the complete polypeptide encoded by the HMCDX48 cDNA contained in ATCC Deposit No. 209197, wherein said isolated protein is capable of specifically binding an antibody that specifically also binds to a protein whose sequence consists of the complete polypeptide encoded by HMCDX48 cDNA contained in ATCC Deposit No. 209197.

43. The isolated protein of claim 42 which comprises at least 50 contiguous amino acid residues of the complete polypeptide encoded by the HMCDX48 cDNA contained in ATCC Deposit No. 209197.

44. The protein of claim 42 which comprises a heterologous polypeptide sequence.

45. A composition comprising the protein of claim 42 and pharmaceutically acceptable carrier.

46. An isolated protein produced by the method comprising:

(a) expressing the protein of claim 42 by a cell; and (b) recovering said protein.

* * * * *